(12) United States Patent
Haaf et al.

(10) Patent No.: US 9,516,880 B2
(45) Date of Patent: Dec. 13, 2016

(54) HERBICIDAL AND FUNGICIDAL 5-OXY-SUBSTITUTED 3-PHENYLISOXAZOLINE-5-CARBOXAMIDES AND 5-OXY-SUBSTITUTED 3-PHENYLISOXAZOLINE-5-THIOAMIDES

(71) Applicant: BAYER CROPSCIENCE AG, Monheim (DE)

(72) Inventors: Klaus Bernhard Haaf, Kelkheim (DE); Lothar Willms, Hofheim (DE); Hansjoerg Dietrich, Liederbach am Taunus (DE); Elmar Gatzweiler, Bad Nauheim (DE); Christopher Hugh Rosinger, Hofheim (DE); Dirk Schmutzler, Hattersheim (DE); Ulrike Wachendorff-Neumann, Neuwied (DE); Marie-Claire Grosjean-Cournoyer, Curis au Mont d'Or (FR); Helene Lachaise, Lyons (FR); Philippe Rinolfi, Chatillon d'Azergues (FR); Stephane Brunet, St Andre de Corcy (FR)

(73) Assignee: Bayer Cropscience AG, Monheim (DE)

( * ) Notice: Subject to any disclaimer, the term of this patent is extended or adjusted under 35 U.S.C. 154(b) by 0 days.

(21) Appl. No.: 14/430,066

(22) PCT Filed: Sep. 23, 2013

(86) PCT No.: PCT/EP2013/069737
§ 371 (c)(1),
(2) Date: Mar. 20, 2015

(87) PCT Pub. No.: WO2014/048882
PCT Pub. Date: Apr. 3, 2014

(65) Prior Publication Data
US 2015/0245616 A1    Sep. 3, 2015

(30) Foreign Application Priority Data
Sep. 25, 2012  (EP) .................................... 12185767

(51) Int. Cl.
*A01N 43/80*   (2006.01)
*C07D 261/04*  (2006.01)
*C07D 413/12*  (2006.01)

(52) U.S. Cl.
CPC ............. *A01N 43/80* (2013.01); *C07D 261/04* (2013.01); *C07D 413/12* (2013.01)

(58) Field of Classification Search
None
See application file for complete search history.

(56) References Cited

U.S. PATENT DOCUMENTS

| | | | |
|---|---|---|---|
| 5,332,175 | A | 7/1994 | Furomoto |
| 9,078,442 | B2 | 7/2015 | Willms et al. |
| 2012/0021903 | A1 | 1/2012 | Ahrens et al. |
| 2015/0223461 | A1 | 8/2015 | Frenzel et al. |
| 2015/0245615 | A1 | 9/2015 | Kuhn et al. |

FOREIGN PATENT DOCUMENTS

| | | |
|---|---|---|
| DE | 4017665 A1 | 12/1991 |
| DE | 4026018 A1 | 2/1992 |
| EP | 0174685 A2 | 3/1986 |
| EP | 0520371 A2 | 12/1992 |
| EP | 10170238 | 7/2010 |
| WO | 9203053 A1 | 3/1992 |
| WO | 9514680 A1 | 6/1995 |
| WO | 9857937 A2 | 12/1998 |
| WO | 2005021516 A1 | 3/2005 |

OTHER PUBLICATIONS

International Search Report from corresponding PCT/EP2013/069737, mailed Oct. 29, 2013.
Gucma et al., "Synthesis of 3-Substituted Isoxazolecarboxamides as Potential Fungicides", Letters in Organic Chemistry, 2010, 7, pp. 502-507.
Gucma et al., "Synthesis and fungicidal activity of substituted ixoxazolecarboxamides", Pestycydy/Pesticides, 2010, (1-4), pp. 21-31, XP008159982.
Gucma et al., "Synthesis and biological activity of 3-substituted isoxazolecarboxamides", Monatsh Chem (2010) 141: pp. 461-469.
Priya et al., "Isoxazoline Derivatives as Antimicrobials" Mysore, India, vol. 12, No. 1, 2006.
U.S. Appl. No. 14/430,018, filed Jul. 14, 2015.
U.S. Appl. No. 14/429,914, filed Mar. 20, 2015.

*Primary Examiner* — Kamal Saeed
(74) *Attorney, Agent, or Firm* — McBee Moore Woodward Vanik IP LLC

(57) ABSTRACT

Herbicidally and fungicidally active 5-oxy-substituted 3-phenylisoxazoline-5-carboxamides and 5-oxy-substituted 3-phenylisoxazoline-5-thioamides of the formula (I) are described.

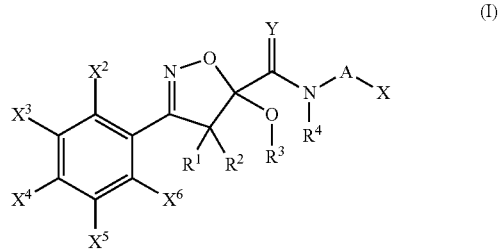

(I)

In this formula (I), X, $X^2$ to $X^6$, $R^1$ to $R^4$ are radicals such as hydrogen, halogen and organic radicals such as substituted alkyl. A is a bond or a divalent unit. Y is a chalcogen.

20 Claims, No Drawings

HERBICIDAL AND FUNGICIDAL 5-OXY-SUBSTITUTED 3-PHENYLISOXAZOLINE-5-CARBOXAMIDES AND 5-OXY-SUBSTITUTED 3-PHENYLISOXAZOLINE-5-THIOAMIDES

CROSS REFERENCE TO RELATED APPLICATIONS

This application is a §371 National Stage Application of PCT/EP2013/069737, filed 23 Sep. 2013 which claims priority to EP 12185767.6 filed 25 Sep. 2012.

BACKGROUND

Field of the Invention

The invention relates to the technical field of herbicides and fungicides, especially that of herbicides for selective control of broad-leaved weeds and weed grasses in crops of useful plants.

Description of Related Art

Specifically, it relates to substituted 5-oxy-substituted 3-phenylisoxazoline-5-carboxamides and 5-oxy-substituted 3-phenylisoxazoline-5-thioamides, to processes for their preparation and to their use as herbicides and fungicides.

DE 4026018 A1, EP 0 520 371 A2 and DE 4017665 disclose 3-phenylisoxazoline-5-carboxamides bearing a hydrogen atom in the 5 position of the isoxazoline ring. These compounds are described therein as agrochemically active safeners, i.e. as compounds which eliminate the unwanted herbicidal action of herbicides on crop plants. No herbicidal action of these compounds is disclosed. European patent application No. 10170238, which has an earlier priority date but was yet to be published at the priority date of the present application, discloses herbicidally and fungicidally active 3-phenylisoxazoline-5-carboxamides and 3-phenylisoxazoline-5-thioamides bearing a hydrogen atom in the 5 position of the isoxazoline ring. Monatshefte Chemie (2010) 141, 461 and Letters in Organic Chemistry (2010), 7, 502 also disclose 3-phenylisoxazoline-5-carboxamides bearing a hydrogen atom in the 5 position of the isoxazoline ring. Fungicidal action, but not herbicidal action, is disclosed for some of the compounds mentioned.

SUMMARY

It is an object of the present invention to provide herbicidally and fungicidally active compounds.

It has been found that 5-oxy-substituted 3-phenylisoxazoline-5-carboxamides and 5-oxy-substituted 3-phenylisoxazoline-5-thioamides are particularly suitable for use as herbicides and fungicides. The present invention provides 5-oxy-substituted 3-phenylisoxazoline-5-carboxamides and 5-oxy-substituted 3-phenylisoxazoline-5-thioamides of the formula (I), or salts thereof,

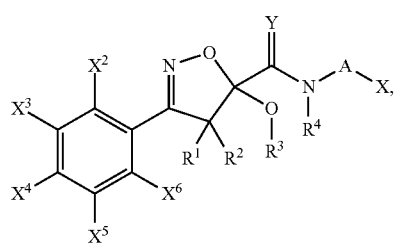

(I)

in which $R^1$ and $R^2$ are each independently hydrogen, fluorine, chlorine, bromine, iodine, cyano, or $(C_1-C_4)$-alkyl or $(C_1-C_4)$-alkoxy each substituted by m radicals from the group consisting of fluorine, chlorine, bromine, iodine and cyano, or $R^1$ and $R^2$ together with the carbon atom to which they are bonded form a saturated or partly or fully unsaturated three-, four- or five-membered ring formed from q carbon atoms and p oxygen atoms;

$R^3$ is $(C_1-C_6)$-alkyl, $(C_3-C_6)$-cycloalkyl, $(C_2-C_6)$-alkenyl or $(C_2-C_6)$-alkynyl each substituted by m radicals from the group consisting of fluorine, chlorine, bromine, iodine, cyano, $(C_1-C_4)$-alkoxy and hydroxyl, $R^4$ is hydrogen, cyano, or $(C_1-C_8)$-alkyl, $(C_3-C_8)$-cycloalkyl, $(C_3-C_8)$-alkenyl or $(C_3-C_8)$-alkynyl each substituted by m radicals from the group consisting of fluorine, chlorine, bromine, iodine, cyano, hydroxyl and $(C_1-C_6)$-alkoxy, A is a bond or a divalent unit from the group consisting of

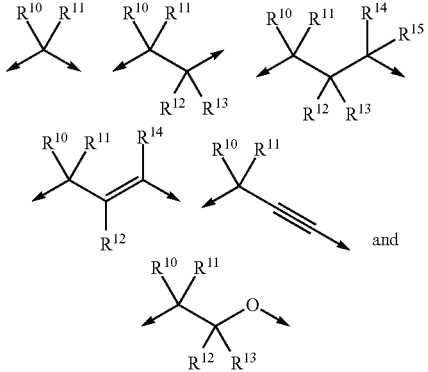

$R^{10}$, $R^{11}$, $R^{12}$, $R^{13}$, $R^{14}$ and $R^{15}$ are each independently hydrogen, fluorine, chlorine, bromine, iodine, hydroxyl, cyano, $CO_2R^8$, $CONR^6R^8$, $R^5$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

Y is oxygen or sulfur;

X is hydrogen, cyano, hydroxyl, $X^1$, or $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, bromine, iodine, cyano, hydroxyl, $OR^7$, $X^1$, $OX^1$, $NHX^1$, $S(O)_nR^5$, $SO_2NR^6R^7$, $SO_2NR^6COR^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)=NOR^8$, or X, A and $R^4$ together with the nitrogen atom to which they are bonded form a saturated or partly or fully unsaturated five-, six- or seven-membered ring containing, as well as this nitrogen atom, k carbon atoms, n oxygen atoms, p sulfur atoms and p elements from the group consisting of $NR^7$ and $NCOR^7$ as ring atoms, where one carbon atom bears p oxo groups;

$X^1$ is a three-, four-, five- or six-membered saturated, partly unsaturated, fully unsaturated or aromatic ring which is formed from r carbon atoms, s nitrogen atoms, n sulfur atoms and n oxygen atoms, and which is substituted by s radicals from the group consisting of $R^6$, $R^{6a}$, $R^8$ and $R^9$, where the sulfur atoms and carbon atoms bear n oxo groups; or $X^1$ is phenyl substituted by m radicals from the group consisting of $R^6$, $R^{6a}$, $R^8$ and $R^9$;

$X^2$, $X^4$ and $X^6$ are each independently hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;

$X^3$ and $X^5$ are each independently hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $S(O)_n R^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$R^5$ is $(C_1-C_6)$-alkyl or $(C_3-C_6)$-cycloalkyl each substituted by m radicals from the group consisting of fluorine, chlorine, bromine, iodine, cyano and hydroxyl;

$R^6$ is hydrogen or $R^5$;

$R^{6a}$ is fluorine, chlorine, bromine, iodine, cyano, hydroxyl, $S(O)_n R^5$, or $(C_1-C_6)$-alkoxy, $(C_3-C_6)$-alkenyloxy or $(C_3-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;

$R^8$ is $R^7$, $R^9$ is $(C_1-C_3)$-alkyl or $(C_1-C_3)$-alkoxy;

k is 3, 4, 5 or 6;
m is 0, 1, 2, 3, 4 or 5;
n is 0, 1 or 2;
p is 0 or 1;
q is 3, 4 or 5;
r is 1, 2, 3, 4 or 5;
s is 0, 1, 2, 3 or 4.

DETAILED DESCRIPTION OF A PREFERRED EMBODIMENT

Alkyl means saturated straight-chain or branched hydrocarbyl radicals having the number of carbon atoms specified in each case, e.g. $C_1-C_6$-alkyl such as methyl, ethyl, propyl, 1-methylethyl, butyl, 1-methylpropyl, 2-methylpropyl, 1,1-dimethylethyl, pentyl, 1-methylbutyl, 2-methylbutyl, 3-methylbutyl, 2,2-dimethylpropyl, 1-ethylpropyl, hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2,2-trimethylpropyl, 1-ethyl-1-methylpropyl and 1-ethyl-2-methylpropyl.

Halogen-substituted alkyl means straight-chain or branched alkyl groups where some or all of the hydrogen atoms in these groups may be replaced by halogen atoms, e.g. $C_1-C_2$-haloalkyl such as chloromethyl, bromomethyl, dichloromethyl, trichloromethyl, fluoromethyl, difluoromethyl, trifluoromethyl, chlorofluoromethyl, dichlorofluoromethyl, chlorodifluoromethyl, 1-chloroethyl, 1-bromoethyl, 1-fluoroethyl, 2-fluoroethyl, 2,2-difluoroethyl, 2,2,2-trifluoroethyl, 2-chloro-2-fluoroethyl, 2-chloro-2,2-difluoroethyl, 2,2-dichloro-2-fluoroethyl, 2,2,2-trichloroethyl, pentafluoroethyl and 1,1,1-trifluoroprop-2-yl.

Alkenyl means unsaturated straight-chain or branched hydrocarbyl radicals having the number of carbon atoms specified in each case and one double bond in any position, e.g. $C_2-C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

Alkynyl means straight-chain or branched hydrocarbyl radicals having the number of carbon atoms specified in each case and one triple bond in any position, e.g. $C_2-C_6$-alkynyl such as ethynyl, 1-propynyl, 2-propynyl (or propargyl), 1-butynyl, 2-butynyl, 3-butynyl, 1-methyl-2-propynyl, 1-pentynyl, 2-pentynyl, 3-pentynyl, 4-pentynyl, 3-methyl-1-butynyl, 1-methyl-2-butynyl, 1-methyl-3-butynyl, 2-methyl-3-butynyl, 1,1-dimethyl-2-propynyl, 1-ethyl-2-propynyl, 1-hexynyl, 2-hexynyl, 3-hexynyl, 4-hexynyl, 5-hexynyl, 3-methyl-1-pentynyl, 4-methyl-1-pentynyl, 1-methyl-2-pentynyl, 4-methyl-2-pentynyl, 1-methyl-3-pentynyl, 2-methyl-3-pentynyl, 1-methyl-4-pentynyl, 2-methyl-4-pentynyl, 3-methyl-4-pentynyl, 1,1-dimethyl-2-butynyl, 1,1-dimethyl-3-butynyl, 1,2-dimethyl-3-butynyl, 2,2-dimethyl-3-butynyl, 3,3-dimethyl-1-butynyl, 1-ethyl-2-butynyl, 1-ethyl-3-butynyl, 2-ethyl-3-butynyl and 1-ethyl-1-methyl-2-propynyl.

Alkoxy means saturated straight-chain or branched alkoxy radicals having the number of carbon atoms stated in each case, for example $C_1-C_6$-alkoxy such as methoxy, ethoxy, propoxy, 1-methylethoxy, butoxy, 1-methylpropoxy, 2-methylpropoxy, 1,1-dimethylethoxy, pentoxy, 1-methylbutoxy, 2-methylbutoxy, 3-methylbutoxy, 2,2-dimethylpropoxy, 1-ethylpropoxy, hexoxy, 1,1-dimethylpropoxy, 1,2-dimethylpropoxy, 1-methylpentoxy, 2-methylpentoxy, 3-methylpentoxy, 4-methylpentoxy, 1,1-dimethylbutoxy, 1,2-dimethylbutoxy, 1,3-dimethylbutoxy, 2,2-dimethylbutoxy, 2,3-dimethylbutoxy, 3,3-dimethylbutoxy, 1-ethylbutoxy, 2-ethylbutoxy, 1,1,2-trimethylpropoxy, 1,2,2-trimethylpropoxy, 1-ethyl-1-methylpropoxy and 1-ethyl-2-methylpropoxy. Halogen-substituted alkoxy means straight-chain or branched alkoxy radicals having the number of carbon atoms specified in each case, where some or all of the hydrogen atoms in these groups may be replaced by halogen atoms as specified above, e.g. $C_1$-$C_2$-haloalkoxy such as chloromethoxy, bromomethoxy, dichloromethoxy, trichloromethoxy, fluoromethoxy, difluoromethoxy, trifluoromethoxy, chlorofluoromethoxy, dichlorofluoromethoxy, chlorodifluoromethoxy, 1-chloroethoxy, 1-bromoethoxy, 1-fluoroethoxy, 2-fluoroethoxy, 2,2-difluoroethoxy, 2,2,2-trifluoroethoxy, 2-chloro-2-fluoroethoxy, 2-chloro-1,2-difluoroethoxy, 2,2-dichloro-2-fluoroethoxy, 2,2,2-trichloroethoxy, pentafluoroethoxy and 1,1,1-trifluoroprop-2-oxy.

According to the nature of the substituents and the way in which they are joined, the compounds of the formula (I) may be present as stereoisomers. If, for example, one or more asymmetrically substituted carbon atoms and/or sulfoxides are present, enantiomers and diastereomers may occur. Stereoisomers can be obtained from the mixtures obtained in the preparation by customary separation methods, for example by chromatographic separation processes. It is likewise possible to selectively prepare stereoisomers by using stereoselective reactions with use of optically active starting materials and/or assistants. The invention also relates to all stereoisomers and mixtures thereof which are encompassed by the formula (I) but not defined specifically. For the sake of simplicity, however, reference is always made hereinafter to compounds of the formula (I), even though this means both the pure compounds and, if appropriate, mixtures having different proportions of isomeric compounds.

According to the nature of the substituents defined above, the compounds of the formula (I) have acidic properties and can form salts, and if appropriate also internal salts or adducts with inorganic or organic bases or with metal ions. If the compounds of the formula (I) bear hydroxyl, carboxyl or other groups which induce acidic properties, these compounds can be reacted with bases to give salts. Suitable bases are, for example, hydroxides, carbonates, hydrogencarbonates of the alkali metals and alkaline earth metals, especially those of sodium, potassium, magnesium and calcium, and also ammonia, primary, secondary and tertiary amines having $C_1$-$C_4$-alkyl groups, mono-, di- and trialkanolamines of $C_1$-$C_4$-alkanols, choline and chlorocholine.

If a group is polysubstituted by radicals, this means that this group is substituted by one or more identical or different radicals from those mentioned.

In all the formulae specified hereinafter, the substituents and symbols have the same definition as in formula (I), unless defined differently. Arrows in a chemical formula denote the points at which it is joined to the rest of the molecule.

Preference is given to 5-oxy-substituted 3-phenylisoxazoline-5-carboxamides and 5-oxy-substituted 3-phenylisoxazoline-5-thioamides of the formula (I) in which
$R^1$ and $R^2$ are each independently hydrogen, fluorine, chlorine, bromine, iodine, cyano, or ($C_1$-$C_4$)-alkyl or ($C_1$-$C_4$)-alkoxy each substituted by m radicals from the group consisting of fluorine, chlorine, bromine, iodine and cyano, or
$R^1$ and $R^2$ together with the carbon atom to which they are bonded form a saturated or partly or fully unsaturated three-, four- or five-membered ring formed from q carbon atoms and p oxygen atoms;
$R^3$ is ($C_1$-$C_6$)-alkyl, ($C_3$-$C_6$)-cycloalkyl, ($C_2$-$C_6$)-alkenyl or ($C_2$-$C_6$)-alkynyl each substituted by m radicals from the group consisting of fluorine, chlorine, bromine, iodine, cyano, ($C_1$-$C_4$)-alkoxy and hydroxyl,
$R^4$ is hydrogen, cyano,
or ($C_1$-$C_8$)-alkyl or ($C_3$-$C_8$)-cycloalkyl each substituted by m radicals from the group consisting of fluorine, chlorine, bromine, iodine, cyano, hydroxyl and ($C_1$-$C_6$)-alkoxy;
A is a bond or a divalent unit from the group consisting of

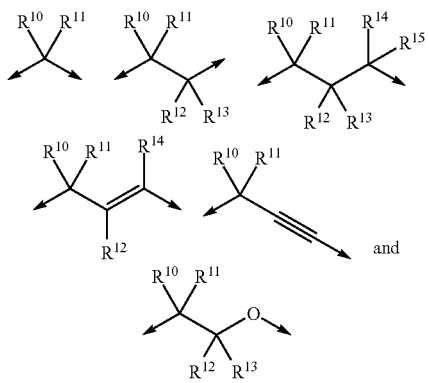

$R^{10}$, $R^{11}$, $R^{12}$, $R^{13}$, $R^{14}$ and $R^{15}$ are each independently hydrogen, fluorine, chlorine, bromine, iodine, hydroxyl, cyano, $CO_2R^8$, $CONR^6R^8$, $R^5$, or ($C_1$-$C_6$)-alkyl, ($C_3$-$C_5$)-cycloalkyl, ($C_2$-$C_6$)-alkenyl, ($C_2$-$C_6$)-alkynyl each substituted by m radicals from the group consisting of fluorine, chlorine, bromine, iodine, hydroxyl and cyano,
or ($C_1$-$C_6$)-alkoxy, ($C_3$-$C_6$)-cycloalkoxy, ($C_2$-$C_6$)-alkenyloxy or ($C_2$-$C_6$)-alkynyloxy each substituted by m radicals from the group consisting of fluorine, chlorine, bromine, iodine, cyano and ($C_1$-$C_2$)-alkoxy;
Y is oxygen or sulfur;
X is hydrogen, cyano, hydroxyl, $X^1$,
or
($C_1$-$C_{12}$)-alkyl, ($C_3$-$C_8$)-cycloalkyl, ($C_2$-$C_{12}$)-alkenyl or ($C_2$-$C_{12}$)-alkynyl each substituted by m radicals from the group consisting of fluorine, chlorine, bromine, iodine, cyano, hydroxyl, $OR^7$, $X^1$, $OX^1$, $NHX^1$, $S(O)_nR^5$, $SO_2NR^6R^7$, $SO_2NR^6COR^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)=NOR^8$,
or
X, A and $R^4$ together with the nitrogen atom to which they are bonded form a saturated or partly or fully unsaturated five-, six- or seven-membered ring containing, as well as this nitrogen atom, k carbon atoms, n oxygen atoms, p sulfur atoms and p elements from the group consisting of $NR^7$ and $NCOR^7$ as ring atoms, where one carbon atom bears p oxo groups;
$X^1$ is a ring, substituted by s radicals from the group consisting of $R^6$, $R^{6a}$, $R^8$ and $R^9$, from the group consisting of

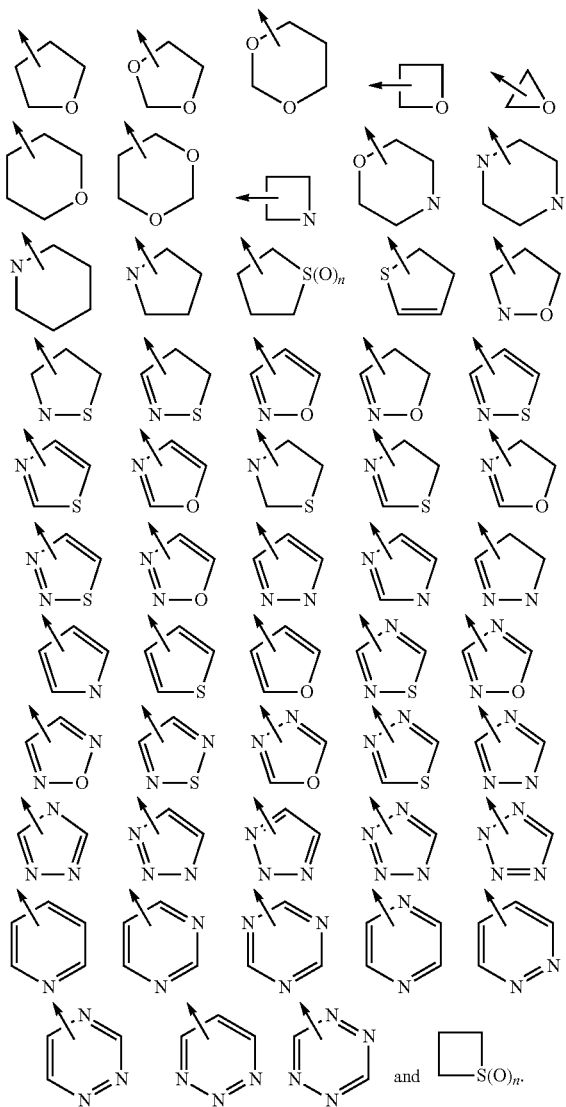

or $X^1$ is phenyl substituted by m radicals from the group consisting of $R^6$, $R^{6a}$, $R^8$ and $R^9$;

$X^2$, $X^4$ and $X^6$ are each independently hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;

$X^3$ and $X^5$ are each independently hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$R^5$ is $(C_1-C_6)$-alkyl or $(C_3-C_6)$-cycloalkyl each substituted by m radicals from the group consisting of fluorine, chlorine, bromine, iodine, cyano and hydroxyl;

$R^6$ is hydrogen or $R^5$;

$R^{6a}$ is fluorine, chlorine, bromine, iodine, cyano, hydroxyl, $S(O)_nR^5$, or $(C_1-C_6)$-alkoxy, $(C_2-C_6)$-alkenyloxy or $(C_2-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;

$R^8$ is $R^7$, $R^9$ is $(C_1-C_3)$-alkyl or $(C_1-C_3)$-alkoxy;

k is 3, 4, 5 or 6;

m is 0, 1, 2, 3, 4 or 5;

n is 0, 1 or 2;

p is 0 or 1;

q is 3, 4 or 5;

s is 0, 1, 2, 3 or 4.

Particular preference is given to 5-oxy-substituted 3-phenylisoxazoline-5-carboxamides and 5-oxy-substituted 3-phenylisoxazoline-5-thioamides of the formula (I) in which $R^1$ and $R^2$ are each independently hydrogen, fluorine, chlorine, bromine, iodine, cyano, or $(C_1-C_4)$-alkyl substituted by m radicals from the group consisting of fluorine, chlorine, bromine, iodine and cyano;

$R^3$ is $(C_1-C_4)$-alkyl, $(C_3-C_4)$-cycloalkyl, $(C_2-C_3)$-alkenyl or $(C_2-C_3)$-alkynyl each substituted by m radicals from the group consisting of fluorine, chlorine, bromine, cyano, $(C_1-C_2)$-alkoxy, A is a bond or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH=CH$, $C(CH_3)_2C\equiv C$, $CH(CF_3)CH_2$, $CH(CH_3)CH_2O$, $CH_2CH_2O$, $CH(cPr)CH_2O$, $CH(CH_2OCH_3)$, $CH(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

$R^4$ is hydrogen or $(C_1-C_8)$-alkyl;

Y is oxygen or sulfur;

X is hydrogen, cyano, hydroxyl, $X^1$, or $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, cyano, hydroxyl, $OR^7$, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring, substituted by s radicals from the group consisting of $R^6$, $R^{6a}$, $R^8$ and $R^9$, from the group consisting of

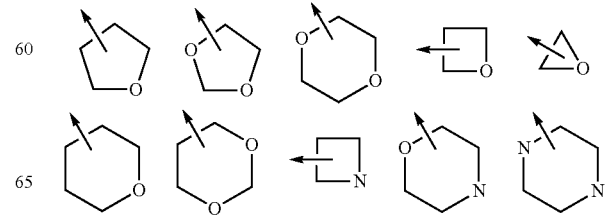

-continued

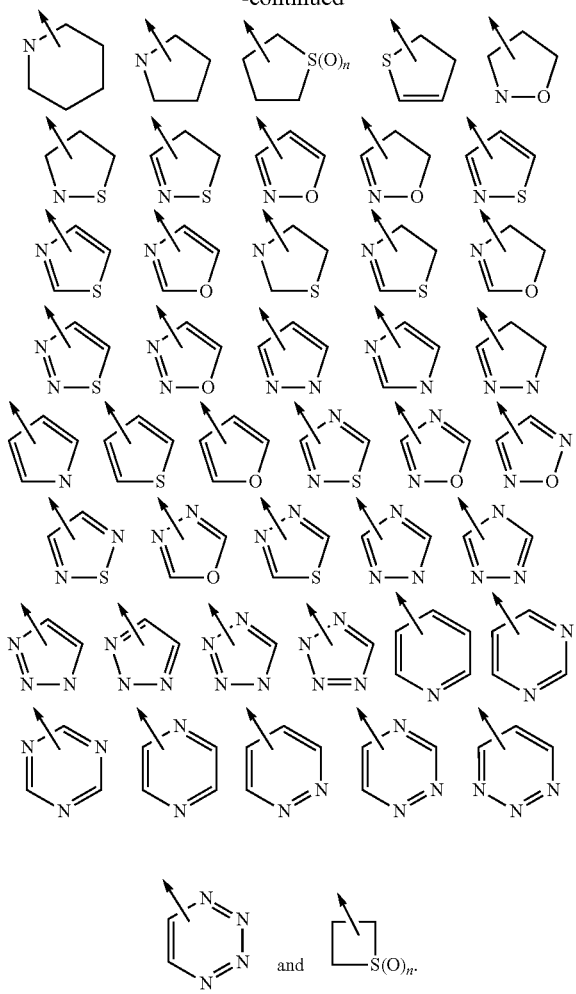

and or X¹ is phenyl substituted by m radicals from the group consisting of R⁶, R⁶ᵃ, R⁸ and R⁹;

X², X⁴ and X⁶ are each independently hydrogen, fluorine, or chlorine, or ($C_1$-$C_4$)-alkyl or ($C_1$-$C_4$)-alkoxy each substituted by m radicals from the group consisting of fluorine, chlorine, cyano and ($C_1$-$C_4$)-alkoxy;

X³ and X⁵ are each independently hydrogen, fluorine, chlorine, bromine, cyano, or ($C_1$-$C_6$)-alkyl substituted by m radicals from the group consisting of fluorine and chlorine, or ($C_1$-$C_6$)-alkoxy substituted by m radicals from the group consisting of fluorine and chlorine;

R⁵ is methyl or ethyl;

R⁶ is hydrogen or R⁵;

R⁶ᵃ is fluorine, chlorine, bromine, iodine, cyano, hydroxyl, $S(O)_n R^5$, or ($C_1$-$C_6$)-alkoxy, ($C_2$-$C_6$)-alkenyloxy or ($C_2$-$C_6$)-alkynyloxy each substituted by m radicals from the group consisting of fluorine, chlorine, bromine, cyano and ($C_1$-$C_2$)-alkoxy;

R⁷ is hydrogen or ($C_1$-$C_6$)-alkyl substituted by m radicals from the group consisting of fluorine and chlorine;

R⁸ is R⁷,

R⁹ is ($C_1$-$C_3$)-alkoxy;

m is 0, 1, 2 or 3;

n is 0, 1 or 2;

s is 0, 1, 2, 3 or 4.

Suitable intermediates for preparation of the inventive compounds of the formula (I) are the compounds of the formula (II):

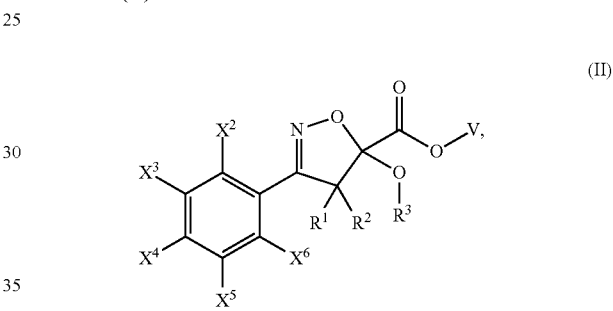

in which the X¹, X², X³, X⁴, X⁵, X⁶, R¹, R² , R³ and R⁵ radicals are each defined as described in the formula (I) and V is hydrogen or R⁵. Compounds of the formula (II) are novel and likewise form part of the subject matter of the present invention.

The inventive compounds can be prepared by reactions known per se to those skilled in the art, for example according to the reaction sequence specified in scheme 1.

Scheme 1:

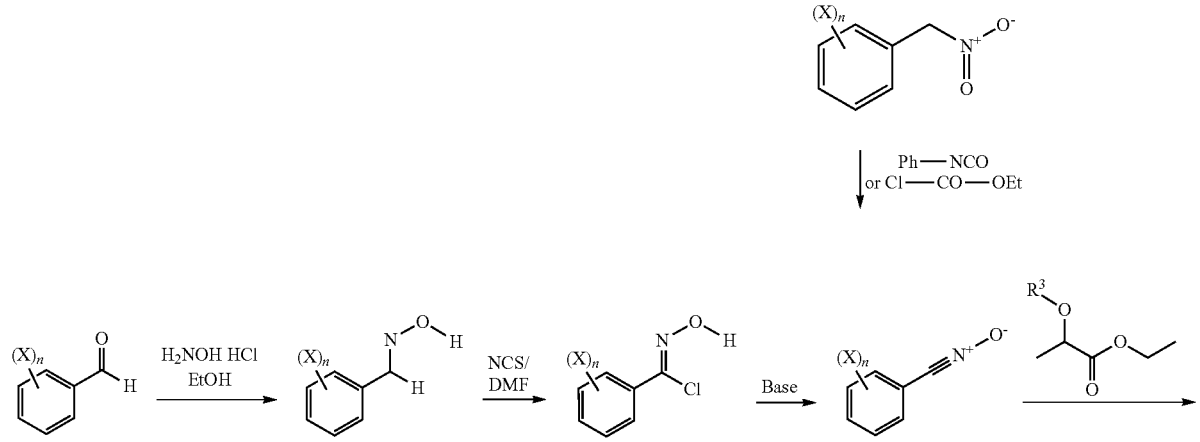

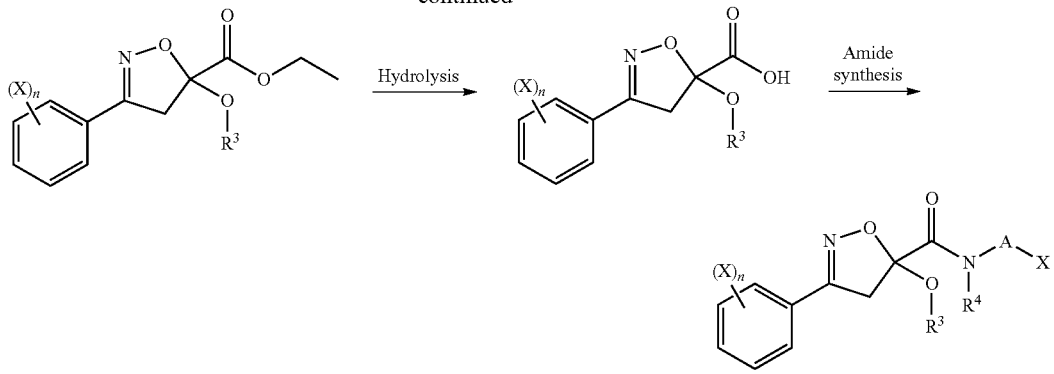

In scheme 1 and the schemes which follow, $(X)_n$ represents the substituents $X^2$, $X^3$, $X^4$, $X^5$ and $X^6$. Such 1,3-dipolar cycloadditions of nitrile oxides with suitable dipolarophiles are described, for example, in reviews: 1,3 dipolar Cycloaddition Chemistry, Padwa, ed. Wiley, New York, 1984; Kanemasa and Tsuge, Heterocycles 1990, 30, 719. For preparation of chloroximes, see Kim, Jae N., Ryu, Eung K. J. Org. Chem. 1992, 57, 6649).

Inventive compounds substituted in the 4 and 5 positions of the isoxazoline ring system can likewise be prepared by 1,3-dipolar cycloaddition by using suitably 1,2-disubstituted olefins as dipolarophiles. Usually, this reaction gives diastereomer mixtures which can be separated by column chromatography. Optically active isoxazolines can be obtained by chiral HPLC of suitable precursors or end products, and likewise by enantioselective reactions, for example enzymatic ester or amide cleavage or through the use of chiral auxiliaries on the dipolarophile, as described by Olssen (J. Org. Chem. 1988, 53, 2468).

The preparation of suitably substituted 2-alkoxyacrylic esters (scheme 2) is possible, for example, by conversion of alpha-keto esters to corresponding ketals (lit.: Wenkert, E; Alonso, M. E.; Buckwalter B. L., Sanchez E. L. J. Am. Chem. Soc. 1983, 105, 2021 and lit.: LaMattina, J. L.; Mularski, C. J., J. Org. Chem. 1984, 49, 4800), and the elimination thereof to give 2-alkoxyacrylic esters (analogously to lit.: Esswein A. et al., Helvetica Chimica Acta 1989, 72(2), 213.)

Scheme 2:

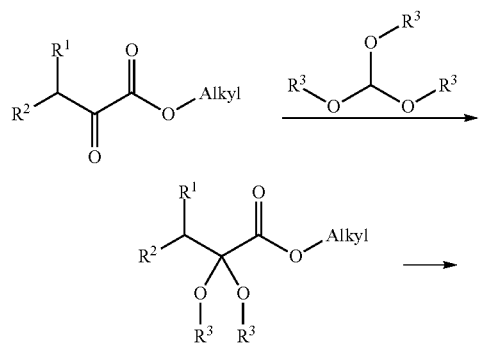

For preparation of the inventive compounds, it is also possible to use suitably substituted 2-alkoxyacrylamides (scheme 3). These are obtainable from the acrylic esters described in scheme 2 after hydrolysis and amide formation.

Scheme 3:

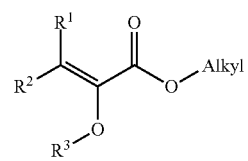

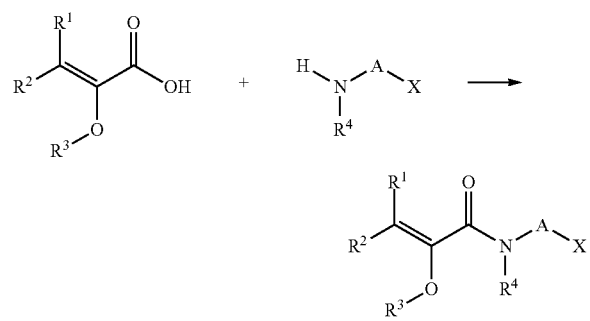

For activation of the alkoxyacrylic acid, carbodiimides such as EDCI, for example, are an option (Chen, F. M. F.; Benoiton, N. L. Synthesis 1979, 709). For preparation of acrylamides, see U.S. Pat. No. 2,521,902, JP60112746, J. of Polymer Science 1979, 17 (6), 1655. Suitably substituted 2-alkoxyacrylamides can be converted in a 1,3-cycloaddition reaction with nitrile oxides to the inventive compounds (scheme 4).

Scheme 4:

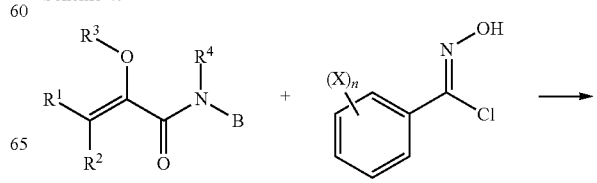

-continued

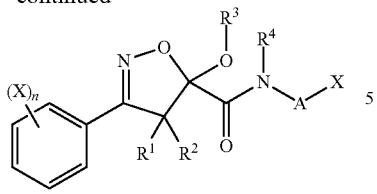

Transformations of the functional groups R³ are possible either at the alkene stage or at the isoxazoline stage.

Scheme 5 describes the route to various R³-substituted isoxazolines.

Scheme 5

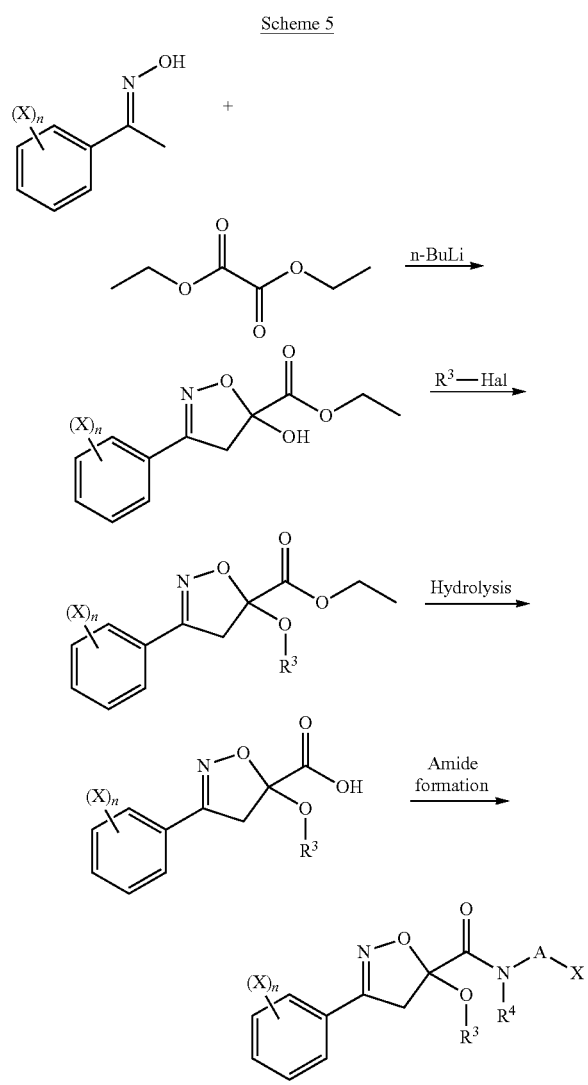

The reaction of oxalic diesters with oximes (scheme 5) leads to 5-hydroxy-3-phenylisoxazolines (lit.: Dang, T. T., Albrecht U., Langer P., Synthesis 2006, 15, 2515). The hydroxyl group can then be derivatized under suitable conditions. The target compounds are obtainable from the esters after hydrolysis and subsequent amide formation.

Scheme 6 describes the route to 5-alkoxy-3-phenylisoxazoline-5-thioamides by conversion of the 5-alkoxy-3-phenylisoxazoline-5-carboxamides through the use of the Lawesson reagent (lit.: WYETH, WO2003/93277, lit.: Wishka D. G., Walker D. P., Tetrahedron Letters 2011, 52, 4713-4715).

Scheme 6

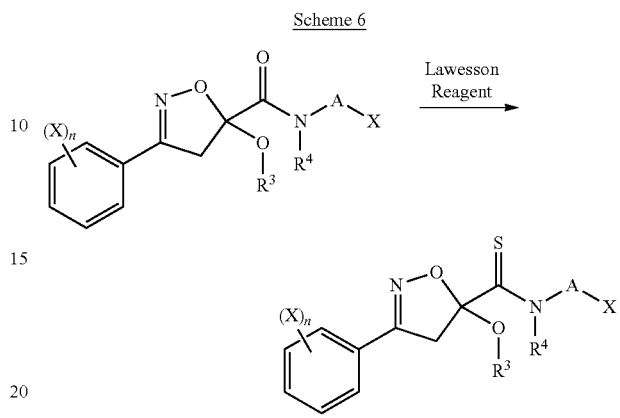

Collections of compounds of the formula (I) and/or salts thereof which can be synthesized by the abovementioned reactions can also be prepared in a parallelized manner, in which case this may be accomplished in a manual, partly automated or fully automated manner. It is possible, for example, to automate the conduct of the reaction, the workup or the purification of the products and/or intermediates. Overall, this is understood to mean a procedure as described, for example, by D. Tiebes in Combinatorial Chemistry—Synthesis, Analysis, Screening (editor: Günther Jung), Wiley, 1999, on pages 1 to 34.

For the parallelized conduct of the reaction and workup, it is possible to use a number of commercially available instruments, for example Calypso reaction blocks from Barnstead International, Dubuque, Iowa 52004-0797, USA or reaction stations from Radleys, Shirehill, Saffron Walden, Essex, CB11 3AZ, England, or MuItiPROBE Automated Workstations from PerkinElmer, Waltham, Mass. 02451, USA. For the parallelized purification of compounds of the formula (I) and salts thereof or of intermediates which occur in the course of preparation, available apparatuses include chromatography apparatuses, for example from ISCO, Inc., 4700 Superior Street, Lincoln, Nebr. 68504, USA.

The apparatuses detailed lead to a modular procedure in which the individual working steps are automated, but manual operations have to be carried out between the working steps. This can be circumvented by using partly or fully integrated automation systems in which the respective automation modules are operated, for example, by robots. Automation systems of this type can be purchased, for example, from Caliper, Hopkinton, Mass. 01748, USA.

The implementation of single or multiple synthesis steps can be supported by the use of polymer-supported reagents/scavenger resins. The specialist literature describes a series of experimental protocols, for example in ChemFiles, Vol. 4, No. 1, Polymer-Supported Scavengers and Reagents for Solution-Phase Synthesis (Sigma-Aldrich).

Aside from the methods described here, the compounds of the formula (I) and salts thereof can be prepared completely or partially by solid-phase supported methods. For this purpose, individual intermediates or all intermediates in the synthesis or a synthesis adapted for the corresponding procedure are bound to a synthesis resin. Solid phase-supported synthesis methods are described adequately in the technical literature, for example Barry A. Bunin in "The Combinatorial Index", Academic Press, 1998 and Combinatorial Chemistry—Synthesis, Analysis, Screening (editor: Günther Jung), Wiley, 1999. The use of solid phase-supported synthesis methods permits a number of protocols known from the literature, and these may again be executed manually or in an automated manner. The reactions can be performed, for example, by means of IRORI technology in microreactors from Nexus Biosystems, 12140 Community Road, Poway, Calif. 92064, USA.

Either on a solid phase or in the liquid phase, the performance of single or multiple synthesis steps can be supported by the use of microwave technology. The technical literature describes a number of experimental protocols, for example Microwaves in Organic and Medicinal Chemistry (editors: C. O. Kappe and A. Stadler), Wiley, 2005.

The preparation by the processes described here gives compounds of the formula (I) and salts thereof in the form of substance collections, which are called libraries. The present invention also provides libraries comprising at least two compounds of the formula (I) and salts thereof.

The inventive compounds of the formula (I) (and/or salts thereof), collectively referred to hereinafter as "inventive compounds", have excellent herbicidal efficacy against a broad spectrum of economically important monocotyledonous and dicotyledonous annual harmful plants. The active ingredients also have good control over perennial harmful plants which are difficult to control and produce shoots from rhizomes, root stocks or other perennial organs.

The present invention therefore also provides a method for controlling unwanted plants or for regulating the growth of plants, preferably in plant crops, in which one or more inventive compound(s) is/are applied to the plants (for example harmful plants such as monocotyledonous or dicotyledonous weeds or unwanted crop plants), to the seeds (for example grains, seeds or vegetative propagules such as tubers or shoot parts with buds) or to the area on which the plants grow (for example the area under cultivation). The inventive compounds can be deployed, for example, prior to sowing (if appropriate also by incorporation into the soil), prior to emergence or after emergence. Specific examples of some representatives of the monocotyledonous and dicotyledonous weed flora which can be controlled by the inventive compounds are as follows, though the enumeration is not intended to impose a restriction to particular species:

Monocotyledonous harmful plants of the genera: *Aegilops, Agropyron, Agrostis, Alopecurus, Apera, Avena, Brachiaria, Bromus, Cenchrus, Commelina, Cynodon, Cyperus, Dactyloctenium, Digitaria, Echinochloa, Eleocharis, Eleusine, Eragrostis, Eriochloa, Festuca, Fimbristylis, Heteranthera, Imperata, Ischaemum, Leptochloa, Lolium, Monochoria, Panicum, Paspalum, Phalaris, Phleum, Poa, Rottboellia, Sagittaria, Scirpus, Setaria, Sorghum*.

Dicotyledonous weeds of the genera: *Abutilon, Amaranthus, Ambrosia, Anoda, Anthemis, Aphanes, Artemisia, Atriplex, Bellis, Bidens, Capsella, Carduus, Cassia, Centaurea, Chenopodium, Cirsium, Convolvulus, Datura, Desmodium, Emex, Erysimum, Euphorbia, Galeopsis, Galinsoga, Galium, Hibiscus, Ipomoea, Kochia, Lamium, Lepidium, Lindernia, Matricaria, Mentha, Mercurialis, Mullugo, Myosotis, Papaver, Pharbitis, Plantago, Polygonum, Portulaca, Ranunculus, Raphanus, Rorippa, Rotala, Rumex, Salsola, Senecio, Sesbania, Sida, Sinapis, Solanum, Sonchus, Sphenoclea, Stellaria, Taraxacum, Thlaspi, Trifolium, Urtica, Veronica, Viola, Xanthium.*

When the inventive compounds are applied to the soil surface before germination, either the weed seedlings are prevented completely from emerging or the weeds grow until they have reached the cotyledon stage, but then stop growing and eventually, after three to four weeks have elapsed, die completely.

If the active ingredients are applied post-emergence to the green parts of the plants, growth stops after the treatment, and the harmful plants remain at the growth stage of the time of application, or die completely after a certain time, such that competition by the weeds, which is harmful to the crop plants, is thus eliminated very early and in a lasting manner.

Although the inventive compounds have excellent herbicidal activity against monocotyledonous and dicotyledonous weeds, crop plants of economically important crops, for example dicotyledonous crops of the genera *Arachis, Beta, Brassica, Cucumis, Cucurbita, Helianthus, Daucus, Glycine, Gossypium, Ipomoea, Lactuca, Linum, Lycopersicon, Nicotiana, Phaseolus, Pisum, Solanum, Vicia*, or monocotyledonous crops of the genera *Allium, Ananas, Asparagus, Avena, Hordeum, Oryza, Panicum, Saccharum, Secale, Sorghum, Triticale, Triticum, Zea*, especially *Zea* and *Triticum*, are damaged only to an insignificant extent, if at all, depending on the structure of the respective inventive compound and the application rate thereof. For these reasons, the present compounds are very suitable for selective control of unwanted plant growth in plant crops such as agriculturally useful plants or ornamentals.

Furthermore, the inventive compounds (depending on their particular structure and the application rate applied) have outstanding growth-regulating properties in crop plants. They intervene to regulate the plant's metabolism and can thus be used for controlled influence on plant constituents and to facilitate harvesting, for example by triggering desiccation and stunted growth. In addition, they are also suitable for general control and inhibition of unwanted vegetative growth without killing the plants. Inhibiting vegetative growth plays a major role for many monocotyledonous and dicotyledonous crops, since, for example, lodging can be reduced or completely prevented.

Because of their herbicidal and plant growth-regulating properties, the active ingredients can also be used to control harmful plants in crops of known genetically modified plants or of those yet to be developed. In general, transgenic plants are notable for special advantageous properties, for example for resistances to certain pesticides, in particular certain herbicides, resistances to plant diseases or organisms that cause plant diseases, such as certain insects or microorganisms such as fungi, bacteria or viruses. Other particular properties relate, for example, to the harvested material with regard to quantity, quality, storability, composition and specific constituents. For instance, there are known transgenic plants with increased starch content or altered starch quality, or those with a different fatty acid composition of the harvested material. Further particular properties lie in tolerance or resistance to abiotic stress factors, for example heat, cold, drought, salinity and ultraviolet radiation.

Preference is given to the use of the inventive compounds of the formula (I) or salts thereof in economically important transgenic crops of useful plants and ornamental plants, for example of cereals such as wheat, barley, rye, oats, sorghum and millet, rice, cassava and corn, or else crops of sugar beet, cotton, soybean, oilseed rape, potatoes, tomatoes, peas and other vegetables.

The compounds of the formula (I) can preferably be used as herbicides in crops of useful plants which are resistant, or have been made resistant by recombinant means, to the phytotoxic effects of the herbicides.

Conventional ways of producing novel plants which have modified properties in comparison to plants which have occurred to date consist, for example, in traditional breeding methods and the generation of mutants. Alternatively, novel plants with altered properties can be generated with the aid of recombinant methods (see, for example, EP 0221044, EP 0131624). For example, there have been descriptions of several cases of genetic modifications of crop plants for the purpose of modifying the starch synthesized in the plants (e.g. WO 92/011376 A, WO 92/014827 A, WO 91/019806 A), transgenic crop plants resistant to particular herbicides of the glufosinate type (cf., for example, EP 0242236 A, EP 0242246 A) or of the glyphosate type (WO 92/000377A) or of the sulfonylurea type (EP 0257993 A, U.S. Pat. No. 5,013,659) or to combinations or mixtures of these herbicides through "gene stacking", such as transgenic crop plants, for example corn or soybean with the tradename or the designation Optimum™ GAT™ (Glyphosate ALS Tolerant), transgenic crop plants, for example cotton, capable of producing Bacillus thuringiensis toxins (Bt toxins), which make the plants resistant to particular pests (EP-A-0142924, EP-A-0193259), transgenic crop plants having a modified fatty acid composition (WO 91/013972 A), genetically modified crop plants having novel constituents or secondary metabolites, for example novel phytoalexins, which cause an increase in disease resistance (EP 0309862 A, EP 0464461 A), genetically modified plants having reduced photorespiration, which have higher yields and higher stress tolerance (EP 0305398 A), transgenic crop plants which produce pharmaceutically or diagnostically important proteins ("molecular pharming"), transgenic crop plants which are notable for higher yields or better quality, transgenic crop plants which are notable for a combination, for example, of the abovementioned novel properties ("gene stacking").

Numerous molecular biology techniques which can be used to produce novel transgenic plants with modified properties are known in principle; see, for example, I. Potrykus and G. Spangenberg (eds.), Gene Transfer to Plants, Springer Lab Manual (1995), Springer Verlag Berlin, Heidelberg or Christou, "Trends in Plant Science" 1 (1996) 423-431).

For such recombinant manipulations, nucleic acid molecules which allow mutagenesis or a sequence change by recombination of DNA sequences can be introduced into plasmids. With the aid of standard methods, it it possible, for example, to undertake base exchanges, remove parts of sequences or add natural or synthetic sequences. For the connection of the DNA fragments to one another, it is possible to add adapters or linkers to the fragments; see, for example, Sambrook et al., 1989, Molecular Cloning, A Laboratory Manual, 2nd ed., Cold Spring Harbor Laboratory Press, Cold Spring Harbor, N.Y.; or Winnacker "Gene and Klone", VCH Weinheim, 2nd edition, 1996.

The production of plant cells with a reduced activity of a gene product can be achieved, for example, by the expression of at least one appropriate antisense RNA, or of a sense RNA for achievement of a cosuppression effect, or the expression of at least one appropriately constructed ribozyme which specifically cleaves transcripts of the abovementioned gene product. For this purpose, it is firstly possible to use DNA molecules which comprise the entire coding sequence of a gene product including any flanking sequences present, or else DNA molecules which comprise only parts of the coding sequence, in which case these parts must be long enough to bring about an antisense effect in the cells. It is also possible to use DNA sequences which have a high degree of homology to the coding sequences of a gene product, but are not completely identical.

When expressing nucleic acid molecules in plants, the protein synthesized may be localized in any desired compartment of the plant cell. However, to achieve localization in a particular compartment, it is possible, for example, to link the coding region with DNA sequences which ensure localization in a particular compartment. Such sequences are known to those skilled in the art (see, for example, Braun et al., EMBO J. 11 (1992), 3219-3227; Wolter et al., Proc. Natl. Acad. Sci. USA 85 (1988), 846-850; Sonnewald et al., Plant J. 1 (1991), 95-106). The nucleic acid molecules can also be expressed in the organelles of the plant cells.

The transgenic plant cells can be regenerated by known techniques to give whole plants. In principle, the transgenic plants may be plants of any desired plant species, i.e. both monocotyledonous and dicotyledonous plants. Thus, it is possible to obtain transgenic plants whose properties are altered by overexpression, suppression or inhibition of homologous (=natural) genes or gene sequences, or expression of heterologous (=foreign) genes or gene sequences.

The inventive compounds (I) can be used with preference in transgenic crops which are resistant to growth regulators, for example 2,4-D, dicamba, or to herbicides which inhibit essential plant enzymes, for example acetolactate synthases (ALS), EPSP synthases, glutamine synthases (GS) or hydroxyphenylpyruvate dioxygenases (HPPD), or to herbicides from the group of the sulfonylureas, the glyphosates, glufosinates or benzoylisoxazoles and analogous active ingredients, or to any desired combinations of these active ingredients.

The inventive compounds can be used with particular preference in transgenic crop plants which are resistant to a combination of glyphosates and glufosinates, glyphosates and sulfonylureas or imidazolinones. Most preferably, the inventive compounds can be used in transgenic crop plants such as corn or soybean with the trade name or the designation Optimum™ GAT™ (glyphosate ALS tolerant), for example.

On employment of the inventive active ingredients in transgenic crops, not only do the effects toward harmful plants observed in other crops occur, but often also effects which are specific to application in the particular transgenic crop, for example an altered or specifically widened spectrum of weeds which can be controlled, altered application rates which can be used for the application, preferably good combinability with the herbicides to which the transgenic crop is resistant, and influencing of growth and yield of the transgenic crop plants.

The invention therefore also provides for the use of the inventive compounds of the formula (I) and of the compounds of the formula (Ia) as herbicides for control of harmful plants in transgenic crop plants.

The inventive compounds can be applied in the form of wettable powders, emulsifiable concentrates, sprayable solutions, dusting products or granules in the customary formulations. The invention therefore also provides herbicidal and plant growth-regulating compositions which comprise the inventive compounds.

The inventive compounds can be formulated in various ways, according to the biological and/or physicochemical parameters required. Possible formulations include, for example: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, oil-miscible solutions, capsule suspensions (CS), dusting products (DP), seed-dressing products, granules for broadcasting and soil application, granules (GR) in the form of microgranules, sprayable granules, coated granules and adsorption granules, water-dispersible granules (WG), water-soluble granules (SG), ULV formulations, microcapsules and waxes. These individual formulation types are known in principle and are described, for example, in: Winnacker-Küchler, "Chemische Technologie" [Chemical Technology], Volume 7, C. Hanser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The necessary formulation auxiliaries, such as inert materials, surfactants, solvents and further additives, are likewise known and are described, for example, in: Watkins, "Handbook of Insecticide Dust Diluents and Carriers", 2nd ed., Darland Books, Caldwell N.J., H.v. Olphen, "Introduction to Clay Colloid Chemistry", 2nd ed., J. Wiley & Sons, N.Y., C. Marsden, "Solvents Guide", 2nd ed., Interscience, N.Y. 1963, McCutcheon's "Detergents and Emulsifiers Annual", MC Publ. Corp., Ridgewood N.J., Sisley and Wood, "Encyclopedia of Surface Active Agents", Chem. Publ. Co. Inc., N.Y. 1964, Schönfeldt, "Grenzflächenaktive Äthylenoxidaddukte" [Interface-active Ethylene Oxide Adducts], Wiss. Verlagsgesell., Stuttgart 1976, Winnacker-Küchler, "Chemische Technologie", Volume 7, C. Hanser Verlag Munich, 4th ed. 1986.

On the basis of these formulations, it is also possible to produce combinations with other active ingredients, for example insecticides, acaricides, herbicides, fungicides, and also with safeners, fertilizers and/or growth regulators, for example in the form of a finished formulation or as a tank mix. Suitable safeners are, for example, mefenpyr-diethyl, cyprosulfamide, isoxadifen-ethyl, cloquintocet-mexyl and dichlormid.

Wettable powders are preparations which can be dispersed uniformly in water and, in addition to the active ingredient, apart from a diluent or inert substance, also comprise surfactants of the ionic and/or nonionic type (wetting agents, dispersants), for example polyoxyethylated alkylphenols, polyoxyethylated fatty alcohols, polyoxyethylated fatty amines, fatty alcohol polyglycol ether sulfates, alkanesulfonates, alkylbenzenesulfonates, sodium lignosulfonate, sodium 2,2' dinaphthylmethane-6,6'-disulfonate, sodium dibutylnaphthalenesulfonate or else sodium oleoylmethyltaurinate. To prepare the wettable powders, the herbicidally active ingredients are ground finely, for example in customary apparatus such as hammer mills, blower mills and air-jet mills, and simultaneously or subsequently mixed with the formulation assistants.

Emulsifiable concentrates are produced by dissolving the active ingredient in an organic solvent, for example butanol, cyclohexanone, dimethylformamide, xylene or else relatively high-boiling aromatics or hydrocarbons or mixtures of the organic solvents, with addition of one or more surfactants of the ionic and/or nonionic type (emulsifiers). The emulsifiers used may, for example, be: calcium alkylarylsulfonate salts such as calcium dodecylbenzenesulfonate, or nonionic emulsifiers such as fatty acid polyglycol esters, alkylaryl polyglycol ethers, fatty alcohol polyglycol ethers, propylene oxide-ethylene oxide condensation products, alkyl polyethers, sorbitan esters, for example sorbitan fatty acid esters, or polyoxyethylene sorbitan esters, for example polyoxyethylene sorbitan fatty acid esters.

Dusting products are obtained by grinding the active ingredient with finely distributed solid substances, for example talc, natural clays, such as kaolin, bentonite and pyrophyllite, or diatomaceous earth.

Suspension concentrates may be water- or oil-based. They can be produced, for example, by wet grinding by means of commercial bead mills with optional addition of surfactants as already listed above, for example, for the other formulation types.

Emulsions, for example oil-in-water emulsions (EW), can be produced, for example, by means of stirrers, colloid mills and/or static mixers using aqueous organic solvents and optionally surfactants as already listed above, for example, for the other formulation types.

Granules can be produced either by spraying the active ingredient onto adsorptive granulated inert material or by applying active ingredient concentrates by means of adhesives, for example polyvinyl alcohol, sodium polyacrylate or mineral oils, to the surface of carrier substances, such as sand, kaolinites or of granulated inert material. Suitable active ingredients can also be granulated in the manner customary for the production of fertilizer granules—if desired as a mixture with fertilizers.

Water-dispersible granules are produced generally by the customary processes such as spray-drying, fluidized bed granulation, pan granulation, mixing with high-speed mixers and extrusion without solid inert material.

For the production of pan granules, fluidized bed granules, extruder granules and spray granules, see, for example, processes in "Spray-Drying Handbook" 3rd ed. 1979, G. Goodwin Ltd., London; J. E. Browning, "Agglomeration", Chemical and Engineering 1967, pages 147 ff.; "Perry's Chemical Engineer's Handbook", 5th ed., McGraw-Hill, New York 1973, p. 8-57.

For further details regarding the formulation of crop protection compositions, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The agrochemical formulations contain generally 0.1 to 99% by weight, especially 0.1 to 95% by weight, of inventive compounds. In wettable powders, the active ingredient concentration is, for example, about 10 to 90% by weight, the remainder to 100% by weight consisting of customary formulation components. In emulsifiable concentrates, the active ingredient concentration may be about 1 to 90% and preferably 5 to 80% by weight. Dust-type formulations contain 1 to 30% by weight of active ingredient, preferably usually 5 to 20% by weight of active ingredient; sprayable solutions contain about 0.05 to 80% by weight, preferably from 2 to 50% by weight, of active ingredient. In the case of water-dispersible granules, the active ingredient content depends partly on whether the active compound is present in liquid or solid form and on which granulation assistants, fillers, etc., are used. In the water-dispersible granules, the content of active ingredient is, for example, between 1 and 95% by weight, preferably between 10 and 80% by weight.

In addition, the active ingredient formulations mentioned optionally comprise the respective customary tackifiers, wetting agents, dispersants, emulsifiers, penetrants, preservatives, antifreeze agents and solvents, fillers, carriers and dyes, defoamers, evaporation inhibitors and agents which influence the pH and the viscosity.

On the basis of these formulations, it is also possible to produce combinations with other pesticidally active substances, for example insecticides, acaricides, herbicides, fungicides, and with safeners, fertilizers and/or growth regulators, for example in the form of a finished formulation or as a tank mix.

For application, the formulations in commercial form are, if appropriate, diluted in a customary manner, for example in the case of wettable powders, emulsifiable concentrates, dispersions and water-dispersible granules with water. Dust-type formulations, granules for soil application or granules for broadcasting and sprayable solutions are not normally diluted further with other inert substances prior to application.

The required application rate of the compounds of the formula (I) varies with the external conditions, including temperature, humidity and the type of herbicide used. It can vary within wide limits, for example between 0.001 and 1.0 kg/ha or more active substance, but it is preferably between 0.005 and 750 g/ha.

In addition to the herbicidal properties, the inventive compounds also have good fungicidal properties. The present invention thus also relates to a composition for controlling unwanted microorganisms, comprising the inventive active ingredients. Preference is given to fungicidal compositions comprising agriculturally usable auxiliaries, solvents, carriers, surfactants or extenders.

In addition, the invention also relates to a method for controlling unwanted microorganisms, which comprises applying the inventive active ingredients to the phytopathogenic fungi and/or their habitat.

According to the invention, a carrier is a natural or synthetic, organic or inorganic substance with which the active ingredients are mixed or combined for better applicability, in particular for application to plants or plant parts or seed. The carrier, which may be solid or liquid, is generally inert and should be suitable for use in agriculture.

Useful solid or liquid carriers include: for example ammonium salts and natural rock dusts, such as kaolins, clays, talc, chalk, quartz, attapulgite, montmorillonite or diatomaceous earth, and synthetic rock dusts, such as finely divided silica, alumina and natural or synthetic silicates, resins, waxes, solid fertilizers, water, alcohols, especially butanol, organic solvents, mineral and vegetable oils, and derivatives thereof. Mixtures of such carriers can likewise be used. Useful solid carriers for granules include: for example crushed and fractionated natural rocks such as calcite, marble, pumice, sepiolite, dolomite, and synthetic granules of inorganic and organic meals, and also granules of organic material such as sawdust, coconut shells, corn cobs and tobacco stalks.

Useful liquefied gaseous extenders or carriers are those liquids which are gaseous at standard temperature and under standard pressure, for example aerosol propellants such as halohydrocarbons, and also butane, propane, nitrogen and carbon dioxide. In the formulations, it is possible to use tackifiers such as carboxymethylcellulose, and natural and synthetic polymers in the form of powders, granules or latices, such as gum arabic, polyvinyl alcohol and polyvinyl acetate, or else natural phospholipids, such as cephalins and lecithins, and synthetic phospholipids. Further additives may be mineral and vegetable oils.

If the extender used is water, it is also possible to use, for example, organic solvents as auxiliary solvents. Useful liquid solvents are essentially: aromatics such as xylene, toluene or alkylnaphthalenes, chlorinated aromatics and chlorinated aliphatic hydrocarbons such as chlorobenzenes, chloroethylenes or dichloromethane, aliphatic hydrocarbons such as cyclohexane or paraffins, for example mineral oil fractions, mineral and vegetable oils, alcohols such as butanol or glycol and their ethers and esters, ketones such as acetone, methyl ethyl ketone, methyl isobutyl ketone or cyclohexanone, strongly polar solvents such as dimethylformamide and dimethyl sulfoxide, and also water.

The inventive compositions may additionally comprise further components, for example surfactants. Useful surfactants are emulsifiers and/or foam formers, dispersants or wetting agents having ionic or nonionic properties, or mixtures of these surfactants. Examples thereof are salts of polyacrylic acid, salts of lignosulfonic acid, salts of phenolsulfonic acid or naphthalenesulfonic acid, polycondensates of ethylene oxide with fatty alcohols or with fatty acids or with fatty amines, substituted phenols (preferably alkylphenols or arylphenols), salts of sulfosuccinic esters, taurine derivatives (preferably alkyl taurates), phosphoric esters of polyethoxylated alcohols or phenols, fatty acid esters of polyols, and derivatives of the compounds containing sulfates, sulfonates and phosphates, for example alkylaryl polyglycol ethers, alkylsulfonates, alkyl sulfates, arylsulfonates, protein hydrolyzates, lignosulfite waste liquors and methylcellulose. The presence of a surfactant is necessary if one of the active ingredients and/or one of the inert carriers is insoluble in water and when application is effected in water. The proportion of surfactants is between 5 and 40 percent by weight of the inventive composition. It is possible to use dyes such as inorganic pigments, for example iron oxide, titanium oxide and Prussian Blue, and organic dyes such as alizarin dyes, azo dyes and metal phthalocyanine dyes, and trace nutrients such as salts of iron, manganese, boron, copper, cobalt, molybdenum and zinc.

If appropriate, it is also possible for other additional components to be present, for example protective colloids, binders, adhesives, thickeners, thixotropic substances, penetrants, stabilizers, sequestrants, complexing agents. In general, the active ingredients can be combined with any solid or liquid additive commonly used for formulation purposes. In general, the inventive compositions and formulations contain between 0.05 and 99% by weight, 0.01 and 98% by weight, preferably between 0.1 and 95% by weight and more preferably between 0.5 and 90% active ingredient, most preferably between 10 and 70 percent by weight. The inventive active ingredients or compositions can be used as such or, depending on their respective physical and/or chemical properties, in the form of the formulations thereof or the use forms prepared therefrom, such as aerosols, capsule suspensions, cold-fogging concentrates, warm-fogging concentrates, encapsulated granules, fine granules, free-flowing concentrates for the treatment of seed, ready-to-use solutions, dustable powders, emulsifiable concentrates, oil-in-water emulsions, water-in-oil emulsions, macrogranules, microgranules, oil-dispersible powders, oil-miscible free-flowing concentrates, oil-miscible liquids, foams, pastes, pesticide-coated seed, suspension concentrates, suspoemulsion concentrates, soluble concentrates, suspensions, spray powders, soluble powders, dusts and granules, water-soluble granules or tablets, water-soluble powders for seed treatment, wettable powders, active ingredient-impregnated natural products and synthetic substances, and also microencapsulations in polymeric substances and in coating materials for seed, and also ULV cold-fogging and warm-fogging formulations.

The formulations mentioned can be produced in a manner known per se, for example by mixing the active ingredients with at least one customary extender, solvent or diluent, emulsifier, dispersant and/or binder or fixative, wetting agent, water repellent, optionally siccatives and UV stabilizers and optionally dyes and pigments, antifoams, preservatives, secondary thickeners, tackifiers, gibberellins and other processing auxiliaries.

The inventive compositions include not only formulations which are already ready for use and can be deployed with a suitable apparatus onto the plant or the seed, but also commercial concentrates which have to be diluted with water prior to use. The inventive active ingredients may be present as such or in their (commercial standard) formulations, or else in the use forms prepared from these formulations as a mixture with other (known) active ingredients, such as insecticides, attractants, sterilants, bactericides, acaricides, nematicides, fungicides, growth regulators, herbicides, fertilizers, safeners or semiochemicals.

The inventive treatment of the plants and plant parts with the active ingredients or compositions is effected directly or by action on their surroundings, habitat or storage space by the customary treatment methods, for example by dipping, spraying, atomizing, irrigating, evaporating, dusting, fogging, broadcasting, foaming, painting, spreading-on, watering (drenching), drip irrigating and, in the case of propagation material, especially in the case of seeds, also by dry seed treatment, wet seed treatment, slurry treatment, incrustation, coating with one or more coats, etc. It is also possible to deploy the active ingredients by the ultra-low volume method or to inject the active ingredient preparation or the active ingredient itself into the soil.

The invention further comprises a method for treating seed.

The invention further relates to seed which has been treated by one of the methods described in the previous paragraph. The inventive seeds are used in methods for protection of seed from unwanted microorganisms. In these methods, seed treated with at least one inventive active ingredient is used. The inventive active ingredients or compositions are also suitable for the treatment of seed. A large part of the damage to crop plants caused by harmful organisms is triggered by the infection of the seed during storage or after sowing, and also during and after germination of the plant. This phase is particularly critical since the roots and shoots of the growing plant are particularly sensitive, and even minor damage may result in the death of the plant. There is therefore a great interest in protecting the seed and the germinating plant by using appropriate compositions.

The control of phytopathogenic fungi by treating the seed of plants has long been known and is the subject of constant improvements. Nevertheless, the treatment of seed gives rise to a series of problems which cannot always be solved in a satisfactory manner. For instance, it is desirable to develop methods for protecting the seed and the germinating plant which dispense with, or at least significantly reduce, the additional deployment of crop protection compositions after sowing or after emergence of the plants. It is additionally desirable to optimize the amount of active ingredient used so as to provide optimum protection for the seed and the germinating plant from attack by phytopathogenic fungi, but without damage to the plant itself by the active ingredient employed. In particular, methods for treatment of seed should also take account of the intrinsic fungicidal properties of transgenic plants in order to achieve optimal protection of the seed and the germinating plant with a minimum expenditure of crop protection compositions.

The present invention therefore also relates to a method for protection of seed and germinating plants from attack by phytopathogenic fungi, by treating the seed with an inventive composition. The invention likewise relates to the use of the inventive compositions for treatment of seed for protection of the seed and the germinating plant from phytopathogenic fungi. The invention further relates to seed which has been treated with an inventive composition for protection from phytopathogenic fungi.

The control of phytopathogenic fungi which damage plants post-emergence is effected primarily by treating the soil and the above-ground parts of plants with crop protection compositions. Owing to the concerns regarding a possible influence of the crop protection compositions on the environment and the health of humans and animals, there are efforts to reduce the amount of active ingredients deployed.

One of the advantages of the present invention is that the particular systemic properties of the inventive active ingredients and compositions mean that treatment of the seed with these active ingredients and compositions protects not only the seed itself but also the resulting plants after emergence from phytopathogenic fungi. In this way, the immediate treatment of the crop at the time of sowing or shortly thereafter can be dispensed with.

It is likewise considered to be advantageous that the inventive active ingredients or compositions can especially also be used for transgenic seed, in which case the plant which grows from this seed is capable of expressing a protein which acts against pests. The treatment of such seed with the inventive active ingredients or compositions, merely through the expression of the protein, for example an insecticidal protein, can result in control of certain pests. Surprisingly, a further synergistic effect can be observed in this case, which additionally increases the effectiveness for protection against attack by pests.

The inventive compositions are suitable for protecting seed of any plant cultivar which is used in agriculture, in greenhouses, in forests or in horticulture and viticulture. In particular, this is the seed of cereals (such as wheat, barley, rye, triticale, sorghum/millet and oats), corn, cotton, soybeans, rice, potatoes, sunflower, bean, coffee, beet (for example sugar beet and fodder beet), peanut, oilseed rape, poppy, olive, coconut, cocoa, sugar cane, tobacco, vegetables (such as tomato, cucumbers, onions and lettuce), turf and ornamentals (see also below). The treatment of the seed of cereals (such as wheat, barley, rye, triticale and oats), corn and rice is of particular significance.

As also described below, the treatment of transgenic seed with the inventive active ingredients or compositions is of particular significance. This relates to the seed of plants containing at least one heterologous gene which enables the expression of a polypeptide or protein having insecticidal properties. The heterologous gene in transgenic seed can originate, for example, from microorganisms of the species *Bacillus, Rhizobium, Pseudomonas, Serratia, Trichoderma, Clavibacter, Glomus* or *Gliocladium*. This heterologous gene preferably originates from *Bacillus* sp., in which case the gene product is effective against the European corn borer and/or the Western corn rootworm. The heterologous gene more preferably originates from *Bacillus thuringiensis*.

In the context of the present invention, the inventive composition is applied to the seed alone or in a suitable formulation. Preferably, the seed is treated in a state in which it is sufficiently stable for no damage to occur in the course of treatment. In general, the seed can be treated at any time between harvest and sowing. It is customary to use seed which has been separated from the plant and freed from cobs, shells, stalks, coats, hairs or the flesh of the fruits. For example, it is possible to use seed which has been harvested, cleaned and dried down to a moisture content of less than 15% by weight. Alternatively, it is also possible to use seed which, after drying, for example, has been treated with water and then dried again.

In general, in the treatment of the seed, it has to be ensured that the amount of the inventive composition and/or further additives applied to the seed is selected such that the germination of the seed is not impaired and the plant which arises therefrom is not damaged. This should be ensured particularly in the case of active ingredients which can exhibit phytotoxic effects at particular application rates.

The inventive compositions can be applied directly, i.e. without containing any other components and without having been diluted. In general, it is preferable to apply the compositions to the seed in the form of a suitable formulation. Suitable formulations and methods for seed treatment are known to those skilled in the art and are described, for example, in the following documents: U.S. Pat. No. 4,272, 417 A, U.S. Pat. No. 4,245,432 A, U.S. Pat. No. 4,808,430, U.S. Pat. No. 5,876,739, US 2003/0176428 A1, WO 2002/080675 A1, WO 2002/028186 A2.

The active ingredients usable in accordance with the invention can be converted to the customary seed dressing formulations, such as solutions, emulsions, suspensions, powders, foams, slurries or other coating compositions for seed, and also ULV formulations.

These formulations are produced in a known manner, by mixing the active ingredients with customary additives, for example customary extenders and solvents or diluents, dyes, wetting agents, dispersants, emulsifiers, antifoams, preservatives, secondary thickeners, adhesives, gibberellins, and also water.

Useful dyes which may be present in the seed dressing formulations usable in accordance with the invention are all dyes which are customary for such purposes. It is possible to use either pigments, which are sparingly soluble in water, or dyes, which are soluble in water. Examples include the dyes known by the names Rhodamine B, C.I. Pigment Red 112 and C.I. Solvent Red 1.

Useful wetting agents which may be present in the seed dressing formulations usable in accordance with the invention are all substances which promote wetting and which are conventionally used for the formulation of active agrochemical ingredients. Alkyl naphthalenesulfonates, such as diisopropyl or diisobutyl naphthalenesulfonates, are usable with preference.

Useful dispersants and/or emulsifiers which may be present in the seed dressing formulations usable in accordance with the invention are all nonionic, anionic and cationic dispersants conventionally used for the formulation of active agrochemical ingredients. Nonionic or anionic dispersants or mixtures of nonionic or anionic dispersants are usable with preference. Suitable nonionic dispersants include especially ethylene oxide/propylene oxide block polymers, alkylphenol polyglycol ethers and tristryrylphenol polyglycol ether, and the phosphated or sulfated derivatives thereof. Suitable anionic dispersants are especially lignosulfonates, polyacrylic salts and arylsulfonate/formaldehyde condensates.

Antifoams which may be present in the seed dressing formulations usable in accordance with the invention are all foam-inhibiting substances conventionally used for the formulation of active agrochemical ingredients. Silicone antifoams and magnesium stearate are usable with preference.

Preservatives which may be present in the seed dressing formulations usable in accordance with the invention are all substances usable for such purposes in agrochemical compositions. Examples include dichlorophene and benzyl alcohol hemiformal.

Secondary thickeners which may be present in the seed dressing formulations usable in accordance with the invention are all substances usable for such purposes in agrochemical compositions. Preferred examples include cellulose derivatives, acrylic acid derivatives, xanthan, modified clays and finely divided silica.

Adhesives which may be present in the seed dressing formulations usable in accordance with the invention are all customary binders usable in seed dressing products. Preferred examples include polyvinylpyrrolidone, polyvinyl acetate, polyvinyl alcohol and tylose.

The seed dressing formulations usable in accordance with the invention can be used, either directly or after previously having been diluted with water, for the treatment of a wide range of different seed, including the seed of transgenic plants. In this case, additional synergistic effects may also occur in interaction with the substances formed by expression.

For treatment of seed with the seed dressing formulations usable in accordance with the invention, or the preparations prepared therefrom by adding water, all mixing units usable customarily for the seed dressing are useful. Specifically, the procedure in the seed dressing is to place the seed into a mixer, to add the particular desired amount of seed dressing formulations, either as such or after prior dilution with water, and to mix everything until the formulation is distributed homogeneously on the seed. If appropriate, this is followed by a drying operation.

The inventive active ingredients or compositions have potent microbicidal activity and can be used for control of unwanted microorganisms, such as fungi and bacteria, in crop protection and in the protection of materials.

Fungicides can be used in crop protection for control of Plasmodiophoromycetes, Oomycetes, Chytridiomycetes, Zygomycetes, Ascomycetes, Basidiomycetes and Deuteromycetes.

Bactericides can be used in crop protection for control of Pseudomonadaceae, Rhizobiaceae, Enterobacteriaceae, Corynebacteriaceae and Streptomycetaceae. The inventive fungicidal compositions can be used for curative or protective control of phytopathogenic fungi. The invention therefore also relates to curative and protective methods for controlling phytopathogenic fungi by the use of the inventive active ingredients or compositions, which are applied to the seed, the plant or plant parts, the fruit or the soil in which the plants grow.

The inventive compositions for controlling phytopathogenic fungi in crop protection comprise an effective but non-phytotoxic amount of the inventive active ingredients. An "effective but non-phytotoxic amount" means an amount of the inventive composition which is sufficient to control the fungal disease of the plant in a satisfactory manner or to eradicate the fungal disease completely, and which, at the same time, does not cause any significant symptoms of phytotoxicity. In general, this application rate may vary within a relatively wide range. It depends on several factors, for example on the fungus to be controlled, the plant, the climatic conditions and the ingredients of the inventive compositions.

The good plant tolerance of the active ingredients in the concentrations required for control of plant diseases allows treatment of above-ground parts of plants, of propagation stock and seeds, and of the soil.

The invention can be used to treat all plants and parts of plants. Plants are understood here to mean all plants and plant populations, such as desired and undesired wild plants or crop plants (including naturally occurring crop plants). Crop plants may be plants which can be obtained by conventional breeding and optimization methods or by biotechnological and genetic engineering methods or combinations of these methods, including the transgenic plants and including the plant cultivars which are protectable and non-protectable by plant breeders' rights. Plant parts shall be understood to mean all parts and organs of plants above and below the ground, such as shoot, leaf, flower and root, examples of which include leaves, needles, stalks, stems, flowers, fruit bodies, fruits, seeds, roots, tubers and rhizomes. Plant parts also include harvested material and vegetative and generative propagation material, for example cuttings, tubers, rhizomes, slips and seeds.

The inventive active ingredients, given good plant compatibility, favorable homeotherm toxicity and good environmental compatibility, are suitable for protection of plants and plant organs, for increasing harvest yields, and for improving the quality of the harvested crop. They can preferably be used as crop protection compositions. They are effective against normally sensitive and resistant species and against all or some stages of development.

Plants which can be treated in accordance with the invention include the following main crop plants: corn, soybean, cotton, *Brassica* oil seeds such as *Brassica napus* (e.g. canola), *Brassica rapa, B. juncea* (e.g. (field) mustard) and *Brassica carinata*, rice, wheat, sugar beet, sugar cane, oats, rye, barley, millet and sorghum, triticale, flax, grapes and various fruit and vegetables from various botanic taxa, for example Rosaceae sp. (for example pome fruits such as apples and pears, but also stone fruits such as apricots, cherries, almonds and peaches, and berry fruits such as strawberries), Ribesioidae sp., Juglandaceae sp., Betulaceae sp., Anacardiaceae sp., Fagaceae sp., Moraceae sp., Oleaceae sp., Actinidaceae sp., Lauraceae sp., Musaceae sp. (for example banana trees and plantations), Rubiaceae sp. (for example coffee), Theaceae sp., Sterculiceae sp., Rutaceae sp. (for example lemons, oranges and grapefruit); Solanaceae sp. (for example tomatoes, potatoes, peppers, aubergines), Liliaceae sp., Compositae sp. (for example lettuce, artichokes and chicory—including root chicory, endive or common chicory), Umbelliferae sp. (for example carrots, parsley, celery and celeriac), Cucurbitaceae sp. (for example cucumbers—including gherkins, pumpkins, watermelons, calabashes and melons), Alliaceae sp. (for example leeks and onions), Cruciferae sp. (for example white cabbage, red cabbage, broccoli, cauliflower, Brussels sprouts, pak choi, kohlrabi, radishes, horseradish, cress and chinese cabbage), Leguminosae sp. (for example peanuts, peas, and beans—for example common beans and broad beans), Chenopodiaceae sp. (for example Swiss chard, fodder beet, spinach, beetroot), Malvaceae (for example okra), Asparagaceae (for example asparagus); useful plants and ornamental plants in the garden and woods; and in each case genetically modified types of these plants.

As mentioned above, it is possible to treat all plants and their parts in accordance with the invention. In a preferred embodiment, wild plant species and plant cultivars, or those obtained by conventional biological breeding, such as crossing or protoplast fusion, and parts thereof, are treated. In a further preferred embodiment, transgenic plants and plant cultivars obtained by genetic engineering methods, if appropriate in combination with conventional methods (genetically modified organisms), and parts thereof are treated. The term "parts" or "parts of plants" or "plant parts" has been explained above. More preferably, plants of the plant cultivars which are each commercially available or in use are treated in accordance with the invention. Plant cultivars are understood to mean plants which have new properties ("traits") and have been obtained by conventional breeding, by mutagenesis or by recombinant DNA techniques. They may be cultivars, varieties, biotypes or genotypes.

The inventive treatment method can be used for the treatment of genetically modified organisms (GMOs), e.g. plants or seeds. Genetically modified plants (or transgenic plants) are plants in which a heterologous gene has been stably integrated into the genome. The expression "heterologous gene" essentially means a gene which is provided or assembled outside the plant and when introduced in the nuclear, chloroplastic or mitochondrial genome gives the transformed plant new or improved agronomic or other properties by expressing a protein or polypeptide of interest or by downregulating or silencing other gene(s) which is/are present in the plant (using for example antisense technology, cosuppression technology or RNAi technology [RNA interference]). A heterologous gene that is present in the genome is also called a transgene. A transgene that is defined by its particular location in the plant genome is called a transformation or transgenic event.

Depending on the plant species or plant cultivars, their location and growth conditions (soils, climate, vegetation period, diet), the treatment according to the invention may also result in superadditive ("synergistic") effects. For example, the following effects which exceed the effects actually to be expected are possible: reduced application rates and/or widened spectrum of activity and/or increased efficacy of the active ingredients and compositions which can be used in accordance with the invention, better plant growth, increased tolerance to high or low temperatures, increased tolerance to drought or to water or soil salinity, increased flowering performance, easier harvesting, accelerated maturation, higher harvest yields, bigger fruits, greater plant height, greener leaf color, earlier flowering, higher quality and/or a higher nutritional value of the harvested products, higher sugar concentration within the fruits, better storage stability and/or processability of the harvested products.

At certain application rates, the inventive active ingredient combinations may also have a fortifying effect in plants. Accordingly, they are also suitable for mobilizing the defense system of the plant against attack by unwanted phytopathogenic fungi and/or microorganisms. This may, if appropriate, be one of the reasons for the enhanced activity of the combinations according to the invention, for example against fungi. Plant-fortifying (resistance-inducing) substances shall be understood to mean, in the present context, also those substances or combinations of substances which are capable of stimulating the defense system of plants in such a way that, when subsequently inoculated with unwanted phytopathogenic fungi, the plants treated display a substantial degree of resistance to these unwanted phytopathogenic fungi.

The inventive substances can therefore be used for protection of plants from attack by the pathogens mentioned within a certain period after treatment. The period within which protection is achieved generally extends for from 1 to 10 days, preferably 1 to 7 days, after the treatment of the plants with the active ingredients.

Plants and plant cultivars which are preferably treated in accordance with the invention include all plants which have genetic material which imparts particularly advantageous, useful traits to these plants (whether obtained by breeding and/or biotechnological means).

Plants and plant cultivars which are likewise preferably treated in accordance with the invention are resistant to one or more biotic stress factors, meaning that these plants have a better defense against animal and microbial pests, such as nematodes, insects, mites, phytopathogenic fungi, bacteria, viruses and/or viroids.

Examples of nematode-resistant plants are described, for example, in the following U.S. patent application Ser. Nos. 11/765,491, 11/765,494, 10/926,819, 10/782,020, 12/032,479, 10/783,417, 10/782,096, 11/657,964, 12/192,904, 11/396,808, 12/166,253, 12/166,239, 12/166,124, 12/166,209, 11/762,886, 12/364,335, 11/763,947, 12/252,453, 12/209,354, 12/491,396 and 12/497,221.

Plants and plant cultivars which may also be treated according to the invention are those plants which are resistant to one or more abiotic stress factors. Abiotic stress conditions may include, for example, drought, cold temperature exposure, heat exposure, osmotic stress, waterlogging, increased soil salinity, increased exposure to minerals, exposure to ozone, exposure to strong light, limited availability of nitrogen nutrients, limited availability of phosphorus nutrients or shade avoidance.

Plants and plant cultivars which may also be treated according to the invention are those plants characterized by enhanced yield characteristics. Enhanced yield in these plants may be the result of, for example, improved plant physiology, improved plant growth and development, such as water use efficiency, water retention efficiency, improved nitrogen use, enhanced carbon assimilation, improved photosynthesis, increased germination efficiency and accelerated maturation. Yield can also be affected by improved plant architecture (under stress and non-stress conditions), including early flowering, flowering control for hybrid seed production, seedling vigor, plant size, internode number and distance, root growth, seed size, fruit size, pod size, pod or ear number, seed number per pod or ear, seed mass, enhanced seed filling, reduced seed dispersal, reduced pod dehiscence and lodging resistance. Further yield traits include seed composition, such as carbohydrate content, protein content, oil content and composition, nutritional value, reduction in anti-nutritional compounds, improved processability and better storage stability.

Plants that may be treated according to the invention are hybrid plants that already express the characteristics of heterosis, or hybrid effect, which results in generally higher yield, vigor, better health and resistance towards biotic and abiotic stress factors. Such plants are typically made by crossing an inbred male-sterile parent line (the female crossbreeding parent) with another inbred male-fertile parent line (the male crossbreeding parent). Hybrid seed is typically harvested from the male-sterile plants and sold to growers. Male-sterile plants can sometimes (e.g. in corn) be produced by detasseling (i.e. the mechanical removal of the male reproductive organs or male flowers) but, more typically, male sterility is the result of genetic determinants in the plant genome. In that case, and especially when seed is the desired product to be harvested from the hybrid plants, it is typically beneficial to ensure that male fertility in hybrid plants, which contain the genetic determinants responsible for male sterility, is fully restored. This can be accomplished by ensuring that the male parents have appropriate fertility restorer genes which are capable of restoring the male fertility in hybrid plants that contain the genetic determinants responsible for male sterility.

Genetic determinants for male sterility may be located in the cytoplasm. Examples of cytoplasmic male sterility (CMS) were for instance described in *Brassica* species. However, genetic determinants for male sterility can also be located in the nuclear genome. Male-sterile plants can also be obtained by plant biotechnology methods such as genetic engineering. A particularly useful means of obtaining male-sterile plants is described in WO 89/10396 in which, for example, a ribonuclease such as barnase is selectively expressed in the tapetum cells in the stamens. Fertility can then be restored by expression in the tapetum cells of a ribonuclease inhibitor such as barstar.

Plants or plant cultivars (obtained by plant biotechnology methods such as genetic engineering) which may be treated according to the invention are herbicide-tolerant plants, i.e. plants made tolerant to one or more given herbicides. Such plants can be obtained either by genetic transformation, or by selection of plants containing a mutation imparting such herbicide tolerance.

Herbicide-tolerant plants are for example glyphosate-tolerant plants, i.e. plants made tolerant to the herbicide glyphosate or salts thereof. Plants can be made tolerant to glyphosate by various methods. For example, glyphosate-tolerant plants can be obtained by transforming the plant with a gene encoding the enzyme 5-enolpyruvylshikimate-3-phosphate synthase (EPSPS). Examples of such EPSPS genes are the AroA gene (mutant CT7) of the bacterium *Salmonella typhimurium* (Comai et al., 1983, Science, 221, 370-371), the CP4 gene of the bacterium *Agrobacterium* sp. (Barry et al., 1992, Curr. Topics Plant Physiol. 7, 139-145), the genes encoding a petunia EPSPS (Shah et al., 1986, Science 233, 478-481), a tomato EPSPS (Gasser et al., 1988, J. Biol. Chem. 263, 4280-4289) or an Eleusine EPSPS (WO 01/66704). It can also be a mutated EPSPS. Glyphosate-tolerant plants can also be obtained by expressing a gene that encodes a glyphosate oxidoreductase enzyme. Glyphosate-tolerant plants can also be obtained by expressing a gene that encodes a glyphosate acetyl transferase enzyme. Glyphosate-tolerant plants can also be obtained by selecting plants containing naturally-occurring mutations of the above-mentioned genes. Plants which express EPSPS genes which impart glyphosate tolerance have been described. Plants which express other genes which impart glyphosate tolerance, for example decarboxylase genes, have been described. Other herbicide resistant plants are for example plants that are made tolerant to herbicides inhibiting the enzyme glutamine synthase, such as bialaphos, phosphinothricin or glufosinate. Such plants can be obtained by expressing an enzyme detoxifying the herbicide or a mutant glutamine synthase enzyme that is resistant to inhibition. One such efficient detoxifying enzyme is, for example, an enzyme encoding a phosphinothricin acetyltransferase (such as the bar or pat protein from *Streptomyces* species). Plants expressing an exogenous phosphinothricin acetyltransferase have been described.

Further herbicide-tolerant plants are also plants that have been made tolerant to the herbicides inhibiting the enzyme hydroxyphenylpyruvate dioxygenase (HPPD). Hydroxyphenylpyruvate dioxygenases are enzymes that catalyze the reaction in which para-hydroxyphenylpyruvate (HPP) is converted to homogentisate. Plants tolerant to HPPD inhibitors can be transformed with a gene encoding a naturally-occurring resistant HPPD enzyme, or a gene encoding a mutated or chimeric HPPD enzyme, as described in WO 96/38567, WO 99/24585, WO 99/24586, WO 2009/144079, WO 2002/046387 or U.S. Pat. No. 6,768,044. Tolerance to HPPD inhibitors can also be obtained by transforming plants with genes encoding certain enzymes enabling the formation of homogentisate despite the inhibition of the native HPPD enzyme by the HPPD inhibitor. Such plants are described in WO 99/34008 and WO 02/36787. Tolerance of plants to HPPD inhibitors can also be improved by transforming plants with a gene encoding an enzyme prephenate dehydrogenase in addition to a gene encoding an HPPD-tolerant enzyme, as described in WO 2004/024928. In addition, plants can be made more tolerant to HPPD inhibitors by inserting into the genome thereof a gene which encodes an enzyme which metabolizes or degrades HPPD inhibitors, for example CYP450 enzymes (see WO 2007/103567 and WO 2008/150473).

Still further herbicide resistant plants are plants that are made tolerant to acetolactate synthase (ALS) inhibitors. Known ALS inhibitors include, for example, sulfonylurea, imidazolinone, triazolopyrimidines, pyrimidinyloxy(thio)benzoates and/or sulfonylaminocarbonyltriazolinone herbicides. It is known that different mutations in the ALS enzyme (also known as acetohydroxy acid synthase, AHAS) confer tolerance to different herbicides and groups of herbicides, as described, for example, in Tranel and Wright (Weed Science 2002, 50, 700-712). The production of sulfonylurea-tolerant plants and imidazolinone-tolerant plants has been described. Further sulfonylurea- and imidazolinone-tolerant plants have also been described.

Further plants tolerant to imidazolinone and/or sulfonylurea can be obtained by induced mutagenesis, by selection in cell cultures in the presence of the herbicide or by mutation breeding (cf., for example, for soybeans U.S. Pat. No. 5,084,082, for rice WO 97/41218, for sugar beet U.S. Pat. No. 5,773,702 and WO 99/057965, for lettuce U.S. Pat. No. 5,198,599 or for sunflower WO 01/065922).

Plants or plant cultivars (obtained by plant biotechnology methods such as genetic engineering) which may also be treated according to the invention are insect-resistant transgenic plants, i.e. plants made resistant to attack by certain target insects. Such plants can be obtained by genetic transformation or by selection of plants containing a mutation imparting such insect resistance.

The term "insect-resistant transgenic plant", as used herein, includes any plant containing at least one transgene comprising a coding sequence encoding:
1) an insecticidal crystal protein from *Bacillus thuringiensis* or an insecticidal portion thereof, such as the insecticidal crystal proteins compiled by Crickmore et al. (Microbiology and Molecular Biology Reviews 1998, 62, 807-813), updated by Crickmore et al. (2005) in the *Bacillus thuringiensis* toxin nomenclature, online at: http://www.lifesci.sussex.ac.uk/Home/Neil_Crickmore/Bt/), or insecticidal portions thereof, for example proteins of the Cry protein classes Cry1Ab, Cry1Ac, Cry1B, Cry1C, Cry1D, Cry1F, Cry2Ab, Cry3Aa, or Cry3Bb or insecticidal portions thereof (e.g. EP-A 1999141 and WO 2007/107302), or those proteins encoded by synthetic genes as described in U.S. patent application Ser. No. 12/249,016; or
2) a crystal protein from *Bacillus thuringiensis* or a portion thereof which is insecticidal in the presence of a second crystal protein other than *Bacillus thuringiensis* or a portion thereof, such as the binary toxin made up of the Cy34 and Cy35 crystal proteins (Nat. Biotechnol. 2001, 19, 668-72; Applied Environm. Microbiol. 2006, 71, 1765-1774) or the binary toxin made up of the Cry1A or Cry1F proteins and the Cry2Aa or Cry2Ab or Cry2Ae proteins (U.S. patent application Ser. No. 12/214,022 and EP08010791.5); or
3) a hybrid insecticidal protein comprising parts of two different insecticidal crystal proteins from *Bacillus thuringiensis*, such as a hybrid of the proteins of 1) above or a hybrid of the proteins of 2) above, for example the Cry1A.105 protein produced by corn event MON98034 (WO 2007/027777); or
4) a protein of any one of 1) to 3) above wherein some, particularly 1 to 10, amino acids have been replaced by another amino acid to obtain a higher insecticidal activity to a target insect species, and/or to expand the range of target insect species affected, and/or because of changes introduced into the encoding DNA during cloning or transformation, such as the Cry3Bb1 protein in corn events MON863 or MON88017, or the Cry3A protein in corn event MIR604; or
5) an insecticidal secreted protein from *Bacillus thuringiensis* or *Bacillus cereus*, or an insecticidal portion thereof, such as the vegetative insecticidal proteins (VIP) listed at: http://www.lifesci.sussex.ac.uk/home/Neil_Crickmore/Bt/vip.html, for example proteins from the VIP3Aa protein class; or
6) a secreted protein from *Bacillus thuringiensis* or *Bacillus cereus* which is insecticidal in the presence of a second secreted protein from *Bacillus thuringiensis* or *B. cereus*, such as the binary toxin made up of the VIP1A and VIP2A proteins (WO 94/21795); or
7) a hybrid insecticidal protein comprising parts from different secreted proteins from *Bacillus thuringiensis* or *Bacillus cereus*, such as a hybrid of the proteins in 1) above or a hybrid of the proteins in 2) above; or
8) a protein of any one of points 5) to 7) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein), such as the VIP3Aa protein in cotton event COT 102; or
9) a secreted protein from *Bacillus thuringiensis* or *Bacillus cereus* which is insecticidal in the presence of a crystal protein from *Bacillus thuringiensis*, such as the binary toxin made up of the proteins VIP3 and Cry1A or Cry1F (US patent applications 61/126083 and 61/195019), or the binary toxin made up of the VIP3 protein and the Cry2Aa or Cry2Ab or Cry2Ae proteins (U.S. patent application Ser. No. 12/214,022 and EP 08010791.5); or
10) a protein according to point 9) above wherein some, particularly 1 to 10, amino acids have been replaced by another amino acid to obtain a higher insecticidal activity to a target insect species, and/or to expand the range of target insect species affected, and/or because of changes induced in the encoding DNA during cloning or transformation (while still encoding an insecticidal protein).

Of course, insect-resistant transgenic plants, as used herein, also include any plant comprising a combination of genes encoding the proteins of any one of the above classes 1 to 10. In one embodiment, an insect-resistant plant contains more than one transgene encoding a protein of any one of the above classes 1 to 10, to expand the range of target insect species affected or to delay insect resistance development to the plants, by using different proteins insecticidal to the same target insect species but having a different mode of action, such as binding to different receptor binding sites in the insect.

In the present context, an "insect-resistant transgenic plant" additionally includes any plant containing at least one transgene comprising a sequence for production of doublestranded RNA which, after consumption of food by an insect pest, prevents the growth of this pest.

Plants or plant cultivars (obtained by plant biotechnology methods such as genetic engineering) which may also be treated according to the invention are tolerant to abiotic stress factors. Such plants can be obtained by genetic transformation, or by selection of plants containing a mutation imparting such stress resistance. Particularly useful stress-tolerant plants include the following:

a. plants which contain a transgene capable of reducing the expression and/or the activity of the poly(ADP-ribose) polymerase (PARP) gene in the plant cells or plants;
b. plants which contain a stress tolerance-enhancing transgene capable of reducing the expression and/or the activity of the PARG-encoding genes of the plants or plant cells;
c. plants which contain a stress tolerance-enhancing transgene coding for a plant-functional enzyme of the nicotinamide adenine dinucleotide salvage biosynthesis pathway, including nicotinamidase, nicotinate phosphoribosyltransferase, nicotinic acid mononucleotide adenyltransferase, nicotinamide adenine dinucleotide synthetase or nicotinamide phosphoribosyltransferase.

Plants or plant cultivars (obtained by plant biotechnology methods such as genetic engineering) which may also be treated according to the invention show altered quantity, quality and/or storage-stability of the harvested product and/or altered properties of specific ingredients of the harvested product such as:

1) Transgenic plants which synthesize a modified starch which is altered with respect to its chemophysical traits, in particular the amylose content or the amylose/amylopectin ratio, the degree of branching, the average chain length, the distribution of the side chains, the viscosity behavior, the gel resistance, the grain size and/or grain morphology of the starch in comparison to the synthesized starch in wild-type plant cells or plants, such that this modified starch is better suited for certain applications.
2) Transgenic plants which synthesize non-starch carbohydrate polymers or which synthesize non-starch carbohydrate polymers with altered properties in comparison to wild-type plants without genetic modification. Examples are plants which produce polyfructose, especially of the inulin and levan type, plants which produce alpha-1,4-glucans, plants which produce alpha-1,6-branched alpha-1,4-glucans, and plants producing alternan.
3) Transgenic plants which produce hyaluronan.
4) Transgenic plants or hybrid plants such as onions with particular properties, such as "high soluble solids content", "low pungency" (LP) and/or "long storage" (LS). Plants or plant cultivars (obtained by plant biotechnology methods such as genetic engineering) which may also be treated according to the invention are plants, such as cotton plants, with altered fiber characteristics. Such plants can be obtained by genetic transformation, or by selection of plants containing a mutation imparting such altered fiber characteristics and include:

a) plants, such as cotton plants, containing an altered form of cellulose synthase genes;
b) plants, such as cotton plants, which contain an altered form of rsw2 or rsw3 homologous nucleic acids, such as cotton plants with an increased expression of sucrose phosphate synthase;
c) plants, such as cotton plants, with increased expression of sucrose synthase;
d) plants, such as cotton plants, wherein the timing of the plasmodesmatal gating at the basis of the fiber cell is altered, for example through downregulation of fiber-selective β-1,3-glucanase;
e) plants, such as cotton plants, which have fibers with altered reactivity, for example through expression of the N-acetylglucosaminetransferase gene, including nodC, and chitin synthase genes.

Plants or plant cultivars (obtained by plant biotechnology methods such as genetic engineering) which may also be treated according to the invention are plants, such as oilseed rape or related *Brassica* plants, with altered oil profile characteristics. Such plants can be obtained by genetic transformation or by selection of plants containing a mutation imparting such altered oil characteristics and include:

a) plants, such as oilseed rape plants, which produce oil having a high oleic acid content;
b) plants, such as oilseed rape plants, which produce oil having a low linolenic acid content;
c) plants, such as oilseed rape plants, producing oil having a low level of saturated fatty acids.

Plants or plant cultivars (which can be obtained by plant biotechnology methods such as genetic engineering) which may also be treated according to the invention are plants such as potatoes which are virus-resistant, for example to the potato virus Y (SY230 and SY233 events from Tecnoplant, Argentina), or which are resistant to diseases such as potato late blight (e.g. RB gene), or which exhibit reduced cold-induced sweetness (which bear the genes Nt-Inh, II-INV) or which exhibit the dwarf phenotype (A-20 oxidase gene).

Plants or plant cultivars (obtained by plant biotechnology methods such as genetic engineering) which may also be treated according to the invention are plants, such as oilseed rape or related *Brassica* plants, with altered seed shattering characteristics. Such plants can be obtained by genetic transformation, or by selection of plants containing a mutation imparting such altered characteristics, and include plants such as oilseed rape with retarded or reduced seed shattering.

Particularly useful transgenic plants which can be treated according to the invention are plants with transformation events or combinations of transformation events which are the subject of granted or pending petitions for nonregulated status in the USA at the Animal and Plant Health Inspection Service (APHIS) of the United States Department of Agriculture (USDA). Information relating to this is available at any time from APHIS (4700 River Road Riverdale, Md. 20737, USA), for example via the website http://www.aphis.usda.gov/brs/not_reg.html. At the filing date of this application, the petitions with the following information were either granted or pending at the APHIS:

Petition: Identification number of the petition. The technical description of the transformation event can be found in the specific petition document available from APHIS on the website via the petition number. These descriptions are hereby disclosed by reference.

Extension of a petition: Reference to an earlier petition for which an extension of scope or term is being requested.

Institution: Name of the person submitting the petition.

Regulated article: The plant species in question.

Transgenic phenotype: The trait imparted to the plant by the transformation event.

Transformation event or line: The name of the event(s) (sometimes also referred to as line(s)) for which non-regulated status is being requested.

APHIS documents: Various documents which have been published by APHIS with regard to the petition or can be obtained from APHIS on request.

Particularly useful transgenic plants which may be treated according to the invention are plants which comprise one or more genes which encode one or more toxins, and are the transgenic plants which are sold under the following trade names: YIELD GARD® (for example corn, cotton, soybeans), KnockOut® (for example corn), BiteGard® (for example corn), BT-Xtra® (for example corn), StarLink® (for example corn), Bollgard® (cotton), Nucotn® (cotton), Nucotn 33B® (cotton), NatureGard® (for example corn), Protecta® and NewLeaf® (potato). Examples of herbicide-tolerant plants which should be mentioned are corn cultivars, cotton cultivars and soybean cultivars which are available under the following trade names: Roundup Ready® (tolerance to glyphosate, for example corn, cotton, soybeans), Liberty Link® (tolerance to phosphinothricin, for example oilseed rape), IMI® (tolerance to imidazolinone) and SOS® (tolerance to sulfonylurea, for example corn). Herbicide-resistant plants (plants bred in a conventional manner for herbicide tolerance) which may be mentioned include the cultivars sold under the name Clearfield® (for example corn).

Particularly useful transgenic plants which may be treated according to the invention are plants containing transformation events, or a combination of transformation events, and that are listed for example in the databases for various national or regional regulatory agencies (see for example http://gmoinfo.jrc.it/gmp_browse.aspx and http://cera-gm-c.org/index.php?evidcode=&hstIDXCode=&gType=&AbbrCode=&atCode=&stCode=& col DCode=&action=gm_crop_database&mode=Submit).

The inventive active ingredients or compositions can also be used in the protection of materials, for protection of industrial materials against attack and destruction by unwanted microorganisms, for example fungi and insects.

In addition, the inventive compounds can be used as antifouling compositions, alone or in combinations with other active ingredients.

Industrial materials in the present context are understood to mean inanimate materials which have been prepared for use in industry. For example, industrial materials which are to be protected by inventive active ingredients from microbial alteration or destruction may be adhesives, sizes, paper, wallpaper and cardboard, textiles, carpets, leather, wood, paints and plastic articles, cooling lubricants and other materials which can be infected with or destroyed by microorganisms. The range of materials to be protected also includes parts of production plants and buildings, for example cooling water circuits, cooling and heating systems, and ventilation and air conditioning systems, which may be impaired by the proliferation of microorganisms. Industrial materials within the scope of the present invention preferably include adhesives, sizes, papers and cardboard, leather, wood, paints, cooling lubricants and heat transfer fluids, more preferably wood. The inventive active ingredients or compositions may prevent adverse effects, such as rotting, decay, discoloration, decoloration or formation of mold. In addition, the inventive compounds can be used for protection of objects which come into contact with saltwater or brackish water, especially hulls, screens, nets, buildings, moorings and signaling systems, from fouling. The inventive method for controlling unwanted fungi can also be employed for protecting storage goods. Storage goods are understood to mean natural substances of vegetable or animal origin or processed products thereof which are of natural origin, and for which long-term protection is desired. Storage goods of vegetable origin, for example plants or plant parts, such as stems, leaves, tubers, seeds, fruits, grains, can be protected freshly harvested or after processing by (pre)drying, moistening, comminuting, grinding, pressing or roasting. Storage goods also include timber, whether unprocessed, such as construction timber, electricity poles and barriers, or in the form of finished products, such as furniture. Storage goods of animal origin are, for example, hides, leather, furs and hairs. The inventive active ingredients may prevent adverse effects, such as rotting, decay, discoloration, decoloration or formation of mold.

Non-limiting examples of pathogens of fungal diseases which can be treated in accordance with the invention include: Diseases caused by powdery mildew pathogens, for example *Blumeria* species, for example *Blumeria graminis*; *Podosphaera* species, for example *Podosphaera leucotricha*; *Sphaerotheca* species, for example *Sphaerotheca fuliginea*; *Uncinula* species, for example *Uncinula necator*; diseases caused by rust disease pathogens, for example *Gymnosporangium* species, for example *Gymnosporangium sabinae*; *Hemileia* species, for example *Hemileia vastatrix*; *Phakopsora* species, for example *Phakopsora pachyrhizi* and *Phakopsora meibomiae*; *Puccinia* species, for example *Puccinia recondita* or *Puccinia triticina*; *Uromyces* species, for example *Uromyces appendiculatus*; diseases caused by pathogens from the group of the oomycetes, for example *Bremia* species, for example *Bremia lactucae*; *Peronospora* species, for example *Peronospora pisi* or *P. brassicae*; *Phytophthora* species, for example *Phytophthora infestans*; *Plasmopara* species, for example *Plasmopara viticola*; *Pseudoperonospora* species, for example *Pseudoperonospora humuli* or *Pseudoperonospora cubensis*; *Pythium* species, for example *Pythium ultimum*; leaf blotch diseases and leaf wilt diseases caused, for example, by *Alternaria* species, for example *Alternaria solani*; *Cercospora* species, for example *Cercospora beticola*; *Cladiosporium* species, for example *Cladiosporium cucumerinum*; *Cochliobolus* species, for example *Cochliobolus sativus* (conidia form: *Drechslera*, Syn: *Helminthosporium*); *Colletotrichum* species, for example *Colletotrichum lindemuthianum*; *Cycloconium* species, for example *Cycloconium oleaginum*; *Diaporthe* species, for example *Diaporthe citri*; *Elsinoe* species, for example *Elsinoe fawcettii*; *Gloeosporium* species, for example *Gloeosporium laeticolor*; *Glomerella* species, for example *Glomerella cingulata*; *Guignardia* species, for example *Guignardia bidwelli*; *Leptosphaeria* species, for example *Leptosphaeria maculans*; *Magnaporthe* species, for example *Magnaporthe grisea*; *Microdochium* species, for example *Microdochium nivale*; *Mycosphaerella* species, for example *Mycosphaerella graminicola* and *M. fijiensis*; *Phaeosphaeria* species, for example *Phaeosphaeria nodorum*; *Pyrenophora* species, for example *Pyrenophora teres*; *Ramularia* species, for example *Ramularia collo-cygni*; *Rhynchosporium* species, for example *Rhynchosporium secalis*; *Septoria* species, for example *Septoria apii*; *Typhula* species, for example *Typhula incarnata*; *Venturia* species, for example *Venturia inaequalis*; root and stem diseases caused, for example, by *Corticium* species, for example *Corticium graminearum*; *Fusarium* species, for example *Fusarium oxysporum*; *Gaeumannomyces* species, for example *Gaeumannomyces graminis*; *Rhizoctonia* species, for example *Rhizoctonia solani*; *Tapesia* species, for example *Tapesia acuformis*; *Thielaviopsis* species, for example *Thielaviopsis basicola*; ear and panicle diseases (including corn cobs) caused, for example, by *Alternaria* species, for example *Alternaria* spp.; *Aspergillus* species, for example *Aspergillus flavus*; *Cladosporium* species, for example *Cladosporium cladosporioides*; *Claviceps* species, for example *Claviceps purpurea*; *Fusarium* species, for example *Fusarium culmorum*; *Gibberella* species, for example *Gibberella zeae*; *Monographella* species, for example *Monographella nivalis*; *Septoria* species, for example, *Septoria nodorum*; diseases caused by smut fungi, for example *Sphacelotheca* species, for example *Sphacelotheca reiliana*; *Tilletia* species, for example *Tilletia caries*; *T. controversa*; *Urocystis* species, for example *Urocystis occulta*; *Ustilago* species, for example *Ustilago nuda*; *U. nuda tritici*; fruit rot caused, for example, by *Aspergillus* species, for example *Aspergillus flavus*; *Botrytis* species, for example *Botrytis cinerea*; *Penicillium* species, for example *Penicillium expansum* and *P. purpurogenum*; *Sclerotinia* species, for example *Sclerotinia sclerotiorum*; *Verticilium* species, for example *Verticilium alboatrum*; seed- and soil-borne rot and wilt diseases, and also diseases of seedlings, caused, for example, by *Fusarium* species, for example *Fusarium culmorum*; *Phytophthora* species, for example *Phytophthora cactorum*; *Pythium* species, for example *Pythium ultimum*; *Rhizoctonia* species, for example *Rhizoctonia solani*; *Sclerotium* species, for example *Sclerotium rolfsii*; cancerous diseases, galls and witches' broom caused, for example, by *Nectria* species, for example *Nectria galligena*; wilt diseases caused, for example, by *Monilinia* species, for example *Monilinia laxa*; deformations of leaves, flowers and fruits caused, for example, by *Taphrina* species, for example *Taphrina deformans*; degenerative diseases of woody plants caused, for example, by *Esca* species, for example *Phaemoniella clamydospora* and *Phaeoacremonium aleophilum* and *Fomitiporia mediterranea*; diseases of flowers and seeds caused, for example, by *Botrytis* species, for example *Botrytis cinerea*; diseases of plant tubers caused, for example, by *Rhizoctonia* species, for example *Rhizoctonia solani*; *Helminthosporium* species, for example *Helminthosporium solani*; diseases caused by bacteriopathogens, for example *Xanthomonas* species, for example *Xanthomonas campestris* pv. *oryzae*; *Pseudomonas* species, for example *Pseudomonas syringae* pv. *lachrymans*; *Erwinia* species, for example *Erwinia amylovora*.

The following diseases of soybeans can be controlled with preference: Fungal diseases on leaves, stems, pods and seeds caused, for example, by alternaria leaf spot (*Alternaria* spec. *atrans tenuissima*), Anthracnose (*Colletotrichum gloeosporoides dematium* var. *truncatum*), brown spot (*Septoria glycines*), cercospora leaf spot and blight (*Cercospora kikuchii*), choanephora leaf blight (*Choanephora infundibulifera trispora* (Syn.)), dactuliophora leaf spot (*Dactuliophora glycines*), downy mildew (*Peronospora manshurica*), drechslera blight (*Drechslera glycini*), frogeye leaf spot (*Cercospora sojina*), leptosphaerulina leaf spot (*Leptosphaerulina trifolii*), phyllostica leaf spot (*Phyllosticta sojaecola*), pod and stem blight (*Phomopsis sojae*), powdery mildew (*Microsphaera diffusa*), pyrenochaeta leaf spot (*Pyrenochaeta glycines*), rhizoctonia aerial, foliage, and web blight (*Rhizoctonia solani*), rust (*Phakopsora pachyrhizi, Phakopsora meibomiae*), scab (*Sphaceloma glycines*), stemphylium leaf blight (*Stemphylium botryosum*), target spot (*Corynespora cassiicola*).

Fungal diseases on roots and the stem base caused, for example, by black root rot (*Calonectria crotalariae*), charcoal rot (*Macrophomina phaseolina*), fusarium blight or wilt, root rot, and pod and collar rot (*Fusarium oxysporum, Fusarium orthoceras, Fusarium semitectum, Fusarium equiseti*), mycoleptodiscus root rot (*Mycoleptodiscus terrestris*), neocosmospora (*Neocosmospora vasinfecta*), pod and stem blight (*Diaporthe phaseolorum*), stem canker (*Diaporthe phaseolorum* var. *caulivora*), phytophthora rot (*Phytophthora megasperma*), brown stem rot (*Phialophora gregata*), pythium rot (*Pythium aphanidermatum, Pythium irregulare, Pythium debaryanum, Pythium myriotylum, Pythium ultimum*), rhizoctonia root rot, stem decay, and damping-off (*Rhizoctonia solani*), sclerotinia stem decay (*Sclerotinia sclerotiorum*), sclerotinia southern blight (*Sclerotinia rolfsii*), thielaviopsis root rot (*Thielaviopsis basicola*).

Microorganisms capable of degrading or altering the industrial materials include, for example, bacteria, fungi, yeasts, algae and slime organisms. The inventive active ingredients preferably act against fungi, especially molds, wood-discoloring and wood-destroying fungi (Basidiomycetes), and against slime organisms and algae. Examples include microorganisms of the following genera: *Alternaria*, such as *Alternaria tenuis*; *Aspergillus*, such as *Aspergillus niger*; *Chaetomium*, such as *Chaetomium globosum*; *Coniophora*, such as *Coniophora puetana*; *Lentinus*, such as *Lentinus tigrinus*; *Penicillium*, such as *Penicillium glaucum*; *Polyporus*, such as *Polyporus versicolor*; *Aureobasidium*, such as *Aureobasidium pullulans*; *Sclerophoma*, such as *Sclerophoma pityophila*; *Trichoderma*, such as *Trichoderma viride*; *Escherichia*, such as *Escherichia coli*; *Pseudomonas*, such as *Pseudomonas aeruginosa*; *Staphylococcus*, such as *Staphylococcus aureus*.

In addition, the inventive active compounds also have very good antimycotic activity. They have a very broad antimycotic activity spectrum, in particular against dermatophytes and yeasts, molds and diphasic fungi, (for example against *Candida* species, such as *Candida albicans, Candida glabrata*), and *Epidermophyton floccosum, Aspergillus* species, such as *Aspergillus niger* and *Aspergillus fumigatus*, *Trichophyton* species, such as *Trichophyton mentagrophytes*, *Microsporon* species such as *Microsporon canis* and *audouinii*. The enumeration of these fungi in no way constitutes a restriction of the mycotic spectrum that can be controlled, and is merely of illustrative character.

The inventive active ingredients can therefore be used both in medical and in non-medical applications.

In the case of use of the inventive active ingredients as fungicides, the application rates can be varied within a relatively wide range, depending on the kind of application. The application rate of the inventive active ingredients is in the case of treatment of plant parts, for example leaves: from 0.1 to 10 000 g/ha, preferably from 10 to 1000 g/ha, more preferably from 50 to 300 g/ha (in the case of application by watering or dripping, it is even possible to reduce the application rate, especially when inert substrates such as rockwool or perlite are used);

in the case of seed treatment: from 2 to 200 g per 100 kg of seed, preferably from 3 to 150 g per 100 kg of seed, more preferably from 2.5 to 25 g per 100 kg of seed, even more preferably from 2.5 to 12.5 g per 100 kg of seed;

in the case of soil treatment: from 0.1 to 10 000 g/ha, preferably from 1 to 5000 g/ha. These application rates are merely illustrative and are not limiting for the purposes of the invention.

The inventive active ingredients or compositions can thus be used to protect plants from attack by the pathogens mentioned for a certain period of time after treatment.

The period for which protection is brought about extends generally for 1 to 28 days, preferably for 1 to 14 days, more preferably for 1 to 10 days, even more preferably for 1 to 7 days, after the treatment of the plants with the active ingredients, or for up to 200 days after a seed treatment.

In addition, the inventive treatment can reduce the mycotoxin content in the harvested material and the foodstuffs and feedstuffs prepared therefrom. Mycotoxins include particularly, but not exclusively, the following: deoxynivalenol (DON), nivalenol, 15-Ac-DON, 3-Ac-DON, T2- and HT2-toxin, fumonisins, zearalenon, moniliformin, fusarin, diaceotoxyscirpenol (DAS), beauvericin, enniatin, fusaroproliferin, fusarenol, ochratoxins, patulin, ergot alkaloids and aflatoxins which can be produced, for example, by the following fungi: *Fusarium* spec., such as *Fusarium acuminatum, F. avenaceum, F. crookwellense, F. culmorum, F. graminearum* (*Gibberella zeae*), *F. equiseti, F. fujikoroi, F. musarum, F. oxysporum, F. proliferatum, F. poae, F. pseudograminearum, F. sambucinum, F. scirpi, F. semitectum, F. solani, F. sporotrichoides, F. langsethiae, F. subglutinans, F. tricinctum, F. verticillioides*, inter alia, and also by *Aspergillus* spec., *Penicillium* spec., *Claviceps purpurea, Stachybotrys* spec., inter alia.

If appropriate, the inventive compounds can, at certain concentrations or application rates, also be used as herbicides, safeners, growth regulators or agents to improve plant properties, or as microbicides, for example as fungicides, antimycotics, bactericides, viricides (including agents against viroids) or as agents against MLO (mycoplasma-like organisms) and RLO (rickettsia-like organisms). If appropriate, they can also be used as intermediates or precursors for the synthesis of other active ingredients.

The examples which follow illustrate the invention in detail.

A. CHEMICAL EXAMPLES

1. Preparation of N-(cyanomethyl)-3-(3,5-dichlorophenyl)-5-methoxy-4,5-dihydro-1,2-oxazole-5-carboxamide (example 1.20-40)

Intermediate 1: 3,5-Dichlorobenzaldehyde oxime 23.82 g (342.8 mmol) of hydroxylamine hydrochloride were admixed with 80 ml of ethanol. After addition of 28.12 g (342.8 mmol) of sodium acetate, a solution of 50.00 g (285.7 mmol) of 3,5-dichlorobenzaldehyde in 100 ml ethanol was added dropwise within 30 min, and the mixture was left to stir for 2 h and then left to stand overnight. The reaction mixture was fully concentrated, then 500 ml of $CH_2Cl_2$ were added, and the mixture was washed with 400 ml of water. The water phase was washed once with 100 ml of $CH_2Cl_2$, and the organic phase was dried over $Na_2SO_4$, filtered and concentrated. The residue was used without further purification. Yield: 56.50 g (98%)

$^1$H NMR ($CDCl_3$): σ=7.36 (s, 1H, Ar—H), 7.47 (s, 2H, Ar—H), 7.63 (s br, 1H, OH), 8.02 (s, 1H, HC=NOH).

Intermediate 2: 3,5-Dichloro-N-hydroxybenzenecarboximidoyl chloride 30.00 g (157.9 mmol) of 3,5-dichlorobenzaldehyde oxime were initially charged in 379 ml of 0.5M HCl in DMF, and 116.7 g (189.5 mmol) of Oxone (potassium peroxomonosulfate) were added in portions at room temperature (RT). In order that the reaction mixture did not heat up to an internal temperature of more than 50° C., it was cooled with an ice bath. After 2 h, the reaction solution was poured into 1 l of ice-water and extracted twice with 500 ml of ether each time. The combined organic phases were then washed with 400 ml of 0.5M aqueous HCl and with 200 ml of saturated NaCl solution, dried over $Na_2SO_4$, filtered and concentrated. The residue was used without further purification. Yield: 28.40 g (80%)

$^1$H NMR ($CDCl_3$): σ=7.43 (s, 1H, Ar—H), 7.74 (s, 2H, Ar—H), 8.03 (s br, 1H, OH).

Intermediate 3: Methyl 3-(3,5-dichlorophenyl)-5-methoxy-4,5-dihydro-1,2-oxazole-5-carboxylate (example A-116)

35.00 g (155.9 mmol) were dissolved in 490 ml of 2-propanol, and 31.61 g (171.5 mmol) of methyl 2-methoxyacrylate were added. At RT, 65.49 g (779.6 mmol) of $NaHCO_3$ were added to this solution, and the mixture was stirred at room temperature for 12 h. The solids were then filtered off, and the filtrate was concentrated on a rotary evaporator. The crude product was dissolved in dichloromethane, dried over $Na_2SO_4$, filtered and concentrated. Subsequently, the solids were dissolved in a little dichloromethane, and isopropanol was added. The product crystallized out of this solvent mixture. Yield: 28.0 g (59%)

$^1$H NMR ($CDCl_3$): σ=3.40 (d $H_A$ of AB, J=19 Hz, 1H, N=C—C$H_A$$H_B$), 3.48 (s, 3H, O—C$H_3$), 3.78 (d, $H_B$ of AB, J=19 Hz, 1H, N=C—C$H_A$$H_B$), 3.90 (s, 3H, OC$H_3$), 7.43 (s, 1H, Ar—H), 7.55 (s, 2H, Ar—H).

Intermediate 4: 3-(3,5-Dichlorophenyl)-5-methoxy-4,5-dihydro-1,2-oxazole-5-carboxylic acid (example A-115)

40.00 g (131.5 mmol) of methyl 3-(3,5-dichlorophenyl)-5-methoxy-4,5-dihydro-1,2-oxazole-5-carboxylate were dissolved in 800 ml of THF, and then 2.99 g of LiOH were added gradually as a 0.5 molar solution in water. After stirring at RT for 2 h, the THF solvent was removed in vacuo, 200 ml of a semisaturated $NaHCO_3$ solution were added and the mixture was extracted with ethyl acetate. Subsequently, the aqueous phase was admixed with 300 ml of methylene chloride and then adjusted to pH 1 by gradual addition of 0.5 n HCl while stirring. The organic phase was dried over $Na_2SO_4$, filtered and concentrated. Yield: 35.4 g (88%)

$^1$H NMR ($CDCl_3$): σ=3.45 (d $H_A$ of AB, J=19 Hz, 1H, N=C—C$H_A$$H_B$), 3.51 (s, 3H$_2$OC$H_3$), 3.85 (d $H_B$ of AB, J=19 Hz, 1H,N=C—C$H_A$$H_B$), 7.45 (s, 1H, Ar—H), 7.56 (s, 2H, Ar—H), 93 (s br., 1H, COOH).

Example 1.20-40

N-(Cyanomethyl)-3-(3,5-dichlorophenyl)-5-methoxy-4,5-dihydro-1,2-oxazole-5-carboxamide 200 mg (0.689 mmol) of 3-(3,5-dichlorophenyl)-5-methoxy-4,5-dihydro-1,2-oxazole-5-carboxylic acid were initially charged in 10 ml of dichloromethane, and 93 mg (0.69 mmol) of HOBT and 57 mg (1.0 mmol) of 2-aminoacetonitrile were added. Subsequently, 172 mg (0.896 mmol) of 1-(3-dimethylaminopropyl)-3-ethylcarbodiimide hydrochloride were added and the mixture was stirred for 30 min. For workup, the mixture was washed with water and chromatographed using silica gel with heptane/ethyl acetate. Yield: 220 mg (92%).

$^1$H NMR ($CDCl_3$): σ=3.36 (d $H_A$ of AB, J=19 Hz, 1H, N=C—C$H_A$$H_B$), 3.37 (s, 3H$_2$OC$H_3$), 3.81 (d, $H_B$ of AB, J=19 Hz, 1H,N=C—C$H_A$$H_B$), 4.27 (d AB, 2H; J AB=16

Hz, JAC=7 Hz, 2H, NH$_C$—C<u>H</u>$_A$H$_B$); 7.17 (t br, J=7 Hz, 1H, N<u>H</u>); 7.45 (s, 1H, Ar—<u>H</u>), 7.56 (s, 2H, Ar—<u>H</u>).

Intermediate 5

Methyl 2,2-dimethoxypropanoate 100 g (979 mmol) of methyl 2-oxopropanoate were admixed with 135 g (1273 mmol) of trimethyl orthoformate in 240 ml of methanol. After addition of 0.96 g (9.79 mmol) of concentrated H$_2$SO$_4$, the mixture was heated to reflux for 4 h. The solvent was distilled off within 2 h, and the crude product was cooled to 10° C. and added to a solution of 2.4 g of KOH in 1200 ml of water at 10° C. After repeated extraction with diethyl ether, the product was dried over Na$_2$SO$_4$, filtered and concentrated. The residue was distilled again. B.p. (10 mbar): 50-55° C. Yield: 118 g (77%)
$^1$H NMR (CDCl$_3$): σ=1.53 (s, 3H,C—C<u>H</u>$_3$), 3.29 (s, 6H, C<u>H</u>$_3$—O—C—O—C<u>H</u>$_3$), 3.82 (s, 3H,COOC<u>H</u>$_3$).

Intermediate 6

Methyl 2-methoxyacrylate 100 g (675 mmol) of methyl 2,2-dimethoxypropanoate were initially charged in 300 ml of DMF, 52.7 g (371 mmol) of P$_2$O$_5$ were added in portions while stirring and then the mixture was heated to 100° C. for 1 h. The reaction solution was then added to 1 l of a saturated NaHCO$_3$ solution cooled to 10° C. This solution was extracted with diethyl ether, and the organic extracts were washed three times with saturated NaCl solution, dried over Na$_2$SO$_4$, filtered and concentrated. The product was used without further purification. Yield: 66.0 g (81%)
$^1$H NMR (CDCl$_3$): σ=3.67 (s, 3H,C—C<u>H</u>$_3$), 3.83 (s, 3H, COOC<u>H</u>$_3$), 4.63 (d, 1H, J=3 Hz,C=C<u>H</u>H), 5.37 (d, 1H, J=3 Hz, C=CH<u>H</u>).

Intermediate 7

Ethyl 2-ethoxyacrylate

Synthesis Analogous to Intermediate 6

$^1$H NMR (CDCl$_3$): σ=1.33 (t, 3H, J=7 Hz, C<u>H</u>$_3$CH$_2$O), 1.40 (t, 3H, J=7 Hz, C<u>H</u>$_3$CH$_2$O) 3.83 (q, 2H, J=7 Hz, CH$_3$C<u>H</u>$_2$O), 4.27 (q, 2H, J=7 Hz, CH$_3$C<u>H</u>$_2$O), 4.58 (d, 1H, J=3 Hz,C=C<u>H</u>H), 5.32 (d, 1H, J=3 Hz, C=CH<u>H</u>).

Example 3.11-9

3-(3,5-Difluorophenyl)-5-methoxy-N-(2,2,2-trifluoroethyl)-4,5-dihydro-1,2-oxazole-5-carbothioamide 400 mg (1.182 mmol) of 3-(3,5-difluorophenyl)-5-methoxy-N-(2,2,2-trifluoroethyl)-4,5-dihydro-1,2-oxazole-5-carboxamide were dissolved in 20 ml of THF, and a total of 478 mg (1.182 mmol) of Lawesson's reagent were added in portions. The clear solution was subsequently heated to 80° C. in a microwave for 2 h. The solvent was removed under reduced pressure, and the residue was taken up in ethyl acetate and extracted with saturated sodium chloride solution. The organic phase was dried over Na$_2$SO$_4$, filtered and concentrated. This was followed by chromatographic purification with ethyl acetate/n-heptane using silica gel. Yield: 150 mg (34%)

1H NMR (CDCl3): σ=3.41 (s, 3H, O—C<u>H</u>$_3$); 3.57 (d H$_A$ of AB, J=19 Hz, 1H, N=C—C<u>H</u>$_A$H$_B$), 4.07 (d H$_B$ of AB, J=19 Hz, 1H,N=C—CH$_A$<u>H</u>$_B$), 4.26-4.41 (m, 1H, C<u>H</u>H—CF$_3$); 4.54-4.71 (m, 1H, CH<u>H</u>—CF$_3$); 6.92 (tt, 1H, phenyl-4<u>H</u>); 7.21 (d, 2H, Ar-2,6<u>H</u>); 8.70 (s br, 1H, N<u>H</u>).

In analogy to the preparation of the abovementioned compounds and in accordance with the general details of the preparation, the compounds specified in the following tables are obtainable. The NMR data of the examples disclosed in these tables are given in the form (δ values, number of hydrogen atoms, multiplet splitting). The δ value/signal intensity number pairs for different signal peaks are listed separated from one another by semicolons.

Table 1.1: Inventive compounds 1.1-1 to 1.1-266 of the general formula (1.1) in which A-X is as defined below.

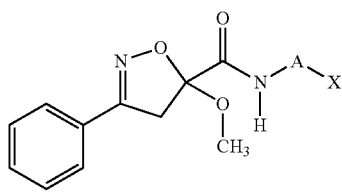

(I.1)

TABLE 1.1

| No. | A—X |
|---|---|
| 1.1-1 | —H |
| 1.1-2 | —CH$_3$ |
| 1.1-3 | (ethyl branched) |
| 1.1-4 | (propyl branched) |
| 1.1-5 | (isopropyl) |
| 1.1-6 | (t-butyl) |
| 1.1-7 | (isobutyl) |

TABLE 1.1-continued
| No. | ⎯A⎯X |
|---|---|
| 1.1-8 | 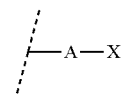 |
| 1.1-9 | 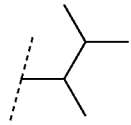 |
| 1.1-10 | 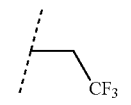 |
| 1.1-11 | 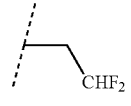 |
| 1.1-12 | 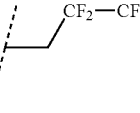 |
| 1.1-13 | 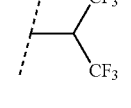 |
| 1.1-14 | 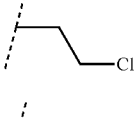 |
| 1.1-15 | 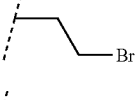 |
| 1.1-16 | 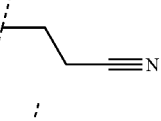 |
| 1.1-17 | 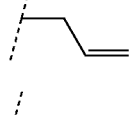 |
| 1.1-18 | 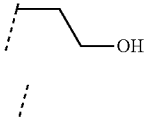 |
| 1.1-19 | 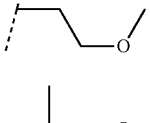 |
| 1.1-20 |  |
| 1.1-21 | 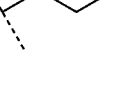 |
| 1.1-22 | 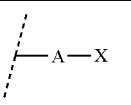 |
| 1.1-23 | 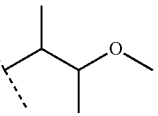 |
| 1.1-24 | 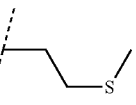 |
| 1.1-25 | 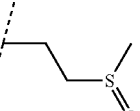 |
| 1.1-26 | 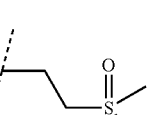 |
| 1.1-27 | 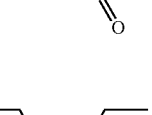 |
| 1.1-28 | 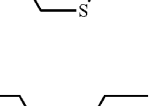 |
| 1.1-29 | 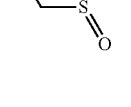 |
| 1.1-30 | 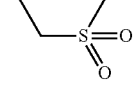 |
| 1.1-31 | 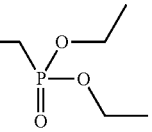 |

TABLE 1.1-continued
| No. | —A—X |
|---|---|
| 1.1-32 | 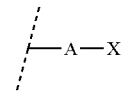 |
| 1.1-33 | 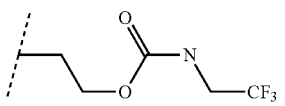 |
| 1.1-34 | 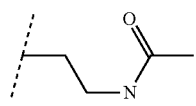 |
| 1.1-35 | 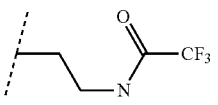 |
| 1.1-36 | 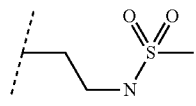 |
| 1.1-37 | 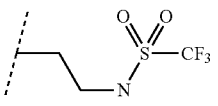 |
| 1.1-38 | 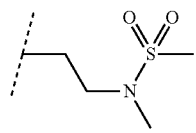 |
| 1.1-39 | 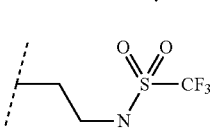 |
| 1.1-40 | 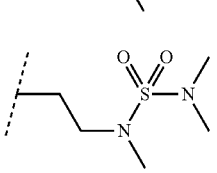 |
| 1.1-41 | 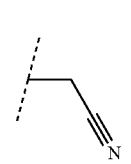 |
| 1.1-42 | 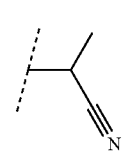 |
| 1.1-43 | 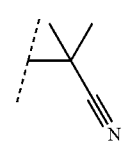 |
| 1.1-44 | 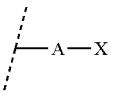 |
| 1.1-45 | 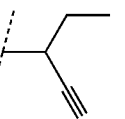 |
| 1.1-46 | 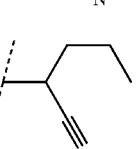 |
| 1.1-47 | 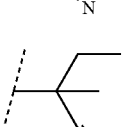 |
| 1.1-48 | 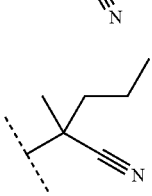 |
| 1.1-49 | 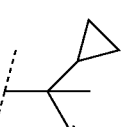 |
| 1.1-50 | 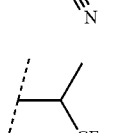 |
| 1.1-51 | 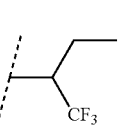 |
| 1.1-52 | 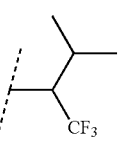 |

TABLE 1.1-continued
| No. | —A—X |
|---|---|
| 1.1-53 | 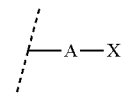 |
| 1.1-54 | 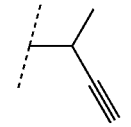 |
| 1.1-55 | 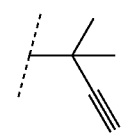 |
| 1.1-56 | 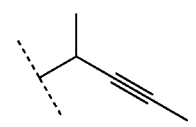 |
| 1.1-57 | 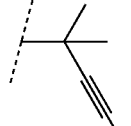 |
| 1.1-58 | 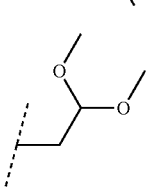 |
| 1.1-59 | 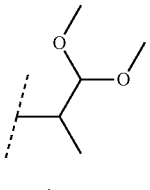 |
| 1.1-60 | 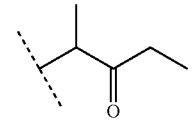 |
| 1.1-61 | 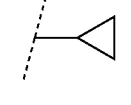 |
| 1.1-62 | 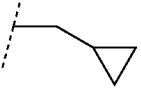 |
| 1.1-63 | 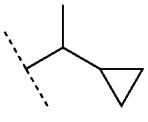 |
| 1.1-64 | 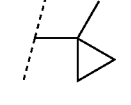 |
| 1.1-65 | 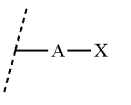 |
| 1.1-66 | 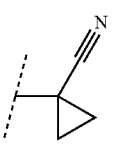 |
| 1.1-67 | 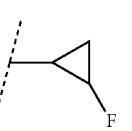 |
| 1.1-68 | 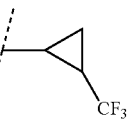 |
| 1.1-69 | 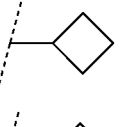 |
| 1.1-70 | 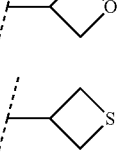 |
| 1.1-71 | 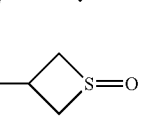 |
| 1.1-72 | 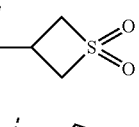 |
| 1.1-73 | 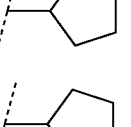 |
| 1.1-74 | 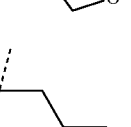 |
| 1.1-75 | 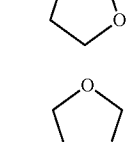 |

TABLE 1.1-continued
| No. | —A—X |
|---|---|
| 1.1-76 | 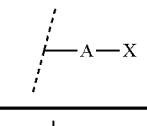 |
| 1.1-77 | 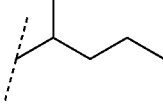 |
| 1.1-78 | 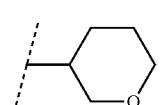 |
| 1.1-79 | 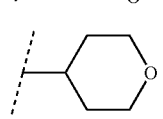 |
| 1.1-80 |  |
| 1.1-81 | 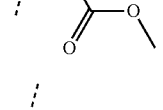 |
| 1.1-82 | 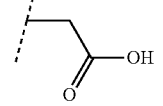 |
| 1.1-83 | 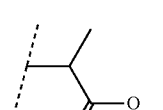 |
| 1.1-84 |  |
| 1.1-85 | 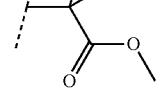 |
| 1.1-86 | 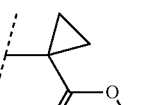 |
| 1.1-87 | 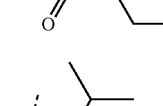 |
| 1.1-88 | 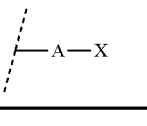 |
| 1.1-89 | 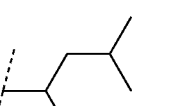 |
| 1.1-90 | 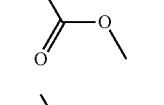 |
| 1.1-91 | 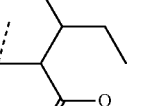 |
| 1.1-92 | 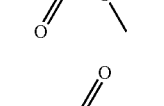 |
| 1.1-93 | 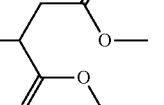 |
| 1.1-94 | 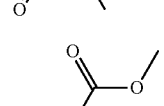 |
| 1.1-95 | 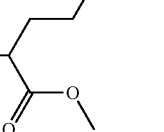 |

TABLE 1.1-continued
| No. | —A—X |
|---|---|
| 1.1-96 | 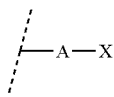 |
| 1.1-97 | 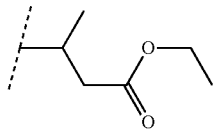 |
| 1.1-98 | 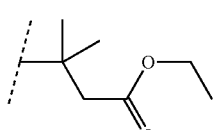 |
| 1.1-99 | 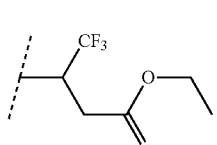 |
| 1.1-100 | 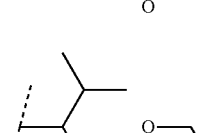 |
| 1.1-101 | 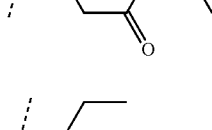 |
| 1.1-102 | 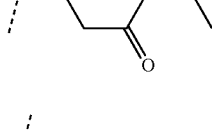 |
| 1.1-103 | 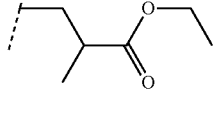 |
| 1.1-104 | 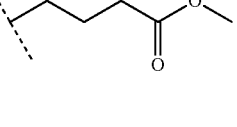 |
| 1.1-105 | 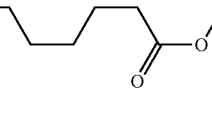 |
TABLE 1.1-continued
| No. | —A—X |
|---|---|
| 1.1-106 | 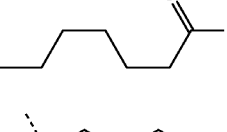 |
| 1.1-107 | 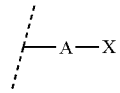 |
| 1.1-108 | 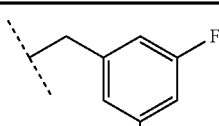 |
| 1.1-109 | 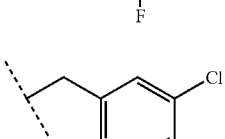 |
| 1.1-110 | 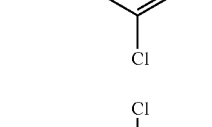 |
| 1.1-111 | 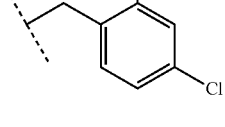 |
| 1.1-112 | 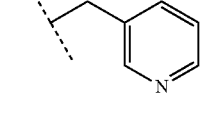 |
| 1.1-113 | 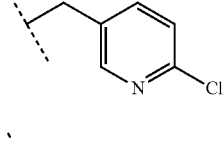 |
| 1.1-114 | 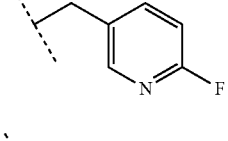 |
| 1.1-115 | 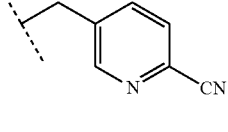 |

TABLE 1.1-continued
| No. | —A—X |
|---|---|
| 1.1-116 | 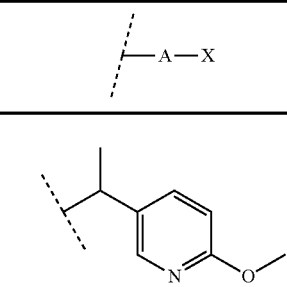 |
| 1.1-117 | 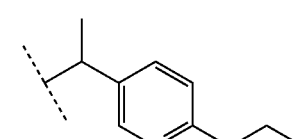 |
| 1.1-118 | 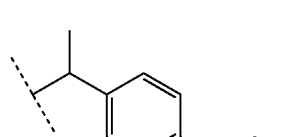 |
| 1.1-119 | 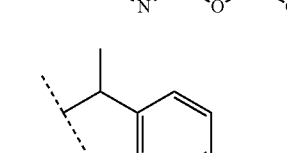 |
| 1.1-120 | 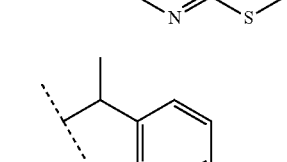 |
| 1.1-121 | 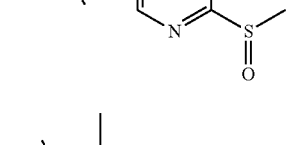 |
| 1.1-122 | 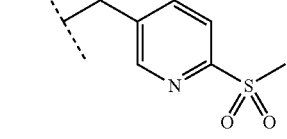 |
| 1.1-123 | 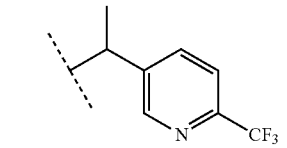 |
| 1.1-124 | 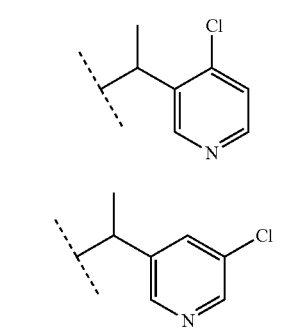 |
| 1.1-125 | (image) |
| 1.1-126 | (image) |
| 1.1-127 | (image) |
| 1.1-128 | (image) |
| 1.1-129 | (image) |
| 1.1-130 | (image) |
| 1.1-131 | (image) |
| 1.1-132 | (image) |
| 1.1-133 | (image) |
| 1.1-134 | (image) |

TABLE 1.1-continued

| No. | —A—X |
|---|---|
| 1.1-135 | 4-pyridylmethyl |
| 1.1-136 | (2-chloropyridin-4-yl)methyl |
| 1.1-137 | (2-fluoropyridin-4-yl)methyl |
| 1.1-138 | (2-bromopyridin-4-yl)methyl |
| 1.1-139 | (2-methylthiopyridin-4-yl)methyl |
| 1.1-140 | (2-methylsulfinylpyridin-4-yl)methyl |
| 1.1-141 | (2-methylsulfonylpyridin-4-yl)methyl |
| 1.1-142 | (2-methoxypyridin-4-yl)methyl |
| 1.1-143 | (2-ethoxypyridin-4-yl)methyl |
| 1.1-144 | (2-(2,2,2-trifluoroethoxy)pyridin-4-yl)methyl |
| 1.1-145 | (2-(difluoromethoxy)pyridin-4-yl)methyl |
| 1.1-146 | (2-(trifluoromethoxy)pyridin-4-yl)methyl |
| 1.1-147 | (2-methylpyridin-4-yl)methyl |
| 1.1-148 | (2-ethylpyridin-4-yl)methyl |
| 1.1-149 | (2-cyclopropylpyridin-4-yl)methyl |
| 1.1-150 | (2-propylpyridin-4-yl)methyl |
| 1.1-151 | (2-tert-butylpyridin-4-yl)methyl |
| 1.1-152 | (2-difluoromethylpyridin-4-yl)methyl (CF$_2$) |
| 1.1-153 | (2-(difluoromethyl)pyridin-4-yl)methyl (CHF$_2$) |
| 1.1-154 | (2-cyanopyridin-4-yl)methyl |
| 1.1-155 | (2-ethynylpyridin-4-yl)methyl |
| 1.1-156 | 1-(pyridin-4-yl)ethyl |

TABLE 1.1-continued
| No. | —A—X |
|---|---|
| 1.1-157 | 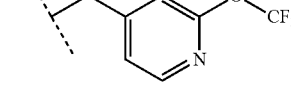 |
| 1.1-158 | |
| 1.1-159 | |
| 1.1-160 | |
| 1.1-161 | |
| 1.1-162 | |
| 1.1-163 | |
| 1.1-164 | |
| 1.1-165 | |
| 1.1-166 | |
TABLE 1.1-continued
| No. | —A—X |
|---|---|
| 1.1-167 |  |
| 1.1-168 | |
| 1.1-169 | |
| 1.1-170 | |
| 1.1-171 | |
| 1.1-172 | |
| 1.1-173 | |
| 1.1-174 | |
| 1.1-175 | |
| 1.1-176 | |

TABLE 1.1-continued

| No. | —A—X |
|---|---|
| 1.1-177 | CH2-(pyridin-2-yl) |
| 1.1-178 | CH2-(3,5-difluoropyridin-2-yl) |
| 1.1-179 | CH2-(3-chloro-5-trifluoromethylpyridin-2-yl) |
| 1.1-180 | CH2CH2-(3-chloro-5-trifluoromethylpyridin-2-yl) |
| 1.1-181 | CH2-(5-fluoropyridin-2-yl) |
| 1.1-182 | CH2-(5-chloropyridin-2-yl) |
| 1.1-183 | CH2-(5-methoxypyridin-2-yl) |
| 1.1-184 | CH2-(6-chloropyridin-2-yl) |
| 1.1-185 | CH2-(6-cyanopyridin-2-yl) |
| 1.1-186 | CH2-(pyrimidin-2-yl) |
| 1.1-187 | CH2-(4-chloropyrimidin-2-yl) |
| 1.1-188 | CH2-(4,6-dichloropyrimidin-2-yl) |
| 1.1-189 | CH2-(4,6-dimethylpyrimidin-2-yl) |
| 1.1-190 | CH2-(4-methoxypyrimidin-2-yl) |
| 1.1-191 | CH2-(4,6-dimethoxypyrimidin-2-yl) |
| 1.1-192 | CH2-(4-methoxypyrimidin-2-yl) |
| 1.1-193 | CH2-(2-chloropyrimidin-4-yl) |
| 1.1-194 | CH2-(pyrimidin-4-yl) |
| 1.1-195 | CH2-(6-chloropyrimidin-4-yl) |
| 1.1-196 | CH2-(2-methyloxazol-4-yl) |
| 1.1-197 | CH2-(2,5-dimethyloxazol-4-yl) |

TABLE 1.1-continued
| No. | —A—X |
|---|---|
| 1.1-198 | 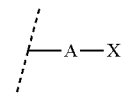 |
| 1.1-199 | 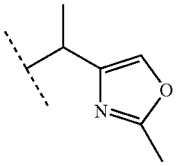 |
| 1.1-200 | 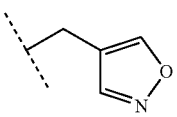 |
| 1.1-201 | 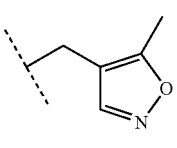 |
| 1.1-202 | 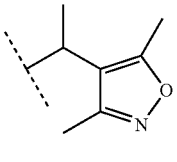 |
| 1.1-203 | 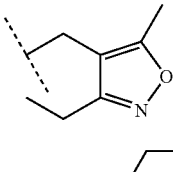 |
| 1.1-204 | 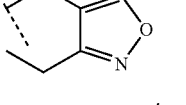 |
| 1.1-205 | 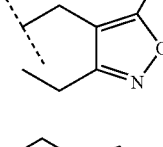 |
| 1.1-206 | 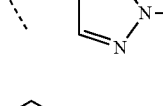 |
| 1.1-207 | 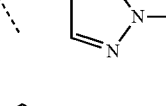 |
| 1.1-208 | 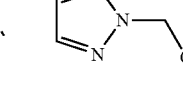 |
| 1.1-209 | 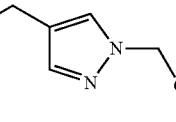 |
| 1.1-210 | 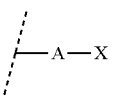 |
| 1.1-211 | 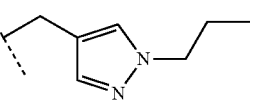 |
| 1.1-212 | 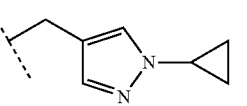 |
| 1.1-213 | 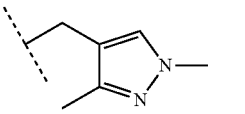 |
| 1.1-214 | 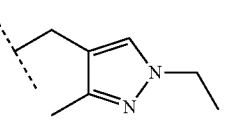 |
| 1.1-215 | 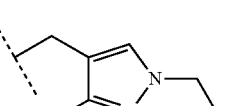 |
| 1.1-216 | 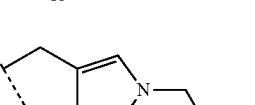 |
| 1.1-217 | 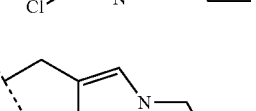 |
| 1.1-218 | 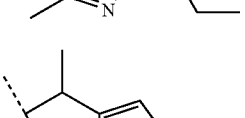 |
| 1.1-219 | 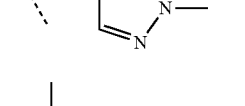 |

TABLE 1.1-continued
| No. | —A—X |
|---|---|
| 1.1-220 |  |
| 1.1-221 | 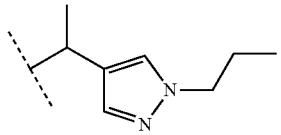 |
| 1.1-222 | 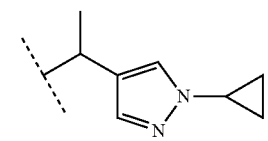 |
| 1.1-223 | 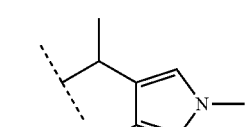 |
| 1.1-224 | 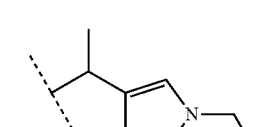 |
| 1.1-225 | 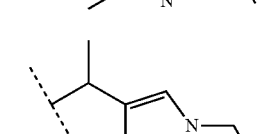 |
| 1.1-226 | 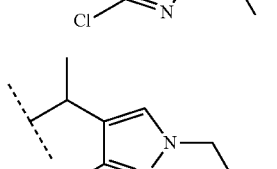 |
| 1.1-227 | 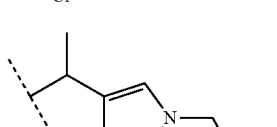 |
| 1.1-228 | 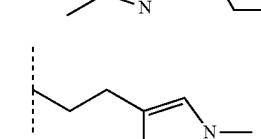 |
| 1.1-229 | 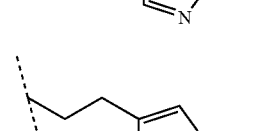 |
TABLE 1.1-continued
| No. | —A—X |
|---|---|
| 1.1-230 | 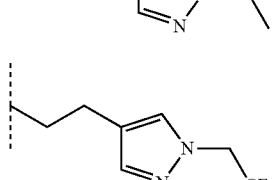 |
| 1.1-231 |  |
| 1.1-232 | 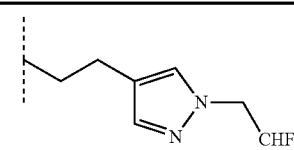 |
| 1.1-233 | 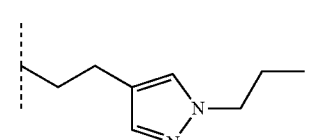 |
| 1.1-234 | 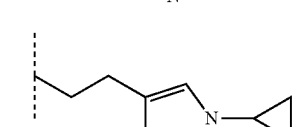 |
| 1.1-235 | 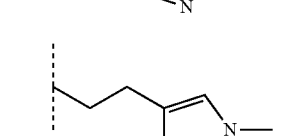 |
| 1.1-236 | 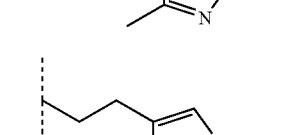 |
| 1.1-237 | 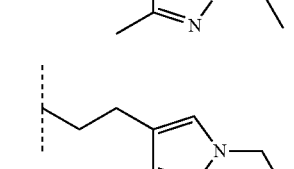 |
| 1.1-238 | 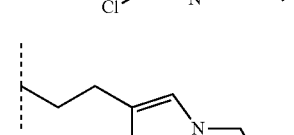 |
| 1.1-239 | 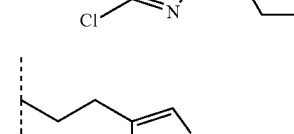 |

TABLE 1.1-continued
| No. | —A—X |
|---|---|
| 1.1-240 | 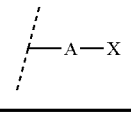 |
| 1.1-241 | 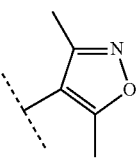 |
| 1.1-242 | 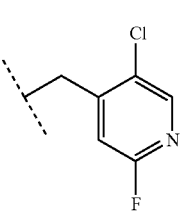 |
| 1.1-243 | 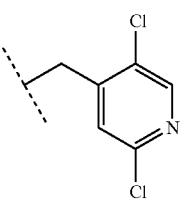 |
| 1.1-244 | 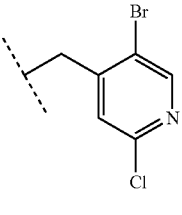 |
| 1.1-245 | 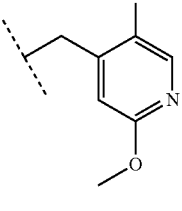 |
| 1.1-246 | 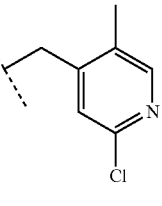 |
| 1.1-247 | 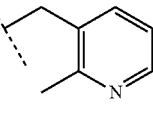 |
| 1.1-248 | 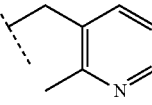 |
| 1.1-249 | 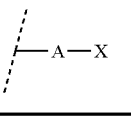 |
| 1.1-250 | 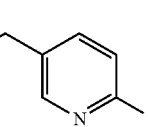 |
| 1.1-251 | 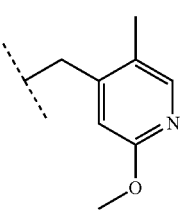 |
| 1.1-252 | 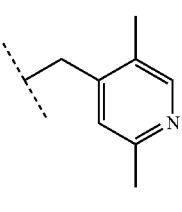 |
| 1.1-253 | 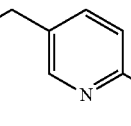 |
| 1.1-254 | 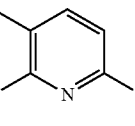 |
| 1.1-255 | 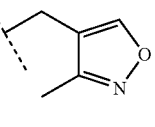 |
| 1.1-256 | 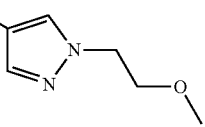 |

TABLE 1.1-continued

| No. | ![A-X] |
|-----|--------|
| 1.1-257 | (pyrazole with ethyl, methoxy) |
| 1.1-258 | (pyrazole with methyl, methoxy) |
| 1.1-259 | (pyrazole with methyl, ethyl) |
| 1.1-260 | (tetrafluoropyridine) |
| 1.1-261 | (chlorotrifluoropyridine) |
| 1.1-262 | (2-cyanophenyl) |
| 1.1-263 | (4-CF$_3$-phenyl) |
| 1.1-264 | (4-OCF$_3$-phenyl) |
| 1.1-265 | (4-Br-phenyl) |

TABLE 1.1-continued

| No. | ![A-X] |
|-----|--------|
| 1.1-266 | (pyrazole with methyl, methoxy) |

Table 1.2: Inventive compounds 1.2-1 to 1.2-266 of the general formula (1.2) in which A-X is as defined in table 1.1.

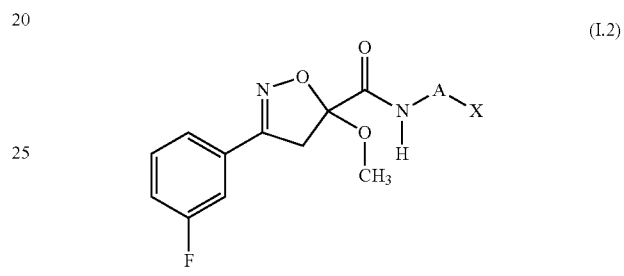

(I.2)

Table 1.3: Inventive compounds 1.3-1 to 1.3-266 of the general formula (1.3) in which A-X is as defined in table 1.1.

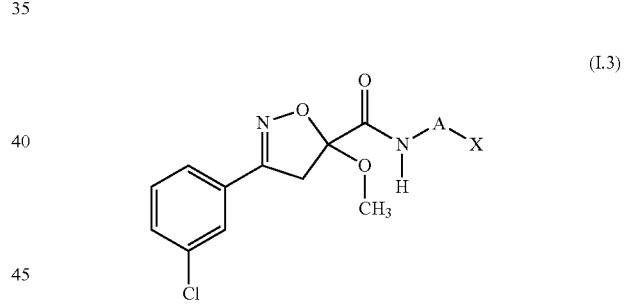

(I.3)

Table 1.4: Inventive compounds 1.4-1 to 1.4-266 of the general formula (1.4) in which A-X is as defined in table 1.1.

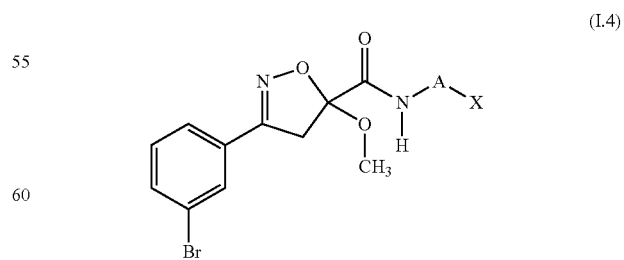

(I.4)

Table 1.5: Inventive compounds 1.5-1 to 1.5-266 of the general formula (1.5) in which A-X is as defined in table 1.1.

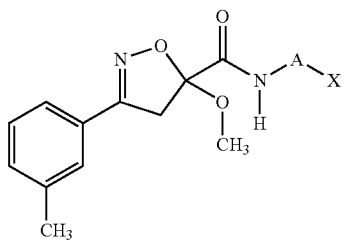

(I.5)

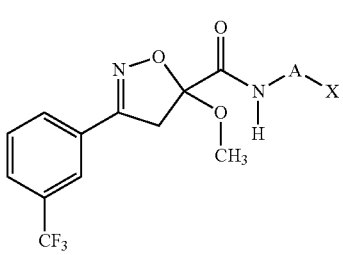

(I.9)

Table 1.6: Inventive compounds 1.6-1 to 1.6-266 of the general formula (1.6) in which A-X is as defined in table 1.1.

Table 1.10: Inventive compounds 1.10-1 to 1.10-266 of the general formula (1.10) in which A-X is as defined in table 1.1.

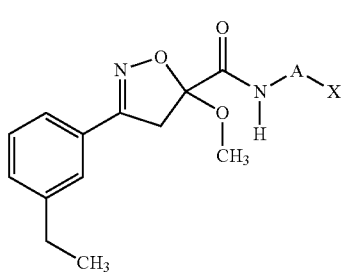

(I.6)

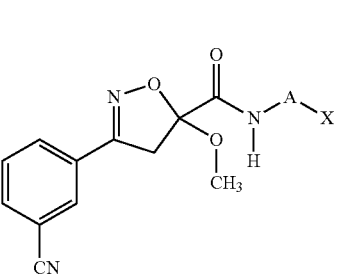

(I.10)

Table 1.7: Inventive compounds 1.7-1 to 1.7-266 of the general formula (1.7) in which A-X is as defined in table 1.1.

Table 1.11: Inventive compounds 1.11-1 to 1.11-266 of the general formula (1.11) in which A-X is as defined in table 1.1.

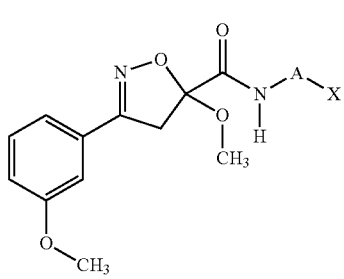

(I.7)

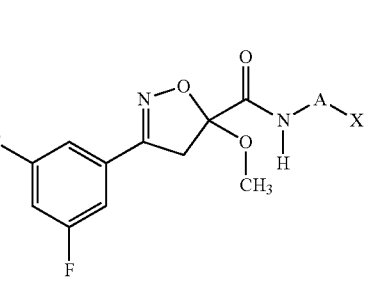

(I.11)

Table 1.8: Inventive compounds 1.8-1 to 1.8-266 of the general formula (1.8) in which A-X is as defined in table 1.1.

Table 1.12: Inventive compounds 1.12-1 to 1.12-266 of the general formula (1.12) in which A-X is as defined in table 1.1.

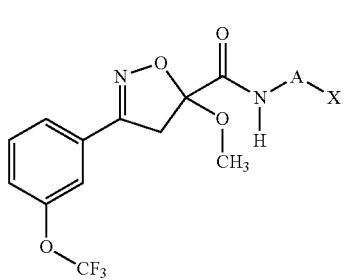

(I.8)

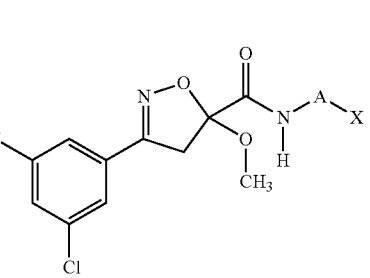

(I.12)

Table 1.9: Inventive compounds 1.9-1 to 1.9-266 of the general formula (1.9) in which A-X is as defined in table 1.1.

Table 1.13: Inventive compounds 1.13-1 to 1.13-266 of the general formula (1.13) in which A-X is as defined in table 1.1.

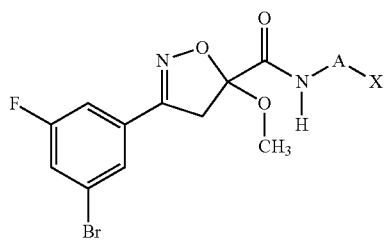

Table 1.14: Inventive compounds 1.14-1 to 1.14-266 of the general formula (1.14) in which A-X is as defined in table 1.1.

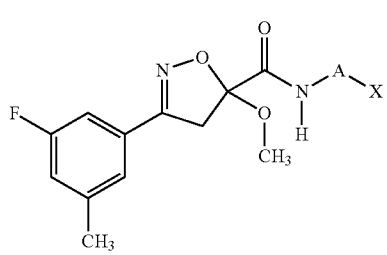

Table 1.15: Inventive compounds 1.15-1 to 1.15-266 of the general formula (1.15) in which A-X is as defined in table 1.1.

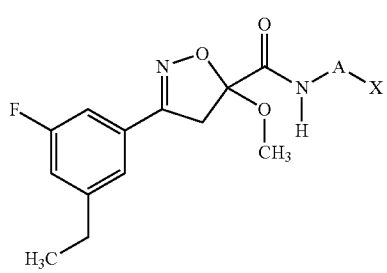

Table 1.16: Inventive compounds 1.16-1 to 1.16-266 of the general formula (1.16) in which A-X is as defined in table 1.1.

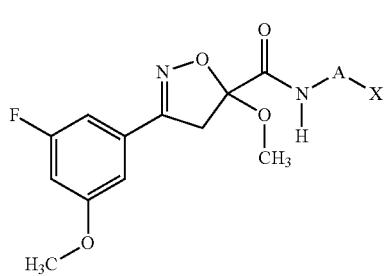

Table 1.17: Inventive compounds 1.17-1 to 1.17-266 of the general formula (1.17) in which A-X is as defined in table 1.1.

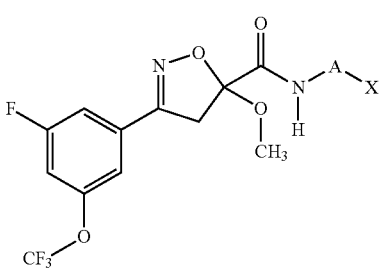

Table 1.18: Inventive compounds 1.18-1 to 1.18-266 of the general formula (1.18) in which A-X is as defined in table 1.1.

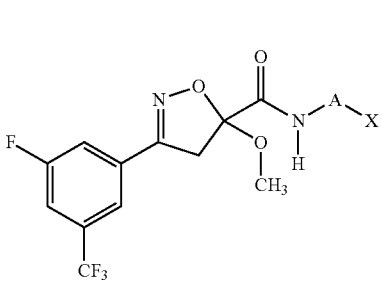

Table 1.19: Inventive compounds 1.19-1 to 1.19-266 of the general formula (1.19) in which A-X is as defined in table 1.1.

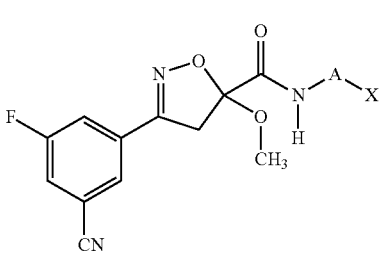

Table 1.20: Inventive compounds 1.20-1 to 1.20-266 of the general formula (1.20) in which A-X is as defined in table 1.1.

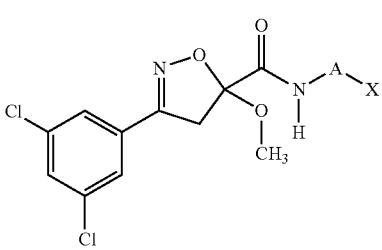

Table 1.21: Inventive compounds 1.21-1 to 1.21-266 of the general formula (1.21) in which A-X is as defined in table 1.1.

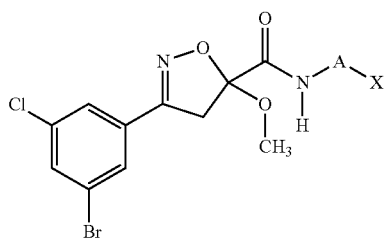

(I.21)

Table 1.22: Inventive compounds 1.22-1 to 1.22-266 of the general formula (1.22) in which A-X is as defined in table 1.1.

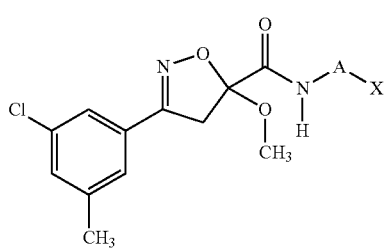

(I.22)

Table 1.23: Inventive compounds 1.23-1 to 1.23-266 of the general formula (1.23) in which A-X is as defined in table 1.1.

(I.23)

Table 1.24: Inventive compounds 1.24-1 to 1.24-266 of the general formula (1.24) in which A-X is as defined in table 1.1.

(I.24)

Table 1.25: Inventive compounds 1.25-1 to 1.25-266 of the general formula (1.25) in which A-X is as defined in table 1.1.

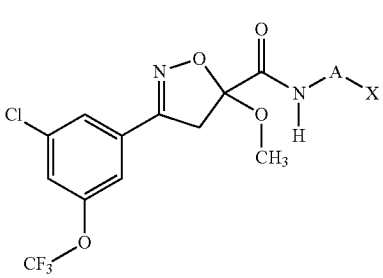

(I.25)

Table 1.26: Inventive compounds 1.26-1 to 1.26-266 of the general formula (1.26) in which A-X is as defined in table 1.1.

(I.26)

Table 1.27: Inventive compounds 1.27-1 to 1.27-266 of the general formula (1.27) in which A-X is as defined in table 1.1.

(I.27)

Table 1.28: Inventive compounds 1.28-1 to 1.28-266 of the general formula (1.28) in which A-X is as defined in table 1.1.

(I.28)

Table 1.29: Inventive compounds 1.29-1 to 1.29-266 of the general formula (1.29) in which A-X is as defined in table 1.1.

Table 1.30: Inventive compounds 1.30-1 to 1.30-266 of the general formula (1.30) in which A-X is as defined in table 1.1.

Table 1.31: Inventive compounds 1.31-1 to 1.31-266 of the general formula (1.31) in which A-X is as defined in table 1.1.

Table 1.32: Inventive compounds 1.32-1 to 1.32-266 of the general formula (1.32) in which A-X is as defined in table 1.1.

Table 1.33: Inventive compounds 1.33-1 to 1.33-266 of the general formula (1.33) in which A-X is as defined in table 1.1.

Table 1.34: Inventive compounds 1.34-1 to 1.34-266 of the general formula (1.34) in which A-X is as defined in table 1.1.

Table 1.35: Inventive compounds 1.35-1 to 1.35-266 of the general formula (1.35) in which A-X is as defined in table 1.1.

Table 1.36: Inventive compounds 1.36-1 to 1.36-266 of the general formula (1.36) in which A-X is as defined in table 1.1.

Table 1.37: Inventive compounds 1.37-1 to 1.37-266 of the general formula (1.37) in which A-X is as defined in table 1.1.

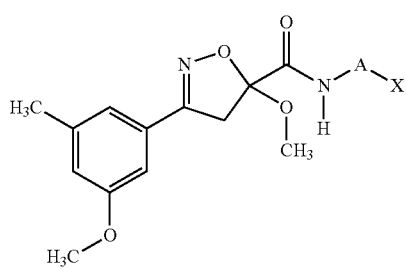

(I.37)

Table 1.38: Inventive compounds 1.38-1 to 1.38-266 of the general formula (1.38) in which A-X is as defined in table 1.1.

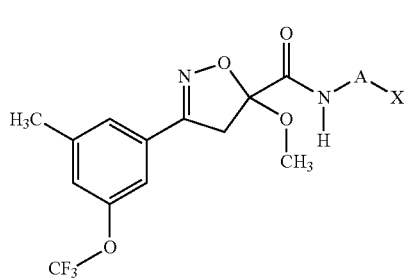

(I.38)

Table 1.39: Inventive compounds 1.39-1 to 1.39-266 of the general formula (1.39) in which A-X is as defined in table 1.1.

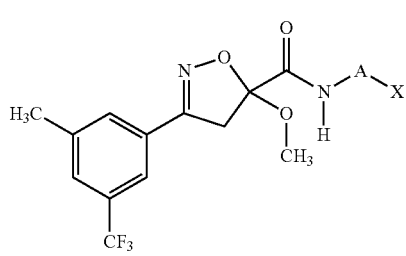

(I.39)

Table 1.40: Inventive compounds 1.41-1 to 1.41-266 of the general formula (1.41) in which A-X is as defined in table 1.1.

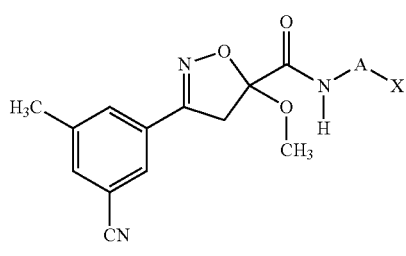

(I.40)

Table 1.41: Inventive compounds 1.41-1 to 1.41-266 of the general formula (1.41) in which A-X is as defined in table 1.1.

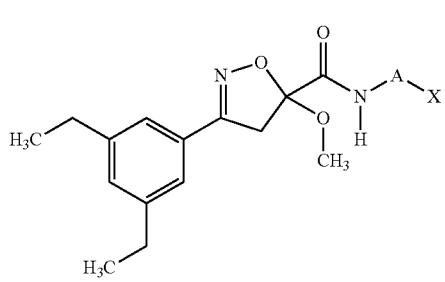

(I.41)

Table 1.42: Inventive compounds 1.42-1 to 1.42-266 of the general formula (1.42) in which A-X is as defined in table 1.1.

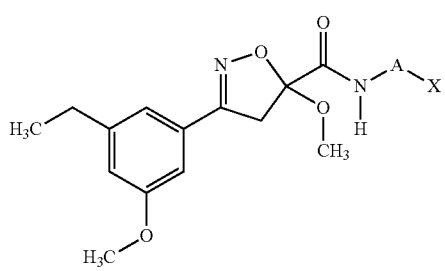

(I.42)

Table 1.43: Inventive compounds 1.43-1 to 1.43-266 of the general formula (1.43) in which A-X is as defined in table 1.1.

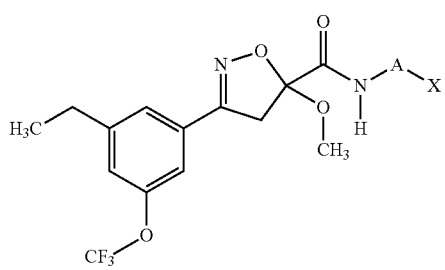

(I.43)

Table 1.44: Inventive compounds 1.44-1 to 1.44-266 of the general formula (1.44) in which A-X is as defined in table 1.1.

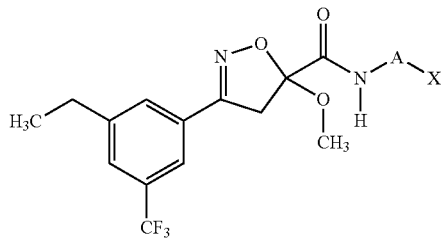

(I.44)

Table 1.45: Inventive compounds 1.45-1 to 1.45-266 of the general formula (1.45) in which A-X is as defined in table 1.1.

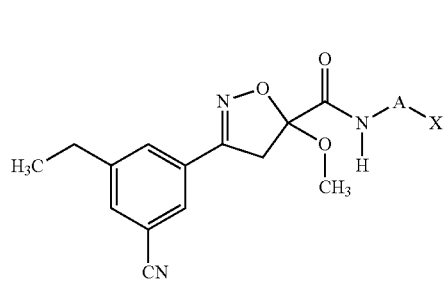
(I.45)

Table 1.46: Inventive compounds 1.46-1 to 1.46-266 of the general formula (1.46) in which A-X is as defined in table 1.1.

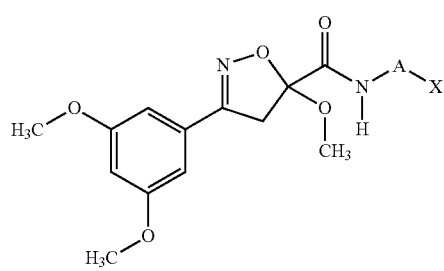
(I.46)

Table 1.47: Inventive compounds 1.47-1 to 1.47-266 of the general formula (1.47) in which A-X is as defined in table 1.1.

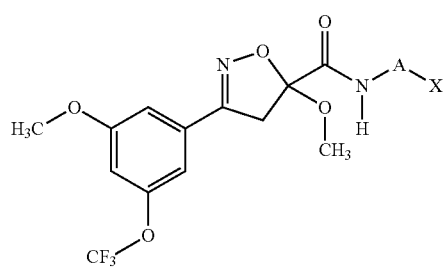
(I.47)

Table 1.48: Inventive compounds 1.48-1 to 1.48-266 of the general formula (1.48) in which A-X is as defined in table 1.1.

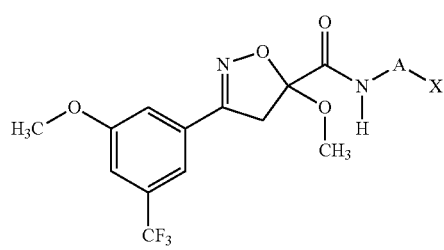
(I.48)

Table 1.49: Inventive compounds 1.49-1 to 1.49-266 of the general formula (1.49) in which A-X is as defined in table 1.1.

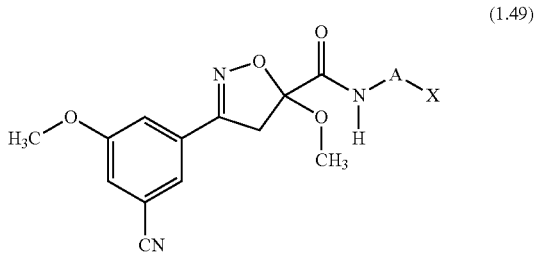
(1.49)

Table 1.50: Inventive compounds 1.50-1 to 1.50-266 of the general formula (1.50) in which A-X is as defined in table 1.1.

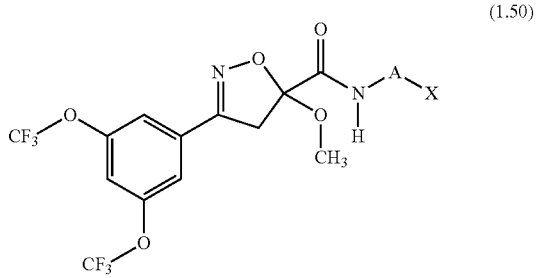
(1.50)

Table 1.51: Inventive compounds 1.51-1 to 1.51-266 of the general formula (1.51) in which A-X is as defined in table 1.1.

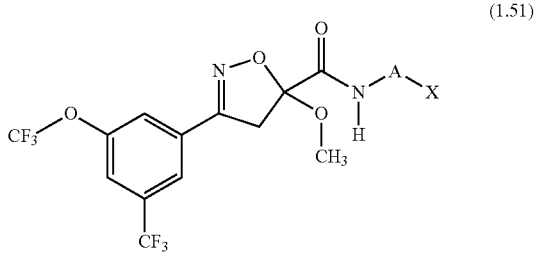
(1.51)

Table 1.52: Inventive compounds 1.52-1 to 1.52-266 of the general formula (1.52) in which A-X is as defined in table 1.1.

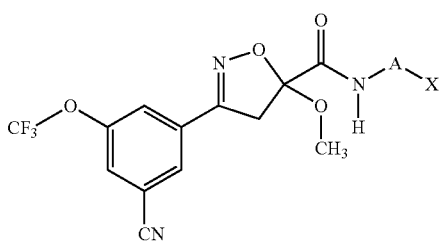

(1.52)

Table 1.53: Inventive compounds 1.53-1 to 1.53-266 of the general formula (1.53) in which A-X is as defined in table 1.1.

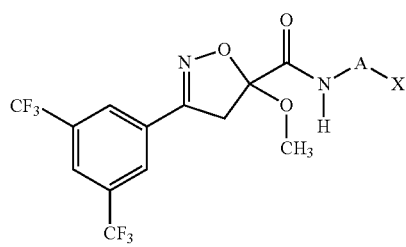

(1.53)

Table 1.54: Inventive compounds 1.54-1 to 1.54-266 of the general formula (1.54) in which A-X is as defined in table 1.1.

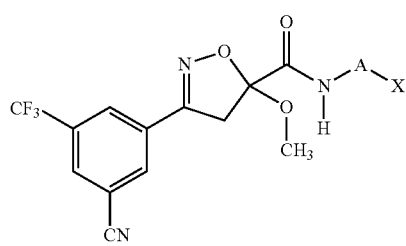

(1.54)

Table 1.55: Inventive compounds 1.55-1 to 1.55-266 of the general formula (1.55) in which A-X is as defined in table 1.1.

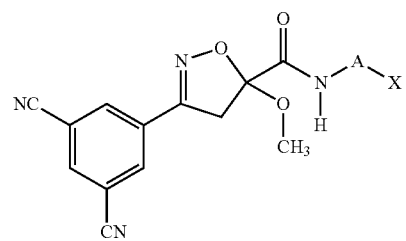

(1.55)

Table 1.56: Inventive compounds 1.56-1 to 1.56-266 of the general formula (1.56) in which A-X is as defined in table 1.1.

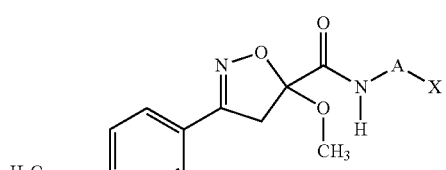

(1.56)

Table 1.57: Inventive compounds 1.57-1 to 1.57-266 of the general formula (1.57) in which A-X is as defined in table 1.1.

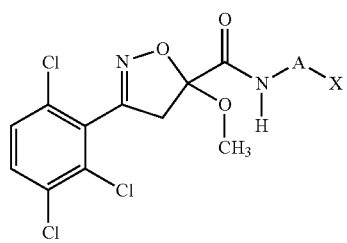

(1.57)

Analogous methods to those for the inventive compounds specified in tables 1.1 to 1.57 give rise correspondingly to the inventive compounds of tables 2.1 to 2.57 in which Y is oxygen, $R^3$ is ethyl, and the other substituents are each as defined in tables 1.1 to 1.57.

Analogous methods to those for the inventive compounds specified in tables 1.1 to 1.57 give rise correspondingly to the inventive compounds of tables 3.1 to 3.57 in which Y is sulfur, $R^3$ is methyl, and the other substituents are each as defined in tables 1.1 to 1.57.

Analogous methods to those for the inventive compounds specified in tables 1.1 to 1.57 give rise correspondingly to the inventive compounds of tables 4.1 to 4.57 in which Y is sulfur, $R^3$ is ethyl, and the other substituents are each as defined in tables 1.1 to 1.57.

The abbreviations used mean:

| Ac | acetoxy | Bu | butyl | Et | ethyl | Me | methyl |
|---|---|---|---|---|---|---|---|
| Pr | propyl | Pen | pentyl | Hex | hexyl | Ph | phenyl |
| c | cyclo | s | secondary | i | iso | t | tertiary |
| THF | tetrahydrofuran | | | | | | |

E1, E2, E3, E4 denote enantiomerically pure compounds. D1, D2, D3, D4 denote diastereomers of a diastereomer pair present as a racemate of two enantiomers.

TABLE 1.2

Analytical data

| No. | NMR |
|---|---|
| 1.2-7 | [CDCl₃] 0.89-0.97 (m, 3H); 1.17-1.21 (m, 3H); 1.52 (m, 2H); 3.38 (s, 3H); 3.42 (m, 1H); 3.84 (m, 1H); 3.96 (m, 1H); 6.58 (d, 1H); 7.16 (m, 1H); 7.42 (m, 3H). |
| 1.2-8 | [CDCl₃] 0.93 (m, 6H); 1.14 (m, 3H); 1.76 (m, 1H); 3.38 (s, 3H); 3.42 (m, 1H); 3.78-3.86 (m, 1H); 3.91 (m, 1H); 6.61 (d, 1H); 7.16 (m, 1H); 7.41 (m, 3H). |
| 1.2-10 | [CDCl₃] 3.38 (s, 3H); 3.44 (d, 1H); 3.62-3.79 (m, 2H); 3.90 (d, 1H); 5.77-6.05 (tt, 1H); 7.06 (s, 1H); 7.15 (m, 1H); 7.42 (m, 3H). |
| 1.2-11 | [CDCl₃] 3.39 (s, 3H); 3.44 (d, 1H); 3.85 (d, 1H); 3.90-4.00 (m, 1H); 4.10-4.20 (m, 1H); 7.05 (s, 1H); 7.17 (m, 1H); 7.42 (m, 3H). |
| 1.2-15 | [CDCl₃] 2.67-2.73 (m, 2H); 3.38 (s, 3H); 3.42 (d, 1H); 3.59-3.68 (m, 2H); 3.91 (d, 1H); 7.18 (m, 2H); 7.42 (m, 3H). |
| 1.2-16 | [CDCl₃] 3.39 (s, 3H); 3.44 (d, 1H); 3.89 (d, 1H); 3.92-4.03 (m, 2H); 5.18-5.27 (m, 2H); 5.82-5.91 (m, 1H); 6.88 (s, 1H); 7.15 (m, 1H); 7.41 (m, 3H). |
| 1.2-20 | [CDCl₃] 1.43 (m, 3H); 2.57-2.67 (m, 1H); 2.75-2.90 (m, 1H); 3.38 (s, 3H); 3.40 (m, 1H); 3.88 (m, 1H); 4.29 (m, 1H); 6.86 (t, 1H); 7.16 (m, 1H); 7.42 (m, 3H). |
| 1.2-21 | [CDCl₃] 1.13 (m, 6H); 1.22 (m, 1H); 3.34-3.44 (m, 7H); 3.77-3.87 (m, 1H); 4.05 (m, 1H); 7.02 (t, 1H); 7.13 (m, 1H); 7.41 (m, 3H). |
| 1.2-24 | [CDCl₃] 3.00 (s, 3H); 3.26-3.38 (m, 6H); 3.81-3.95 (m, 3H); 7.16 (m, 1H); 7.41 (m, 4H). |
| 1.2-25 | [CDCl₃] 1.28 (t, 3H); 2.58 (q, 2H); 2.72 (t, 2H); 3.39 (s, 3H); 3.42 (d, 1H); 3.55 (m, 2H); 3.88 (d, 1H); 7.13 (m, 2H); 7.41 (m, 3H). |
| 1.2-40 | [CDCl₃] 3.38 (s, 3H); 3.44 (d, 1H); 3.94 (d, 1H); 4.18-4.24 (m, 1H); 4.32-4.38 (m, 1H); 7.19 (m, 2H); 7.41 (m, 3H). |
| 1.2-41 D1 | [CDCl₃] D1: 1.65 (d, 3H); 3.37 (s, 3H); 3.45 (d, 1H); 3.89 (d, 1H); 4.95 (m, 1H); 7.09 (d, 1H); 7.17 (m, 1H); 7.42 (m, 3H). |
| 1.2-41 D2 | [CDCl₃] D2: 1.63 (d, 3H); 3.39 (s, 3H); 3.41 (d, 1H); 3.97 (d, 1H); 4.93 (m, 1H); 7.08 (d, 1H); 7.17 (m, 1H); 7.43 (m, 3H). |
| 1.2-42 | [CDCl₃] 1.78 (s, 6H); 3.38 (s, 3H); 3.40 (d, 1H); 3.99 (d, 1H); 6.73 (s, 1H); 7.17 (m, 1H); 7.42 (m, 3H). |
| 1.2-45 | [CDCl₃] 1.09-1.17 (m, 3H); 1.73 (s, 3H); 1.96-2.12 (m, 2H); 3.38 (s, 3H); 3.40 (m, 1H); 3.94-4.00 (m, 1H); 6.80 (d, 1H); 7.16 (m, 1H); 7.43 (m, 3H). |
| 1.2-46 | [CDCl₃] 1.03 (m, 3H); 1.53-1.59 (m, 2H); 1.75 (s, 3H); 1.88-2.07 (m, 2H); 3.38 (s, 3H); 3.40 (m, 1H); 3.98 (m, 1H); 6.81 (d, 1H); 7.16 (m, 1H); 7.42 (m, 3H). |
| 1.2-47 | [CDCl₃] 0.71-0.78 (m, 4H); 1.31 (m, 1H); 1.83 (d, 3H); 3.38 (s, 3H); 3.41 (m, 1H); 3.90-4.01 (m, 1H), 7.01 (d, 1H); 7.17 (m, 1H); 7.42 (m, 3H). |
| 1.2-48 D1 | [CDCl₃] D1: 1.40 (d, 3H); 3.39 (s, 3H); 3.45 (d, 1H); 3.83 (d, 1H); 4.73 (m, 1H); 6.83 (d, 1H); 7.18 (m, 1H); 7.42 (m, 3H). |
| 1.2-48 D2 | [CDCl₃] D2: 1.39 (d, 3H); 3.38 (s, 3H); 3.41 (d, 1H); 3.87 (d, 1H); 4.73 (m, 1H); 6.89 (d, 1H); 7.18 (m, 1H); 7.42 (m, 3H). |
| 1.2-49 D1 | [CDCl₃] D1: 1.04 (t, 3H); 1.58-1.65 (m, 1H); 1.90-1.98 (m, 1H); 3.40 (s, 3H); 3.49 (d, 1H); 3.80 (d, 1H); 4.55 (m, 1H); 6.73 (d, 1H); 7.17 (m, 1H); 7.42 (m, 3H). |
| 1.2-49 D2 | [CDCl₃] D2: 1.02 (t, 3H); 1.56-1.65 (m, 1H); 1.90-1.98 (m, 1H); 3.39 (s, 3H); 3.45 (d, 1H); 3.92 (d, 1H); 4.55 (m, 1H); 6.78 (d, 1H); 7.18 (m, 1H); 7.43 (m, 3H). |
| 1.2-50 | [CDCl₃] 1.00-1.07 (m, 6H); 2.22 (m, 1H); 3.39 (d, 3H); 3.45 (m, 1H); 3.75-3.92 (dd, 1H); 4.53 (m, 1H); 6.88 (m, 1H); 7.17 (m, 1H); 7.42 (m, 3H). |
| 1.2-51 | [CDCl₃] 1.61-1.66 (m, 1H); 1.91 (m, 2H); 2.09 (m, 1H); 3.38 (s, 3H); 3.42 (d, 1H); 3.85-3.99 (m, 3H); 4.30 (t, 1H), 4.65 (quint, 1H); 7.17 (m, 1H); 7.42 (m, 3H). |
| 1.2-53 | [CDCl₃] 1.49 (t, 3H); 2.30 (dd, 1H); 3.38 (d, 3H); 3.43 (m, 1H); 3.85 (m, 1H); 4.84 (m, 1H); 6.96 (s, 1H); 7.15 (m, 1H); 7.41 (m, 3H). |
| 1.2-55 | [CDCl₃] 1.43 (m, 3H); 1.81 (m, 3H); 3.38 (d, 3H); 3.41 (m, 1H); 3.83 (m, 1H); 4.78 (m, 1H); 6.91 (s, 1H); 7.17 (m, 1H); 7.40 (m, 3H). |
| 1.2-58 | [CDCl₃] 1.19 (m, 3H); 3.38 (s, 3H); 3.41-3.47 (m, 7H); 3.88 (m, 1H), 4.21 (m, 2H), 6.89 (s, 1H), 7.15 (m, 1H); 7.41 (m, 3H). |
| 1.2-59 | [CDCl₃] 1.12 (q, 3H); 1.42 (m, 3H); 2.49-2.68 (m, 2H); 3.37 (s, 3H); 3.42 (m, 1H); 3.84 (m, 1H); 4.63 (m, 1H); 7.15 (m, 1H); 7.39-7.47 (m, 4H). |
| 1.2-60 | [CDCl₃] 0.57-0.61 (m, 2H); 0.82-0.87 (m, 2H); 2.82 (m, 1H); 3.36 (s, 3H); 3.41 (m, 1H); 3.88 (d, 1H); 6.82 (s, 1H); 7.14 (m, 1H); 7.41 (m, 3H). |
| 1.2-62 | [CDCl₃] 0.22-0.30 (m, 1H); 0.32-0.40 (m, 1H); 0.44-0.56 (m, 2H); 0.87 (m, 1H); 1.27 (m, 3H); 3.38-3.48 (m, 5H); 3.78-3.84 (m, 1H); 6.79 (s, 1H); 7.15 (m, 1H); 7.42 (m, 3H). |
| 1.2-64 | [CDCl₃] 1.33 (m, 2H); 1.62 (m, 2H); 3.35 (s, 3H); 3.40 (d, 1H); 3.99 (d, 1H); 7.17 (m, 1H); 7.23 (s, 1H); 7.41 (m, 3H). |
| 1.2-69 | [CDCl₃] 3.36 (d, 1H); 3.37 (s, 3H); 3.40(m, 4H); 3.87(d, 1H); 5.22-5.33 (m, 1H);7.12-7.20 (m, 1H); 7.22(s br, 1H); 7.42 (m, 3H). |
| 1.2-70 | [CDCl₃] 3.24-3.34(m, 2H); 3.40 (s, 3H); 3.41 (d, 1H); 3.49-3.59 (m, 1H); 3.67-3.74(m, 1H); 3.91 (dd, 1H); 4.09-4.19 (m, 2H); 4.42-4.54 (m, 1H); 5.15-5.25 (m, 1H); 7.13-7.20(m, 1H); 7.32 (s br, 1H); 7.40 (m, 1H). |
| 1.2-71 | [CDCl₃] 3.36 (d, 1H); 3.37 (s, 3H); 3.94 (d, 1H); 4.02-4.13 (m, 2H); 4.53-4.13 (m, 2H); 4.70-4.80 (m, 1H); 7.13-7.20 (m, 1H); 7.38 (d br, 1H); 7.42 (m, 3H). |
| 1.2-73 | [CDCl₃] 1.83-1.92 (m, 1H); 2.26-2.38 (m, 1H); 3.36 (s, 3H); 3.38 (dd, 1H); 3.70-3.76 (m, 1H); 3.78-3.91 (m, 3H); 3.94-4.02 (m, 1H); 4.51-4.61 (m, 1H); 6.95 (s br, 1H); 7.18 (m, 1H); 7.42 (m, 3H). |

TABLE 1.2-continued

Analytical data

| No. | NMR |
|---|---|
| 1.2-76 | [CDCl₃] 0.89-0.96 (m, 3H); 1.19 (m, 3H); 1.32-1.40 (m, 2H); 1.42-1.50 (m, 2H); 3.38 (s, 3H); 3.41 (m, 1H); 3.79-3.86 (m, 1H); 4.04 (m, 1H); 6.54 (d, 1H); 7.15 (m, 1H); 7.41 (m, 3H). |
| 1.2-94 | [CDCl₃] 1.28 (t, 3H); 2.59 (t, 2H); 3.36 (s, 3H); 3.40 (d, 1H); 3.62 (m, 2H); 3.83 (d, 1H); 4.17 (q, 2H); 7.15 (m, 1H); 7.28 (s, 1H); 7.41 (m, 3H). |
| 1.2-96 | [CDCl₃] 1.24-1.32 (m, 6H); 2.57 (m, 2H); 3.37 (s, 3H); 3.40 (d, 1H); 3.84 (d, 1 H); 4.12-4.20 (m, 2H); 4.37-4.44 (m, 1H); 7.14 (m, 1H); 7.41 (m, 3H). |
| 1.2-102 | [CDCl₃] 1.88-1.95 (quint, 2H); 2.40 (t, 2H); 3.37-3.43 (m, 6H); 3.69 (s, 3H); 3.84 (d, 1H); 6.94 (s, 1H); 7.15 (m, 1H); 7.41 (m, 3H). |
| 1.2-119 | [CDCl₃] 3.38 (s, 3H); 3.42 (d, 1H); 3.96 (d, 1H); 4.62 (m, 1H); 7.17 (m, 1H); 7.28 (s, 1H); 7.41 (m, 3H); 7.68 (d, 1H); 7.86 (d, 1H); 8.69 (s, 1H). |
| 1.2-138 | [CDCl₃] 3.39 (s, 3H), 3.44 (d, 1H); 3.99 (d, 1H); 4.47-4.58 (m, 2H); 7.19 (m, 3H); 7.43 (m, 4H); 8.34 (d, 1H). |
| 1.2-142 | [CDCl₃] 3.39 (s, 3H); 3.42 (d, 1H); 3.93 (s, 3H); 3.93 (d, 1H); 4.42-4.56 (m, 2H); 6.65 (s, 1H); 6.30 (d, 1H); 7.13-7.20 (m, 2H); 7.43 (m, 3H); 8.13 (d, 1H). |
| 1.2-147 | [CDCl₃] 2.58 (s, 3H); 3.39 (s, 3H); 3.42 (d, 1H); 3.95 (d, 1H), 4.51 (m, 2H); 7.05 (s, 1H); 7.10 (s, 1H); 7.18 (m, 2H); 7.41 (m, 3H); 7.48 (d, 1H). |
| 1.2-148 | [CDCl₃] 1.30 (t, 3H); 2.83 (q, 2H); 3.39 (s, 3H); 3.42 (d, 1H); 3.95 (d, 1H); 4.51 (m, 2H); 7.05 (d, 1H); 7.09 (s, 1H); 7.17 (m, 2H); 7.42 (m, 3H); 8.50 (d, 1H). |
| 1.2-149 | [CDCl₃] 1.01 (m, 4H); 2.03 (m, 1H); 3.39 (s, 3H); 3.42 (d, 1H); 3.97 (d, 1H); 4.50 (m, 2H); 6.95 (d, 1H); 7.06 (s, 1H); 7.17 (m, 2H); 7.41 (m, 3H); 8.40 (d, 1H). |
| 1.2-150 | [CDCl₃] 0.97 (t, 3H); 1.70-1.80 (m, 2H); 2.78 (t, 2H); 3.39 (s, 3H); 3.42 (d, 1H); 3.94 (d, 1H); 4.51 (m, 2H); 7.05 (d, 1H); 7.08 (s, 1H); 7.18 (m, 2H); 7.41 (m, 3H); 8.50 (d, 1H). |
| 1.2-200 | [CDCl₃] 2.46 (s, 3H); 3.35 (s, 3H); 3.39 (d, 1H); 3.88 (d, 1H); 4.22-4.38 (m, 2H); 7.01 (s br, 1H); 7.11-7.20 (m, 1H); 7.42 (m, 3H); 8.20 (s, 1H). |
| 1.2-201 | [CDCl₃] 2.27 (s, 3H); 2.42 (s, 3H); 3.34 (s, 3H); 3.40 (d, 1H); 3.93 (d, 1H); 4.27 (m, 2H); 6.81 (s, 1H); 7.17 (m, 1H); 7.41 (m, 3H). |
| 1.2-202 | [CDCl₃] 1.30 (t, 3H); 2.42 (s, 3H); 2.66 (q, 2H); 3.34 (s, 3H), 3.40 (d, 1H); 3.92 (d, 1H); 4.28 (m, 2H); 6.80 (s, 1H); 7.17 (m, 1H); 7.41 (m, 3H). |
| 1.2-203 | [CDCl₃] 1.30 (m, 6H); 2.66 (q, 2H); 2.79 (q, 2H); 3.34 (s, 3H); 3.40 (d, 1H); 3.92 (d, 1H); 4.28 (m, 2H); 6.79 (s, 1H); 7.16 (m, 1H); 7.42 (m, 3H). |
| 1.2-206 | [CDCl₃] 1.48 (t, 3H); 3.35 (s, 3H); 3.42 (d, 1H); 3.89 (d, 1H); 4.14 (q, 2H); 4.38 (m, 2H); 6.96 (s, 1H); 7.16 (m, 1H); 7.40 (m, 4H); 7.46 (s, 1H). |
| 1.2-207 | [CDCl₃] 3.35 (s, 3H); 3.41 (d, 1H); 3.90 (d, 1H); 4.37-4.43 (m, 2H); 4.68 (q, 2H); 7.02 (s, 1H); 7.18 (m, 1H); 7.41 (m, 3H); 7.53 (s, 1H); 7.56 (s, 1H). |
| 1.2-210 | [CDCl₃] 1.02 (m, 2H); 1.11 (m, 2H); 3.35 (s, 3H); 3.41 (d, 1H); 3.57 (m, 1H); 3.89 (d, 1H); 4.36 (m, 2H); 6.95 (s, 1H); 7.17 (m, 1H); 7.39-7.56 (m, 5H). |
| 1.2-211 | [CDCl₃] 2.24 (s, 3H); 3.35 (s, 3H); 3.39 (d, 1H); 3.81 (s, 3H); 3.87 (d, 1H); 4.26-4.38 (m, 2H); 6.83 (s br, 1H); 7.15 (m, 1H); 7.28 (s, 1H); 7.40 (m, 3H). |
| 1.2-212 | [CDCl₃] 1.46 (t, 3H); 2.26 (s, 3H); 3.35 (s, 3H); 3.39 (d, 1H); 4.09 (q, 2H); 4.27-4.39 (m, 2H); 6.83 (s br, 1H); 7.16 (m, 1H); 7.32 (s, 1H); 7.41 (m, 3H). |
| 1.2-241 | [CDCl₃] 3.40 (s, 3H); 3.41 (d, 1H); 3.97(d, 1H); 4.56-4.68 (m, 2H); 6.95(s, 1H); 7.16 (m, 1H); 7.28 (s br, 1H); 7.92 (m, 3H); 8.19 (s, 1H). |
| 1.2-257 | [CDCl₃] 1.42 (t, 3H); 3.36 (s, 3H); 3.39 (d, 1H); 3.81(d, 1H); 3.91 (s, 3H); 3.96 (q, 2H); 4.20-4.32 (m, 2H); 7.03 (s br, 1H); 7.15 (m, 1H); 7.20 (s, 1H); 7.40 (m, 3H). |
| 1.2-258 | [CDCl₃] 3.35 (s, 3H); 3.39 (d, 1H); 3.71 (s, 3H); 3.82 (d, 1H); 3.90 (s, 3H); 4.25 (d, 1H); 7.03 (s br, 1H); 7.15 (m, 1H); 7.17 (s, 1H); 7.40 (m, 3H). |

Analytical data table 1.3

| No. | NMR |
|---|---|
| 1.3-1 | [CDCl₃] 3.41 (s, 3H); 3.42 (d, 1H); 3.88 (d, 1H); 5.85 (s, 1H); 6.72 (s, 1H); 7.38 (t, 1H); 7.41 (d, 1H); 7.53 (d, 1H); 7.69 (s, 1H). |
| 1.3-9 | [CDCl₃] 3.39-3.46 (m, 4H); 3.85-3.94 (m, 2H); 4.06-4.14 (m, 1H); 7.07 (s, 1H); 7.38 (m, 1H); 7.43 (m, 1H); 7.56 (m, 1H); 7.69 (m, 1H). |
| 1.3-16 | [CDCl₃] 3.38 (s, 3H); 3.40 (d, 1H); 3.89 (d, 1H); 3.90-4.03 (m, 2H); 5.18-5.27 (m, 2H); 5.80-5.91 (m, 1H); 6.86 (s, 1H); 7.37 (m, 1H); 7.42 (m, 1H); 7.52 (m, 1H); 7.69 (s, 1H). |
| 1.3-60 | [CDCl₃] 0.60 (m, 2H); 0.85 (m, 2H); 2.82 (m, 1H); 3.35 (s, 3H); 3.39 (d, 1H); 3.86 (d, 1H); 6.81 (s, 1H); 7.37 (t, 1H); 7.42 (d, 1H); 7.53 (d, 1H); 7.69 (s, 1H). |
| 1.3-94 | [CDCl₃] 1.28 (m, 3H); 2.60 (t, 2H); 3.36 (s, 3H); 3.39 (d, 1H); 3.62 (m, 2H); 3.86 (d, 1H); 4.18 (q, 2H); 7.31 (s, 1H); 7.38 (t, 1H); 7.41 (d, 1H); 7.53 (d, 1H); 7.68 (s, 1H). |
| 1.3-96 | [CDCl₃] 1.22-1.30 (m, 6H); 2.52-2.60 (m, 2H); 3.37 (s, 3H); 3.39 (d, 1H); 3.86 (d, 1H); 4.11-4.20 (m, 2H); 4.40 (m, 1H); 7.25 (s, 1H); 7.36 (t, 1H); 7.43 (d, 1H); 7.52 (d, 1H); 7.68 (s, 1H). |

Analytical data table 1.3

| No. | NMR |
|---|---|
| 1.3-102 | [CDCl₃] 1.92 (quint, 2H); 2.40 (t, 2H); 3.35-3.43 (m, 6H); 3.69 (s, 3H); 3.88 (d, 1H); 6.93 (s, 1H); 7.31-7.43 (m, 2H); 7.52 (d, 1H); 7.68 (s, 1H). |
| 1.3-110 | [CDCl₃] 3.36 (s, 3H); 3.40 (d, 1H); 3.92 (d, 1H); 4.52 (m, 2H); 7.18 (s, 1H); 7.31-7.77 (m, 3H); 7.52 (m, 1H); 7.67 (m, 2H); 8.35 (s, 1H). |
| 1.3-206 | [CDCl₃] 1.48 (t, 3H); 3.35 (s, 3H); 3.40 (d, 1H); 3.88 (d, 1H); 4.14 (q, 2H), 4.38 (m, 2H); 6.95 (s, 1H); 7.36-7.46 (m, 4H); 7.53 (m, 1H); 7.68 (s, 1H). |
| 1.3-212 | [CDCl₃] 1.46 (t, 3H); 2.25 (s, 3H); 3.35 (s, 3H); 3.38 (d, 1H); 3.88 (d, 1H); 4.08 (m, 2H); 4.32 (m, 2H); 6.81 (s, 1H); 7.31 (s, 1H); 7.38 (t, 1H); 7.41 (t, 1H); 7.53 (d, 1H); 7.68 (s, 1H). |

Analytical data table 1.5

| No. | NMR |
|---|---|
| 1.5-1 | [CDCl₃] 2.39 (s, 3H); 3.41 (s, 3H); 3.46 (d, 1H); 3, 86 (d, 1H); 5.73 (s br, 1H); 6.72 (s br, 1H); 7.27 (d, 1H); 7.32 (t, 1H); 7.44 (d, 1H); 7.51 (s, 1H). |
| 1.5-9 | [CDCl₃] 2.39 (s, 3H); 3.39 (s, 3H); 3.47 (d, 1H); 3.88 (d, 1H); 3.82-3.97 (m, 1H); 4.02-4.17 (m, 1H); 7.10 (s br, 1H); 7.25 (d, 1H); 7.31 (t, 1H); 7.44 (d, 1H); 7.52 (s, 1H). |
| 1.5-16 | [CDCl₃] 2.39 (s, 3H); 3.38 (s, 3H); 3.45 (d, 1H); 3.87 (d, 1H); 3.90-4.07 (m, 2H); 5.20 (d, 1H); 5.24 (d, 1H); 5.81-5.92 (m, 1H); 6.89 (s br, 1H); 7.25 (d, 1H); 7.31 (t, 1H); 7.45 (d, 1H); 7.51 (1H). |
| 1.5-60 | [CDCl₃] 0.54-0.64 (m, 2H); 0.79-0.87 (m, 2H); 2.38 (s, 3H); 2.77-2.86 (m, 1H); 3.35 (s, 3H); 3.41 (d, 1H); 3.86 (d, 1H); 6.83 (s br, 1H); 7.25 (d, 1H); 7.31 (t, 1H); 7.43 (d, 1H); 7.50 (s, 1H). |
| 1.5-94 | [CDCl₃] 1.27 (t, 3H); 2.38 (s, 3H); 2.59 (t, 2H); 3.36 (s, 3H); 3.41 (d, 1H); 3.57-3.66 (m, 2H); 3.85 (d, 1H); 4.17 (d, 2H); 7.21-7.33 (3H); 7.44 (d, 1H); 7.51 (s, 1H). |
| 1.5-96 | [CDCl₃] D 1: 1.26 (t, 3H); 1.30 (d, 3H); 2.38 (s, 3H); 2.55 (d, 2H); 3.36 (s, 3H); 3.41 (d, 1H); 3.83 (d, 1H); 4.15 (q, 2H); 4.33-4.46 (m, 1H); 7.22 (s br, 1H); 7.25 (d, 1H); 7.31 (t, 1H); 7.45 (d, 1H); 7.51 (s, 1H). D 2: 1.27 (t, 3H); 1.30 (d, 3H); 2.38 (s, 3H); 2.57 (d, 2H); 3.36 (s, 3H); 3.41 (d, 1H); 3.84 (d, 1H); 4.16 (q, 2H); 4.33-4.46 (m, 1H); 7.22 (s br, 1H); 7.25 (d, 1H); 7.31 (t, 1H); 7.45 (d, 1H); 7.51 (s, 1H). |
| 1.5-102 | [CDCl₃] 1.91 (pent, 2H); 2.38 (q, 2H); 2.39 (s, 3H); 3.37 (s, 3H); 3.30-3.43 (m, 2H); 3.42 (d, 1H); 3.67 (s, 3H); 3.84 (d, 1H); 6.94 (s br, 1H); 7.25 (d, 1H); 7.31 (t, 1H); 7.44 (d, 1H); 7.51 (s, 1H). |
| 1.5-206 | [CDCl₃] 1.48 (t, 3H); 2.38 (s, 3H); 3.35 (s, 3H); 3.43 (d, 1H); 3.86 (d, 1H); 4.14 (q, 2H); 4.31-4.42 (m, 2H); 6.97 (s br, 1H); 7.25 (d, 1H); 7.31 (t, 1H); 7.40 s, 1H); 7.44 (d, 1H); 7.45 (s, 1H); 7.50 (s, 1H). |
| 1.5-212 | [CDCl₃] 1.26 (t, 3H); 2.24 (s, 3H); 2.38 (s, 3H); 3.35 (s, 3H); 3.43 (d, 1H); 3.86 (d, 1H); 4.06 (q, 2H); 4.25-4.38 (m, 2H); 6.83 (s br, 1H); 7.25 (d, 1H); 7.31 (t, 1H); 7.44 (d, 1H); 7.50 (s, 1H). |

Analytical data table 1.6

| No. | NMR |
|---|---|
| 1.6-1 | [CDCl₃] 1.25 (t, 3H); 2.68 (q, 2H); 4.41 (s, 3H); 3.47 (d, 1H); 3.88 (d, 1H); 5.66 br, 1H); 6.72 (s br, 1H); 7.29 (d, 1H); 7.34 (t, 1H); 7.45 (d, 1H); 7.54 (s, 1H). |
| 1.6-9 | [CDCl₃] 1.25 (t, 3H); 2.68 (q, 2H); 3.39 (s, 3H); 3.47 (d, 1H); 3.82-3.97 (m, 1H); 3.86 (d, 1H); 4.02-4.16 (m, 1H); 7.09 (s br, 1H); 7.28 (d, 1H); 7.34 (t, 1H); 7.45 (d, 1H); 7.53 (s, 1H). |
| 1.6-16 | [CDCl₃] 1.25 (t,, 3H); 2.68 (q, 1H); 3.39 (s, 3H); 3.45 (d, 1H); 3.87 (d, 1H); 3.90-4.04 (m, 2H); 5.18 (d, 1H); 5.24 (d, 1H); 5.81-5.92 (m, 1H); 6.88 (s br, 1H); 7.29 (d, 1H); 7.33 (t, 1H); 7.44 (d, 1H); 7.54 (s, 1H). |
| 1.6-60 | [CDCl₃] 0.59 (m, 2H); 0.84 (m, 2H); 1.25 (t, 3H); 2.68 (q, 2H); 2.81-2.84 (m, 1H); 3.36 (s, 3H); 3, 43 (d, 1H); 3.87 (d, 1H); 6.85 (s br, 1H); 2.27 (d, 1H); 7.33 (t, 1H); 7.44 (d, 1H); 7.53 (s, 1H). |
| 1.6-94 | [CDCl₃] 1.25 (t, 3H); 1.28 (t, 3H); 2.59 (q, 2H); 2.67 (q, 2H); 3.36 (s, 3H); 3.42 (d, 1H); 3.58-3.66 (m, 2H); 3.86 (d, 1H); 4.17 (q, 2H); 7.27 (d, 1H); 7.30 (s br, 1H); 7.34 (t, 1H); 7.44 (d, 1H); 7.54 (s, 1H). |
| 1.6-96 | [CDCl₃] 1.23-1.33 (m, 6H); 2.51-2.63 (m, 2H); 2.68 (q, 2H); 3.37 (s, 3H); 3.43 (d, 1H); 3.85 (d, 1H); 4.12-4.20 (m, 2H); 4.36-4.44 (m, 1H); 7.25 (t br, 1H); 7.27 (d, 1H); 7.34 (t, 1H); 7.44 (d, 1H); 7.54 (s, 1H). |
| 1.6-110 | [CDCl₃] 1.25 (t, 3H); 2.68 (q, 2H); 3.36 (s, 3H); 3.44 (d, 1H); 3.91 (d, 1H); 4.46-4.58 (m, 2H); 7.19 (t br, 1H); 7.27-7.37 (m, 3H); 7.45 (d, 1H); 7.53 (s, 1H); 7.64 (d, 1H); 8.35 (s, 1H). |
| 1.6-206 | [CDCl₃] 1.25 (t, 3H); 1.48 (t, 3H); 2.68 (q, 2H); 3.36 (s, 3H); 3.44 (d, 1H); 4.14 (q, 2H); 4.31-4.43 (m, 2H); 6.96 (s br, 1H); 7.29 (d, 1H); 7.33 (t, 1H); 7.40 (s, 1H); 7.43 (s, 1H); 7.44 (s, 1H); 7.54 (s, 1H). |
| 1.6-212 | [CDCl₃] 1.25 (t, 3H); 1.45 (t, 3H); 2.26 (s, 3H); 2.67 (q, 2H); 3.35 (s, 3H); 3.44 (d, 1H); 3.87 (d, 1H); 4.08 (q, 2H); 4.28-4.37 (m, 2H); 6.85 (s br, 1H); 7.27 (d, 1H); 7.33 (s, 1H); 7.34 (t, 1H); 7.44 (d, 1H); 7.53 (s, 1H). |

Analytical data table 1.7

| No. | NMR |
|---|---|
| 1.7-1 | [CDCl₃] 3.41 (s, 3H); 3.46 (d, 1H); 3.84 (s, 3H); 3.86 (d, 1H); 5.79 (s br, 1H); 6.72 (s br, 1H); 7.00 (d, 1H); 7.18 (d, 1H); 7.26 (s, 1H); 7.34 (t, 1H). |
| 1.7-9 | [CDCl₃] 3.39 (s, 3H); 3.45 (d, 1H); 3.86 (s, 3H); 3.87 (d, 1H); 3.86-3.95 (m, 1H); 4.01-4.18 (m, 1H); 7.01 (d, 1H); 7.09 (s br, 1H); 7.18 (d, 1H); 7.26 (s, 1H); 7.34 (t, 1H). |
| 1.7-16 | [CDCl₃] 3.38 (s, 3H); 3.43 (d, 1H); 3.84 (s, 3H); 3.86 (d, 1H); 3.80-4.06 (m, 2H); 5.19 (d, 1H); 5.25 (d, 1H); 5.81-5.90 (m, 1H); 6.88 (s br, 1H); 7.00 (d, 1H); 7.17 (d, 1H); 7.26 (s, 1H); 7.33 (t, 1H). |
| 1.7-60 | [CDCl₃] 0.59 (m, 2H); 0.84 (m, 2H); 2.82 (m, 1H); 3.36 (s, 3H); 3.41 (d, 1H); 3.84 (s, 3H); 3.86 (d, 1H); 6.85 (s br, 1H); 7.00 (d, 1H); 7.17 (d, 1H); 7.26 (s, 1H); 7.33 (t, 1H). |
| 1.7-94 | [CDCl₃] 1.28 (t, 3H); 2.60 (t, 2H); 3.36 (s, 3H); 3.40 (d, 1H); 3.57-3.68 (m, 2H); 3.84 (s, 3H); 3.86 (d, 1H); 4.16 (q, 2H); 6.69 (d, 1H); 7.18 (d, 1H); 7.30 (s br, 1H); 7.31 (t, 1H). |
| 1.7-96 | [CDCl₃] D1: 1.24 (t, 3H); 1.29 (d, 3H); 2.55 (m, 2H); 3.37 (s, 3H); 3.41 (d, 1H); 3.85 (s, 3H); 3.85 (d, 1H); 4.10-4.20 (m, 2H); 4.35-4.43 (m, 1H); 6.99 (d, 1H); 7.18 (d, 1H); 7.25 (s, 1H); 7.26 (s br, 1H); 7.33 (t, 1H). D2: 1.26 (t, 3H); 1.30 (d, 3H); 2.58 (m, 2H); 3.37 (s, 3H); 3.41 (d, 1H); 3.85 (s, 3H); 3.85 (d, 1H); 4.10-4.20 (m, 2H); 4.35-4.43 (m, 1H); 6.99 (d, 1H); 7.18 (d, 1H); 7.25 (s, 1H); 7.26 (s, 1H); 7.33 (t, 1H). |
| 1.7-110 | [CDCl₃] 3.36 (s, 3H); 3.43 (d, 1H); 3.84 (s, 3H); 3.92 (d, 1 H); 4.47-4.56 (m, 2H); 7.00 (d, 1H); 7.18 (d, 1H); 7.23 (t br, 1H); 7.25 (s, 1H); 7.33 (t, 1H); 7.34 (d, 1H); 7.66 (d, 1 H); 8.35 (s, 1H). |
| 1.7-206 | [CDCl₃] 1.48 (t, 3H); 3.36 (s, 3H); 3.43 (d, 1H); 3.84 (s, 3H); 3.87 (d, 1H); 4.15 (q, 2H); 4.33-4.42 (m, 2H); 6.97 (s br, 1H); 7.00 (d, 1H); 7.18 (d, 1H); 7.26 (s, 1H); 7.33 (t, 1H); 7.41 (s, 1H); 7.46 (s, 1H). |
| 1.7-212 | [CDCl₃] 1.46 (t, 3H); 2.26 (s, 3H); 3.35 (s, 3H); 3.42 (d, 1H); 3.84 (s, 3H); 3.88 (d, 1H); 4.08 (q, 2H); 4.29-4.37 (m, 2H); 6.85 (s br, 1H); 7.01 (d, 1H); 7.17 (d, 1H); 7.26 (s, 1H); 7.33 (s, 1H); 7.36 (t, 1H). |

Analytical data table 1.11

| No. | NMR |
|---|---|
| 1.11-4 | [CDCl₃] 0.96 (t, 3H); 1.54-1.66 (m, 2H); 3.22-3.38 (m, 2H); 3.34 (d, 1H); 3.37 (s, 3H); 3.83 (d, 1H); 6.78 (s br, 1H); 6.90 (t, 1H); 7.20 (d, 2H). |
| 1.11-7 | [CDCl₃] D1: 0.93 (t, 3H); 1.19 (d, 3H); 1.52 (m, 2H); 3.35 (d, 1H); 3.37 (s, 3H); 3.81(d, 1H); 3.96 (m, 1H); 6.55 (d, br, 1H); 6.90 (t, 1H); 7.19 (d, 2H). D2: 0.95 (t, 3H); 1.20 (d, 3H); 1.52 (m, 2H); 3.36 (d, 1H); 3.37 (s, 3H); 3.83(d, 1H); 3.96 (m, 1H); 6.55 (d br, 1H); 6.90 (t, 1H); 7.19 (d, 2H). |
| 1.11-8 | [CDCl₃] D1: 0.92 (d, 6H); 1.14 (d, 3H); 1.75 (sept, 1H); 3.34 (d, 1H); 3.39 (s, 3H); 3.80 (d, 1H); 3.86-3.94 (m, 1H); 6.60 (d br, 1H); 6.90 (t, 1H); 7.20 (d, 2H). D2: 0.96 (d, 6H); 1.15 (d, 3H); 1.75 (sept, 1H); 3.36 (d, 1H); 3.38 (s, 3H); 3.83 (d, 1H); 3.86-3.94 (m, 1H); 6.60 (d br, 1H); 6.90 (t, 1H); 7.20 (d, 2H). |
| 1.11-9 | [CDCl₃] 3.39 (d, 1H); 3.39 (s, 3H); 3.84 (d, 1H); 3.84-3.96 (m, 1H); 4.04-4.16 (m, 1H); 6.90 (t, 1H); 7.1 (t br, 1H); 7.20 (d, 2H). |
| 1.11-10 | [CDCl₃] 3.36 (d, 1H); 3.38 (s, 3H); 3.61-3.87 (m, 2H); 3.86 (d, 1H); 5.91 (tt, 1H); 6.92 (t, 1H); 7.04 (t br, 1H); 7.21 (d, 1H). |
| 1.11-11 | [CDCl₃] 3.38 (d, 1H); 3.39 (s, 3H); 3.84 (d, 1H); 3.88-4.03 (m, 1H); 4.06-4.22(m, 1H); 6.90 (t, 1H); 7.03 (s br, 1 H); 7.20 (d, 2H). |
| 1.11-15 | [CDCl₃] 2.62-2.80 (m, 2H); 3.36(d, 1H); 3.38 (s, 3H); 3.55-3.72 (m, 2H); 3.88 (d, 1H); 6.90 (t, 1H); 7.18 (s br, 1H); 7.20 (d, 2H). |
| 1.11-16 | [CDCl₃] 3.36 (d, 1H); 3.38 (s, 3H); 3.87 (d, 1H); 3.90-4.06 (m, 2H); 5.20 (d, 1H); 5.25 (d, 1H); 5.81-5.92 (m, 1H); 6.86 (s br, 1H); 6.90 (t, 1H); 7.20 (d, 2H). |
| 1.11-19 D1 | [CDCl₃] D1: 1.25 (d, 3H); 3.34 (d, 1H); 3.40 (s, 3H); 3.35-3.44 (m, 2H); 3.37 (s, 3H); 3.37 (s, 3H); 3.82 (d, 1H); 4.20 (m, 1H); 6.90 (t, 1H); 6.94 (d br, 1H); 7.20 (d, 2H). |
| 1.11-19 D2 | [CDCl₃] D2: 1.24 (d, 3H); 3.34 (d, 1H); 3.37 (s, 3H); 3.38 (s, 3H); 3.41 (m, 2H); 3.37 (s, 3H); 3.82 (d, 1H); 4.21 (m, 1H); 6.90 (t, 1H); 6.91(d br, 1H); 7.20 (d, 2H). |
| 1.11-20 | [CDCl₃] D1: 1.43 (d, 3H); 2.55-2.66 (m, 1H); 2.73-2.90 (m, 1H); 3.34 (d, 1H); 3.37 (s, 1H); 3.86 (d, 1H); 4.23-4.32 (m, 1H); 6.84 (t br, 1H); 6.90 (t br, 1H); 7.20 (d, 2H). D2: 1.44 (d, 3H); 2.55-2.66 (m, 1H); 2.73-2.90 (m, 1H); 3.34 (d, 1H); 3.37 (s, 1H); 3.88 (d, 1H); 4.23-4.32 (m, 1H); 6.84 (t br, 1H); 6.90 (t br, 1H); 7.20 (d, 2H). |
| 1.11-21 | [CDCl₃] 1.10-1.19 (m, 7H); 1.20-1.28 (m, 1H); 3.30-3.45 (m, 8H); 3.74-3.86 (m, 1H); 4.00-4.13(m, 1H); 6.90 (t, 1H); 7.04 (t br, 1H); 7.19 (d, 2H). |
| 1.11-24 | [CDCl₃] 3.00 (s, 3H); 3.23-3.39 (m, 2H); 3.32 (d, 1H); 3.37 (s, 3H); 3.80-3.94 (m, 2H); 3.90 (d, 1H); 6.91 (t, 1H); 7.20 (d, 2H); 7.41 (t br, 1H). |
| 1.11-25 | [CDCl₃] 1.28 (t, 3H); 2.58 (quart, 2H); 2.73 (t, 2H); 3.35 (d, 1H); 3.38 (s, 3H); 3.48-3.63 (m, 2H); 3.85 (d, 1H); 6.91 (t, 1H); 7.13 (s br, 1H); 7.21 (d, 2H). |
| 1.11-40 | [CDCl₃] 3.37 (d, 1H); 3.38 (s, 3H); 3.92 (d, 1H); 4.19-4.39 (m, 2H); 6.92 (t, 1H); 7.18 (s br, 1H); 7.20 (d, 2H). |
| 1.11-41 D2 | [CDCl₃] D2: 1.65 (d, 3H); 3.37 (d, 1H); 3.37 (s, 3H); 3.86 (d, 1H); 4.90-5.00 (m, 1H); 6.92 (t, 1H); 7.07 (s br, 1H); 7.20 (d, 2H). |
| 1.11-41 D1 | [CDCl₃] D1: 1.64 (d, 3H); 3.34 (d, 1H); 3.38 (s, 3H); 3.94 (d, 1H); 4.88-4.98 (m, 1H); 6.92 (t, 1H); 7.04 (s br, 1H); 7.20 (d, 2H). |
| 1.11-42 | [CDCl₃] 1.78 (s, 6H); 3.33 (d, 1H); 3.37 (s, 3H); 3.96 (d, 1H); 6.82 (s, 1H); 6.92 (t, 1H); 7.20 (d, 2H). |
| 1.11-45 | [CDCl₃] D1: 1.11 (t, 3H); 1.73 (s, 3H); 1.90-2.19 (m, 2H); 3.32 (d, 1H); 3.37 (s, 3H); 3.94 (d, 1H); 6.28 (d br, 1H); 6.90 (t, 1H); 7.20 (d, 2H). D2: 1.15 (t, 3H); 1.74 (s, 3H); 1.90-2.19 (m, 2H); 3.34 (d, 1H); 3.37 (s, 3H); 3.97 (d, 1H); 6.28 (d br, 1H); 6.90 (t, 1H); 7.20 (d, 2H). |
| 1.11-46 D1 | [CDCl₃] D1: 1.04 (t, 3H); 1.50-1.63 (m, 2H); 1.75 (s, 3H); 1.82-2.06 (m, 2H); 3.33 (d, 1H); 3.37 (s, 3H); 3.97 (d, 1H); 6.82 (s br, 1H); 6.92 (t, 1H); 7.21 (d, 2H). |
| 1.11-46 D2 | [CDCl₃] D2: 1.01 (t, 3H); 1.48-1.60 (m, 2H); 1.74 (s, 3H); 1.85-1.88 (m, 2H); 2.01-2.11 (m, 2H); 3.33 (d, 1H); 3.37 (s, 3H); 3.96 (d, 1H); 6.79 (s br, 1H); 6.92 (t, 1H); 7.21 (d, 2H). |
| 1.11-47 | [CDCl₃] D1: 0.75 (m, 4H); 1.31(m, 1H); 1.83 (s, 3H); 3.32 (d, 1H); 3.38 (s, 3H); 3.91 (d, 1H); 6.92 (t, 1H); 7.01 (s br, 1H); 7.20 (d, 1H). D2: 0.75 (m, 4H); 1.31 (m, 1H); 1.82 (s, 3H); 3.36 (d, 1H); 3.38 (s, 3H); 3.99 (d, 1H); 6.92 (t, 1H); 7.01 (s br, 1H); 7.20 (d, 1H). |
| 1.11-48 D1 | [CDCl₃] D1: 1.41 (d, 3H); 3.37 (d, 1H); 3, 38 (s, 3H); 3.80 (d, 1H); 4.65-4.79 (m, 1H); 6.83 (d br, 1H); 6.91 (t, 1H); 7.20 (d, 2H). |
| 1.11-48 D2 | [CDCl₃] D2: 1.40 (d, 3H); 3.37 (d, 1H); 3.38 (s, 3H); 3.87 (d, 1H); 4.66-4.78 (m, 1H); 6.87 (d br, 1H); 6.90 (t, 1H); 7.20 (d, 2H). |
| 1.11-49 D1 | [CDCl₃] D1 1.04 (t, 3H); 1.54-1.68 (m, 1H); 1.90-2.01(m, 1H); 3.39 (s, 3H); 3.42 (d, 1H); 3.77 (d, 1H); 4.46-4.60 (m, 1H); 6.7 (d br, 1H); 6.91 (t, 1H); 7.20 (d, 2H). |
| 1.11-49 D2 | [CDCl₃] D2: 1.02 (t, 3H); 1.55-1.68 (m, 1H); 1.89-2.00 (m, 1H); 3.39 (s, 3H); 3.37 (d, 1H); 3.89 (d, 1H); 4.47-4.60 (m, 1H); 6.75 (d br, 1H); 6.91 (t, 1H); 7.20 (d, 2H). |
| 1.11-50 | [CDCl₃] D1: 1.02 (m, 6H); 2.16-2.28 (m, 1H); 3.38 (d, 1H); 3.39 (s, 3H); 3.78 (d, 1H); 4.46-4.59 (m, 1H); 6.83 (d br, 1H); 6.91 (t, 1H); 7.21 (d, 2H). D2: 1.05 (m, 6H); 2.16-2.28 (m, 1H); 3.43 (d, 1H); 3.39 (s, 3H); 3.89 (d, 1H); 4.46-4.59 (m, 2H); 6.88 (d br, 1H); 6.91 (t, 1H); 7.21 (d, 2H). |
| 1.11-51 | [CDCl₃] 1.58-1.69 (m, 1H); 1.34-1.98 (m, 2H); 2.05-2.15 (m, 1H); 3.36 (d, 1H); 3.38 (s, 3H); 3.81-3.96 (m, 2H); 3.95 (d, 1H); 4.25-4.33 (m, 1H); 4.57-4.68 (m, 1H); 6.91 (t, 1H); 7.21 (d, 2H); 7.21 (s br, 1H). |
| 1.11-53 | [CDCl₃] D1: 1.47 (d, 3H); 2.31 (d, 1H); 3.34 (d, 1H); 3.37 (s, 3H); 3.81 (d, 1H); 4.78-4.88 (m, 1H); 6.90 (t, 1H); 6.95 (s br, 1H); 7.20 (d, 2H). D2: 1.50 (d, 3H); 2.32 (d, 1H); 3.36 (d, 1H); 3.37 (s, 3H); 3.86 (d, 1H); 4.78-4.88 (m, 1H); 6.90 (t, 1H); 6.95 (s br, 1H); 7.20 (d, 2H). |
| 1.11-55 | [CDCl₃] D1: 1.41 (d, 3H); 1.82 (d, 3H); 3.34 (d, 1H); 3.38 (s, 3H); 3.80 (d, 1H); 4.72-4.82 (m, 1H); 6.86-6.94 (m, 2H); 7.20 (d, 2H). D2: 1.44 (d, 3H); 1.82 (d, 3H); 3.36 (d, 1H); 3.39 (s, 3H); 3.85 (d, 1H); 4.72-4.82 (m, 1H); 6.86-6.94 (m, 2H); 7.20 (d, 2H). |
| 1.11-58 | [CDCl₃] D1: 1.19 (d, 3H); 3.34 (d, 1H); 3.38(s, 3H); 3.43 (s, 3H); 3.46 (s, 3H); 3.80 (d, 1H); 4.16-4.28 (m, 2H); 6.85 (s br, 1H); 6.90 (t, 1H); 7.20 (d, 2H). D2: 1.21 (d, 1H); 3.35 (d, 1H); 3.38(s, 3H); 3.44 (s, 3H); 3.46 (s, 3H); 3.81 (d, 1H); 4.16-4.28 (m, 2H); 6.85 (s br, 1H); 6.90 (t, 1H); 7.20 (d, 2H). |
| 1.11-59 | [CDCl₃] D1: 1.12 (t, 3H); 1.42 (d, 3H); 2.44-2.69 (m, 2H); 3.33 (d, 1H); 3.38 (s, 3H); 3.81 (d, 1H); 4.59-4.68 (m, 1H); 6.90 (t, 1H); 7.20 (d, 2H); 7.45 (d br, 1H). D2: 1.13 (t, 3H); 1.41 (d, 3H); 2.44-2.69 (m, 2H); 3.36 (d, 1H); 3.38 (s, 3H); 3.84 (d, 1H); 4.59-4.68 (m, 1H); 6.90 (t, 1H); 7.20 (d, 2H); 7.45 (d br, 1H). |
| 1.11-60 | [CDCl₃] 0.56-0.63 (m, 2H); 0.82-0.88 (m, 2H); 2.78-2.86 (m, 1H); 3.33 (d, 1H); 3.37 (s, 3H); 3.85 (d, 1H); 6.80 (s br, 1H); 6.90 (t, 1H); 7.20 (d, 2H). |
| 1.11-62 | [CDCl₃] D1: 0.22-0.32 (m, 2H); 0.43-0.54 (m, 2H); 0.83-0.93 (m, 1H); 1.27 (d, 3H); 3.35 (d, 1H); 3.39 (s, 3H); 3.38-3.48 (m, 1H); 3.81 (d, 1H); 6.26 (s br, 1H); 6.90 (t, 1H); 7.21 (d, 2H). D2: 0.32-0.43 (m, 2H); 0.54-0.63 (m, 2H); 0.83-0.93 (m, 1H); 1.28 (d, 3H); 3.35 (d, 1H); 3.38 (s, 3H); 3.38-3.48 (m, 1H); 3.82 (d, 1H); 6.26 (s br, 1H); 6.90 (t, 1H); 7.21 (d, 2H). |
| 1.11-64 | [CDCl₃] 1.29-1.40 (m, 2H); 1.57-1.68 (m, 2H); 3.34 (d, 1H); 3.35 (s, 3H); 3.96 (d, 1H); 6.92 (t, 1H); 7.20 (d, 2H); 7.24 (s br, 1H). |
| 1.11-70 | [CDCl₃] 3.19-3.28 (m, 2H); 3.32 (d, 1H); 3.37 (s, 3H); 3.90 (d, 1H); 4.10-4.19 (m, 2H); 4.40-4.54 (m, 1H) 6.91 (t, 1H); 7.23 (d br, 1H); 7.21(d, 2H). |
| 1.11-71 | [CDCl₃] 3.32 (d, 1H); 3.37 (s, 3H); 3.92 (d, 1H); 4.02-4.11 (m, 2H); 4.54-4.62 (m, 2H); 4.71-4.80 (m, 1H); 6.90 (t, 1H); 7.20 (d, 2H); 7.37 (d br, 1H). |
| 1.11-73 | [CDCl₃] 1.83-1.92 (m, 1H); 2.26-2.38 (m, 1H); 3.33 (dd, 1H); 3.36 (s(3H); 3.70-3.76 (m, 1H); 3.78-3.91(m, 3H); |

Analytical data table 1.11

| No. | NMR |
|---|---|
| | 3.94-4.02(m, 1H); 4.51-4.61 (m, 1H); 6.91 (t, 1H); 6.94 (s br, 1H); 7.21 (d, 2H). |
| 1.11-74 | [CDCl₃] 1.60-1.70 (m, 1H); 2.02-2.13 (m, 1H); 2.48-2.60 (m, 1H); 3.34 (d, 1H); 3.38 (s, 3H); 3.32-3.44 (m, 1H); 3.54-3.58 (m, 1H); 3.71-3.95 (m, 3H); 3.85 (d, 1H); 6.90 (t, 1H); 6.91(s br, 1H); 7.20 (d, 2H). |
| 1.11-76 | [CDCl₃] D1: 0.92 (t, 3H); 1.18 (d, 3H); 1.29-1.43 (m, 2H); 3.34 (d, 1H); 3.37 (s, 3H); 3.81 (d, 1H); 3.97-4.10 (m, 1H); 6.53 (d br, 1H); 6.90 (t, 1H); 7.21 (d, 2H). D2: 0.94 (t, 3H); 1.20 (d, 3H); 1.43-1.53 (m, 2H); 3.35 (d, 1H); 3.37 (s, 3H); 3.83 (d, 1H); 3.97-4.10 (m, 1H); 6.53 (d br, 1H); 6.90 (t, 1H); 7.21 (d, 2H). |
| 1.11-93 | [CDCl₃] 2.61 (t, 2H); 3.33 (d, 1H); 3.36 (s, 3H); 3.62 (q, 2H); 3.72 (s, 3H); 3.84 (d, 1H); 6.90 (t, 1H); 7.20 (d, 2H); 2.29 (s br, 1H). |
| 1.11-96 | [CDCl₃] D1: 1.25 (t, 3H); 1.30 (d, 3H); 2.50-2.62 (m, 2H); 3.32 (d, 1H); 3.36 (s, 3H); 3.83 (d, 1H); 4.17 (q, 2H); 4.40 (m, 1H); 6.91 t, 1H); 7.20 (d, 2H); 7.25 (s br, 1H). D2: 1.26 (t, 3H); 1.31 (d, 3H); 2.50-2.62 (m, 2H); 3.32 (d, 1H); 3.36 (s, 3H); 3.84 (d, 1H); 4.18 (q, 2H); 4.40 (m, 1H); 6.91 (t, 1H); 7.20 (d, 2H); 7.25 (s br, 1H) |
| 1.11-102 | [CDCl₃] 1.92 (pent, 2H); 2.40 (t, 2H); 3.34 (d, 1H); 3.39 (s, 3H); 3.38-3.42 (m, 2H); 3.69 (s, 3H); 3.85 (d, 1H); 6.90 (t, 1H); 6.94 (s br, 1H); 7.20 (d, 2H). |
| 1.11-110 | [CDCl₃] 3.35 (d, 1H); 3.36 (s, 3H); 3.92 (d, 1H); 4.49-4.56 (m, 2H); 6.92 (t, 1H); 7.19 (d, 2H); 7.33 (d, 1H); 7.65 (d, 1H); 8.35 (s, 1H). |
| 1.11-111 | [CDCl₃] 3.34 (d, 1H); 3.35 (s, 3H); 3.92 (d, 1H); 4.45-4.58 (m, 2H); 6.88-6.96 (m, 2H); 7.18 (s br, 1H); 7.20 (d, 2H); 7.79 (m, 1H); 8.18 (s, 1H). |
| 1.11-113 | [CDCl₃] 3.35 (d, 1H); 3.35 (s, 3H); 3.88 (d, 1H); 3.93 (s, 3H); 4.40-4.52 (m2H); 6.73 (d, 1H); 6.91 (t, 1H); 7.04 (t br, 1H); 7.20 (d, 1H); 7.56 (dd, 1H); 8.11 (d, 1H). |
| 1.11-119 | [CDCl₃] 3.35 (d, 1H); 3.37 (s, 3H); 4.58-4.67 (m, 2H); 6.92 (t, 1H); 7.20 (d, 2H); 7.22 (s br, 1H); 7.68 (d, 1H); 7.84 (d, 1H); 8.69 (s, 1H). |
| 1.11-135 | [CDCl₃] 3.37 (d, 1H); 3.38 (s, 3H); 3.95 (d, 1H); 4.49-4.61 (m, 2H); 6.92 (t, 1H); 7.20 (d, 2H); 7.28 (s, 2H); 8.59 (s, 2H). |
| 1.11-136 | [CDCl₃] 3.37 (d, 1H); 3.39 (s, 3H); 3.97 (d, 1H); 4.51-4.62 (m, 2H); 6.87 (s, 1H); 6.93 (t, 1H); 7.12 (d, 1H); 7.22 (d, 2H); 7.25 (s br, 1H); 8.20 (d, 1H). |
| 1.11-137 | [CDCl₃] 3.37 (d, 1H); 3.39 (s, 3H); 3.97 (d, 1H); 4.51-4.62 (m, 2H); 6.87 (s, 1H); 6.93 (t, 1H); 7.12 (d, 1H); 7.22 (d, 2H); 7.25 (s br, 1H); 8.20 (d, 1H). |
| 1.11-138 | [CDCl₃] 3.36 (d, 1H); 3.39 (s, 3H); 3.97 (d, 1H); 4.44-4.59 (m, 2H); 6.92 (t, 1H); 7.19 (d, 1H); 7.20 (s br, 1H), 7.20 (d, 2H); 7.42 (s, 1H); 8.34 (d, 1H). |
| 1.11-142 | [CDCl₃] 3.36 (d, 1H); 3.38 (s, 3H); 3.92 (d, 1H); 3.93 (s, 3H); 4.42-4.56 (m, 2H); 6.65 (s, 1H); 6.79 (d, 1H); 6.91 (t, 1H); 7.12 (t br, 1H); 7.20 (d, 2H); 8.13 (d, 1H). |
| 1.11-147 | [CDCl₃] 2.56 (s, 3H); 3.36 (d, 1H); 3.39 (s, 3H); 3.95 (d, 1H); 4.43-4.58 (m, 2H); 6.91 (t, 1H); 7.02 (d, 1H); 7.08 (s, 1H); 7.16 (t br, 1H); 7.21 (d, 2H); 8.47 (d, 1H). |
| 1.11-148 | [CDCl₃] 1.31 (t, 3H); 2.83 (d, 3H); 3.37 (d, 1H); 3.39 (s, 3H); 3.94 (d, 1H); 4.45-4.58 (m, 2H); 6.90 (t, 1H); 7.03 (d, 1H); 7.08 (s, 1H); 7.16 (s br, 1H); 7.20 (d, 2H); 8.50 (d, 1H). |
| 1.11-149 | [CDCl₃] 1.21 (m, 2H); 1.42 (m, 2H); 2.57 (m, 1H); 3.35 (d, 1H); 3.39 (s, 3H); 4.01 (d, 1H); 4.55-4.73 (m, 2H); 6.92 (t, 1H); 7.15 (d, 1H); 7.22 (d, 2H); 7.41(d, 1H); 7.63 (t br, 1H); 8.57 (d, 1H). |
| 1.11-150 | [CDCl₃] 0.97 (t, 3H); 1.70-1.82 (m, 2H); 2.77 (t, 2H); 3.37 (d, 1H); 3.39 (s, 3H); 3.94 (d, 1H); 4.44-4.58 (m, 2H); 6.92 (t, 1H); 7.04 (d, 1H); 7.07 (s, 1H); 7.16 (t br, 1H); 7.21 (d, 2H); 8.50 (d, 1H). |
| 1.11-152 | [CDCl₃] 3.37 (d, 1H); 3.39 (s, 3H); 3.97 (d, 1H); 4.55-4.69 (m, 2H); 6.91 (t, 1H); 7.21 (d, 2H); 7.30 (t br, 1H); 7.44 (d, 1H); 7.60 (s, 1H); 8.71 (d, 1H). |
| 1.11-179 | [CDCl₃] 3.41 (d, 1H); 3.44 (s, 3H); 3.88 (d, 1H); 4.74-4.86 (m, 2H); 6.91 (t, 1H); 7.22 (d, 2H); 7.97 (s, 1H); 8.20 (s br, 1H); 8.76 (s, 1H). |
| 1.11-180 | [CDCl₃] 3.26 (t, 2H); 3.33 (d, 1H); 3.33 (s, 3H); 3.80 (d, 1H); 3.84-3.92 (m, 2H); 6.90 (t, 1H); 7.20 (d, 2H); 7.52 (s br, 1H); 7.91 (s, 1H); 8.72 (s, 1H). |
| 1.11-189 | [CDCl₃] 2.48 (s, 6H); 3.42 (d, 1H); 3.46 (s, 3H); 3.86 (d, 1H); 4.62-4.73 (m, 2H); 6.90 (t, 1H); 7.21 (d, 2H); 8.04 (s br, 1H). |
| 1.11-191 | [CDCl₃] 3.40 (d, 1H); 3.43 (s, 3H); 3.86 (d, 1H); 3.95 (s, 6H); 4.51-4.15 (m-2H); 6.90 (t, 1H); 7.20 (d, 2H); 7.95 (s br, 1H). |
| 1.11-194 | [CDCl₃] 3.39 (d, 1H); 3.42 (s, 3H); 3.92 (d, 1H); 4.65 (m, 2H); 6.90 (t, 1H); 7.21 (d, 2H); 7.32 (d, 1H); 7.84 (br, 1H); 8.71 (d, 1H); 9.20 (s, 1H). |
| 1.11-197 | [CDCl₃] 2.29 (s, 3H); 2.38 (s, 3H); 3.33 (d, 1H); 3.35 (s, 3H); 3.83 (d, 1H); 4.28 (d, 2H); 6.90 (t, 1H); 7.19 (s br, 1H); 7.20 (d, 2H). |
| 1.11-199 | [CDCl₃] 3.34 (d, 1H); 3.35 (s, 3H); 3.89 (d, 1H); 4.34-4.47 (m, 2H); 6.91 (t, 1H); 7.09 (t br, 1H); 7.20 (d, 2H); 8.31 (s, 1H); 8.45 (s, 1H). |
| 1.11-200 | [CDCl₃] 2.46 (s, 3H); 3.33 (d, 1H); 3.34 (s, 3H); 3.87 (d, 1H); 4.24-4.37 (m, 2H); 6.91 (t, 1H); 6.93 (t br, 1H); 7.20 (d, 2H). |
| 1.11-201 | [CDCl₃] 2.26 (s, 3H); 2.42 (s, 3H); 3.33 (d, 1H); 3.34 (s, 3H); 3.89 (d, 1H); 4.26 (m, 2H); 6.8 (s br, 1H); 6.91 (t, 1H); 7.19 (d, 1H). |
| 1.11-202 | [CDCl₃] 1.30 (t, 3H); 2.42 (s, 3H); 2.65 (q, 2H); 3.33 (d, 1H); 3.34 (s, 3H); 3.90 (d, 1H); 4.21-4.33 (m, 2H); 6.77 (t br, 1H); 6.90 (t, 1H); 7.20 (d, 2H). |
| 1.11-203 | [CDCl₃] 1.29 (t, 3H); 1.30 (t, 3H); 2.66 (q, 2H); 2.79 (q, 2H); 3.33 (d, 1H); 3.34 (s, 3H); 3.80 (d, 1H); 4.22-4.33 (m, 2H); 6.26 (s, 1H); 6.91 (t, 1H); 7.19 (d, 2H). |
| 1.11-206 | [CDCl₃] 1.48 (t, 3H); 3.34 (d, 1H); 3.35 (s, 3H); 3.86 (d, 1H); 4.15 (q, 2H); 4.33-4.43 (m, 2H); 6.88 (t, 1H); 6.94 (s br, 1H); 7.18 (d, 2H); 7.41 (s, 1H); 7.46 (s, 1H). |
| 1.11-207 | [CDCl₃] 3.34 (d, 1H); 3.35 (s, 3H); 3.87 (d, 1H); 4.33-4.46 (m, 2H); 4.69 (q, 2H); 6.90 (t, 1H); 7.02 (t br, 1H); 7.20 (d, 2H); 7.53 (s, 1H); 7.56 (s, 1H). |
| 1.11-208 | [CDCl₃] 3.34 (d, 1H); 3.35 (s, 3H); 3.87 (d, 1H); 4.32-4.48 (m, 2H); 6.07 (tt, 1H); 6.90 (t, 1H); 6.98 (t br, 1H); 7.20 (d, 2H); 7.48 (s, 1H); 7.54 (s, 1H). |
| 1.11-210 | [CDCl₃] 0.98-1.08 (m, 2H); 1.10-1.17 (m, 2H); 3.34 (d, 1H); 3.35 (s, 3H); 3.52-3.59 (m, 1H); 3.86 (d, 1H); 4.30-4.41 (m, 2H); 6.91 (t, 1H); 6.93 (s br, 1H); 7.20 (d, 2H); 7.43 (s, 1H); 7.46 (s, 1H). |
| 1.11-211 | [CDCl₃] 2.24 (s, 3H); 3.33 (d, 1H); 3.34 (s, 3H); 3.81 (s, 3H); 3.87 (d, 1H); 4.26-4.38 (m, 2H); 6.82 (s br, 1H); 6.90 (t, 1H); 7.20 (d, 2H); 7.28 (s, 1H). |
| 1.11-212 | [CDCl₃] 1.45 (t, 3H); 2.24 (s, 3H); 3.34 (d, 1H); 3.35 (s, 3H); 3.86 (d, 1H); 4.08 (q, 2H); 4.27-4.39 (m, 2H); 6.80 (s br, 1H); 6.91 (t, 1H); 7.21 (d, 2H); 7.33 (s, 1H). |
| 1.11-213 | [CDCl₃] 1.47 (t, 3H); 3.33 (d, 1H); 3.35 (s, 3H); 3.84 (d, 1H); 4.08 (q, 2H); 4.33 (d, 2H); 6.90 (t, 1H); 7.03 (s br, 1H); 7.20 (d, 2H); 7.72 (s, 1H). |
| 1.11-238 | [CDCl₃] 3.34 (d, 1H); 3.36 (s, 3H); 3.80 (d, 1H); 4.60 (d, 2H); 6.91 (t, 1H); 7.20 (d, 2H); 7.26 (d, 1H); 7.33 (t br, 1H); 7.76 (d, 1H); 8.35 (d, 1H). |
| 1.11-239 | [CDCl₃] 3.37 (d, 1H); 3.40 (s, 3H); 3.95 (d, 1H); 4.62 (d, 2H); 6.91 (t, 1H); 7.20 (d, 2H); 7.28 (s , 1H); 7.30 (d, 1H); 8.48 (d, 1H); 8.58 (s, 1H). |
| 1.11-240 | [CDCl₃] 2.22 (s, 3H); 2.36 (s, 3H); 3.33 (d, 1H); 3.40 (s, 3H); 6.93 (d, 1H); 7.21 (d, 2H), 7.76 (s br, 1H). |
| 1.11-241 | [CDCl₃] 3.36 (d, 1H); 3.39 (s, 3H); 3.97(d, 1H); 4.56-4.69 (m, 2H); 6.91(t, 1H); 6.93 (m, 1H); 7.21 (d, 2H); 7.28 (s br, 1H); 8.19 (s, 1H). |
| 1.11-242 | [CDCl₃] 3.36 (d, 1H); 3.39 (s, 3H); 3.95 (d, 1H); 4.52-4.66 (m, 2H); 6.90 (t, 1H); 7.20 (d, 2H); 7.23 (s br, 1H); 7.32 (s, 1H); 8.36 (s, 1H). |
| 1.11-243 | [CDCl₃] 3.36 (d, 1H); 3.40 (s, 3H); 3.96 (d, 1H); 4.51-4.64 (m, 2H); 6.91 (t, 1H); 7.22 (d, 2H); 7.31 (s, 1H); 8.49 (s, 1H). |
| 1.11-244 | [CDCl₃] 3.35 (d, 1H); 3.39 (s, 3H); 3.91 (s, 3H); 3.92 (d, 1H); 4.45-4.60 (m, 2H); 6.73 (s, 1H); 6.91 (t, 1H); 7.20 (s br, 1H); 7.21 (d, 2H); 8.23 (s, 1H). |
| 1.11-245 | [CDCl₃] 2.29 (s, 3H); 3.37 (d, 1H); 3.40 (s, 3H); 3.97 (d, 1H); 4.42-4.57 (m, 2H); 6.92 (t, 1H); 7.10 (s br, 1H); 7.18 (s, 1H); 7.21 (d, 2H); 8.18 (s, 1H). |

Analytical data table 1.11

| No. | NMR |
|---|---|
| 1.11-246 | [CDCl₃] 2.55 (s, 3H); 3.34 (d, 1H); 3.36 (s, 3H); 3.94 (d, 1H); 4.50 (d, 2H); 6.91 (t, 1H); 7.03 (t br, 1H); 7.16 (d, 1H); 7.20 (d, 2H); 7.53 (d, 1H). |
| 1.11-247 | [CDCl₃] 2.58 (s, 3H); 3.36 (d, 1H); 3.37 (s, 3H); 3.94 (d, 1H); 4.48-4.60 (m, 2H); 6.90 (t, 1H); 7.02 (t br, 1H); 7.15 (dd, 1H); 7.21 (d, 1H); 7.56 (d, 1H); 8.45 (d, 1H). |
| 1.11-248 | [CDCl₃] 3.34 (d, 1H); 3.35 (s, 3H); 3.90 (d, 1H); 4.43-4.55 (m, 2H); 6.90 (t, 1H); 7.19 (s br, 1H); 7.20 (d, 2H); 7.48 (d, 1H); 7.54 (d, 1H); 8.33 (s, 1H). |
| 1.11-249 | [CDCl₃] 2.21 (s, 3H); 3.36 (d, 1H); 3.39 (s, 3H); 3.91 (s, 3H); 3.94 (d, 1H); 4.47 (qd, 2H); 6.62 (s, 1H); 6.91 (t, 1H); 7.03 (t br, 1H); 7.21 (d, 2H); 7.94 (s, 1H). |
| 1.11-250 | [CDCl₃] 2.28 (s, 3H); 2.53 (s, 3H); 3.36 (d, 1H); 3.39 (s, 3H); 3.96 (d, 1H); 4.43-4.54 (m, 2H); 6.90 (t, 1H); 7.02 (s br, 1H), 7.02 (s, 1H); 7.21 (d, 2H); 8.30 (s, 1H). |
| 1.11-251 | [CDCl₃] 2.56 (s, 3H); 3.35 (d, 1H); 3.36 (s, 3H); 3.88 (d, 1H); 4.44-4.57 (m, 2H); 6.90 (t, 1H); 7.08 (s br, 1H); 7.15 (d, 1H); 7.20 (d, 2H); 7.56 (d, 1H); 8.45 (s, 1H). |
| 1.11-252 | [CDCl₃] 3.34 (d, 1H); 3.34 (s, 3H); 3.80 (d, 1H); 3.91 (s, 3H); 3.98 (s, 3H); 4.32-4.47 (m, 2H); 6.27 (d, 1H); 6.90 (t, 1H); 7.17 (s br, 1H); 7.19 (d, 2H); 7.49 (d, 1H). |
| 1.11-253 | [CDCl₃] 2.32 (s, 3H); 3.33 (d, 1H); 3.35 (s, 3H); 3.91 (d, 1H); 4.36 (d, 2H); 6.91 (t, 1H); 6.95 (s br, 1H); 7.20 (d, 2H); 8.34 (s, 1H). |
| 1.11-254 | [CDCl₃] 3.34 (s, 3H); 3.35 (s, 3H); 3.35 (d, 1H); 3.74 (t, 2H); 3.85 (d, 1H); 4.26 (t, 2H); 4.32-4.46 (m, 2H); 6.91 (t, 1H); 6.93 (s br, 1H); 7.20 (d, 2H); 7.47 (s, 2H). |
| 1.11-255 | [CDCl₃] 1.47 (t, 3H); 3.34 (s, 3H); 3.35 (d, 1H); 3.84 (d, 1H); 4.11 (q, 2H); 4.32 (d, 2H); 6.90 (t, 1H); 7.03 (t br, 1H); 7.20 (d, 2H); 7.40 (s, 1H). |
| 1.11-256 | [CDCl₃] 1.44 (t, 3H); 3.33 (d, 1H); 3.35 (s, 3H); 3.83 (d, 1H); 4.00 (q, 2H); 4.30 (d, 2H); 6.90 (t, 1H); 6.90 (t, 1H); 7.03 (t br, 1H); 7.19 (d, 2H); 7.32 (s, 1H). |
| 1.11-257 | [CDCl₃] 1.42 (t, 3H); 3.34 (d, 1H); 3.35 (s, 3H); 3.80 (d, 1H); 3.91 (s, 3H); 3.96 (q, 2H); 4.21-4.32 (m, 2H); 6.90 (t, 1H); 7.02 (s br, 1H); 7.19 (d, 2H); 7.20 (s, 1H). |
| 1.11-258 | [CDCl₃] 3.33 (d, 1H); 3.35 (s, 3H); 3.78 (s, 3H); 3.86 (d, 1H); 3.90 (s, 3H); 4.20-4.30 (m, 2H); 6.89 (t, 1H); 7.02 (s br, 1H); 7.16 (s, 1H); 7.19 (d, 2H). |
| 1.11-259 | [CDCl₃] 1.25 (t, 3H); 2.58 (q, 2H); 3.36 (s, 3H); 3.37 (s, 3H); 3.74 (s, 3H); 3.83 (d, 1H); 4.40-4.52 (m, 2H); 5.98 (s, 1H); 6.90 (t, 1H); 7.18 (s br, 1H); 7.20 (d, 2H). |

Analytical data table 1.14

| No. | NMR |
|---|---|
| 1.14-1 | [CDCl₃] 2.39 (s, 3H); 3.40 (s, 3H); 3.43 (d, 1H); 3.85 (d, 1H); 5.90 (s br, 1H); 6.72 (s br, 1H); 6.98 (d, 1H); 7.20 (d, 1H); 7.24 (s, 1H). |
| 1.14-9 | 2.39 (s, 3H); 3.38 (s, 3H); 3.42 (d, 1H); 3.86 (d, 1H); 3.85-3.96 (m, 1H); 4.03-4.17 (m, 1H); 6.98 (d, 1H); 7.08 (t br, 1H); 7.20 (d, 1H); 7.25 (s, 1H). |
| 1.14-16 | [CDCl₃] 2.38 (s, 3H); 3.38 (s, 3H); 3.40 (d, 1H); 3.86 (d, 1H); 3.90-4.05 (m, 2H); 5.19 (d, 1H); 5.24 (d, 1H); 5.81-5.92 (m, 1H); 6.86 (s br, 1H); 6.97 (d, 1H); 7.20 (d, 1H); 7.24 (s, 1H). |
| 1.14-60 | [CDCl₃] 0.60 (m, 2H); 0.84 (m, 2H); 2.38 (s, 3H); 2.82 (s, 1H); 3.35 (s, 3H); 3.37 (d, 1H); 3.84 (d, 1H); 6.83 (s br, 1H); 6.97 (d, 1H); 7.19 (d, 1H); 7.23 (s, 1H). |
| 1.14-94 | [CDCl₃] 1.27 (t, 3H); 2.38 (s, 3H); 2.59 m, 2H); 3.36 (s, 3H); 3.37 (d, 1H); 3.57-3.66 (m, 2H); 3.84 (d, 1H); 4.17 (q, 2H); 6.97 (d, 1H); 7.19 (d, 1H); 7.24 (s, 1H); 7.32 (s br, 1H). |
| 1.14-96 | [CDCl₃] 1.12-1.34 (m, 6H); 2.38 (s, 3H); 2.51-2.62 (m, 2H); 3.37 (s, 3H); 3.38 (d, 1H); 3.83 (d, 1H); 4.10-4.22 (m, 2H); 4.36-4.44 (m, 1H); 6.96 (d, 1H); 7.20 (d, 1H); 7.24 (s, 1H); 7.26 (s br, 1H). |
| 1.14-102 | [CDCl₃] 1.91 (quin, 2H); 2.38 (m, 5H); 3.38 (s, 3H); 3.38 (d, 1H); 3.33-3.45 (m, 2H); 3.69 (d, 3H); 3.85 (d, 1H); 6.92 (t br, 1H); 6.97 (d, 1H); 7.20 (d, 1H); 7.25 (s, 1H). |

Analytical data table 1.14

| No. | NMR |
|---|---|
| 1.14-110 | [CDCl₃] 2.39 (s, 3H); 3.35 (s, 3H); 3.38 (d, 1H); 4.49-4.56 (m, 2H); 6.98 (d, 1H); 7.20 (d, 1H); 7.21 (s br, 1H); 7.24 (s, 1H); 7.32 (d, 1H); 7.65 (d, 1H); 8.35 (s, 1H). |
| 1.14-136 | [CDCl₃] 2.39 (s, 3H); 3.39 (s, 3H); 3.41 (d, 1H); 3.97 (d, 1 H); 4.48-4.59 (m, 2H); 6.98 (d, 1H); 7.16 (d, 1H); 7.21 (d, 1H); 7.25 (s, 2H); 7.26 (s br, 1H); 8.36 (d, 1H). |
| 1.14-206 | [CDCl₃] 1.48 (t, 3H); 2.38 (s, 3H); 3.34 (s, 3H); 3.37 (d, 1H); 3.85 (d, 1H); 4.14 (q, 2H); 4.31-4.43 (m, 2H); 6.94 (s br, 1H); 6.97 (d, 1H); 7.18 (d, 1H); 7.24 (s, 1H); 7.40 (s, 1H); 7.45 (s, 1H). |
| 1.14-212 | [CDCl₃] 1.43 (t, 3H); 2.25 (s, 3H); 2.38 (s, 3H); 3.35 (s, 3H); 3.39 (d, 1H); 3.86 (d, 1H); 4.10 (q, 2H); 4.29-4.38(m, 2H); 6.83 (s br, 1H); 6.97 (d, 1H); 7.19 (d, 1H); 7.24 (s, 1H); 7.41 (s, 1H). |

Analytical data table 1.16

| No. | NMR |
|---|---|
| 1.16-1 | [CDCl₃] 3.39 (d, 1H); 3.41 (s, 3H); 3.83 (s, 3H); 3.84 (d, 1H); 5.68 (s br, 1H); 6.70 (s br 1H); 6.71 (d, 1H); 6.96 (d, 1H); 7.01 (s, 1H). |
| 1.16-60 | [CDCl₃] 0.60 (m, 2H); 0.84 (m, 2H); 2.81-2.84 (m, 1H); 3.35 (s, 3H); 3.36 (d, 1H); 3.83 (s, 3H); 3.85 (d, 1H); 6.69 (d, 1H); 6.82 (s br, 1H); 6.94 (d, 1H); 7.00 s, 1H). |
| 1.16-94 | [CDCl₃] 1.28 (t, 3H); 2.59 (m, 2H); 3.35 (d, 1H); 3.36 (s, 3H); 3.58-3.67 (m, 2H); 3.83 (s, 3H); 3.84 (d, 1H); 4.17 (q, 2H); 6-70 (d, 1H); 6.97 (d, 1H); 7.01 (s, 1H); 7.31 (t br, 1H). |
| 1.16-96 | [CDCl₃] 1.24-1.32 (m, 6H); 2.52-2.62 (m, 2H); 3.35 (d, 1H); 3.37 (s, 3H); 3.82 (d, 1H); 3.84 (s, 3H); 4.11-4.21 (m, 2H); 4.36-4.43 (m, 1H); 6.69 (d, 1H); 6.95 (d, 1H); 7.01 (s, 1H). |
| 1.16-110 | [CDCl₃] 3.35 (s, 3H); 3.37 (d, 1H); 3.83 (s, 3H); 3.89 (d, 1H); 4.47-4.56 (m, 2H); 6.70 (d, 1H); 6.95 (d, 1H); 7.01 (s, 1H); 7.21 (t br, 1H); 7.32 (d, 1H); 7.65 (d, 1H); 8.35 (s, 1H). |
| 1.16-136 | [CDCl₃] 3.39 (d, 1H); 3.39 (s, 3H); 3.84 (s, 3H); 3.96 (d, 1H); 4.48-4.59 (m, 2H); 6.71 (d, 1H); 6.97 (d, 1H); 7.02 (s, 1H); 7.16 (d, 1H); 7.27 (s br, 2H); 8.36 (d, 1H). |
| 1.16-212 | [CDCl₃] 1.45 (t, 3H); 2.26 (s, 3H); 3.35 (s, 3H); 3.37 (d, 1H); 3.84 (s, 3H); 3.86 (d, 1H); 4.10 (q, 2H); 4.30-4.36 (m, 2H); 6.71 (d, 1H); 6.82 (t br, 1H); 6.94 (d, 1H); 7.00 (s, 1H); 7.32 (s, 1H). |

Analytical data table 1.18

| No. | NMR |
|---|---|
| 1.18-1 | [CDCl₃] 3.42 (s, 3H); 3.43 (d, 1H); 3.92 (d, 1H); 5.86 (s br, 1H); 6.70 (s br, 1H); 7.43 (d, 1H); 7.61 (d, 1H); 7.70 (s, 1H). |
| 1.18-9 | [CDCl₃] 3.40 (s, 3H); 3.43 (d, 1H); 3.83-3.98 (m, 1H); 3.82 (d, 1H); 4.03-4.19 (m, 1H); 7.08 (s br, 1H); 7.43 (d, 1H); 7.60 (d, 1H); 7.69 (s, 1H). |
| 1.18-16 | [CDCl₃] 3.39 (s, 3H); 3.40 (d, 1H); 3.93 (d, 1H); 3.92-4.06 (m, 2H); 5.19 (d, 1H); 5.25 (d, 1H); 5.82-5.93 (m, 1H); 6.87 (s br, 1H); 7.42 (d, 1H); 7.60 (d, 1H); 7.70 (s, 1H). |
| 1.18-60 | [CDCl₃] 0.60 (m, 2H); 0.85 (m, 2H); 2.80-2.84 (m, 1H); 3.36 (s, 3H); 3.38 (d, 1H); 3.92 (d, 1H); 6.82 (s br, 1H); 7.41 (d, 1H); 7.59 (d, 1H); 7.69 (s, 1H). |
| 1.18-94 | [CDCl₃] 1.28 (t, 3H); 2.60 (m, 2H); 3.37 (s, 3H); 3.37 (d, 1H); 3.63 (q, 2H); 3.90 (d, 1H); 4.18 (q, 2H); 7.30 (t br, 1H); 7.42 (d, 1H); 7.60 (d, 1H); 7.69 (s, 1H). |
| 1.18-96 | [CDCl₃] 1.25-1.32 (m, 6H); 2.50-2.51 (m, 2H); 3.37 (d, 1H); 3.38 (s, 3H); 3.89 (d, 1H); 4.13-4.21 (m, 2H); 4.31-4.46 (m, 1 H); 7.27 (s br, 1H); 7.41 (d, 1H); 7.60 (d, 1H); 7.70 (s, 1H). |

Analytical data table 1.18

| No. | NMR |
|---|---|
| 1.18-102 | [CDCl$_3$] 1.92 (quin, 2H); 2.41 (t, 2H); 3.38 (s, 3H); 3.36-3.43 (m, 3H); 3.91 (d, 1H); 6.96 (s br, 1H); 7.41 (d, 1H); 7.60 (d, 1H); 7.70 (s, 1H). |
| 1.18-110 | [CDCl$_3$] 3.37 (s, 3H); 3.40 (d, 1H); 3.98 (d, 1H); 4.48-4.56 (m, 2H); 7.21 (t br, 1H); 7.33 (d, 1H); 7.42 (d, 1H); 7.60 (d, 1H); 7.65 (d, 1H); 7.69 (s, 1H); 8.35 (s, 1H). |
| 1.18-136 | [CDCl$_3$] 3.41 (s, 3H) 3.42 (d, 1H); 4.04 (d, 1H); 4.49-4.59 (m, 2H); 7.16 (d, 1H); 7.43 (d, 1H); 7.62 (d, 1H); 7.71 (s, 1H); 8.36 (d, 1H). |
| 1.18-206 | [CDCl$_3$] 1.48 (t, 3H); 3.36 (s, 3H); 3.38 (d, 1H); 3.92 (d, 1H); 4.15 (q, 2H); 4.31-4.43 (m, 2H); 6.95 (s br, 1H); 7.40 (s, 1H); 7.41 (d, 1H); 7.46 (s, 1H); 7.58 (d, 1H); 7.69 (s, 1H). |
| 1.18-212 | [CDCl$_3$] 1.46 (t, 3H); 2.25 (s, 3H); 3.36 (s, 3H); 3.38 (d, 1H); 3.93 (d, 1H); 4.10 (q, 2H); 4.28-4.39 (m, 2H); 6.81 (s br, 1H); 7.32 (s, 1H); 7.42 (d, 1H); 7.60 (d, 1H); 7.69 (d, 1H). |

Analytical data table 1.20

| No. | NMR |
|---|---|
| 1.20-1 | [CDCl$_3$] 3.38 (d, 1H); 3.39 (s, 3H); 3.86 (d, 1H); 5.85 (s br, 1H); 6.70 (s br, 1H); 7.44 (s, 1H); 7.56 (s, 2H). |
| 1.20-4 | [CDCl$_3$] 0.96 (t, 3H); 1.59 (m, 2H); 3.27-3.33 (m, 3H); 3.37 (s, 3H); 3.85 (d, 1H); 6.78 (s, 1H); 7.43 (s, 1H); 7.55 (s, 2H). |
| 1.20-5 | [CDCl$_3$] 1.21 (d, 3H); 1.23 (d, 3H); 3.33 (d, 1H); 3.36 (s, 3H); 3.84 (d, 1H); 4.04-4.18 (m, 1H); 6.58 (d br, 1H); 7.43 (s, 1H); 7.55 (s, 2H). |
| 1.20-7 | [CDCl$_3$] D1: 0.93 (t, 3H); 1.18 (d, 3H); 1.48-1.58 (m, 2H); 3.34 (d, 1H); 3.36 (s, 3H); 3.83 (d, 1H); 3.90-4.02 (m, 1H); 6.55 (d br, 1H); 7.43 (s, 1H); 7.55 (s, 2H). D2: 0.96 (t, 3H); 1.20 (d, 3H); 1.48-1.58 (m, 2H); 3.35 (d, 1H); 3.36 (s, 3H); 3.86 (d, 1H); 3.90-4.02 (m, 1H); 6.55 (d br, 1H); 7.43 (s, 1H); 7.55 (s, 2H). |
| 1.20-8 | [CDCl$_3$] D1: 0.93 (d, 6H); 1.13 (d, 3H); 1.69-1.81 (m, 1H); 3.33 (d, 1H); 3.37 (s, 3H); 3.82 (d, 1H); 3.83-3.96 (m, 1H); 6.58 (d br, 1H); 7.44 (s, 1H); 7.55 (s, 2H). D2: 0.95 0 (d, 6H); 1.15 (d, 3H); 1.69-1.81 (m, 1H); 3.34 (d, 1H); 3.38 (s, 3H); 3.85 (d, 1H); 3.83-3.96 (m, 1H); 6.58 (d br, 1H); 7.44 (s, 1H); 7.55 (s, 2H). |
| 1.20-9 | [CDCl$_3$] 3.36 (d, 1H); 3.38 (s, 3H); 3.86 (d, 1H); 3.84-3.97 (m, 1H); 4.02-4.17 (m, 1H); 7.05 (s br, 1H); 7.45 (s, 1H); 7.55 (s, 2H). |
| 1.20-10 | [CDCl$_3$] 3.33 (d, 1H); 3.38 (s, 3H); 3.66-3.80 (m, 2H); 3.89 (d, 1H); 5.78-6.05 (tt, 1H); 7.02 (s, 1H); 7.45 (s, 1H); 7.56 (s, 2H). |
| 1.20-11 | [CDCl$_3$] 3.38 (s, 3H); 3.40 (d, 1H); 3.84 (d, 1H); 3.91-4.01 (m, 1H); 4.08-4.20 (m, 1H); 7.03 (s, 1H); 7.45 (s, 1H); 7.56 (s, 2H). |
| 1.20-15 | [CDCl$_3$] 2.67-2.73 (m, 2H); 3.32 (d, 1H); 3.37 (s, 3H); 3.59-3.68 (m, 2H); 3.89 (d, 1H); 7.20 (m, 1H); 7.45 (s, 1H); 7.55 (s, 2H). |
| 1.20-16 | [CDCl$_3$] 3.34 (d, 1H); 3.38 (s, 3H); 3.87 (d, 1H); 3.90-4.06 (m, 2H); 5.20 (d, 1H); 5.25 (d, 1H); 5.80-5.93 (m, 1H); 6.85 s br, 1H); 7.44 (s, 1H); 7.55 (s, 2H). |
| 1.20-19 D1 | [CDCl$_3$] D1: 1.26 (d, 3H); 3.34 (d, 1H); 3.37 (s, 3H); 3.37-3.45 (m, 2H); 3.83 (d, 1H); 4.13-4.26 (m, 1H); 6.93 (d br, 1H); 7.43 (s, 1H); 7.55 (s, 2H). |
| 1.20-19 D2 | [CDCl$_3$] D2: 1.23 (d, 3H); 3.34 (d, 1H); 3.40 (s, 3H); 3.37-3.45 (m, 2H); 3.83 (d, 1H); 4.14-4.27 (m, 1H); 6.91 (d br, 1H); 7.43 (s, 1H); 7.55 (s, 2H). |
| 1.20-20 | [CDCl$_3$] 1.43 (t, 3H); 2.57-2.66 (m, 1H); 2.75-2.89 (m, 1H); 3.31 (d, 1H); 3.37 (s, 3H); 3.84-3.91 (m, 1H); 4.29 (m, 1H); 6.83 (s, 1H); 7.44 (s, 1H); 7.55 (s, 2H). |
| 1.20-21 | [CDCl$_3$] 1.11-1.20 (m, 6H); 3.30-3.42 (m, 8H); 3.77-3.85 (m, 1H); 4.02 (m, 1H); 7.02 (m, 1H); 7.42 (m, 1H); 7.55 (m, 2H). |
| 1.20-24 | [CDCl$_3$] 3.00 (s, 3H); 3.29-3.36 (m, 3H); 3.38 (s, 3H); 3.86-3.93 (m, 3H); 7.43 (m, 3H); 7.55 (s, 2H). |

Analytical data table 1.20

| No. | NMR |
|---|---|
| 1.20-25 | [CDCl$_3$] 1.28 (t, 3H); 2.58 (q, 2H); 2.73 (t, 2H); 3.35 (d, 1H); 3.38 (s, 3H); 3.48-3.61 (m, 2H); 3.85 (d, 1H); 7.12 (s br, 1H); 7.43 (s, 1H); 7.55 (s, 2H). |
| 1.20-40 | [CDCl$_3$] 3.36 (d, 1H); 3.37 (s, 3H); 3.92 (d, 1H); 4.17-4.89(m, 2H); 7.18 (t br, 1H); 7.45 (s, 1H); 7.55 (s, 2H). |
| 1.20-41 D1 | [CDCl$_3$] D1: 1.65 (d, 3H); 3.37 (s, 3H); 3.37 (d, 1H); 3.86 (d, 1H); 4.90-4.99 (m, 1H); 7.05 (s br, 1H); 7.45 (s, 1H); 7.55 (s, 2H). |
| 1.20-41 D2 | [CDCl$_3$] D2: 1.64 (d, 3H); 3.36 (s, 3H); 3.34 (d, 1H); 3.95 (d, 1H); 4.89-4.98 (m, 1H); 7.05 (s br, 1H); 7.45 (s, 1H); 7.55 (s, 2H). |
| 1.20-42 | [CDCl$_3$] 1.78 (s, 6H); 3.35 (d, 1H); 3.38 (s, 3H); 3.99 (d, 1H); 6.80 (s, 1H); 7.45 (s, 1H); 7.55 (s, 2H). |
| 1.20-45 | [CDCl$_3$] 1.09-1.18 (m, 3H); 1.73 (d, 3H); 1.98-2.13 (m, 2H); 3.30 (d, 1H); 3.37 (s, 3H); 3.92-4.00 (m, 1H); 6.79 (d, 1H); 7.45 (s, 1H); 7.56 (s, 2H). |
| 1.20-46 D1 | [CDCl$_3$] D1 1.04 (t, 3H); 1.59 (m, 2H); 1.75 (s, 3H); 1.89 (m, 1H); 2.00 (m, 1H); 3.34 (d, 1H); 3.36 (s, 3H); 3.98 (d, 1H); 6.80 (s, 1H); 7.45 (s, 1H); 7.56 (s, 2H). |
| 1.20-46 D2 | [CDCl$_3$] D2 1.01 (t, 3H); 1.52 (m, 2H); 1.74 (s, 3H); 1.92 (m, 1H); 2.05 (m, 1H); 3.35 (d, 1H); 3.36 (s, 3H); 3.97 (d, 1H); 6.78 (s, 1H); 7.45 (s, 1H); 7.56 (s, 2H). |
| 1.20-47 | [CDCl$_3$] 0.70-0.80 (m, 4H); 1.26-1.33 (m, 1H); 1.82 (d, 3H); 3.30-3.34 (m, 1H); 3.38 (s, 3H); 3.90-4.02 (m, 1H); 7.00 (m, 1H); 7.45 (s, 1H); 7.56 (s, 2H). |
| 1.20-48 D1 | [CDCl$_3$] D1 1.40 (d, 3H); 3.38 (s, 3H), 3.39 (d, 1H), 3.88 (d, 1H); 4.73 (m, 1H); 6.85 (d, 1H); 7.45 (s, 1H); 7.56 (s, 2H). |
| 1.20-48 D2 | [CDCl$_3$] D2 1.40 (d, 3H); 3.38 (s, 3H), 3.39 (d, 1H), 3.80 (d, 1H); 4.72 (m, 1H); 6.80 (d, 1H); 7.45 (s, 1H); 7.56 (s, 2H). |
| 1.20-49 D1 | [CDCl$_3$] D1 1.03 (t, 3H); 1.58-1.64 (m, 1H); 1.90-2.00 (m, 1H); 3.38 (s, 3H); 3.42 (d, 1H); 3.80 (d, 1H); 4.55 (m, 1H); 6.70 (d, 1H); 7.45 (s, 1H); 7.55 (s, 2H). |
| 1.20-49 D2 | [CDCl$_3$] D2 1.02 (t, 3H); 1.58-1.64 (m, 1H); 1.90-2.00 (m, 1H); 3.38 (s, 3H); 3.40 (d, 1H); 3.90 (d, 1H); 4.55 (m, 1H); 6.75 (d, 1H); 7.45 (s, 1H); 7.56 (s, 2H). |
| 1.20-50 | [CDCl$_3$] D1: 0.98-1.07 (m, 6H); 2.16-2.28 (m, 1H); 3.39 (s, 3H); 3.36 (d, 1H); 3.78 (d, 1H); 3.46-4.58 (m, 1H); 6.84 (d br, 1H); 7.44 (s, 1H); 7.56 (s, 2H). D2: 0.98-1.07 (m, 6H); 2.16-2.28 (m, 1H); 3.40 (s, 3H); 3.42 (d, 1H); 3.90 (d, 1H); 3.46-4.58 (m, 1H); 6.88 (d br, 1H); 7.44 (s, 1H); 7.56 (s, 2H). |
| 1.20-51 D1 | [CDCl$_3$] D1 1.80 (m, 1H); 1.95 (m, 2H); 2.09 (m, 1H); 3.38 (s, 3H), 3.39 (d, 1H); 3.80-3.91 (m, 3H); 4.18 (q, 1H), 4.72 (m, 1H); 7.00 (m, 1H); 7.45 (s, 1H); 7.56 (s, 2H). |
| 1.20-51 D2 | [CDCl$_3$] D2 1.60 (m, 1H); 1.93 (m, 2H); 2.14 (m, 1H); 3.38 (s, 3H), 3.42 (d, 1H); 3.80 (d, 1H); 3.83-3.97 (m, 2H); 4.30 (m, 1H), 4.65 (m, 1H); 7.20 (d, 1H); 7.45 (s, 1H); 7.56 (s, 2H). |
| 1.20-51 D3 | [CDCl$_3$] D3 1.62 (m, 1H); 1.91 (m, 2H); 2.10 (m, 1H); 3.37 (s, 3H), 3.38 (d, 1H); 3.84-3.97 (m, 3H); 4.30 (m, 1H), 4.64 (m, 1H); 7.21 (s, 1H); 7.45 (s, 1H); 7.56 (s, 2H). |
| 1.20-51 D4 | [CDCl$_3$] D4 1.80 (m, 1H); 1.93 (m, 2H); 2.08 (m, 1H); 3.38 (s, 3H), 3.39 (d, 1H); 3.81-3.91 (m, 2H); 4.18 (q, 1H), 4.73 (m, 1H); 7.00 (m, 1H); 7.45 (s, 1H); 7.56 (s, 2H) |
| 1.20-53 | [CDCl$_3$] 1.49 (t, 3H); 2.30 (m, 1H); 3.33 (m, 1H); 3.37 (s, 3H); 3.80-3.90 (m, 1H); 4.83 (m, 1H); 6.93 (s, 1H); 7.44 (s, 1H); 7.55 (s, 2H). |
| 1.20-55 | [CDCl$_3$] D1: 1.42 (d, 3H); 1.81 (s, 3H); 3.33 (d, 1H); 3.38 (s, 3H); 3.80 (d, 1H); 4.71-4.81 (m, 1H); 6.88 (d br, 1H); 7.43 (s, 1H); 7.55 (s, 2H). D2: 1.45 (d, 3H); 1.82 (s, 3H); 3.35 (d, 1H); 3.38 (s, 3H); 3.85 (d, 1H); 4.71-4.81 (m, 1H); 6.88 (d br, 1H); 7.43 (s, 1H); 7.55 (s, 2H). |
| 1.20-58 | [CDCl$_3$] D1: 1.18 (d, 3H); 3.32 (d, 1H); 3.37 (s, 3H); 3.43 (s, 3H); 3.46 (s, 3H); 3.81 (d, 1H); 4.16-4.28 (m, 2H); 6.87 (t br, 1H); 7.43 (s, 1H); 7.55 (s, 2H). D2: 1.20 (d, 3H); 3.34 (d, 1H); 3.37 (s, 3H); 3.43 (s, 3H); 3.44 (s, 3H); 3.82 (d, 1H); 4.16-4.28 (m, 2H); 6.87 (t br, 1H); 7.43 (s, 1H); 7.55 (s, 2H). |

Analytical data table 1.20

| No. | NMR |
|---|---|
| 1.20-59 | [CDCl$_3$] 1.11 (m, 3H); 1.42 (m, 3H); 2.48-2.63 (m, 2H); 3.32 (m, 1H); 3.38 (s, 3H); 3.79-3.88 (m, 1H); 4.62 (m, 1H); 7.43-7.50 (m, 2H); 7.55 (m, 2H). |
| 1.20-60 | [CDCl$_3$] 0.59 (m, 2H); 0.84 (m, 2H); 2.82 (m, 1H); 3.34 (s, 3H); 3.34 (d, 1H); 3.88 (d, 1H); 6.79 (s, 1H); 7.43 (m, 1H); 7.54 (m, 2H). |
| 1.20-60 E1 | [CDCl$_3$] 0.56-0.62 (m, 2H); 0.82-0.89 (m, 2H); 2.77-2.86 (m-1H); 3.33 (d, 1H); 3.86 (d, 1H); 6.78 (s br, 1H); 7.43 (s, 1H); 7.54 (s, 2H). |
| 1.20-60 E2 | [CDCl$_3$] 0.56-0.62 (m, 2H); 0.82-0.89 (m, 2H); 2.77-2.86 (m-1H); 3.33 (d, 1H); 3.86 (d, 1H); 6.78 (s br, 1H); 7.43 (s, 1H); 7.54 (s, 2H). |
| 1.20-62 | [CDCl$_3$] D1: 0.27-0.32 (m, 2H); 0.43-0.53 (m, 2H); 0.82-0.93 (m, 1H); 1.26 (d, 3H); 3.34 (d, 1H); 3.39 (s, 3H); 3.37-3.46 (m, 1H); 3.82 (d, 1H); 6.76 (s br, 1H); 7.43 (s, 1H); 7.56 (s, 2H). D2: 0.33-0.43 (m, 2H); 0.53-0.62 (m, 2H); 0.82-0.93 (m, 1H); 1.28 (d, 3H); 3.35 (d, 1H); 3.41 (s, 3H); 3.37-3.46 (m, 1H); 3.83 (d, 1H); 6.76 (s br, 1H); 7.43 (s, 1H); 7.56 (s, 2H). |
| 1.20-64 | [CDCl$_3$] 1.26-1.38 (m, 2H); 1.58-1.68 (m, 2H); 3.30 (d, 1H); 3.35 (s, 3H); 3.96 (d, 1H); 7.23 (s, 1H); 7.45 (s, 1H); 7.55 (s, 2H). |
| 1.20-69 | [CDCl$_3$] 3.30 (d, 1H); 3.36 (s, 3H); 3.39(dd, 4H); 3.87(d, 1H); 5.22-5.33 (m, 1H); 7.18 (d br, 1H); 7.44 (s, 1H); 7.55 (s, 1H). |
| 1.20-70 | [CDCl$_3$] D1 3.20-3.30 (m, 2H); 3, 32 (d, 1H); 3.36 (s, 3H); 3.49-3.58 (m, 1H); 3.67-3.74 (m, 1H); 3.90 (d, 1H); 4.10-4.18 (m, 2H); 4.41-4.53 (m, 1H); 7.19 (s br, 1H); 7.45 (s, 1H);7.55 (s, 2H). D2 3.20-3.30 (m, 2H); 3.32 (d, 1H); 3.36 (s, 3H); 3.49-3.58 (m, 1H); 3.67-3.74 (m, 1H); 3.91 (d, 1H); 4.10-4.18 (m, 2H); 5.14-5.23 (m, 1H); 7.12 (s br, 1H); 7.45 (s, 1H); 7.55 (s, 2H). |
| 1.20-71 | [CDCl$_3$] 3.31 (d, 1H); 3.37 (s, 3H); 3.93 (d, 1H); 4.00-4.11 (m, 2H); 4.52-4.63 (m, 2H); 4.71-4.79 (m, 1H); 7.35 (d br, 1H); 7.45 (s, 1H); 7.55 (s, 2H). |
| 1.20-73 | [CDCl$_3$] 1.83-1.92 (m, 1H); 2.26-2.38 (m, 1H); 3.32 (dd, 1H); 3.34 (s, 3H); 3.70-3.76 (m, 1H); 3.78-3.91(m, 3H); 3.93-4.03(m,1H); 4.51-4.61 (m, 1H); 6.93 (s br, 1H); 7.44 (s, 1H); 7.55 (s, 2H). |
| 1.20-74 | [CDCl$_3$] 1.59-1.68 (m, 1H); 2.02-2.14 (m, 1H); 2.47-2.59 (m, 1H); 3.34 (d, 1H); 3.37 (s, 3H); 3.33-3.45 (m, 2H); 3.56 (dd, 1H); 3.72-3.79 (m, 1H); 3.81-3.94 (m, 2H); 3.87 (d, 1H); 6.91 (t br, 1H); 7.44 (s, 1H); 7.55 (s, 2H). |
| 1.20-76 | [CDCl$_3$] D1: 0.92 (t, 3H); 1.18 (d, 3H); 1.32-1.43 (m, 2H); 1.43-1.52 (m, 2H); 3.33 (d, 1H); 3.40 (s, 3H); 3.82 (d, 1H); 3.97-4.09 (m, 1H); 6.53 (d br, 1H); 7.44 (s, 1H); 7.55 (s, 2H). D2: 0.94 (t, 3H); 1.20 (d, 3H); 1.32-1.43 (m, 2H); 1.43-1.52 (m, 2H); 3.34 (d, 1H); 3.40 (s, 3H); 3.84 (d, 1H); 3.97-4.09 (m, 1H); 6.53 (d br, 1H); 7.44 (s, 1H); 7.55 (s, 2H). |
| 1.20-93 | [CDCl$_3$] 2.63 (t, 2H); 3.33 (d, 1H); 3.36 (s, 3H); 3.62 (d, 2H); 3.73 (s, 3H); 3.85(d, 1H); 7.27 (t br, 1H); 7.43 (s, 1H); 7.56 (2H). |
| 1.20-96 | [CDCl$_3$] 1.28 (m, 6H); 2.56 (m, 2H); 3.34 (d, 1H); 3.36 (s, 3H); 3.85 (d, 1H); 4.16 (m, 2H); 4.39 (m, 1H); 7.24 (s, 1H); 7.42 (s, 1H); 7.55 (s, 2H). |
| 1.20-102 | [CDCl$_3$] 1.91 (quint, 2H); 2.40 (t, 2H); 3.30 (d, 1H); 3.37 (s, 3H); 3.39 (m, 2H); 3.69 (s, 3H); 3.86 (d, 1H); 6.90 (s, 1H); 7.44 (s, 1H); 7.55 (s, 2H). |
| 1.20-110 | [CDCl$_3$] 3.35 (s, 3H); 3.36 (d, 1H); 3.92 (d, 1H); 4.52 (m, 2H); 7.20 (s, 1H); 7.32 (d, 1H); 7.45 (s, 1H); 7.55 (s, 2H); 7.65 (d, 1H); 8.35 (s, 1H). |
| 1.20-119 | [CDCl$_3$] 3.35 (d, 1H); 3.36 (s, 3H); 3.94 (d, 1H); 4.56-4.68 (m, 2H); 7.25 (s br, 1H); 7.44 (s, 1H); 7.55 (s, 2H); 7.68 (d, 1H); 7.85 (d, 1H); 8.68 (s, 1H). |
| 1.20-135 | [CDCl$_3$] 3.34 (d, 1H); 3.38 (s, 3H); 3.96 (d, 1H); 4.55 (d, 2H); 7.21 (d, 3H); 7.44 (s, 1H); 7.56 (s, 2H); 8.59 (d, 2H). |
| 1.20-136 | [CDCl$_3$] 3.86 (d, 1H); 3.38 (s, 3H); 3.95 (d, 1H); 4.45-4.60 (m, 2H); 7.16 (m, 1H); 7.23 (s br, 1H); 7.24 (s, 1H); 7.44 (s, 1H); 7.56 (s, 2H); 8.36 (d, 1H). |
| 1.20-137 | [CDCl$_3$] 3.34 (d, 1H); 3.38 (s, 3H); 3.96 (d, 1H); 4.57 (m, 2H); 6.86 (m, 1H); 7.11 (m, 1H); 7.20 (s, 1H); 7.47 (s, 1H); 7.57 (s, 2H); 8.20 (d, 1H). |
| 1.20-138 | [CDCl$_3$] 3.37 (d, 1H); 3.38 (s, 3H); 3.97 (d, 1H); 4.45-4.58 (m, 2H); 7.18 (d, 1H); 7.23 (t br, 1H); 7.41 (s, 1H); 7.44 (s, 1H); 7.57 (s, 2H); 8.34 (d, 1H). |
| 1.20-142 | [CDCl$_3$] 3.36 (d, 1H); 3.38 (s, 3H); 3.92 (d, 1H); 3.93 (s, 3H); 4.41-4.56 (m, 2H); 6.65 (s, 1H); 6.79 (d, 1H); 7.13 (t br, 1H); 7.44 (s, 1H); 7.56 (s, 2H); 8.13 (d, 1H). |
| 1.20-147 | [CDCl$_3$] 2.56 (s, 3H); 3.35 (d, 1H); 3.38 (s, 3H); 3.95 (d, 1H); 4.44-4.56 (m, 2H); 7.02 (d, 1H); 7.08 (s, 1H); 7.14 (t br, 1H); 7.45 (s, 1H); 7.56 (s, 2H); 8.47 (d, 1H). |
| 1.20-148 | [CDCl$_3$] 1.31 (t, 3H); 2.81 (q, 2H); 3.36 (d, 1H); 3.38 (s, 3H); 3.95 (d, 1H); 4.45-4.58 (m, 2H); 7.03 (d, 1H); 7.08 (s, 1H); 7.15 (t br, 1H); 7.45 (s, 1H); 7.56 (s, 2H); 8.50 (d, 1H). |
| 1.20-149 | [CDCl$_3$] 0.94-1.06 (m, 4H); 1.97-2.06 (m, 1H); 3.37 (d, 1H); 3.38 (s, 3H); 3.95 (d, 1H); 4.42-4.56 (m, 2H); 6.95 (d, 1H); 7.05 (s, 1H); 7.13 (t br, 1H); 7.44 (s, 1H); 7.56 (s, 2H); 8.40 (d, 1H). |
| 1.20-150 | [CDCl$_3$] o.97 (t, 3H); 1.70-1.82 (m, 2H); 2.73-2.83 (m, 2H); 3.37 (d, 1H); 3.38 (s, 3H); 3.94 (d, 1H); 4.43-4.58 (m, 2H); 7.04 (d, 1H); 7.07 (s, 1H); 7.15 (s br, 1H); 7.45 (s, 1H); 7.56 (s, 2H); 8.50 (d, 1H). |
| 1.20-152 | [CDCl$_3$] 3.36 (d, 1H); 3.38 (s, 3H); 3.97 (d, 1H); 4.55-4.69 (m, 2H); 7.28 (t br, 1H); 7.42 (d, 1H); 7.45 (s, 1H); 7.56 (s, 2H); 7.61 (s, 1H); 8.71 (d, 1H). |
| 1.20-191 | [CDCl$_3$] 3.39 (d, 1H); 3.43 (s, 3H); 3.87 (d, 1H); 3.95 (s, 6H); 4.50-4.64 (m, 2H); 7.43 (s, 1H); 7.56 (s, 2H); 7.45 (s br, 1H). |
| 1.20-199 | [CDCl$_3$] 3.33 (d, 1H); 3.34 (s, 3H); 3.89 (d, 1H); 4.33-4.47 (m, 2H); 7.08 (t br, 1H); 7.44 (s, 1H); 7.56 (s, 2H); 8.31 (s, 1H); 8.45 (s, 1H). |
| 1.20-200 | [CDCl$_3$] 2.46 (s, 3H); 3.32 (d, 1H); 3.33 (s, 3H); 3.88 (d, 1H); 4.23-4.37 (m, 2H); 7.00 (s br, 1H); 7.44 (s, 1H); 7.56 (s, 2H); 8.19 (s, 1H). |
| 1.20-201 | [CDCl$_3$] 2.26 (s, 3H); 2.42 (s, 3H); 3.32 (d, 1H); 3.33 (s, 3H); 3.91 (d, 1H); 4.22-4.33 (m, 2H); 6.80 (t br, 1H); 7.46 (s, 1H); 7.55 (s, 2H). |
| 1.20-202 | [CDCl$_3$] 1.30 (t, 3H); 2.42 (s, 3H); 2.65 (q, 2H); 3.32 (d, 1H); 3.90 (d, 1H); 4.21-4.34 (m, 2H); 6.75 (s br, 1H); 7.44 (s, 1H); 7.55 (s, 2H). |
| 1.20-203 | [CDCl$_3$] 1.29 (t, 3H); 1.30 (t, 3H); 2.66 (q, 2H); 2.78 (q, 2H); 3.32 (d, 1H); 3.33 (s, 3H); 3.89 (d, 1H); 4.24-4.33 (m, 2H); 7.75 (s br, 1H); 7.44 (s, 1H); 7.55 (s, 2H). |
| 1.20-206 | [CDCl$_3$] 1.49 (t, 3H); 3.34 (s, 3H); 3.35 (d, 1H); 3.88 (d, 1H); 4.14 (m, 2H); 4.38 (m, 2H); 6.90 (s, 1H); 7.40 (s, 1H); 7.43 (m, 2H); 7.54 (s, 2H). |
| 1.20-207 | 3.33 (d, 1H); 3.34 (s, 3H); 3.88 (d, 1H); 4.33-4.46 (m, 2H); 4.68 (q, 2H); 7.01 (s br, 1H); 7.43 (s, 1H); 7.53 (s, 1H); 7.55 (s, 2H); 7.56 (s, 1H). |
| 1.20-208 | [CDCl$_3$] 3.34 (s, 3H); 3.36 (d, 1H); 3.89 (d, 1H); 4.38-4.48 (m, 4H); 5.93-6.21 (tt, 1H); 6.98 (s, 1H); 7.42 (m, 1H); 7.49 (s, 1H); 7.54 (m, 3H). |
| 1.20-210 | [CDCl$_3$] 0.98-1.08 (m, 2H); 1.09-1.14 (m, 2H); 3.33 (d, 0 (m, 1H); 3.86 (d, 1H); 4.30-4.42 (m, 2H); 6.92 (s br, 1H); 7.44 (s, 2H); 7.46 (s, 1H); 7.55 (s, 2H). |
| 1.20-211 | [CDCl$_3$] 2.24 (s, 3H); 3.33 (d, 1H); 3.34 (s, 3H); 3.81 (s, 3H); 3.87 (d, 1H); 4.26-4.38 (m, 2H); 6.82 (s br, 1H); 7.28 (s, 1H); 7.43 (s, 1H); 7.54 (s, 2H). |
| 1.20-212 | [CDCl$_3$] 1.46 (t, 3H); 2.25 (s, 3H); 3.33 (s, 3H); 3.36 (d, 1H); 3.86 (d, 1H); 4.08 (q, 2H); 4.33 (m, 2H); 6.80 (s, 1H); 7.31 (s, 1H); 7.43 (s, 1H); 7.54 (s, 2H). |
| 1.20-213 | [CDCl$_3$] 1.47 (t, 3H); 3.34 (d, 1H); 3.35 (s, 3H); 3.84 (d, 1H); 4.08 (q, 2H); 4.33 (m, 2H); 6.90 (t, 1H); 7.03 (s br, 1H); 7.21 (d, 2H); 7.42 (s, 1H). |
| 1.20-241 | [CDCl$_3$] 3.36 (d, 1H); 3.38 (s, 3H); 3.97 (d, 1H); 4.54-4.68 (m, 2H); 6.94 (d, 1H); 7.27 (s br, 1H); 7.45 (s, 1H); 7.57 (s, 2H); 8.19 (s, 1H). |
| 1.20-242 | [CDCl$_3$] 3.36 (d, 1H); 3.39 (s, 3H); 3.96 (d, 1H); 4.51-4.64 (m, 2H); 7.23 (s br, 1H); 7.31 (s, 1H); 7.45 (s, 1 H); 7.57 (s, 2H); 8.36 (s, 1H). |
| 1.20-243 | [CDCl$_3$] 3.36 (d, 1H); 3.39 (s, 3H); 3.96 (d, 1H); 4.51-4.63 (m, 2H); 7.25 (s br, 1H); 7.30 (s, 1H); 7.45 (s, 1H); 7.57 (s, 2H); 8.46 (s, 1H). |

Analytical data table 1.20

| No. | NMR |
|---|---|
| 1.20-244 | [CDCl₃] 3.36 (d, 1H); 3.38 (s, 3H); 3.91 (s, 3H); 3.92 (d, 1H); 4.45-4.59 (m, 2H); 6.73 (s, 1H); 7.21 (t br, 1H); 7.44 (s, 1H); 7.56 (s, 2H); 8.23 (s, 1H). |
| 1.20-255 | [CDCl₃] 1.47 (t, 3H); 3.33 (d, 1H); 3.34 (s, 3H); 3.85 (d, 1H); 4.11 (q, 2H); 4.32 (d, 2H); 7.03 (s br, 1H); 7.40 (s, 1H); 7.43 (s, 1H); 7.55 (s, 2H). |
| 1.20-257 | [CDCl₃] 1.42 (t, 3H); 3.33 (d, 1H); 3.34 (s, 3H); 3.81 (d, 1H); 3.91 (s, 3H); 3.96 (d, 2H); 4.21-4.32 (m, 2H); 7.00 (s br, 1H); 7.20 (s, 1H); 7.43 (s, 1H); 7.54 (s, 2H). |

Analytical data table 1.25

| No. | NMR |
|---|---|
| 1.25-1 | [CDCl₃] 3.37 (d, 1H); 3.41 (s, 3H); 3.87 (d, 1H); 5.60 (s br, 1H); 6.76 (s br, 1H); 7.32 (s, 1H); 7.45 (s, 1H); 7.58 (s, 1H). |
| 1.25-9 | [CDCl₃] 3.39 (s, 3H); 3.39 (d, 1H); 3.37 (d, 1H); 3.33-3.46 (m, 1H); 4.02-4.18 (m, 1H); 7.05 (t br, 1H); 7.32 (s, 1H); 7.45 (s, 1H); 7.58 (s, 1H). |
| 1.25-16 | [CDCl₃] 3.36 (d, 1H); 3.38 (s, 3H); 3.89 (d, 1H); 3.90-4.06 (m, 2H); 5.20 (d, 1H); 5.25 (d, 1H); 5.81-5.92 (m, 1H); 6.84 (s br, 1H); 7.31 (s, 1H); 7.45 (s, 1H); 7.58 (s, 1H). |
| 1.25-60 | [CDCl₃] 0.57-0.61 (m, 2H); 0.81-0.87 (m, 2H); 2.78-2.86 (m, 1H); 3.34 (d, 1H); 3.35 (s, 3H); 3.87 (d, 1H); 6.78 (s br, 1H); 7.31 (s, 1H); 7.44 (s, 1H); 7.57 (s, 1H). |
| 1.25-94 | [CDCl₃] 1.28 (t, 3H); 2.59 (t, 2H); 3.33 (d, 1H); 3.36 (s, 3H); 3.62 (q, 2H); 3.85 (d, 1H); 4.18 (q, 2H); 7.28 (s br, 1H); 7.31 (s, 1H); 7.44 (s, 1H); 7.58 (s, 1H). |
| 1.25-96 | [CDCl₃] 1.23-1.32 (m, 6H); 2.50-2.62 (m, 2H); 3.33 (d, 1H); 3.37 (s, 3H); 3.85 (d, 1H); 4.11-4.21 (m, 2H); 4.33-4.45 (m, 1H); 7.25 (s br, 1H); 7.45 (s, 1H); 7.52 (s, 1H); 7.58 (s, 1H). |
| 1.25-102 | [CDCl₃] 1.92 (quin, 2H); 2.40 (t, 2H); 3.34 (d, 1H); 3.38 (s, 3H); 3.36-3.43 (m, 2H); 3.69 (s, 3H); 3.87 (d, 1H); 6.92 (s br, 1H); 7.31 (s, 1H); 7.44 (s, 1H); 7.58 (s, 1H). |
| 1.25-110 | [CDCl₃] 3.35 (d, 1H); 3.36 (s, 3H); 3.92 (d, 1H); 4.45-4.57 (m, 2H); 7.15 (t br, 1H); 7.32 (d, 1H); 7.34 (s, 1H); 7.45 (s, 1H); 7.58 (s, 1H); 6.64 (d, 1H); 8.35 (s, 1H). |
| 1.25-136 | [CDCl₃] 3.37 (d, 1H); 3.39 (s, 3H); 3.98 (d, 1H); 4.46-4.60 (m, 2H); 7.17 (d, 1H); 7.33 (s, 1H); 7.46 (s, 1H); 7.59 (s, 1H); 8.36 (d, 1H). |
| 1.25-206 | [CDCl₃] 1.48 (t, 1H); 3.34 (d, 1H); 3, 35 (s, 3H); 3.87 (d, 1H); 4.15 (q, 2H); 4.32-4.43 (m, 2H); 6.92 (s br, 1H); 7.31 (s, 1H); 7.40 (s, 1H); 7.44 (s, 1H); 7.46 (s, 1H); 7.57 (s, 1H). |
| 1.25-212 | [CDCl₃] 1.45 (t, 3H); 2.24 (s, 3H); 3.32 (d, 1H); 3.33 (s, 3H); 3.89 (d, 1H); 4.08 (q, 2H); 4.28-4.38 (m, 2H); 6.79 (t br, 1H); 7.31 (s, 1H); 7.44 (s, 1H); 7.57 (s, 1H). |

Analytical data table 1.29

| No. | NMR |
|---|---|
| 1.29-9 | [CDCl₃] 2.37 (s, 3H); 3.38 (s, 3H); 3.42 (d, 1H); 3.83-3.90 (m, 2H); 4.02-4.13 (m, 1H); 7.08 (s, 1H); 7.40 (m, 2H); 7.60 (s, 1H). |
| 1.29-41 D1 | [CDCl₃] D1: 1.63 (d, 3H); 2.37 (s, 3H); 3.36 (d, 1H); 3.38 (s, 3H); 3.81-3.91 (m, 1H); 4.95 (quint, 1H); 7.03 (d, 1H); 7.41 (m, 2H); 7.61 (s, 1H). |
| 1.29-41 D2 | [CDCl₃] D2: 1.63 (d, 3H); 2.37 (s, 3H); 3.36 (d, 1H); 3.38 (s, 3H); 3.95 (d, 1H); 4.93 (quint, 1H); 7.06 (d, 1H); 7.40 (m, 2H); 7.61 (s, 1H). |
| 1.29-48 | [CDCl₃] 1.40 (t, 3H); 2.37 (s, 3H); 3.38 (s, 3H); 3.41 (d, 1H); 3.77-3.89 (m, 1H); 4.68-4.76 (m, 1H); 6.86 (m, 1H); 7.41 (m, 2H); 7.61 (1H). |
| 1.29-60 | [CDCl₃] 0.59 (m, 2H); 0.83 (m, 2H); 2.36 (s, 3H); 2.82 (m, 1H); 3.34 (s, 3H); 3.37 (d, 1H); 3.87 (d, 1H); 6.80 (s, 1H); 7.40 (m, 2H); 7.60 (s, 1H). |
| 1.29-73 | [CDCl₃] 1.88 (m, 1H); 2.28-2.35 (m, 1H); 2.37 (s, 3H); 3.32 (d, 1H); 3.36 (s, 3H); 3.72 (m, 1H); 3.78-3.88 (m, 3H); 3.98 (q, 1H); 4.55 (m, 1H); 6.93 (d, 1H); 7.41 (s, 2H); 7.61 (s, 1H). |
| 1.29-93 | [CDCl₃] 2.36 (s, 3H); 2.61 (t, 2H); 3.35 (s, 3H); 3.37 (d, 1H); 3.62 (q, 2H); 3.72 (s, 3H); 3.86 (d, 1H); 7.40 (m, 2H); 7.60 (s, 1H). |
| 1.29-96 | [CDCl₃] 1.25-1.31 (m, 6H); 2.36 (s, 3H); 2.57 (m, 2H); 3.32 (d, 1H); 3.37 (s, 3H); 3.85 (d, 1H); 4.11-4.20 (m, 2H); 4.39 (m, 1H); 7.22 (s, 1H); 7.41 (s, 2H); 7.61 (s, 1H); |
| 1.29-136 | [CDCl₃] 2.37 (s, 3H); 3.38 (s, 3H); 3.41 (d, 1H); 3.98 (d, 1H), 4.53 (t, 2H); 7.16 (t, 1H); 7.26 (m, 1H); 7.42 (s, 2H); 7.61 (s, 1H); 8.36 (d, 1H). |
| 1.29-137 | [CDCl₃] 2.37 (s, 3H); 3.38 (s, 3H); 3.41 (d, 1H); 3.96 (d, 1H); 4.57 (t, 2H); 6.86 (s, 1H); 7.11 (m, 1H); 7.41 (s, 2H); 7.61 (s, 1H); 8.20 (d, 1H). |
| 1.29-142 | [CDCl₃] 2.37 (s, 3H); 3.37 (s, 3H); 3.41 (d, 1H); 3.89 (d, 1H); 3.93 (s, 3H); 4.46-4.51 (m, 2H); 6.65 (s, 1H); 6.80 (d, 1H); 7.16 (s, 1H); 7.41 (s, 2H); 7.61 (s, 1H); 8.12 (d, 1H). |
| 1.29-148 | [CDCl₃] 1.30 (t, 3H); 2.37 (s, 3H); 2.82 (q, 2H); 3.38 (s, 3H); 3.41 (d, 1H); 3.63 (d, 1H); 4.51 (t, 2H); 7.02 (d, 1H); 7.08 (s, 1H); 7.19 (s, 1H); 7.41 (s, 2H); 7.62 (s, 1H); 8.50 (d, 1H). |
| 1.29-149 | [CDCl₃] 0.97-1.03 (m, 4H); 2.00 (m, 1H); 2.37 (s, 3H); 3.38 (s, 3H); 3.41 (d, 1H); 3.94 (d, 1H); 4.49 (m, 2H); 6.96 (d, 1 H); 7.05 (s, 1H); 7.14 (s, 1H); 7.41 (s, 2H); 7.61 (s, 1H); 8.40 (d, 1H). |
| 1.29-150 | [CDCl₃] 0.96 (t, 3H); 1.76 (sext, 2H); 2.37 (s, 3H); 2.75 (m, 2H); 3.38 (s, 3H); 3.41 (d, 1H); 3.93 (d, 1H); 4.50 (t, 2H); 7.02 (d, 1H); 7.06 (s, 1H); 7.18 (s, 1H); 7.41 (s, 2H); 7.61 (s, 1H); 8.50 (d, 1H). |
| 1.29-152 | [CDCl₃] 2.37 (s, 3H); 3.38 (s, 3H); 3.41 (d, 1H); 3.96 (d, 1H); 4.58-4.64 (m, 2H); 7.30 (s, 1H); 7.44 (m, 3H); 7.61 (d, 2H); 8.70 (d, 1H). |
| 1.29-206 | [CDCl₃] 1.48 (t, 3H); 2.36 (s, 3H); 3.34 (s, 3H); 3.38 (d, 1 H); 3.88 (d, 1H); 4.16 (q, 2H); 4.38 (m, 2H); 6.93 (s, 1H); 7.40 (s, 3H); 7.46 (s, 1H); 7.60 (s, 1H). |
| 1.29-207 | [CDCl₃] 2.36 (s, 3H); 3.34 (s, 3H); 3.38 (d, 1H); 3.88 (d, 1H); 4.40 (t, 2H); 4.67 (q, 2H); 7.03 (s, 1H); 7.41 (m, 2H); 7.53 (s, 1H); 7.56 (s, 1H); 7.61 (s, 1H). |
| 1.29-208 | [CDCl₃] 2.36 (s, 3H); 3.34 (s, 3H); 3.35 (d, 1H); 3.85 (d, 1 H); 4.31-4.50 (m, 4H); 6.07 (tt, 1H); 6.99 (t br, 1H); 7.39 (s, 2H); 7.48 (s, 1H); 7.53 (s, 1H); 7.60 (s, 1H). |
| 1.29-212 | [CDCl₃] 1.46 (t, 3H); 2.25 (s, 3H); 2.36 (s, 3H); 3.34 (s, 3H); 3.38 (d, 1H); 3.88 (d, 1H); 4.07 (q, 2H); 4.33 (m, 2H); 6.80 (s, 1H); 7.31 (s, 1H); 7.40 (s, 2H); 7.61 (s, 1H). |

Analytical data table 1.32

| No. | NMR |
|---|---|
| 1.32-1 | [CDCl₃] 3.36 (d, 1H); 3.41 (s, 3H); 3.87 (d, 1H); 5.68 (s br, 1 H); 6.66 (s br, 1H); 7.47 (s, 1H); 7.49 (s, 1H); 7.73 (s, 1H). |
| 1.32-9 | [CDCl₃] 3.39 (s, 3H); 3.39 (d, 1H); 3.88 (d, 1H); 3.85-3.97 (m, 1H); 4.01-4.18 (m, 1H); 7.05 (t br, 1H); 7.48 (s, 1H); 7.49 (s, 1H); 7.73 (s, 1H). |
| 1.32-16 | 3.36 (d, 1H); 3.38 (s, 3H); 3.88 (d, 1H); 3.90-4.05 (m, 2H); 5.20 (d, 1H); 5.24 (d, 1H); 5.80-5.92 (m, 1H); 6.85 (s br, 1H); 7.47 (s, 1H); 7.49 (s, 1H); 7.73 (s, 1H). |
| 1.32-60 | [CDCl₃] 0.60 (m, 2H); 0.84 (m, 2H); 2.81 (m, 1H); 3.32 (d, 1H); 3.35 (s, 3H); 3.87 (d, 1H); 6.78 (s br, 1H); 7.46 (s, 1H); 7.48 (s, 1H); 7.72 (s, 1H). |

Analytical data table 1.32

| No. | NMR |
|---|---|
| 1.32-94 | [CDCl₃] 1.28 (t, 3H); 2.59 (t, 2H); 3.32 (d, 1H); 3.36 (s, 3H); 3.62 (q, 2H); 3.86 (d, 1H); 4.18 (q, 2H); 7.28 (s br, 1H); 7.46 (s, 1H); 7.48 (s, 1H); 7.73 (s, 1H). |
| 1.32-96 | [CDCl₃] 1.22-1.33 (m, 6H); 2.49-2.12 (m, 2H); 3.33 (d, 1H); 3.37 (d, 1H); 3.84 (d, 1H); 4.10-4.23 (m, 2H); 4.34-4.44 (m, 1H); 7.25 (s br, 1H); 7.46 (s, 1H); 7.49 (s, 1H); 7.73 (s, 1H). |
| 1.32-102 | [CDCl₃] 1.92 (pent, 2H); 2.40 (t, 2H); 3.35 (d, 1H); 3.40 (s, 3H); 3.35-3.44 (m, 2H); 3.69 (s, 3H); 3.87 (d, 1H); 6.92 (s br, 1H); 7.46 (s, 1H); 7.49 (s, 1H); 7.73 (s, 1H). |
| 1.32-110 | [CDCl₃] 3.34 (d, 1H); 3.37 (s, 3H); 3.92 (d, 1H); 4.46-4.59 (m, 2H); 7.15 (t br, 1H); 7.33 (d, 1H); 7.47 (s, 1H); 7.49 (s, 1H); 7.64 (d, 1H); 7.73 (s, 1H); 8.35 (s, 1H) |

Analytical data table 1.32

| No. | NMR |
|---|---|
| 1.32-136 | [CDCl₃] 3.37 (d, 1H); 3.39 (s, 3H); 3.99 (d, 1H); 4.48-4.58 (m, 2H); 7.16 (d, 1H); 7.24 (s br, 1H); 7.48 (s, 1H); 7.51 (s, 1H); 7.75 1H); 8.36 (d, 1H). |
| 1.32-206 | [CDCl₃] 1.48 (t, 3H); 3.34 (d, 1H); 3.35 (s, 3H); 3.89 (d, 1H); 4.15 (q, 2H); 4.31-4.43 (m, 2H); 6.92 (s br, 1H); 7.41 (s, 1H); 7.47 (s, 2H); 7.48 (s, 1H); 7.72 (s, 1H). |
| 1.32-212 | [CDCl₃] 1.44 (t, 3H); 2.25 (s, 3H); 3.34 (d, 1H); 3.35 (s, 3H); 3.88 (d, 1H); 4.03-4.18 (m, 2H); 4.28-4.38 (m, 2H); 6.79 (s br, 1H); 7.32 (s, 1H); 7.46 (s, 1H); 7.72 (s, 1H). |

Analytical data table 1.33

| No. | NMR |
|---|---|
| 1.33-1 | [CDCl₃] 3.40 (d, 1 H); 3.41 (s, 3 H); 3.93 (d, 1 H); 5.64 (s br, 1 H); 6.66 (s br, 1 H); 7.84 (s, 1 H); 7.85 (s, 1 H); 8.01 (s, 1 H). |
| 1.33-9 | 3.38 (s, 3 H); 3.43 (d, 1 H); 3.83-3.98 (m, 1 H); 3.42 (d, 1 H); 4.03-4.18 (m, 1 H); 7.06 (s br, 1 H);7.85 (s, 2 H); 8.01 (s, 1 H). |
| 1.33-16 | [CDCl₃] 3.38 (s, 3 H); 3.39 (d, 1 H); 3.91 (d, 1 H); 3.91-4.06 (m, 2 H); 5.20 (d, 1 H); 5.28 (d, 1 H); 5.80-5.92 (m, 1 H); 6.84 (s br, 1 H); 7.83 (s, 1 H); 7.84 (s, 1 H); 8.00 (s, 1 H). |
| 1.33-60 | [CDCl₃] 0.60 (m, 2 H); 0.84 (m, 2 H); 2.81 (m, 1 H); 3.35 (s, 3 H); 3.36 (d, 1 H); 3.91 (d, 1 H); 6.79 (s br, 1 H); 7.83 (s, 1 H); 7.84 (s, 1 H); 7.99 (s, 1 H). |
| 1.33-94 | [CDCl₃] 1.28 (t, 3 H); 2.56 ( t, 2 H); 3.37 (d, 1 H); 3.38 (s, 3 H); 3.63 (q, 2 H); 3.89 (d, 1 H); 4.18 (q, 2 H); 7.28 (s br, 1 H); 7.83 (s, 1 H); 7.84 (s, 1 H); 8.00 (s, 1 H). |
| 1.33-96 | [CDCl₃] 1.24-1.35 (m, 6 H); 2.50-2.64 (m, 2 H); 3.36 (d, 1 H); 3.38 (s, 3 H); 3.89 (d, 1 H); 4.12-4.23 (m, 2 H); 4.34-4.45 (m, 1 H); 7.27 (s br, 1 H); 7.83 (s, 1 H); 7.85 (s, 1 H); 8.00 (s, 1 H). |
| 1.33-102 | [CDCl₃] 1.92 (pent, 2 H); 2.40 it, 2 H); 3.39 (s, 3 H); 3.39 (d, 1 H); 3.39 (t, 2 H); 3.69 (s, 3 H); 3.91 (d, 1 H); 6.93 (s br, 1 H); 7.83 (s, 1 H); 7.85 (s, 1 H); 8.00 (s, 1 H). |
| 1.33-110 | [CDCl₃] 3.36 (s, 3 H); 3.38 (d, 1 H); 3.97 (d, 1 H); 4.45-4.59 (m, 2 H); 7.15 (t br, 1 H); 7.33( d, 1 H); 7.65 (dd, 1 H); 7.84 (s, 2 H); 8.00 (s, 1 H); 8.36 (d, 1 H). |
| 1.33-136 | [CDCl₃] 3.39 (s, 3 H); 3.41 (d, 1 H); 4.03 (d, 1 H); 4.49-4.59(m, 2 H); 7.17 (d, 1 H); 7.25 (s br, 1 H); 7.85 (s, 1 H); 7, 86 (s, 1 H); 8.02 (s, 1 H); 8.37 (d, 1 H). |
| 1.33-206 | [CDCl₃] 1.49 (t, 3 H); 3.35 (s, 3 H); 3.37 (d, 1 H); 3.92 (d, 1 H); 4.15 (q, 2 H); 4.32-4.43 (m, 2 H); 6.92 (s br, 1 H); 7.41 (s, 1 H); 7.46 (s, 1 H); 7.84 (s, 2 H); 8.00 (s, 1 H). |
| 1.33-212 | [CDCl₃] 1.46 (t, 3 H); 2.25 (s, 3 H); 3.35 (s, 3 H); 3.37 (d, 1 H); 3.43 (d, 1 H); 4.08 (q, 2 H); 4.26-4.38 (m, 2 H); 6.79 (s br, 1 H); 7.31 (s, 1 H); 7.83 (s, 1 H); 7.84 (s, 1 H); 8.00 (s, 1 H). |

Analytical data table 1.56

| No. | NMR |
|---|---|
| 1.56-260 | [CDCl₃] 1.26 (t, 3 H); 2.70 (q, 2 H); 3.47 (s, 3 H); 3.53 (d, 1 H); 4.03 (d, 1 H); 7.28 (d, 2 H); 7.61 (d, 2 H); 8.51 (s br, 1 H). |
| 1.56-261 | [CDCl₃] 1.26 (t, 3 H); 2.70 (q, 2 H); 3.48 (s, 3 H); 3.55 (d, 1 H); 4.01 (d, 1 H); 7.27 (d, 2 H); 7.61 (d, 2 H); 8.57 (s br, 1 H). |
| 1.56-262 | [CDCl₃] 1.26 (t, 3 H); 2.70 (q, 2 H); 3.47 (d, 1 H); 3, 48 (s, 3 H); 4.08 (d, 1 H); 7.20-7.30 (m, 2 H); 7.6-7.66 (m, 4 H); 8.44 (d, 1 H); 9.20 (s br, 1 H). |
| 1.56-263 | [CDCl₃] 1.26 (t, 3 H); 2.69 (q, 2 H); 3.45 (s, 3 H); 3.49 (d, 1 H); 4.00 (d, 1 H); 7.27 (d, 2 H); 7.62 (m, 4 H); 7.75 (d, 2 H); 8.67 (s br, 1 H). |

| Analytical data table 1.57 | |
|---|---|
| No. | NMR |
| 1.57-264 | [CDCl$_3$] 3.37 (d, 1 H); 3.60 (s, 3 H); 4.05 (d, 1 H); 7.23 (d, 2 H); 7.36 (d, 1 H); 7.51 (d, 1 H); 7.67 (d 2 H); 8.58 (s br, 1 H). |
| 1.57-265 | [CDCl$_3$] 3.36 (d, 1 H); 3.59 (s, 3 H); 4.05 (d, 1 H); 7.36 (d, 1 H); 7.45-7.56 (m, 5 H)8.53 (s br, 1 H). |

| Analytical data table 2.2 | |
|---|---|
| No. | NMR |
| 2.2-1 | [CDCl$_3$] 1.26 (t, 3 H); 3.42 (d, 1 H); 3.63 (m, 2 H); 3.86 (d, 1 H); 5.70 (s br, 1 H); 6.70 (s br, 1 H); 7.16 (m, 1 H); 7.40 (m, 3 H). |
| 2.2-9 | [CDCl$_3$] 1.25 (t, 3 H); 3.43 (d, 1 H); 3.60 (q, 2 H); 3.82 (d, 1 H); 3.90 (m, 1 H); 4.03-4.14 (m, 1 H); 7.10 (s br, 1 H); 7.13-7.18 (m, 1 H); 7.40 (m, 3 H). |
| 2.2-16 | [CDCl$_3$] 1.25 (t, 3 H); 3.40 (d, 1 H); 3.60 (m, 2 H); 3.85 (d, 1 H); 3.90-4.02 (m, 2 H); 5.17-5.27 (m, 2 H); 5.87 (m, 1 H); 6.90 (s br, 1 H); 7.17 (m, 1 H); 7.40 (m, 3 H). |
| 2.2-60 | [CDCl$_3$] 0.60 (m, 2 H); 0.82 (m, 2 H); 1.24 (t, 3 H); 2.80 (m, 2 H); 3.40 (d, 1 H); 3.58 (m, 2 H); 3.82 (d, 1 H); 6.82 (s br, 1 H); 7.15 (m, 1 H); 7.41 (m, 2 H). |
| 2.2-94 | [CDCl$_3$] 1.26 (m, 6 H); 2.59 (t, 2 H); 3.39 (d, 1 H); 3.60 (m, 4 H); 3.82 (d, 1 H); 4.18 (q, 2 H); 7.14 (m, 1 H); 7.31 (s br, 1 H); 7.40 (m, 3 H). |
| 2.2-96 | [CDCl$_3$] 1.23-1.31 (m, 9 H); 2.56 (m, 2 H); 3.40 (d, 1 H), 3.60 (m, 2 H); 3.80 (d, 1 H); 4.18 (m, 2 H); 4.40 (m, 1 H); 7.13 (m, 1 H); 7.27 (s br, 1 H); 7.40 (m, 3 H). |
| 2.2-102 | [CDCl$_3$] 1.25 (t, 3 H); 1.92 (quin, 2 H); 2.40 (t, 2 H); 3.39 (m, 3 H); 3.57 (m, 2 H); 3.70 (s, 3 H); 3.84 (d, 1 H); 6.98 (s br, 1 H); 7.16 (m, 1 H); 7.40 (m, 3 H). |
| 2.2-206 | [CDCl$_3$] 1.24 (t, 3 H); 1.48 (t, 3 H); 3.40 (d, 1 H); 3.58 (m, 2 H); 3.84 (d, 1 H); 4.16 (q, 2 H); 4.39 (d, 2 H); 6.98 (s br, 1 H); 7.12 (m, 1 H); 7.40 (m, 4 H); 7.46 (s, 1 H). |
| 2.2-212 | [CDCl$_3$] 1.23 (t, 3 H); 1.44 (m, 3 H); 2.26 (s, 3 H); 3.40 (d, 1 H); 3.58 (m, 2 H); 3.82 (d, 1 H), 4.08 (m, 2 H); 4.33 (d, 2 H); 6.85 (s br, 1 H); 7.15 (m, 1 H); 7.30 (s, 1 H); 7.40 (m, 3 H). |

| Analytical data table 2.5 | |
|---|---|
| No. | NMR |
| 2.5-9 | [CDCl$_3$] 1.25 (t, 3 H); 2.40 (s, 3 H); 3.48 (d, 1 H); 3.60 (q, 2 H); 3.83 (d, 1 H); 3.86-3.95 (m, 1 H), 4.05-4.12 (m, 1 H); 7.10 (s br, 1 H); 7.30 (m, 2 H); 7.45 (d, 1 H); 7.51 (s, 1 H). |
| 2.5-16 | [CDCl$_3$] 1.25 (t, 3 H); 2.39 (s, 3 H); 3.42 (d, 1 H); 3.61 (q, 2 H); 3.85 (d, 1 H); 3.92-4.02 (m, 2 H); 5.17-5.30 (m, 2 H); 5.82-5.92 (m, 1 H); 6.90 (s br, 1 H); 7.24-7.33 (m, 2 H); 7.44 (d, 1 H); 7.51 (s, 1 H). |
| 2.5-60 | [CDCl$_3$] 0.58 (m, 2 H); 0.84 (m, 2 H); 1.23 (t, 3 H); 2.39 (s, 3 H); 2.82 (ml H); 3.40 (d, 1 H); 3.58 (m, 2 H); 3.84 (d, 1 H); 6.85 (s br, 1 H); 7.24-7.32 (m, 2 H); 7.43 (d, 1 H); 7.50 (s, 1 H). |
| 2.5-94 | [CDCl$_3$] 1.22-1.29 (m, 6 H); 2.38 (s, 3 H); 2.61 (t, 2 H); 3.42 (d, 1 H); 3.55-3.63 (m, 4 H); 3.84 (d, 1 H); 4.19 (q, 2 H); 7.24-7.32 (m, 3 H); 7.44 (d, 1 H); 7.51 (s, 1 H). |
| 2.5-96 | [CDCl$_3$] 1.22-1.31 (m, 9 H); 2.38 (s, 3 H); 2.57 (m, 2 H); 3.40 (d, 1 H); 3.60 (m, 2 H); 3.80 (d, 1 H); 4.11-4.20 (m, 2 H); 4.43 (m, 1 H); 7.24-7.32 (m, 2 H); 7.45 (d, 1 H); 7.51 (s, 1 H). |
| 2.5-102 | [CDCl$_3$] 1.25 (t, 3 H); 1.91 (quin, 2 H); 2.39 (m, 5 H); 3.36-3.44 (m, 3 H); 3.57 (m, 2 H); 3.69 (s, 3 H); 3.84 (d, 1 H); 6.98 (s br, 1 H); 7.24-7.33 (m, 2 H); 7.45 (d, 1 H); 7.51 (s, 1 H). |
| 2.5-206 | [CDCl$_3$] 1.23 (t, 3 H); 1.48 (t, 3 H); 2.39 (s, 3 H); 3.42 (d, 1 H); 3.57 (m, 2 H); 3.83 (d, 1 H), 4.15 (q, 2 H); 4.38 (d, 2 H); 6.99 (s br, 1 H); 7.22-7.32 (m, 2 H); 7.40-7.46 (m, 3 H); 7.50 (s, 1 H). |
| 2.5-212 | [CDCl$_3$] 1.22 (t, 3 H); 1.45 (t, 3 H); 2.26 (s, 3 H); 2.39 (s, 3 H); 3.42 (d, 1 H); 3.58 (m, 2 H); 3.84 (d, 1 H); 4.07 (m, 2 H); 4.32 (d, 2 H); 6.86 (s br, 1 H); 7.22-7.30 (m, 3 H); 7.43 (m, 1 H); 7.50 (s, 1 H). |

| Analytical data table 2.11 | |
|---|---|
| No. | NMR |
| 2.11-4 | [CDCl$_3$] 0.98 (t, 3 H); 1.27 (t, 3 H); 1.62 (d, 2 H); 3.22-3.38 (m, 2 H); 3.37 (d, 1 H); 3.52-3.65 (m, 2 H); 3.80 (d, 1 H); 6.80 (s br, 1 H); 6.89 (t, 1 H); 7.19 (d, 2 H). |
| 2.11-9 | [CDCl$_3$] 1.29 (t, 3 H); 3.39 (d, 1 H); 3.53-3.65 (m, 2 H); 3.82 (d, 1 H); 3.85-3.98 (m, 1 H); 4.01-4.15 (m, 1 H); 6.90 (t, 1 H); 7.05 (t br, 1 H); 7.20 (d, 2 H). |
| 2.11-60 | [CDCl$_3$] 0.59 (t, 2 H); 0.87 (m, 2 H); 1.26 (t, 3 H); 2.81 (m, 1 H); 3.32 (d, 1 H); 3.50-3.63 (m, 2 H); 3.82 (d, 1 H); 6.80 (s br, 1 H); 6.89 (t, 1 H); 7.18 (d, 2 H). |
| 2.11-93 | [CDCl$_3$] 1.25 (t, 3 H); 2.60 (t, 2 H); 3.32 (d, 1 H); 3.50-3.60 (m, 2 H); 3.62 (q, 2 H); 3.71 (s, 3 H); 3.82 (d, 1 H); 6.89 (t, 1 H); 7.18 (d, 2 H); 7.28 (t br, 1 H). |
| 2.11-96 | [CDCl$_3$] 1.22-1.36 (m, 9 H); 2.50-2.61 (m, 2 H); 3.34 (d, 1 H); 3.53-3.65 (m, 2 H); 3.80 (d, 1 H); 4.11-4.22 (m, 2 H); 4.34-4.45 (ml H); 6.89 (t, 1 H); 7.18 (d, 2 H); 7.25 (s br, 1 H). |
| 2.11-102 | [CDCl$_3$] 1.26 (t, 3 H); 1.93 (q, 2 H); 2.40 (t, 2 H); 3.34 (d, 1 H); 3.40 (q, 2 H); 3.51-3.65 (m, 2 H); 3.69 (s, 3 H); 3.83 (d, 1 H); 6.85-6.93 (m, 1 H); 6.95 (t br, 1 H); 7.19 (d, 2 H). |
| 2.11-135 | [CDCl$_3$] 1.28 (t, 3 H); 3.38 (d, 1 H); 3.50-3.70 (m, 2 H); 3.95 (d, 1 H); 4.62 (t, 2 H); 6.90 (t, 1 H); 7.20 (d, 2 H); 7.38 (t br, 1 H); 7.45 (d, 2 H); 8.68 (d, 2 H). |
| 2.11-206 | [CDCl$_3$] 1.27 (t, 3 H); 1.49 (t, 3 H); 3.35 (d, 1 H); 3.50-3.63 (m, 2 H); 3.83 (d, 1 H); 4.15 (q, 2 H); 4.38 (d, 2 H); 6.89 (t, 1 H); 6.95 (t br, 1 H); 7.18 (d, 2 H); 7.40 (s, 1 H); 7.46 (s, 1 H). |
| 2.11-212 | [CDCl$_3$] 1.24 (t, 3 H); 1.48 (t, 3 H); 2.25 (s, 3 H); 3.35 (d, 1 H); 3.50-3.64 (m, 2 H); 3.85 (d, 1 H); 4.08 (q, 2 H); 4.34 (d, 2 H); 6.82 (t, 1 H); 6.90 (t, 1 H); 7.18 (d, 2 H); 7.32 (s, 1 H). |

| Analytical data table 2.20 | |
|---|---|
| No. | NMR |
| 2.20-4 | [CDCl$_3$] 0.96 (t, 3 H); 1.25 (t, 3 H); 1.55-1.64 (m, 2 H); 3.23-3.35 (m, 2 H); 3.34 (d, 1 H); 3.51-3.65 (m, 2 H); 3.80 (d, 1 H); 6.79 (t br, 1 H); 7.43 (s, 1 H); 7.55 (s, 2 H). |
| 2.20-9 | [CDCl$_3$] 1.27 (t, 3 H); 3.39 (d, 1 H); 3.52-3.65 (m, 2 H); 3.83 (d, 1 H); 3.83-3.97 (m, 1 H); 4.01-4.18 (m, 1 H); 7.05 (t br, 1 H); 7.44 (s, 1 H); 7.55 (s, 2 H). |
| 2.20-60 | [CDCl$_3$] 0.60 (m, 2 H); 0.85 (m, 2 H); 1.24 (t, 3 H); 2.80 (m, 1 H); 3.32 (d, 1 H); 3.50-3.63 (m, 2 H); 3.84 (d, 1 H); 6.80 (s br, 1 H); 7.42 (s, 1 H); 7.54 (s, 2 H). |
| 2.20-93 | [CDCl$_3$] 1.25 (t, 3 H); 2.61 (t, 2 H); 3.36 (d, 1 H); 3.50-3.65 (m, 4 H); 3.72 (s, 3 H); 3.83 (d, 1 H); 7.30 (t br, 1 H); 7.42 (s, 1 H); 7.55 (d, 2 H). |
| 2.20-96 | [CDCl$_3$] 1.23-1.31 (m, 9 H); 2.55 (m, 2 H); 3.31 (d, 1 H); 3.57 (m, 2 H); 3.80 (d, 1 H); 4.14 (m, 2 H); 4.39 (m, 1 H); 7.28 (s br, 1 H); 7.42 (s, 1 H); 7.55 (s, 2 H). |
| 2.20-102 | [CDCl$_3$] 1.26 (t, 3 H); 1.92 (quin, 2 H); 2.40 (t, 2 H); 3.32 (d, 1 H); 3.39 (q, 2 H); 3.50-3.64 (m, 2 H); 3.69 (s, 3 H); 3.83 (d, 1 H); 6.96 (t br, 1 H); 7.43 (s, 1 H); 7.55 (s, 2 H). |
| 2.20-135 | [CDCl$_3$] 1.27 (t, 3 H); 3.39 (d, 1 H); 3.52-3.67 (m, 2 H); 3.93 (d, 1 H); 4.55 (d, 2 H); 7.23 (m, 3 H); 7.44 (s, 1 H); 7.56 (s, 2 H); 8.60 (d, 2 H). |
| 2.20-206 | [CDCl$_3$] 1.25 (t, 3 H); 1.50 (t, 3 H); 3.34 (d, 1 H); 3.50-3.64 (m, 2 H); 3.85 (d, 1 H); 4.15 (q, 2 H); 4.38 (d, 2 H); 6.95 (t br, 1 H); 7.40 (s, 1 H); 7.44 (s, 1 H); 7.48 (s, 1 H); 7.55 (s, 2 H). |
| 2.20-212 | [CDCl$_3$] 1.23 (t, 3 H); 1.43 (t, 3 H); 2.26 (s, 3 H); 3.34 (d, 1 H); 3.48-3.64 (m, 2 H); 3.83 (d, 1 H); 4.08 (q, 2 H); 4.33 (d, 2 H); 6.82 (s br, 1 H); 7.32 (s, 1 H); 7.42 (s, 1 H); 7.54 (s, 2 H). |

| Analytical data table 3.11 | |
|---|---|
| No. | NMR |
| 3.11-9 | [CDCl$_3$] 3.41 (s, 3 H); 3.57 (d, 1 H), 4.08 (d, 1 H); 4.34 (m, 1 H); 4.62 (m, 1 H); 6.91 (m, 1 H); 7.20 (m, 2 H); 8.70 (s br, 1 H). |
| 3.11-60 | [CDCl$_3$] 0.73 (m, 2 H); 1.01 (m, 2 H); 3.30 (m, 1 H); 3.38 (s, 3 H); 3.54 (d, 1 H); 4.10 (d, 1 H); 6.90 (m, 1 H); 7.19 (m, 2 H); 8.50 (s br, 1 H). |
| 3.11-93 | [CDCl$_3$] 2.76 (m, 2 H); 3.38 (s, 3 H); 3.51 (d, 1 H); 3.73 (s, 3 H); 4.02 (m, 2 H); 4.10 (d, 1 H), 6.90 (m, 1 H); 7.20 (m, 2 H); 9.12 (s br, 1 H). |

-continued

Analytical data table 3.11

| No. | NMR |
|---|---|
| 3.11-212 | [CDCl$_3$] 1.47 (t, 3 H); 2.25 (s, 3 H); 3.38 (s, 3 H); 3.55 (d, 1 H); 4.09-4.14 (m, 3 H); 4.63 (m, 2 H); 6.90 (m, 1 H); 7.19 (m, 2 H); 7.39 (s, 1 H); 8.50 (s br, 1 H). |

Table A describes compounds of the general formula (II) in which R$^1$ and R$^2$ are each hydrogen, and the X$^2$, X$^3$, X$^4$, X$^5$, X$^6$, R$^3$ and V radicals are each as defined in the table.

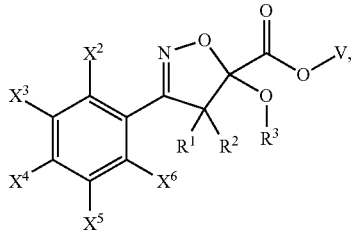

(II)

TABLE A

| No. | X$^2$ | X$^3$ | X$^4$ | X$^5$ | X$^6$ | R$^3$ | V |
|---|---|---|---|---|---|---|---|
| A-1 | H | H | H | H | H | Me | H |
| A-2 | H | H | H | H | H | Me | Me |
| A-3 | H | H | H | H | H | Me | Et |
| A-4 | H | H | H | H | H | Et | H |
| A-5 | H | H | H | H | H | Et | Me |
| A-6 | H | H | H | H | H | Et | Et |
| A-7 | H | H | H | F | H | Me | H |
| A-8 | H | H | H | F | H | Me | Me |
| A-9 | H | H | H | F | H | Me | Et |
| A-10 | H | H | H | F | H | Et | H |
| A-11 | H | H | H | F | H | Et | Me |
| A-12 | H | H | H | F | H | Et | Et |
| A-13 | H | H | H | Cl | H | Me | H |
| A-14 | H | H | H | Cl | H | Me | Me |
| A-15 | H | H | H | Cl | H | Me | Et |
| A-16 | H | H | H | Cl | H | Et | H |
| A-17 | H | H | H | Cl | H | Et | Me |
| A-18 | H | H | H | Cl | H | Et | Et |
| A-19 | H | H | H | Br | H | Me | H |
| A-20 | H | H | H | Br | H | Me | Me |
| A-21 | H | H | H | Br | H | Me | Et |
| A-22 | H | H | H | Br | H | Et | H |
| A-23 | H | H | H | Br | H | Et | Me |
| A-24 | H | H | H | Br | H | Et | Et |
| A-25 | H | H | H | Me | H | Me | H |
| A-26 | H | H | H | Me | H | Me | Me |
| A-27 | H | H | H | Me | H | Me | Et |
| A-28 | H | H | H | Me | H | Et | H |
| A-29 | H | H | H | Me | H | Et | Me |
| A-30 | H | H | H | Me | H | Et | Et |
| A-31 | H | H | H | Et | H | Me | H |
| A-32 | H | H | H | Et | H | Me | Me |
| A-33 | H | H | H | Et | H | Me | Et |
| A-34 | H | H | H | Et | H | Et | H |
| A-35 | H | H | H | Et | H | Et | Me |
| A-36 | H | H | H | Et | H | Et | Et |
| A-37 | H | H | H | OMe | H | Me | H |
| A-38 | H | H | H | OMe | H | Me | Me |
| A-39 | H | H | H | OMe | H | Me | Et |
| A-40 | H | H | H | OMe | H | Et | H |
| A-41 | H | H | H | OMe | H | Et | Me |
| A-42 | H | H | H | OMe | H | Et | Et |
| A-43 | H | H | H | OCF$_3$ | H | Me | H |
| A-44 | H | H | H | OCF$_3$ | H | Me | Me |
| A-45 | H | H | H | OCF$_3$ | H | Me | Et |
| A-46 | H | H | H | OCF$_3$ | H | Et | H |
| A-47 | H | H | H | OCF$_3$ | H | Et | Me |
| A-48 | H | H | H | OCF$_3$ | H | Et | Et |
| A-49 | H | H | H | CF$_3$ | H | Me | H |
| A-50 | H | H | H | CF$_3$ | H | Me | Me |
| A-51 | H | H | H | CF$_3$ | H | Me | Et |
| A-52 | H | H | H | CF$_3$ | H | Et | H |
| A-53 | H | H | H | CF$_3$ | H | Et | Me |
| A-54 | H | H | H | CF$_3$ | H | Et | Et |
| A-55 | H | H | H | CN | H | Me | H |
| A-56 | H | H | H | CN | H | Me | Me |
| A-57 | H | H | H | CN | H | Me | Et |
| A-58 | H | H | H | CN | H | Et | H |
| A-59 | H | H | H | CN | H | Et | Me |
| A-60 | H | H | H | CN | H | Et | Et |
| A-61 | H | F | H | F | H | Me | H |
| A-62 | H | F | H | F | H | Me | Me |
| A-63 | H | F | H | F | H | Me | Et |
| A-64 | H | F | H | F | H | Et | H |
| A-65 | H | F | H | F | H | Et | Me |
| A-66 | H | F | H | F | H | Et | Et |
| A-67 | H | F | H | Cl | H | Me | H |
| A-68 | H | F | H | Cl | H | Me | Me |
| A-69 | H | F | H | Cl | H | Me | Et |
| A-70 | H | F | H | Cl | H | Et | H |
| A-71 | H | F | H | Cl | H | Et | Me |
| A-72 | H | F | H | Cl | H | Et | Et |
| A-73 | H | F | H | Br | H | Me | H |
| A-74 | H | F | H | Br | H | Me | Me |
| A-75 | H | F | H | Br | H | Me | Et |
| A-76 | H | F | H | Br | H | Et | H |
| A-77 | H | F | H | Br | H | Et | Me |
| A-78 | H | F | H | Br | H | Et | Et |
| A-79 | H | F | H | Me | H | Me | H |
| A-80 | H | F | H | Me | H | Me | Me |
| A-81 | H | F | H | Me | H | Me | Et |
| A-82 | H | F | H | Me | H | Et | H |
| A-83 | H | F | H | Me | H | Et | Me |
| A-84 | H | F | H | Me | H | Et | Et |
| A-85 | H | F | H | Et | H | Me | H |
| A-86 | H | F | H | Et | H | Me | Me |
| A-87 | H | F | H | Et | H | Me | Et |
| A-88 | H | F | H | Et | H | Et | H |
| A-89 | H | F | H | Et | H | Et | Me |
| A-90 | H | F | H | Et | H | Et | Et |
| A-91 | H | F | H | OMe | H | Me | H |
| A-92 | H | F | H | OMe | H | Me | Me |
| A-93 | H | F | H | OMe | H | Me | Et |
| A-94 | H | F | H | OMe | H | Et | H |
| A-95 | H | F | H | OMe | H | Et | Me |
| A-96 | H | F | H | OMe | H | Et | Et |
| A-97 | H | F | H | OCF$_3$ | H | Me | H |
| A-98 | H | F | H | OCF$_3$ | H | Me | Me |
| A-99 | H | F | H | OCF$_3$ | H | Me | Et |
| A-100 | H | F | H | OCF$_3$ | H | Et | H |
| A-101 | H | F | H | OCF$_3$ | H | Et | Me |
| A-102 | H | F | H | OCF$_3$ | H | Et | Et |
| A-103 | H | F | H | CF$_3$ | H | Me | H |
| A-104 | H | F | H | CF$_3$ | H | Me | Me |
| A-105 | H | F | H | CF$_3$ | H | Me | Et |

TABLE A-continued

| Intermediate No. | $X^2$ | $X^3$ | $X^4$ | $X^5$ | $X^6$ | $R^3$ | V |
|---|---|---|---|---|---|---|---|
| A-106 | H | F | H | CF$_3$ | H | Et | H |
| A-107 | H | F | H | CF$_3$ | H | Et | Me |
| A-108 | H | F | H | CF$_3$ | H | Et | Et |
| A-109 | H | F | H | CN | H | Me | H |
| A-110 | H | F | H | CN | H | Me | Me |
| A-111 | H | F | H | CN | H | Me | Et |
| A-112 | H | F | H | CN | H | Et | H |
| A-113 | H | F | H | CN | H | Et | Me |
| A-114 | H | F | H | CN | H | Et | Et |
| A-115 | H | Cl | H | Cl | H | Me | H |
| A-116 | H | Cl | H | Cl | H | Me | Me |
| A-117 | H | Cl | H | Cl | H | Me | Et |
| A-118 | H | Cl | H | Cl | H | Et | H |
| A-119 | H | Cl | H | Cl | H | Et | Me |
| A-120 | H | Cl | H | Cl | H | Et | Et |
| A-121 | H | Cl | H | Br | H | Me | H |
| A-122 | H | Cl | H | Br | H | Me | Me |
| A-123 | H | Cl | H | Br | H | Me | Et |
| A-124 | H | Cl | H | Br | H | Et | H |
| A-125 | H | Cl | H | Br | H | Et | Me |
| A-126 | H | Cl | H | Br | H | Et | Et |
| A-127 | H | Cl | H | Me | H | Me | H |
| A-128 | H | Cl | H | Me | H | Me | Me |
| A-129 | H | Cl | H | Me | H | Me | Et |
| A-130 | H | Cl | H | Me | H | Et | H |
| A-131 | H | Cl | H | Me | H | Et | Me |
| A-132 | H | Cl | H | Me | H | Et | Et |
| A-133 | H | Cl | H | Et | H | Me | H |
| A-134 | H | Cl | H | Et | H | Me | Me |
| A-135 | H | Cl | H | Et | H | Me | Et |
| A-136 | H | Cl | H | Et | H | Et | H |
| A-137 | H | Cl | H | Et | H | Et | Me |
| A-138 | H | Cl | H | Et | H | Et | Et |
| A-139 | H | Cl | H | OMe | H | Me | H |
| A-140 | H | Cl | H | OMe | H | Me | Me |
| A-141 | H | Cl | H | OMe | H | Me | Et |
| A-142 | H | Cl | H | OMe | H | Et | H |
| A-143 | H | Cl | H | OMe | H | Et | Me |
| A-144 | H | Cl | H | OMe | H | Et | Et |
| A-145 | H | Cl | H | OCF$_3$ | H | Me | H |
| A-146 | H | Cl | H | OCF$_3$ | H | Me | Me |
| A-147 | H | Cl | H | OCF$_3$ | H | Me | Et |
| A-148 | H | Cl | H | OCF$_3$ | H | Et | H |
| A-149 | H | Cl | H | OCF$_3$ | H | Et | Me |
| A-150 | H | Cl | H | OCF$_3$ | H | Et | Et |
| A-151 | H | Cl | H | CF$_3$ | H | Me | H |
| A-152 | H | Cl | H | CF$_3$ | H | Me | Me |
| A-153 | H | Cl | H | CF$_3$ | H | Me | Et |
| A-154 | H | Cl | H | CF$_3$ | H | Et | H |
| A-155 | H | Cl | H | CF$_3$ | H | Et | Me |
| A-156 | H | Cl | H | CF$_3$ | H | Et | Et |
| A-157 | H | Cl | H | CN | H | Me | H |
| A-158 | H | Cl | H | CN | H | Me | Me |
| A-159 | H | Cl | H | CN | H | Me | Et |
| A-160 | H | Cl | H | CN | H | Et | H |
| A-161 | H | Cl | H | CN | H | Et | Me |
| A-162 | H | Cl | H | CN | H | Et | Et |
| A-163 | H | Br | H | Br | H | Me | H |
| A-164 | H | Br | H | Br | H | Me | Me |
| A-165 | H | Br | H | Br | H | Me | Et |
| A-166 | H | Br | H | Br | H | Et | H |
| A-167 | H | Br | H | Br | H | Et | Me |
| A-168 | H | Br | H | Br | H | Et | Et |
| A-169 | H | Br | H | Me | H | Me | H |
| A-170 | H | Br | H | Me | H | Me | Me |
| A-171 | H | Br | H | Me | H | Me | Et |
| A-172 | H | Br | H | Me | H | Et | H |
| A-173 | H | Br | H | Me | H | Et | Me |
| A-174 | H | Br | H | Me | H | Et | Et |
| A-175 | H | Br | H | Et | H | Me | H |
| A-176 | H | Br | H | Et | H | Me | Me |
| A-177 | H | Br | H | Et | H | Me | Et |
| A-178 | H | Br | H | Et | H | Et | H |
| A-179 | H | Br | H | Et | H | Et | Me |
| A-180 | H | Br | H | Et | H | Et | Et |
| A-181 | H | Br | H | OMe | H | Me | H |
| A-182 | H | Br | H | OMe | H | Me | Me |
| A-183 | H | Br | H | OMe | H | Me | Et |
| A-184 | H | Br | H | OMe | H | Et | H |
| A-185 | H | Br | H | OMe | H | Et | Me |
| A-186 | H | Br | H | OMe | H | Et | Et |
| A-187 | H | Br | H | OCF$_3$ | H | Me | H |
| A-188 | H | Br | H | OCF$_3$ | H | Me | Me |
| A-189 | H | Br | H | OCF$_3$ | H | Me | Et |
| A-190 | H | Br | H | OCF$_3$ | H | Et | H |
| A-191 | H | Br | H | OCF$_3$ | H | Et | Me |
| A-192 | H | Br | H | OCF$_3$ | H | Et | Et |
| A-193 | H | Br | H | CF$_3$ | H | Me | H |
| A-194 | H | Br | H | CF$_3$ | H | Me | Me |
| A-195 | H | Br | H | CF$_3$ | H | Me | Et |
| A-196 | H | Br | H | CF$_3$ | H | Et | H |
| A-197 | H | Br | H | CF$_3$ | H | Et | Me |
| A-198 | H | Br | H | CF$_3$ | H | Et | Et |
| A-199 | H | Br | H | CN | H | Me | H |
| A-200 | H | Br | H | CN | H | Me | Me |
| A-201 | H | Br | H | CN | H | Me | Et |
| A-202 | H | Br | H | CN | H | Et | H |
| A-203 | H | Br | H | CN | H | Et | Me |
| A-204 | H | Br | H | CN | H | Et | Et |
| A-205 | H | Me | H | Me | H | Me | H |
| A-206 | H | Me | H | Me | H | Me | Me |
| A-207 | H | Me | H | Me | H | Me | Et |
| A-208 | H | Me | H | Me | H | Et | H |
| A-209 | H | Me | H | Me | H | Et | Me |
| A-210 | H | Me | H | Me | H | Et | Et |
| A-211 | H | Me | H | Et | H | Me | H |
| A-212 | H | Me | H | Et | H | Me | Me |
| A-213 | H | Me | H | Et | H | Me | Et |
| A-214 | H | Me | H | Et | H | Et | H |
| A-215 | H | Me | H | Et | H | Et | Me |
| A-216 | H | Me | H | Et | H | Et | Et |
| A-217 | H | Me | H | OMe | H | Me | H |
| A-218 | H | Me | H | OMe | H | Me | Me |
| A-219 | H | Me | H | OMe | H | Me | Et |
| A-220 | H | Me | H | OMe | H | Et | H |
| A-221 | H | Me | H | OMe | H | Et | Me |
| A-222 | H | Me | H | OMe | H | Et | Et |
| A-223 | H | Me | H | OCF$_3$ | H | Me | H |
| A-224 | H | Me | H | OCF$_3$ | H | Me | Me |
| A-225 | H | Me | H | OCF$_3$ | H | Me | Et |
| A-226 | H | Me | H | OCF$_3$ | H | Et | H |
| A-227 | H | Me | H | OCF$_3$ | H | Et | Me |
| A-228 | H | Me | H | OCF$_3$ | H | Et | Et |
| A-229 | H | Me | H | CF$_3$ | H | Me | H |
| A-230 | H | Me | H | CF$_3$ | H | Me | Me |
| A-231 | H | Me | H | CF$_3$ | H | Me | Et |
| A-232 | H | Me | H | CF$_3$ | H | Et | H |
| A-233 | H | Me | H | CF$_3$ | H | Et | Me |
| A-234 | H | Me | H | CF$_3$ | H | Et | Et |
| A-235 | H | Me | H | CN | H | Me | H |
| A-236 | H | Me | H | CN | H | Me | Me |
| A-237 | H | Me | H | CN | H | Me | Et |
| A-238 | H | Me | H | CN | H | Et | H |
| A-239 | H | Me | H | CN | H | Et | Me |
| A-240 | H | Me | H | CN | H | Et | Et |
| A-241 | H | Et | H | Et | H | Me | H |
| A-242 | H | Et | H | Et | H | Me | Me |
| A-243 | H | Et | H | Et | H | Me | Et |
| A-244 | H | Et | H | Et | H | Et | H |
| A-245 | H | Et | H | Et | H | Et | Me |
| A-246 | H | Et | H | Et | H | Et | Et |
| A-247 | H | Et | H | OMe | H | Me | H |
| A-248 | H | Et | H | OMe | H | Me | Me |
| A-249 | H | Et | H | OMe | H | Me | Et |
| A-250 | H | Et | H | OMe | H | Et | H |
| A-251 | H | Et | H | OMe | H | Et | Me |
| A-252 | H | Et | H | OMe | H | Et | Et |
| A-253 | H | Et | H | OCF$_3$ | H | Me | H |
| A-254 | H | Et | H | OCF$_3$ | H | Me | Me |
| A-255 | H | Et | H | OCF$_3$ | H | Me | Et |
| A-256 | H | Et | H | OCF$_3$ | H | Et | H |
| A-257 | H | Et | H | OCF$_3$ | H | Et | Me |

TABLE A-continued

| No. | X² | X³ | X⁴ | X⁵ | X⁶ | R³ | V |
|---|---|---|---|---|---|---|---|
| A-258 | H | Et | H | OCF₃ | H | Et | Et |
| A-259 | H | Et | H | CF₃ | H | Me | H |
| A-260 | H | Et | H | CF₃ | H | Me | Me |
| A-261 | H | Et | H | CF₃ | H | Me | Et |
| A-262 | H | Et | H | CF₃ | H | Et | H |
| A-263 | H | Et | H | CF₃ | H | Et | Me |
| A-264 | H | Et | H | CF₃ | H | Et | Et |
| A-265 | H | Et | H | CN | H | Me | H |
| A-266 | H | Et | H | CN | H | Me | Me |
| A-267 | H | Et | H | CN | H | Me | Et |
| A-268 | H | Et | H | CN | H | Et | H |
| A-269 | H | Et | H | CN | H | Et | Me |
| A-270 | H | Et | H | CN | H | Et | Et |
| A-271 | H | OMe | H | OMe | H | Me | H |
| A-272 | H | OMe | H | OMe | H | Me | Me |
| A-273 | H | OMe | H | OMe | H | Me | Et |
| A-274 | H | OMe | H | OMe | H | Et | H |
| A-275 | H | OMe | H | OMe | H | Et | Me |
| A-276 | H | OMe | H | OMe | H | Et | Et |
| A-277 | H | OMe | H | OCF₃ | H | Me | H |
| A-278 | H | OMe | H | OCF₃ | H | Me | Me |
| A-279 | H | OMe | H | OCF₃ | H | Me | Et |
| A-280 | H | OMe | H | OCF₃ | H | Et | H |
| A-281 | H | OMe | H | OCF₃ | H | Et | Me |
| A-282 | H | OMe | H | OCF₃ | H | Et | Et |
| A-283 | H | OMe | H | CF₃ | H | Me | H |
| A-284 | H | OMe | H | CF₃ | H | Me | Me |
| A-285 | H | OMe | H | CF₃ | H | Me | Et |
| A-286 | H | OMe | H | CF₃ | H | Et | H |
| A-287 | H | OMe | H | CF₃ | H | Et | Me |
| A-288 | H | OMe | H | CF₃ | H | Et | Et |
| A-289 | H | OMe | H | CN | H | Me | H |
| A-290 | H | OMe | H | CN | H | Me | Me |
| A-291 | H | OMe | H | CN | H | Me | Et |
| A-292 | H | OMe | H | CN | H | Et | H |
| A-293 | H | OMe | H | CN | H | Et | Me |
| A-294 | H | OMe | H | CN | H | Et | Et |
| A-295 | H | OCF₃ | H | OCF₃ | H | Me | H |
| A-296 | H | OCF₃ | H | OCF₃ | H | Me | Me |
| A-297 | H | OCF₃ | H | OCF₃ | H | Me | Et |
| A-298 | H | OCF₃ | H | OCF₃ | H | Et | H |
| A-299 | H | OCF₃ | H | OCF₃ | H | Et | Me |
| A-300 | H | OCF₃ | H | OCF₃ | H | Et | Et |
| A-301 | H | OCF₃ | H | CF₃ | H | Me | H |
| A-302 | H | OCF₃ | H | CF₃ | H | Me | Me |
| A-303 | H | OCF₃ | H | CF₃ | H | Me | Et |
| A-304 | H | OCF₃ | H | CF₃ | H | Et | H |
| A-305 | H | OCF₃ | H | CF₃ | H | Et | Me |
| A-306 | H | OCF₃ | H | CF₃ | H | Et | Et |
| A-307 | H | OCF₃ | H | CN | H | Me | H |
| A-308 | H | OCF₃ | H | CN | H | Me | Me |
| A-309 | H | OCF₃ | H | CN | H | Me | Et |
| A-310 | H | OCF₃ | H | CN | H | Et | H |
| A-311 | H | OCF₃ | H | CN | H | Et | Me |
| A-312 | H | OCF₃ | H | CN | H | Et | Et |
| A-313 | H | CF₃ | H | CF₃ | H | Me | H |
| A-314 | H | CF₃ | H | CF₃ | H | Me | Me |
| A-315 | H | CF₃ | H | CF₃ | H | Me | Et |
| A-316 | H | CF₃ | H | CF₃ | H | Et | H |
| A-317 | H | CF₃ | H | CF₃ | H | Et | Me |
| A-318 | H | CF₃ | H | CF₃ | H | Et | Et |
| A-319 | H | CF₃ | H | CN | H | Me | H |
| A-320 | H | CF₃ | H | CN | H | Me | Me |
| A-321 | H | CF₃ | H | CN | H | Me | Et |
| A-322 | H | CF₃ | H | CN | H | Et | H |
| A-323 | H | CF₃ | H | CN | H | Et | Me |
| A-324 | H | CF₃ | H | CN | H | Et | Et |
| A-325 | H | CN | H | CN | H | Me | H |
| A-326 | H | CN | H | CN | H | Me | Me |
| A-327 | H | CN | H | CN | H | Me | Et |
| A-328 | H | CN | H | CN | H | Et | H |
| A-329 | H | CN | H | CN | H | Et | Me |
| A-330 | H | CN | H | CN | H | Et | Et |
| A-331 | H | H | Et | H | H | Me | H |
| A-332 | H | H | Et | H | H | Me | Me |
| A-333 | H | H | Et | H | H | Me | Et |
| A-334 | Cl | Cl | H | H | Cl | Me | H |
| A-335 | Cl | Cl | H | H | Cl | Me | Me |
| A-336 | Cl | Cl | H | H | Cl | Me | Et |

Analytical data table A:

| No. | NMR |
|---|---|
| A-1 | [CDCl₃] 3.50 (s, 3 H); 3.50-3.55 (d, 1 H), 3.90 (d, 1 H), 7.45 (m, 3 H); 7.68 (m, 2 H). |
| A-2 | [CDCl₃] 3.48 (d, 1 H); 3.48 (s, 3 H); 3.83 (d, 1 H); 3.89 (s, 3 H); 7.42 (m, 3 H); 7.68 (m, 2 H). |
| A-7 | [CDCl₃] 3.49 (d, 1 H); 3.51 (s, 3 H); 3.90 (d, 1 H); 7.18 (m, 1 H); 7.42-7.51 (m, 2 H); 7.60 (m, 1 H). |
| A-8 | [CDCl₃] 3.45 (d, 1 H), 3.48 (s, 3 H); 3.80 (d, 1 H); 3.89 (s, 3 H); 7.16 (m, 1 H); 7.37-7.43 (m, 3 H). |
| A-10 | [CDCl₃] 1.27 (m, 3 H); 3.50 (d, 1 H); 3.77 (q, 2 H); 3.88 (d, 1 H), 5.74 (s br, 1 H); 7.16 (m, 1 H), 7.40 (m, 2 H); 7.60 (m, 1 H). |
| A-12 | [CDCl₃] 1.23 (t, 3 H); 1.36 (t, 3 H); 3.42 (d, 1 H); 3.70-3.85 (m, 3 H); 4.34 (m, 2 H); 7.13 (m, 1 H); 7.40 (m, 3 H). |
| A-13 | [CDCl₃] 3.49 (d, 1 H); 3.50 (s, 3 H), 3.89 (d, 1 H); 7.39 (t, 1 H); 7.42 (d, 1 H); 7.56 (d, 1 H); 7.69 (s, 1 H). |
| A-14 | [CDCl₃] 3.43 (d, 1 H); 3.48 (s, 3 H); 3.80 (d, 1 H); 3.89 (s, 3 H); 7.37 (t, 1 H); 7.41 (m, 1 H); 7.54 (m, 1 H); 7.67 (m, 1 H). |
| A-25 | [CDCl₃] 2.39 (s, 3 H); 3.50 (s, 3 H); 3.54 (d, 1 H); 3.88 (d, 1 H); 7.30-7.68 (m, 4 H). |
| A-26 | [CDCl₃] 2.38 (s, 3 H); 3.47 (s, 3 H); 3.44-3.49 (d, 1 H); 3.83 (d, 1 H); 3.89 (s, 3 H); 7.25-7.33 (m, 2 H), 7.45 (d, 1 H); 7.51 (s, 1 H). |
| A-30 | [CDCl₃] 1.22 (t, 3 H); 1.35 (t, 3 H); 2.39 (s, 3 H); 3.49 (d, 1 H); 3.70-3.81 (m, 3 H); 4.33 (m, 2 H); 7.24-7.32 (m, 2 H), 7.45 (d, 1 H); 7.52 (s, 1 H). |
| A-31 | [CDCl₃] 1.25 (m, 3 H); 2.69 (q, 2 H), 3.49 (s, 3 H); 3.50 (d, 1 H); 3.90 (d, 1 H); 7.30 (d, 1 H); 7.33 (t, 1 H); 7.46 (d, 1 H); 7.54 (s, 1 H). |
| A-32 | [CDCl₃] 1.25 (t, 3 H); 2.68 (q, 2 H); 3.45-3.50 (d, 1 H); 3.47 (s, 3 H); 3.83 (d, 1 H); 3.88 (s, 3 H); 7.26-7.35 (m, 2 H); 7.45 (d, 1 H); 7.54 (s, 1 H). |

-continued

| Analytical data table A: | |
|---|---|
| No. | NMR |

A-36 [CDCl₃] 1.23 (m, 6 H); 1.35 (t, 3 H); 2.68 (q, 2 H); 3.49 (d, 1 H); 3.70-3.85 (m, 3 H); 4.43 (m, 2 H); 7.29-7.35 (m, 2 H); 7.45 (d, 1 H); 7.55 (s, 1 H).

A-37 [CDCl₃] 3.50 (s, 3 H); 3.51 (d, 1 H); 3.83 (s, 3 H); 3.90 (d, 1 H); 7.01 (d, 1 H); 7.19 (d, 1 H); 7.28 (s, 1 H); 7.33 (t, 1 H).

A-38 [CDCl₃] 3.44 (d, 1 H); 3.48 (s, 3 H); 3.79-3.87 (d, 1 H); 3.84 (s, 3 H); 3.89 (s, 3 H); 6.99 (d, 1 H); 7.17 (d, 1 H); 7.26-7.34 (m, 2 H).

A-42 [CDCl₃] 1.23 (t, 3 H); 1.36 (t, 3 H), 3.44 (d, 1 H); 3.70-3.80 (m, 3 H); 3.82 (s, 3 H); 4.32 (m, 2 H); 6.99 (d, 1 H); 7.19 (d, 1 H); 7.28-7.34 (m, 2 H).

A-62 [CDCl₃] 3.40 (d, 1 H); 3.48 (s, 3 H); 3.78 (d, 1 H); 3.89 (s, 3 H); 6.90 (t, 1 H); 7.20 (d, 2 H).

A-61 [CDCl₃] 3.45 (d, 1 H); 3.51 (s, 3 H); 3.86 (d, 1 H); 6.91 (m, 1 H); 7.21 (m, 2 H).

A-64 [CDCl₃] 1.27 (t, 3 H); 3.45 (d, 1 H), 3.75 (q, 2 H); 3.83 (d, 1 H); 6.90 (m, 1 H); 7.20 (m, 2 H).

A-66 [CDCl₃] 1.23 (t, 3 H); 1.34 (t, 3 H); 3.40 (d, 1 H); 3.70-3.77 (m, 2 H); 3.82 (m, 1 H); 4.35 (m, 2 H); 6.89 (m, 1 H); 7.20 (m, 2 H).

A-79 [CDCl₃] 2.39 (s, 3 H); 3.46 (d, 1 H); 3.49 (s, 3 H); 3.88 (d, 1 H); 6.99 (d, 1 H), 7.20 (d, 1 H); 7.25 (s, 1 H).

A-80 [CDCl₃] 2.38 (s, 3 H); 3.43 (d, 1 H), 3.47 (s, 3 H); 3.80 (d, 1 H); 3.90 (s, 3 H); 6.97 (d, 1 H); 7.19 (d, 1 H); 7.26 (s, 1 H).

A-84 [CDCl₃] 1.22 (t, 3 H); 1.35 (t, 3 H); 2.39 (s, 3 H); 3.42 (d, 1 H); 3.72 (m, 2 H); 3.80 (quin, 1 H); 4.33 (m, 2 H); 6.97 (d, 1 H); 7.20 (d, 1 H), 7.26 (s, 1 H).

A-91 [CDCl₃] 3.47 (d, 1 H); 3.50 (s, 3 H); 3.83 (s, 3 H); 3.85 (d, 1 H); 6.71 (d, 1 H); 6.96 (d, 1 H); 7.02 (s, 1 H).

A-92 [CDCl₃] 3.40 (d, 1 H); 3.48 (s, 3 H); 3.78 (d, 1 H); 3.83 (s, 3 H); 3.89 (s, 3 H); 6.70 (d, 1 H); 6.94 (d, 1 H); 7.02 (s, 1 H).

A-103 [CDCl₃] 3.46-3.51 (d, 1 H); 3.51 (s, 3 H); 3.92 (d, 1 H); 7.42 (d, 1 H); 7.61 (d, 1 H); 7.69 (s, 1 H).

A-104 [CDCl₃] 3.45 (d, 1 H); 3.50 (s, 3 H); 3.83 (d, 1 H); 3.90 (s, 3 H); 7.40 (d, 1 H); 7.60 (d, 1 H), 7.68 (s, 1 H).

A-115 [CDCl₃] 3.35 (d, 1 H); 3.41 (s, 3 H); 3.78 (d, 1 H); 7.38 (s, 1 H); 7.48 (s, 2 H).

A-116 [CDCl₃] 3.40 (d, 1 H); 3.48 (s, 3 H); 3.78 (d, 1 H); 3.89 (s, 3 H); 7.43 (s, 1 H); 7.55 (s, 2 H).

A-118 [CDCl₃] 1.27 (t, 3 H), 3.45 (d, 1 H); 3.75 (q, 2 H); 3.85 (d, 1 H); 7.45 (s, 1 H); 7.56 (s, 2 H).

A-120 [CDCl₃] 1.23 (t, 3 H); 1.37 (t, 3 H); 3.40 (d, 1 H); 3.70-3.82 (m, 3 H); 4.35 (m, 2 H); 7.43 (s, 1 H); 7.56 (s, 2 H).

A-145 [CDCl₃] 3.45 (d, 1 H); 3.50 (s, 3 H); 3.87 (d, 1 H); 7.33 (s, 1 H); 7.46 (s, 1 H); 7.59 (s, 1 H).

A-146 [CDCl₃] 3.41 0, 1 H); 3.49 (s, 3 H); 3.80 0, 1 H); 3.89 (s, 3 H); 7.31 (s, 1 H); 7.45 (s, 1 H); 7.58 (s, 1 H).

A-169 [CDCl₃] 2.37 (s, 3 H), 3.47 (d, 1 H); 3.48 (s, 3 H); 3.87 (d, 1 H); 7.43 (s, 2 H); 7.61 (s, 1 H).

A-170 [CDCl₃] 2.36 (s, 3 H); 3.41 (d, 1 H); 3.47 (s, 3 H), 3.79 (d, 1 H); 3.89 (s, 3 H); 7.42 (d, 2 H); 7.60 (s, 1 H).

A-187 [CDCl₃] 3.45 (d, 1 H); 3.50 (s, 3 H); 3.87 (d, 1 H); 7.49 (d, 2 H); 7.73 (s, 1 H).

A-188 [CDCl₃] 3.41 (d, 1 H); 3.49 (s, 3 H); 3.79 (d, 1 H); 3.89 (s, 3 H); 7.47 (s, 1 H); 7.50 (s, 1 H); 7.73 (s, 1 H).

A-193 [CDCl₃] 3.47 (d, 1 H), 3.50 (s, 3 H); 3.90 (d, 1 H); 7.85 (s, 2 H); 8.02 (s, 1 H).

A-194 [CDCl₃] 3.45 (d, 1 H); 3.49 (s, 3 H); 3.81 (d, 1 H); 3.90 (s, 3 H); 7.83 (m, 2 H); 8.01 (s, 1 H).

A-331 [CDCl₃] 1.25 (t, 3 H); 2.69 (q, 2 H); 3.49 (s, 3 H); 3.51 (d, 1 H); 3.89 (d, 1 H); 7.26 (d, 2 H); 7.59 (d, 2 H); 8.0 (s br, 1 H).

A-332 [CDCl₃] 1.25 (t, 3 H); 2.68 (q, 2 H); 3.36 (d, 1 H); 3.47 (s, 3 H); 3.82 (d, 1 H); 3.88 (s, 3 H); 7.25 (d, 2 H); 7.58 (d, 2 H).

A-334 [CDCl₃] 3.39 (d, 1 H); 3.61 (s, 3 H); 3.91 (d, 1 H); 7.36 (d, 1 H); 7.51 (d, 1 H).

A-335 [CDCl₃] 3.35 (d, 1 H); 3.56 (s, 3 H); 3.82 (d, 1 H); 3.91 (s, 3 H); 7.34 (d, 1 H); 7.50 (d, 1 H).

B. FORMULATION EXAMPLES

1. Dusting Products

A dusting product is obtained by mixing 10 parts by weight of a compound of the formula (I) and 90 parts by weight of talc as an inert substance and comminuting the mixture in a hammer mill.

2. Dispersible Powder

A readily water-dispersible wettable powder is obtained by mixing 25 parts by weight of a compound of the formula (I), 64 parts by weight of kaolin-containing quartz as an inert substance, 10 parts by weight of potassium lignosulfonate and 1 part by weight of sodium oleoylmethyltaurate as a wetting agent and dispersant, and grinding the mixture in a pinned-disk mill.

3. Dispersion Concentrate

A readily water-dispersible dispersion concentrate is obtained by mixing 20 parts by weight of a compound of the formula (I) with 6 parts by weight of alkylphenol polyglycol ether (®Triton X 207), 3 parts by weight of isotridecanol polyglycol ether (8 EO) and 71 parts by weight of paraffinic mineral oil (boiling range for example about 255 to above 277° C.) and grinding the mixture in a ball mill to a fineness of below 5 microns.

4. Emulsifiable Concentrate

An emulsifiable concentrate is obtained from 15 parts by weight of a compound of the formula (I), 75 parts by weight of cyclohexanone as a solvent and 10 parts by weight of ethoxylated nonylphenol as an emulsifier.

5. Water-Dispersible Granules

Water-dispersible granules are obtained by mixing
75 parts by weight of a compound of the formula (I),
10 parts by weight of calcium lignosulfonate,
5 parts by weight of sodium laurylsulfate,
3 parts by weight of polyvinyl alcohol and
7 parts by weight of kaolin,
grinding the mixture in a pinned-disk mill, and granulating the powder in a fluidized bed by spray application of water as a granulating liquid.
Water-dispersible granules are also obtained by homogenizing and precomminuting, in a colloid mill,
25 parts by weight of a compound of the formula (I),
5 parts by weight of sodium 2,2'-dinaphthylmethane-6,6'-disulfonate,
2 parts by weight of sodium oleoylmethyltaurinate,
1 part by weight of polyvinyl alcohol,
17 parts by weight of calcium carbonate and
50 parts by weight of water,
then grinding the mixture in a bead mill and atomizing and drying the suspension thus obtained in a spray tower by means of a one-phase nozzle.

C. BIOLOGICAL EXAMPLES

1. Pre-Emergence Herbicidal Action Against Harmful Plants

Seeds or rhizome pieces of mono- and dicotyledonous harmful plants are placed in sandy loam soil in pots having a diameter of 9 to 13 cm and covered with soil. The herbicides, formulated as emulsifiable concentrates or dusting products, are then applied in various dosages in the form of aqueous dispersions or suspensions or emulsions at an application rate of 300 to 800 l of water/ha (converted) to the surface of the covering soil. For further cultivation of the plants, the pots are then kept under optimal conditions in a greenhouse. After the test plants have been left to stand in the greenhouse for 3 to 4 weeks under optimal growth conditions, the activity of the inventive compounds is scored visually. For example, compounds No. 1.2-7, 1.2-11, 1.2-42, 1.2-46, 1.2-62, 1.2-148, 1.2-202, 1.3-206, 1.3-110, 1.5-212, 1.6-206, 1.7-9, 1.11-9, 1.11-11, 1.11-16, 1.11-21, 1.11-40, 1.11-41 D1, 1.11-42, 1.11-46 D2, 1.11-147, 1.11-48 D1, 1.11-48 D2, 1.11-53, 1.11-59, 1.11-60, 1.11-110, 1.11-119, 1.11-136, 1.11-137, 1.11-142, 1.11-150, 1.11-197, 1.11-199, 1.11-200, 1.11-201, 1.11-202, 1.11-210, 1.11-212, 1.11-229, 1.14-16, 1.14-212, 1.18-9, 1.18-16, 1.18-96, 1.18-212, 1.20-7, 1.20-19 D2, 1.20-20, 1.20-21, 1.20-42, 1.20-48 D2, 1.20-55, 1.20-74, 1.20-200, 1.20-208, 1.25-206, 1.29-73, 1.29-212, 1.32-206, 1.33-212 and 2.11-212 at an application rate of 320 grams per hectare each show at least 90% efficacy against *Echinochloa crus galli, Lolium multiflorum, Stellaria media* and *Veronica persica*.

2. Post-Emergence Herbicidal Action Against Harmful Plants

Seeds of monocotyledonous and dicotyledonous harmful plants are laid out in sandy loam in cardboard pots, covered with soil and cultivated in a greenhouse under good growth conditions. Two to three weeks after sowing, the test plants are treated at the three-leaf stage. The inventive compounds, formulated as wettable powders or as emulsion concentrates, are sprayed onto the surface of the green parts of the plants at an application rate of 600 to 800 l of water/ha (converted). After the test plants have been left to stand in the greenhouse for 3 to 4 weeks under optimal growth conditions, the activity of the inventive compounds is scored visually. For example, compounds No. 1.2-11, 1.2-53, 1.20-93, 1.2-102, 1.2-138, 1.2-200, 1.3-9, 1.3-206, 1.6-206, 1.7-96, 1.11-11, 1.11-20, 1.11-40, 1.11-53, 1.11-60, 1.11-93, 1.11-110, 1.11-119, 1.11-200, 1.11-212, 1.11-137, 1.11-142, 1.11-149, 1.14-96, 1.14-136, 1.16-110, 1.18-96, 1.18-206, 1.20-16, 1.20-40, 1.20-58, 1.20-200, 1.20-208, 1.25-102, 1.25-206, 1.29-73, 1.32-96, 1.33-102, 2.2-102, 2.11-96 and 2.11-212 at an application rate of 320 grams per hectare each show at least 90% efficacy against *Alopecurus myosuroides* and *Polygonum convolvulus*.

3. Fungicidal Action

Example: In vivo protective test, *Sphaerotheca fuliginea* (powdery mildew in gherkins) To produce an appropriate active ingredient formulation, active ingredient is mixed with acetone/Tween/DMSO and diluted with water to the appropriate concentration.

Gherkin plants (cultivar: Vert petit de Paris) are cultivated in 50/50 peat/pozzolan substrate at 24° C. and sprayed at the Z11 cotyledon stage with the active ingredient formulation specified above. Plants which serve as a control are treated with an aqueous solution without active ingredient.

After 24 hours, the plants are sprayed with a spore suspension of *Sphaerotheca fuliginea* (100 000 spores/ml). The spores are collected from infected plants. The inoculated plants are placed at 20/25° C. and at 60/70% relative humidity.

Evaluation is carried out 12 days after the inoculation. 0% means an efficacy which corresponds to that of the control, whereas 100% means that no infection is observed.

At an application rate of 500 ppm, the following efficacies are found with the following compounds:

| Example No. | Efficacy [%] |
|---|---|
| 1.3-206 | 94 |
| 1.5-206 | 80 |
| 1.6-206 | 94 |
| 1.7-9 | 98 |
| 1.7-206 | 72 |
| 1.11-19 D1 | 100 |
| 1.11-110 | 78 |
| 1.11-238 | 83 |
| 1.14-16 | 100 |
| 1.14-206 | 98 |
| 1.16-60 | 94 |
| 1.16-96 | 78 |
| 1.16-110 | 89 |
| 1.16-136 | 78 |
| 1.16-212 | 94 |
| 1.18-110 | 98 |
| 1.18-212 | 98 |
| 1.18-206 | 95 |
| 1.33-60 | 100 |
| 1.33-96 | 100 |
| 1.33-212 | 100 |
| 1.33-102 | 100 |
| 1.32-60 | 100 |
| 1.32-96 | 100 |
| 1.20-19 D2 | 100 |
| 1.20-64 | 98 |
| 1.20-206 | 100 |
| 1.20-212 | 100 |
| 1.20-135 | 98 |
| 1.25-9 | 100 |
| 1.25-16 | 95 |
| 1.25-60 | 100 |
| 1.25-110 | 90 |
| 1.25-136 | 100 |
| 1.32-9 | 100 |
| 1.32-16 | 100 |
| 1.32-110 | 100 |
| 1.32-212 | 100 |
| 1.33-9 | 100 |
| 1.33-16 | 100 |
| 1.33-206 | 100 |

Example 2

In Vivo Protective Test, *Phytophthora infestans* (Late Blight in Tomatoes)

To produce an appropriate active ingredient formulation, active ingredient is mixed with acetone/Tween/DMSO and diluted with water to the appropriate concentration.

Tomato plants (cultivar: Rentita) are cultivated in 50/50 peat/pozzolan substrate at 20-25° C. and sprayed at the Z12 stage with the active ingredient formulation specified above. Plants which serve as a control are treated with an aqueous solution without active ingredient.

After 24 hours, the plants are sprayed with a spore suspension of *Phytophthora infestans* (20 000 spores/ml). The spores are collected from infected plants. The inoculated plants are placed at 16-18° C. and in a humid atmosphere for 5 days.

Evaluation is carried out 5 days after the infection. 0% means an efficacy which corresponds to that of the control, whereas an efficacy of 100% means that no infection is observed.

At an application rate of 500 ppm, the following efficacies are found with the following compounds:

| Example No. | Efficacy [%] |
|---|---|
| 1.11-19 D1 | 100 |
| 1.11-110 | 100 |
| 1.11-136 | 100 |
| 1.11-238 | 99 |
| 1.11-239 | 100 |
| 1.11-189 | 100 |
| 1.14-110 | 100 |
| 1.14-206 | 100 |
| 1.16-212 | 100 |
| 1.18-206 | 90 |
| 1.18-212 | 99 |
| 1.20-19 D2 | 100 |
| 1.20-64 | 100 |
| 1.20-206 | 100 |
| 1.20-212 | 95 |
| 1.25-212 | 100 |
| 1.33-212 | 97 |
| 2.11-206 | 100 |
| 2.11-212 | 98 |
| 2.20-206 | 85 |

Example 3

In Vivo Protective Test, *Botrytis cinerea* (Gray Mold in Gherkins)

To produce an appropriate active ingredient formulation, active ingredient is mixed with acetone/Tween/DMSO and diluted with water to the appropriate concentration.

Gherkin plants (Vert petit de Paris) are cultivated in 50/50 peat/pozzolan substrate at 24° C. and sprayed at the Z11 stage with the active ingredient formulation specified above. Plants which serve as a control are treated with an aqueous solution without active ingredient.

After 24 hours, the plants are sprayed with a spore suspension of *Botrytis cinerea* (50 000 spores/ml). The spores are suspended in a nutrient solution consisting of 10 g/L PDB, 50 g/L D-Fructose, 2 g/L $NH_4NO_3$ and 1 g/L $KH_2PO_4$.

The inoculated gherkin plants are incubated at 17° C. and at 80% relative air humidity.

Evaluation is carried out 4-5 days after the infection. 0% means an efficacy which corresponds to that of the control, whereas an efficacy of 100% means that no infection is observed.

At an application rate of 500 ppm, the following efficacies are found with the following compounds:

| Example No. | Efficacy [%] |
|---|---|
| 1.3-110 | 98 |
| 1.5-206 | 100 |
| 1.6-96 | 95 |
| 1.6-110 | 100 |
| 1.6-206 | 100 |
| 1.7-9 | 95 |
| 1.7-110 | 100 |
| 1.7-206 | 99 |
| 1.11-19 D1 | 100 |
| 1.11-110 | 90 |
| 1.11-238 | 100 |
| 1.11-239 | 98 |
| 1.14-16 | 99 |

| Example No. | Efficacy [%] |
|---|---|
| 1.14-110 | 100 |
| 1.14-136 | 88 |
| 1.14-206 | 100 |
| 1.16-60 | 100 |
| 1.16-94 | 75 |
| 1.16-96 | 85 |
| 1.16-110 | 100 |
| 1.16-136 | 96 |
| 1.16-212 | 100 |
| 1.18-110 | 91 |
| 1.18-206 | 100 |
| 1.18-212 | 100 |
| 1.20-19 D2 | 100 |
| 1.20-64 | 70 |
| 1.20-110 | 83 |
| 1.20-135 | 100 |
| 1.20-206 | 100 |
| 1.20-212 | 100 |
| 1.25-9 | 99 |
| 1.25-16 | 100 |
| 1.25-60 | 100 |
| 1.25-110 | 98 |
| 1.25-136 | 79 |
| 1.25-206 | 100 |
| 1.25-212 | 97 |
| 1.32-9 | 100 |
| 1.32-16 | 100 |
| 1.32-60 | 100 |
| 1.32-94 | 95 |
| 1.32-110 | 100 |
| 1.32-102 | 100 |
| 1.32-206 | 96 |
| 1.32-212 | 100 |
| 1.33-9 | 89 |
| 1.33-16 | 100 |
| 1.33-60 | 100 |
| 1.33-96 | 100 |
| 1.33-110 | 81 |
| 1.33-206 | 100 |
| 1.33-212 | 100 |

Example 4

In Vivo Protective Test, *Septoria tritici* (Blotch in Wheat)

To produce an appropriate active ingredient formulation, active ingredient is mixed with acetone/Tween/DMSO and diluted with water to the appropriate concentration.

Wheat plants (cultivar: Scipion) are cultivated in 50/50 peat/pozzolan substrate at 22° C. (12 h)/20° C. (12 h) and sprayed at the 1-leaf stage (height 10 cm) with the active ingredient formulation specified above. Control plants are sprayed with an aqueous solution without added active ingredient.

After 24 hours, the plants are sprayed with a spore suspension of cryopreserved *Septoria tritici* (500 000 spores/ml). The inoculated plants are placed at 18° C. and at 100% relative humidity for 72 h and then at 90% relative air humidity for a further 21-28 days.

21-28 days after the inoculation, the evaluation is conducted in comparison with the control plants. 0% means an efficacy which corresponds to that of the control, whereas an efficacy of 100% means that no infection is observed.

At an application rate of 500 ppm, the following efficacies are found with the following compounds:

| Example No. | Efficacy [%] |
|---|---|
| 1.3-206 | 100 |
| 1.3-110 | 98 |
| 1.5-206 | 100 |
| 1.6-96 | 75 |
| 1.6-110 | 100 |
| 1.6-206 | 100 |
| 1.7-9 | 100 |
| 1.7-110 | 100 |
| 1.7-206 | 100 |
| 1.11-19 D1 | 100 |
| 1.11-110 | 100 |
| 1.11-136 | 100 |
| 1.11-238 | 100 |
| 1.11-239 | 100 |
| 1.14-16 | 100 |
| 1.14-110 | 100 |
| 1.14-206 | 100 |
| 1.16-60 | 100 |
| 1.16-96 | 88 |
| 1.16-110 | 100 |
| 1.16-212 | 100 |
| 1.18-110 | 100 |
| 1.18-212 | 100 |
| 1.20-19 D2 | 100 |
| 1.20-64 | 100 |
| 1.20-110 | 100 |
| 1.20-135 | 100 |
| 1.20-206 | 83 |
| 1.20-212 | 100 |
| 2.11-206 | 83 |
| 2.11-212 | 83 |
| 2.20-206 | 100 |
| 1.25-206 | 100 |
| 1.25-60 | 100 |
| 1.25-212 | 100 |
| 1.25-9 | 100 |
| 1.25-16 | 97 |
| 1.25-110 | 97 |
| 1.32-1 | 98 |
| 1.32-9 | 100 |
| 1.32-16 | 100 |
| 1.32-60 | 100 |
| 1.32-94 | 100 |
| 1.32-96 | 100 |
| 1.32-102 | 100 |
| 1.32-110 | 100 |
| 1.32-206 | 100 |
| 1.32-212 | 100 |
| 1.33-1 | 100 |
| 1.33-9 | 100 |
| 1.33-16 | 100 |
| 1.33-60 | 100 |
| 1.33-94 | 100 |
| 1.33-96 | 100 |
| 1.33-102 | 100 |
| 1.33-110 | 100 |
| 1.33-206 | 100 |
| 1.33-212 | 100 |

Example 5

*Venturia* Test (Apple)/Protective

Solvents: 24.5 parts by weight of acetone
24.5 parts by weight of dimethylacetamide
Emulsifier: 1 part by weight of alkylaryl polyglycol ether To produce an appropriate active ingredient formulation, 1 part by weight of active ingredient is mixed with the stated amounts of solvent and emulsifier, and the concentrate is diluted with water to the desired concentration.

To test for protective efficacy, young plants are sprayed with the active ingredient formulation at the stated application rate. After the spray coating has dried on, the plants are inoculated with an aqueous conidia suspension of the apple scab pathogen *Venturia inaequalis* and then remain in an incubation cabin at about 20° C. and 100% relative air humidity for 1 day.

The plants are then placed in a greenhouse at about 21° C. and a relative air humidity of about 90%.

Evaluation follows 10 days after the inoculation. 0% means an efficacy which corresponds to that of the control, whereas an efficacy of 100% means that no infection is observed.

In this test, the following inventive compounds show, at an active ingredient concentration of 100 ppm, an efficacy of 70% or more:

| Example No. | Efficacy [%] |
|---|---|
| 1.11-212 | 100 |
| 1.20-5 | 96 |
| 1.25-206 | 90 |
| 1.25-212 | 98 |

Example 6

*Plasmopara* Test (Grapevine)/Protective

Solvents: 24.5 parts by weight of acetone
24.5 parts by weight of dimethylacetamide
Emulsifier: 1 part by weight of alkylaryl polyglycol ether To produce an appropriate active ingredient formulation, 1 part by weight of active ingredient is mixed with the stated amounts of solvent and emulsifier, and the concentrate is diluted with water to the desired concentration.

To test for protective efficacy, young plants are sprayed with the active ingredient formulation at the stated application rate. After the spray coating has dried on, the plants are inoculated with an aqueous spore suspension of *Plasmopara viticola* and then remain in an incubation cabin at about 20° C. and 100% relative air humidity for 1 day. Subsequently, the plants are placed in a greenhouse at about 21° C. and about 90% air humidity for 4 days. The plants are then moistened and placed in an incubation cabin for 1 day.

Evaluation follows 6 days after the inoculation. 0% means an efficacy which corresponds to that of the control, whereas an efficacy of 100% means that no infection is observed.

In this test, the following inventive compounds show, at an active ingredient concentration of 100 ppm, an efficacy of 70% or more:

| Example No. | Efficacy [%] |
|---|---|
| 1.20-5 | 99 |
| 1.25-206 | 98 |
| 1.25-212 | 100 |

The invention claimed is:

1. A 5-oxy-substituted 3-phenylisoxazoline-5-carboxamide and/or 5-oxy-substituted 3-phenylisoxazoline-5-thioamide of the formula (I) and/or a salt thereof

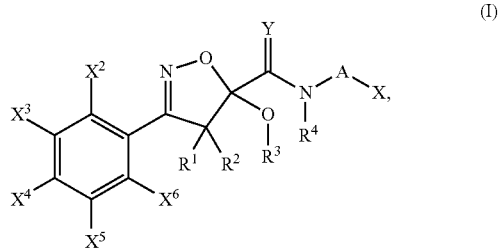

in which $R^1$ and $R^2$ are each independently hydrogen, fluorine, chlorine, bromine, iodine, cyano, or $(C_1$-$C_4)$-alkyl or $(C_1$-$C_4)$-alkoxy each substituted by m radicals from the group consisting of fluorine, chlorine, bromine, iodine and cyano, or $R^1$ and $R^2$ together with the carbon atom to which they are bonded form a saturated or partly or fully unsaturated three-, four- or five-membered ring formed from q carbon atoms and p oxygen atoms;

$R^3$ is $(C_1$-$C_6)$-alkyl, $(C_3$-$C_6)$-cycloalkyl, $(C_2$-$C_6)$-alkenyl or $(C_2$-$C_6)$-alkynyl each substituted by m radicals from the group consisting of fluorine, chlorine, bromine, iodine, cyano, $(C_1$-$C_4)$-alkoxy and hydroxyl, $R^4$ is hydrogen, cyano, or $(C_1$-$C_8)$-alkyl, $(C_3$-$C_8)$-cycloalkyl, $(C_3$-$C_8)$-alkenyl or $(C_3$-$C_8)$-alkynyl each substituted by m radicals from the group consisting of fluorine, chlorine, bromine, iodine, cyano, hydroxyl and $(C_1$-$C_6)$-alkoxy, A is a bond or a divalent unit from the group consisting of

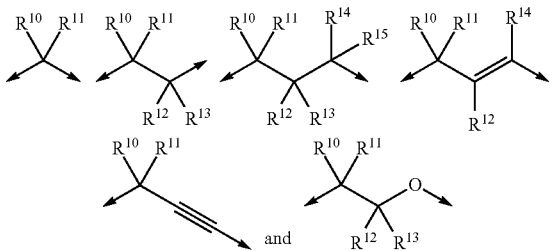

$R^{10}$, $R^{11}$, $R^{12}$, $R^{13}$, $R^{14}$ and $R^{15}$ are each independently hydrogen, fluorine, chlorine, bromine, iodine, hydroxyl, cyano, $CO_2R^8$, $CONR^6R^8$, $R^5$, or $(C_1$-$C_6)$-alkyl, $(C_3$-$C_5)$-cycloalkyl, $(C_2$-$C_6)$-alkenyl, $(C_2$-$C_6)$-alkynyl each substituted by m radicals from the group consisting of fluorine, chlorine, bromine, iodine, hydroxyl and cyano, or $(C_1$-$C_6)$-alkoxy, $(C_3$-$C_6)$-cycloalkoxy, $(C_2$-$C_6)$-alkenyloxy or $(C_2$-$C_6)$-alkynyloxy each substituted by m radicals from the group consisting of fluorine, chlorine, bromine, iodine, cyano and $(C_1$-$C_2)$-alkoxy;

Y is oxygen or sulfur;

X is hydrogen, cyano, hydroxyl, $X^1$, or $(C_1$-$C_{12})$-alkyl, $(C_3$-$C_8)$-cycloalkyl, $(C_2$-$C_{12})$-alkenyl or $(C_2$-$C_{12})$-alkynyl each substituted by m radicals from the group consisting of fluorine, chlorine, bromine, iodine, cyano, hydroxyl, $OR^7$, $X^1$, $OX^1$, $NHX^1$, $S(O)_nR^5$, $SO_2NR^6R^7$, $SO_2NR^6COR^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)=NOR^8$, or X, A and $R^4$ together with the nitrogen atom to which they are bonded form a saturated or partly or fully unsaturated five-, six- or seven-membered ring containing, as well as this nitrogen atom, k carbon atoms, n oxygen atoms, p sulfur atoms and p elements from the group consisting of $NR^7$ and $NCOR^7$ as ring atoms, where one carbon atom bears p oxo groups;

$X^1$ is a three-, four-, five- or six-membered saturated, partly unsaturated, fully unsaturated or aromatic ring which is formed from r carbon atoms, s nitrogen atoms, n sulfur atoms and n oxygen atoms, and which is substituted by s radicals from the group consisting of $R^6$, $R^{6a}$, $R^8$ and $R^9$, where the sulfur atoms and carbon atoms bear n oxo groups;

or $X^1$ is phenyl substituted by m radicals from the group consisting of $R^6$, $R^{6a}$, $R^8$ and $R^9$;

$X^2$, $X^4$ and $X^6$ are each independently hydrogen, fluorine, chlorine, bromine, iodine, cyano, nitro, or $(C_1-C_4)$-alkyl, $(C_3-C_5)$-cycloalkyl, $(C_2-C_4)$-alkenyl, $(C_2-C_4)$-alkynyl, $(C_1-C_4)$-alkoxy, $(C_2-C_4)$-alkenyloxy, $(C_2-C_4)$-alkynyloxy or $(C_1-C_4)$-alkylcarbonyl each substituted by m radicals from the group consisting of fluorine, chlorine, bromine, iodine, cyano and $(C_1-C_4)$-alkoxy;

$X^3$ and $X^5$ are each independently hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)=NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $S(O)_nR^5$, $SO_2NR^6R^8$, $OSO_2NR^6R^8$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

$R^5$ is $(C_1-C_6)$-alkyl or $(C_3-C_6)$-cycloalkyl each substituted by m radicals from the group consisting of fluorine, chlorine, bromine, iodine, cyano and hydroxyl;

$R^6$ is hydrogen or $R^5$;

$R^{6a}$ is fluorine, chlorine, bromine, iodine, cyano, hydroxyl, $S(O)_nR^5$, or $(C_1-C_6)$-alkoxy, $(C_3-C_6)$-alkenyloxy or $(C_3-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl, $(C_3-C_6)$-cycloalkyl, $(C_2-C_4)$-alkenyl or $(C_2-C_4)$-alkynyl each substituted by m radicals from the group consisting of fluorine, chlorine, bromine, cyano and $(C_1-C_2)$-alkoxy;

$R^8$ is $R^7$;

$R^9$ is $(C_1-C_3)$-alkyl or $(C_1-C_3)$-alkoxy;

k is 3, 4, 5 or 6;
m is 0, 1, 2, 3, 4 or 5;
n is 0, 1 or 2;
p is 0 or 1;
q is 3, 4 or 5;
r is 1, 2, 3, 4 or 5;
s is 0, 1, 2, 3 or 4.

2. A 5-oxy-substituted 3-phenylisoxazoline-5-carboxamide or 5-oxy-substituted 3-phenylisoxazoline-5-thioamide and/or salt as claimed in claim 1, in which $R^1$ and $R^2$ are each independently hydrogen, fluorine, chlorine, bromine, iodine, cyano, or $(C_1-C_4)$-alkyl or $(C_1-C_4)$-alkoxy each substituted by m radicals from the group consisting of fluorine, chlorine, bromine, iodine and cyano, or $R^1$ and $R^2$ together with the carbon atom to which they are bonded form a saturated or partly or fully unsaturated three-, four- or five-membered ring formed from q carbon atoms and p oxygen atoms;

$R^3$ is $(C_1-C_6)$-alkyl, $(C_3-C_6)$-cycloalkyl, $(C_2-C_6)$-alkenyl or $(C_2-C_6)$-alkynyl each substituted by m radicals from the group consisting of fluorine, chlorine, bromine, iodine, cyano, $(C_1-C_4)$-alkoxy and hydroxyl, $R^4$ is hydrogen, cyano, or $(C_1-C_8)$-alkyl or $(C_3-C_8)$-cycloalkyl each substituted by m radicals from the group consisting of fluorine, chlorine, bromine, iodine, cyano, hydroxyl and $(C_1-C_6)$-alkoxy;

A is a bond or a divalent unit from the group consisting of

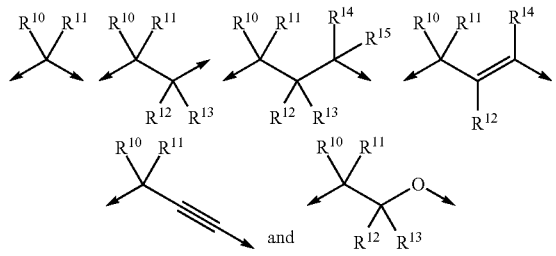

$R^{10}$, $R^{11}$, $R^{12}$, $R^{13}$, $R^{14}$ and $R^{15}$ are each independently hydrogen, fluorine, chlorine, bromine, iodine, hydroxyl, cyano, $CO_2R^8$, $CONR^6R^8$, $R^5$, or $(C_1-C_6)$-alkyl, $(C_3-C_5)$-cycloalkyl, $(C_2-C_6)$-alkenyl, $(C_2-C_6)$-alkynyl each substituted by m radicals from the group consisting of fluorine, chlorine, bromine, iodine, hydroxyl and cyano, or $(C_1-C_6)$-alkoxy, $(C_3-C_6)$-cycloalkoxy, $(C_2-C_6)$-alkenyloxy or $(C_2-C_6)$-alkynyloxy each substituted by m radicals from the group consisting of fluorine, chlorine, bromine, iodine, cyano and $(C_1-C_2)$-alkoxy;

Y is oxygen or sulfur;

X is hydrogen, cyano, hydroxyl, $X^1$, or $(C_1-C_{12})$-alkyl, $(C_3-C_8)$-cycloalkyl, $(C_2-C_{12})$-alkenyl or $(C_2-C_{12})$-alkynyl each substituted by m radicals from the group consisting of fluorine, chlorine, bromine, iodine, cyano, hydroxyl, $OR^7$, $X^1$, $OX^1$, $NHX^1$, $S(O)_nR^5$, $SO_2NR^6R^7$, $SO_2NR^6COR^8$, $CO_2R^8$, $CONR^6R^8$, $COR^6$, $CONR^8SO_2R^5$, $NR^6R^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OCSNR^6R^8$, $POR^9R^9$ and $C(R^6)=NOR^8$, or X, A and $R^4$ together with the nitrogen atom to which they are bonded form a saturated or partly or fully unsaturated five-, six- or seven-membered ring containing, as well as this nitrogen atom, k carbon atoms, n oxygen atoms, p sulfur atoms and p elements from the group consisting of MC and $NCOR^7$ as ring atoms, where one carbon atom bears p oxo groups;

$X^1$ is a ring, substituted by s radicals from the group consisting of $R^6$, $R^{6a}$, $R^8$ and $R^9$, from the group consisting of

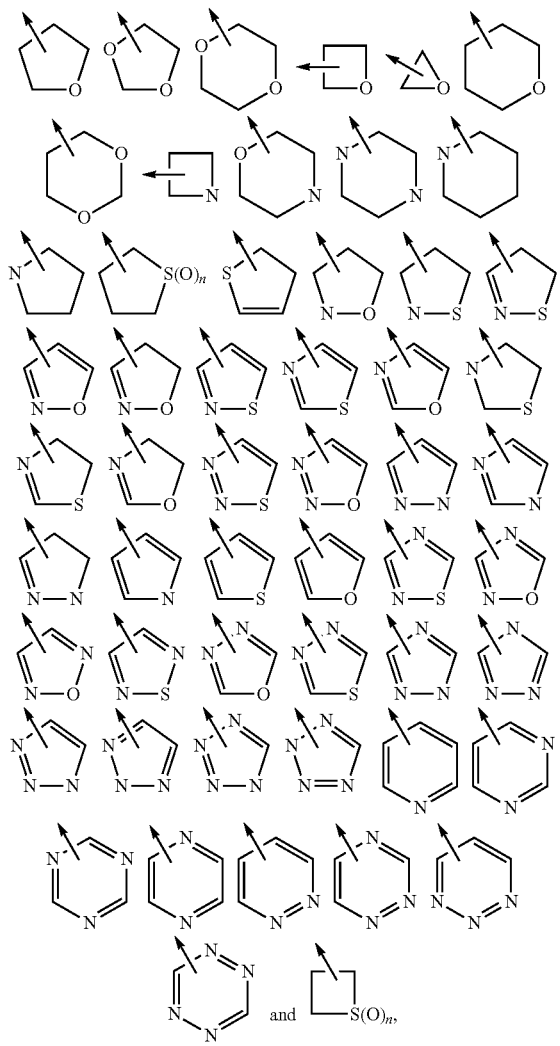

or $X^1$ is phenyl substituted by m radicals from the group consisting of $R^6$, $R^{6a}$, $R^8$ and $R^9$;

$X^2$, $X^4$ and $X^6$ are each independently hydrogen, fluorine, chlorine, bromine, iodine, cyano, nitro, or $(C_1\text{-}C_4)$-alkyl, $(C_3\text{-}C_5)$-cycloalkyl, $(C_2\text{-}C_4)$-alkenyl, $(C_2\text{-}C_4)$-alkynyl, $(C_1\text{-}C_4)$-alkoxy, $(C_2\text{-}C_4)$-alkenyloxy, $(C_2\text{-}C_4)$-alkynyloxy or $(C_1\text{-}C_4)$-alkylcarbonyl each substituted by m radicals from the group consisting of fluorine, chlorine, bromine, iodine, cyano and $(C_1\text{-}C_4)$-alkoxy;

$X^3$ and $X^5$ are each independently hydrogen, fluorine, chlorine, bromine, iodine, hydroxyl, cyano, nitro, $SF_5$, $CONR^8SO_2R^5$, $CONR^6R^8$, $COR^6$, $CO_2R^8$, $CONR^6R^8$, $C(R^6)\!=\!NOR^8$, $NR^6COR^8$, $NR^6CONR^8R^8$, $NR^6CO_2R^8$, $NR^6SO_2R^8$, $NR^6SO_2NR^6R^8$, $OCONR^6R^8$, $OSO_2R^5$, $S(O)_nR^5$, $SO_2NR^6R^8$, $OSO_2NR^6R^8$, or $(C_1\text{-}C_6)$-alkyl, $(C_3\text{-}C_5)$-cycloalkyl, $(C_2\text{-}C_6)$-alkenyl, $(C_2\text{-}C_6)$-alkynyl each substituted by m radicals from the group consisting of fluorine, chlorine, bromine, iodine, hydroxyl and cyano;

or $(C_1\text{-}C_6)$-alkoxy, $(C_3\text{-}C_6)$-cycloalkoxy, $(C_2\text{-}C_6)$-alkenyloxy or $(C_2\text{-}C_6)$-alkynyloxy each substituted by m radicals from the group consisting of fluorine, chlorine, bromine, iodine, cyano and $(C_1\text{-}C_2)$-alkoxy;

$R^5$ is $(C_1\text{-}C_6)$-alkyl or $(C_3\text{-}C_6)$-cycloalkyl each substituted by m radicals from the group consisting of fluorine, chlorine, bromine, iodine, cyano and hydroxyl;

$R^6$ is hydrogen or $R^5$;

$R^{5a}$ is fluorine, chlorine, bromine, iodine, cyano, hydroxyl, $S(O)_nR^5$, or $(C_1\text{-}C_6)$-alkoxy, $(C_2\text{-}C_6)$-alkenyloxy or $(C_2\text{-}C_6)$-alkynyloxy each substituted by m radicals from the group consisting of fluorine, chlorine, bromine, cyano and $(C_1\text{-}C_2)$-alkoxy;

$R^7$ is hydrogen or $(C_1\text{-}C_6)$-alkyl, $(C_3\text{-}C_6)$-cycloalkyl, $(C_2\text{-}C_4)$-alkenyl or $(C_2\text{-}C_4)$-alkynyl each substituted by m radicals from the group consisting of fluorine, chlorine, bromine, cyano and $(C_1\text{-}C_2)$-alkoxy;

$R^8$ is $R^7$, $R^9$ is $(C_1\text{-}C_3)$-alkyl or $(C_1\text{-}C_3)$-alkoxy;

k is 3, 4, 5 or 6;

m is 0, 1, 2, 3, 4 or 5;

n is 0, 1 or 2;

p is 0 or 1;

q is 3, 4 or 5;

s is 0, 1, 2, 3 or 4.

3. A 5-oxy-substituted 3-phenylisoxazoline-5-carboxamide or 5-oxy-substituted 3-phenylisoxazoline-5-thioamide and/or salt as claimed in claim 1, in which $R^1$ and $R^2$ are each independently hydrogen, fluorine, chlorine, bromine, iodine, cyano, or $(C_1\text{-}C_4)$-alkyl substituted by m radicals from the group consisting of fluorine, chlorine, bromine, iodine and cyano;

$R^3$ is $(C_1\text{-}C_4)$-alkyl, $(C_3\text{-}C_4)$-cycloalkyl, $(C_2\text{-}C_3)$-alkenyl or $(C_2\text{-}C_3)$-alkynyl each substituted by m radicals from the group consisting of fluorine, chlorine, bromine, cyano, $(C_1\text{-}C_2)$-alkoxy, A is a bond or a divalent unit from the group consisting of $CH_2$, $CH_2CH_2$, $CHCH_3$, $CH_2CH_2CH_2$, $CH(CH_2CH_3)$, $CH(CH_3)CH_2$, $C(CH_3)_2$, $C(CH_3)_2CH_2$, $C(iPr)CH_3$, $CH(CH_2iPr)CH_2$, $CH_2CH\!=\!CH$, $C(CH_3)_2C\!\equiv\!C$, $CH(CF_3)CH_2$, $CH(CH_3)CH_2O$, $CH_2CH_2O$, $CH(cPr)CH_2O$, $CH(CH_2OCH_3)$, $CH(CH_2CH_2SCH_3)$, $CH(COOH)$, $CH(COOCH_3)$, $CH(COOH)CH_2$, $CH(COOCH_3)CH_2$, $CH_2COH(CF_3)$, $CH(CONHCH_3)$, $CH(CONHCH_3)CH_2$ and $CH_2CH_2CONHCH_2$;

$R^4$ is hydrogen or $(C_1\text{-}C_8)$-alkyl;

Y is oxygen or sulfur;

X is hydrogen, cyano, hydroxyl, $X^1$, or $(C_1\text{-}C_{12})$-alkyl, $(C_3\text{-}C_8)$-cycloalkyl, $(C_2\text{-}C_{12})$-alkenyl or $(C_2\text{-}C_{12})$-alkynyl each substituted by m radicals from the group consisting of fluorine, chlorine, cyano, hydroxyl, $OR^7$, $X^1$, $OX^1$, $NHX^1$, $S(O)_nR^5$, $CO_2R^8$, $CONR^6R^8$, $CONR^8SO_2R^5$ and $POR^9R^9$;

$X^1$ is a ring, substituted by s radicals from the group consisting of $R^6$, $R^{6a}$, $R^8$ and $R^9$, from the group consisting of

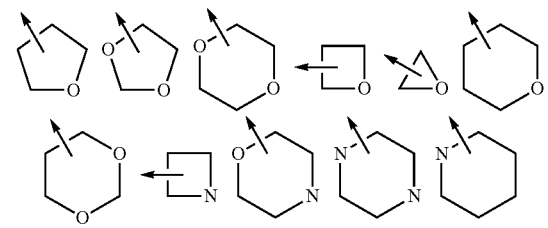

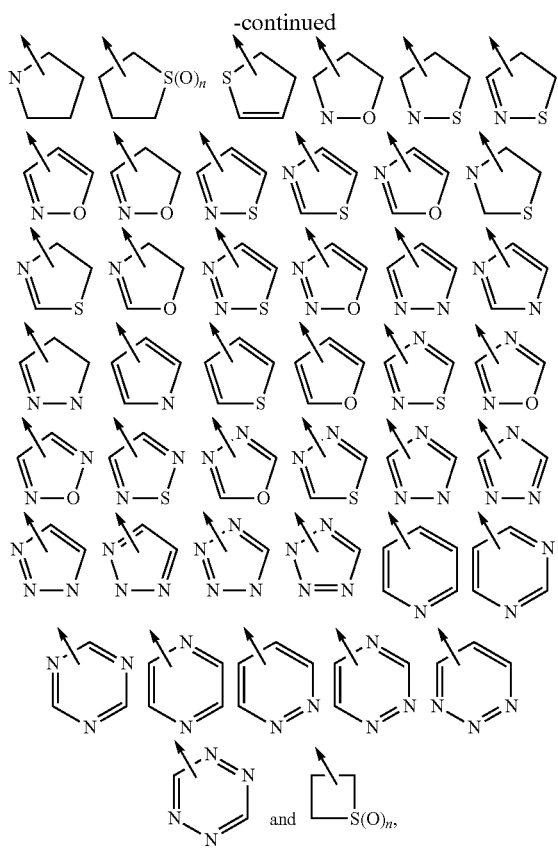

or X¹ is phenyl substituted by m radicals from the group consisting of $R^6$, $R^{6a}$, $R^8$ and $R^9$;

$X^2$, $X^4$ and $X^6$ are each independently hydrogen, fluorine, or chlorine, or $(C_1-C_4)$-alkyl or $(C_1-C_4)$-alkoxy each substituted by m radicals from the group consisting of fluorine, chlorine, cyano and $(C_1-C_4)$-alkoxy;

$X^3$ and $X^5$ are each independently hydrogen, fluorine, chlorine, bromine, cyano, or $(C_1-C_6)$-alkyl substituted by m radicals from the group consisting of fluorine and chlorine, or $(C_1-C_6)$-alkoxy substituted by m radicals from the group consisting of fluorine and chlorine;

$R^5$ is methyl or ethyl;

$R^6$ is hydrogen or $R^5$;

$R^{6a}$ is fluorine, chlorine, bromine, iodine, cyano, hydroxyl, $S(O)_nR^5$, or $(C_1-C_6)$-alkoxy, $(C_2-C_6)$-alkenyloxy or $(C_2-C_6)$-alkynyloxy each substituted by m radicals from the group consisting of fluorine, chlorine, bromine, cyano and $(C_1-C_2)$-alkoxy;

$R^7$ is hydrogen or $(C_1-C_6)$-alkyl substituted by m radicals from the group consisting of fluorine and chlorine;

$R^8$ is $R^7$;

$R^9$ is $(C_1-C_3)$-alkoxy;

m is 0, 1, 2 or 3;

n is 0, 1 or 2;

s is 0, 1, 2, 3 or 4.

4. A herbicidal composition, comprising a herbicidally active content of at least one compound of the formula (I) and/or salt as claimed in claim 1.

5. The herbicidal composition as claimed in claim 4 in a mixture with one or more formulation auxiliaries.

6. The herbicidal composition as claimed in claim 4, comprising at least one further pesticidally active substance selected from the group consisting of insecticides, acaricides, herbicides, fungicides, safeners and growth regulators.

7. The herbicidal composition as claimed in claim 6, comprising a safener.

8. The herbicidal composition as claimed in claim 7, in which the safener is selected from the group consisting of mefenpyr-diethyl, cyprosulfamide, isoxadifen-ethyl, cloquintocet-mexyl, benoxacor and dichlormid.

9. The herbicidal composition as claimed in claim 6, comprising a further herbicide.

10. A method for controlling one or more unwanted plants, which comprises applying an effective amount of at least one compound of the formula (I) and/or salt as claimed in claim 1 to the one or more plants and/or a site of unwanted vegetation.

11. A compound of the formula (I) and/or salt as claimed in claim 1 capable of being used for controlling one or more unwanted plants.

12. The method as claimed in claim 10, wherein the compound of the formula (I) and/or salt is used for controlling one or more unwanted plants in one or more crops of one or more useful plants.

13. The method as claimed in claim 12, wherein the useful plants are one or more transgenic useful plants.

14. A fungicidal composition, comprising a fungicidally active amount of at least one compound of the formula (I) and/or salt as claimed in claim 1.

15. The fungicidal composition as claimed in claim 14 in a mixture with one or more formulation auxiliaries.

16. The fungicidal composition as claimed in claim 14, comprising at least one further pesticidally active compound selected from the group consisting of insecticides, acaricides, herbicides, fungicides, safeners and growth regulators.

17. A 5-oxy-substituted 3-phenylisoxazoline-5-carboxamide or 5-oxy-substituted 3-phenylisoxazoline-5-thioamide and/or salt as claimed in claim 1, in which $X^2$, $X^4$, $X^6$, $R^1$, $R^2$, and $R^4$ each represent hydrogen;

$R^3$ represents methyl; and

Y represents oxygen.

18. A 5-oxy-substituted 3-phenylisoxazoline-5-carboxamide or 5-oxy-substituted 3-phenylisoxazoline-5-thioamide and/or salt as claimed in claim 1, in which $X^2$ is hydrogen;

$X^3$ is hydrogen;

$X^4$ is hydrogen;

$X^5$ is cyano;

$X^6$ is hydrogen;

$R^1$ is hydrogen;

$R^2$ is hydrogen;

$R^3$ is methyl;

$R^4$ is hydrogen;

Y is oxygen;

A is a bond; and

X is cyclopropyl.

19. A 5-oxy-substituted 3-phenylisoxazoline-5-carboxamide or 5-oxy-substituted 3-phenylisoxazoline-5-thioamide and/or salt as claimed in claim 1, which is the compound 1.20-5 wherein $X^2$ is hydrogen;

$X^3$ is chlorine;

$X^4$ is hydrogen;

$X^5$ is chlorine;

$X^6$ is hydrogen;

$R^1$ is hydrogen;

$R^2$ is hydrogen;

$R^3$ is methyl;
$R^4$ is hydrogen;
Y is oxygen;
A-X is isopropyl.

20. A 5-oxy-substituted 3-phenylisoxazoline-5-carboxamide or 5-oxy-substituted 3-phenylisoxazoline-5-thioamide and/or salt as claimed in claim 1, which is the compound 1.20-210
$X^2$ is hydrogen;
$X^3$ is chlorine;
$X^4$ is hydrogen;
$X^5$ is chlorine;
$X^6$ is hydrogen;
$R^1$ is hydrogen;
$R^2$ is hydrogen;
$R^3$ is methyl;
$R^4$ is hydrogen;
Y is oxygen;
A-X is

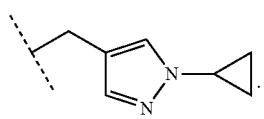
.